(12) United States Patent
Lassen et al.

(10) Patent No.: US 8,663,963 B2
(45) Date of Patent: *Mar. 4, 2014

(54) *HAFNIA* PHYTASE

(75) Inventors: Soeren Flensted Lassen, Farum (DK);
Carsten Sjoeholm, Alleroed (DK); Lars Kobberoee Skov, Ballerup (DK)

(73) Assignee: Novozymes A/S, Bagsvaerd (DK)

( * ) Notice: Subject to any disclaimer, the term of this patent is extended or adjusted under 35 U.S.C. 154(b) by 99 days.

This patent is subject to a terminal disclaimer.

(21) Appl. No.: 13/032,679

(22) Filed: Feb. 23, 2011

(65) Prior Publication Data

US 2011/0154519 A1    Jun. 23, 2011

Related U.S. Application Data

(62) Division of application No. 12/055,694, filed on Mar. 26, 2008, now Pat. No. 7,923,232.

(60) Provisional application No. 60/908,705, filed on Mar. 29, 2007.

(30) Foreign Application Priority Data

Mar. 26, 2007   (EP) .................................. 07104870

(51) Int. Cl.
     *C12N 9/16*     (2006.01)
     *A23J 1/00*     (2006.01)
     *A61K 38/46*     (2006.01)

(52) U.S. Cl.
     USPC ............................. 435/196; 435/19; 536/23.2

(58) Field of Classification Search
     USPC ........................................................ 435/196
See application file for complete search history.

(56) References Cited

U.S. PATENT DOCUMENTS

| | | | |
|---|---|---|---|
| 6,511,699 B1 | 1/2003 | Lei | |
| 6,841,370 B1 | 1/2005 | Lei | |
| 7,923,232 B2* | 4/2011 | Lassen et al. | 435/196 |
| 8,053,221 B2 | 11/2011 | Miasnikov | |
| 8,101,391 B2 | 1/2012 | Sjoeholm | |
| 8,143,045 B2 | 3/2012 | Miasnikov et al. | |
| 8,143,046 B2 | 3/2012 | Cervin et al. | |
| 8,206,962 B2 | 6/2012 | Lassen et al. | |
| 2003/0103958 A1 | 6/2003 | Short et al. | |
| 2003/0190677 A1 | 10/2003 | Lehmann | |
| 2005/0010037 A1 | 1/2005 | Wu et al. | |
| 2010/0136113 A1 | 6/2010 | Steer et al. | |
| 2013/0017185 A1 | 1/2013 | De Maria et al. | |

FOREIGN PATENT DOCUMENTS

| | | |
|---|---|---|
| WO | 03/066847 A2 | 8/2003 |
| WO | WO 2006/043178 A2 | 4/2006 |
| WO | WO 2008/092901 A2 | 8/2008 |
| WO | WO 2008/097619 A2 | 8/2008 |
| WO | WO 2008/116878 A1 | 10/2008 |

OTHER PUBLICATIONS

Miasnikov et al., EBI Accession No. AEH25057 (2006).
Greaves et al., Nature, vol. 200, pp. 1231-1232 (1963).
Gu et al., Chinese J Biotech, vol. 23, No. 6, pp. 1017-1021 (2007).
Huang et al., Biochem Biophys Res Commun, vol. 350, No. 4, pp. 884-889 (2006).
Kim et al., Appl Microbiol Biotechnol, vol. 79, pp. 751-758 (2008).
Lehmann et al., Curr Op Biotechnol, vol. 12, pp. 371-375 (2001).
Lim et al., Nat Struct Biol, vol. 7, No. 2, pp. 108-113 (2000).
Mullaney et al., Biochem Biophys Res Commun, vol. 328, No. 2, pp. 404-408 (2005).
Ryan et al., Com Methods Programs Biomed, vol. 85, No. 1, pp. 69-76 (2006).
Shi et al., Aquaculture, vol. 275, No. 1-4, pp. 70-75 (2008).
Yoon et al., Enzyme Microb Technol, vol. 18, No. 6, pp. 449-454 (1996).
Zinin et al., Biotekhnolgiya vol. 2, pp. 3-10 (2003).
Zinin et al., Database BIOSIS, Accession No. PREV200300308051 (2003).
Zinin et al., FEMS Microbiol Lett, vol. 236, No. 2, pp. 283-290 (2004).

* cited by examiner

*Primary Examiner* — Tekchand Saidha
(74) *Attorney, Agent, or Firm* — Elias Lambiris

(57) ABSTRACT

The present invention relates to isolated polypeptides having phytase activity and isolated polynucleotides encoding the polypeptides. The polypeptides are related to a phytase derived from *Hafnia alvei*, the amino acid sequence of which is shown in the appended sequence listing as SEQ ID NO: 10. The invention also relates to nucleic acid constructs, vectors, and host cells comprising the polynucleotides as well as methods for producing and using the polypeptides, in particular within animal feed.

9 Claims, 54 Drawing Sheets

Residual inositol-phosphate bound phosphorous (mg IP-P/g feed) after *in vitro* incubation. Comparison of the *Hafnia alvei* phytase with a *Citrobacter braakii* phytases dosed from 125-500 FYT/kg feed.

Residual inositol-phosphate bound phosphorous (mg IP-P/g feed) after *in vitro* incubation. Comparison of the *Hafnia alvei* phytase with a *Peniophora lycii* phytases dosed from 250 FYT/kg feed and 500 FYT/kg feed.

Figure 3

Appendix

```
ATOM      1 N     ALA     4      20.713  17.796  42.010  1.00 12.63      PROT
ATOM      2 CA    ALA     4      21.283  17.898  40.629  1.00 11.99      PROT
ATOM      3 C     ALA     4      22.578  17.097  40.593  1.00 11.33      PROT
ATOM      4 O     ALA     4      23.356  17.160  41.535  1.00 11.74      PROT
ATOM      5 CB    ALA     4      21.526  19.352  40.251  1.00 12.20      PROT
ATOM     11 N     PRO     5      22.811  16.324  39.516  1.00 10.64      PROT
ATOM     12 CA    PRO     5      23.904  15.337  39.557  1.00  9.73      PROT
ATOM     13 C     PRO     5      25.274  15.935  39.877  1.00  8.97      PROT
ATOM     14 O     PRO     5      25.533  17.103  39.568  1.00  8.47      PROT
ATOM     15 CB    PRO     5      23.883  14.724  38.150  1.00  9.76      PROT
ATOM     16 CG    PRO     5      22.514  14.991  37.638  1.00  9.88      PROT
ATOM     17 CD    PRO     5      22.102  16.305  38.224  1.00 10.41      PROT
ATOM     25 N     ALA     6      26.125  15.130  40.518  1.00  8.17      PROT
ATOM     26 CA    ALA     6      27.464  15.547  40.907  1.00  7.58      PROT
ATOM     27 C     ALA     6      28.258  16.013  39.692  1.00  7.10      PROT
ATOM     28 O     ALA     6      28.357  15.305  38.687  1.00  6.94      PROT
ATOM     29 CB    ALA     6      28.196  14.414  41.635  1.00  7.58      PROT
ATOM     35 N     GLY     7      28.788  17.227  39.784  1.00  6.31      PROT
ATOM     36 CA    GLY     7      29.579  17.803  38.702  1.00  5.32      PROT
ATOM     37 C     GLY     7      28.790  18.675  37.748  1.00  4.11      PROT
ATOM     38 O     GLY     7      29.382  19.381  36.938  1.00  4.06      PROT
ATOM     42 N     PHE     8      27.455  18.623  37.835  1.00  3.50      PROT
ATOM     43 CA    PHE     8      26.572  19.411  36.970  1.00  2.73      PROT
ATOM     44 C     PHE     8      26.594  20.881  37.404  1.00  2.50      PROT
ATOM     45 O     PHE     8      26.553  21.169  38.592  1.00  2.38      PROT
ATOM     46 CB    PHE     8      25.134  18.885  37.036  1.00  2.80      PROT
ATOM     47 CG    PHE     8      24.777  17.897  35.952  1.00  3.44      PROT
ATOM     48 CD1   PHE     8      25.501  16.720  35.792  1.00  4.43      PROT
ATOM     49 CD2   PHE     8      23.681  18.135  35.119  1.00  3.41      PROT
ATOM     50 CE1   PHE     8      25.156  15.792  34.794  1.00  5.73      PROT
ATOM     51 CE2   PHE     8      23.329  17.221  34.119  1.00  4.46      PROT
ATOM     52 CZ    PHE     8      24.068  16.052  33.959  1.00  3.76      PROT
ATOM     62 N     GLN     9      26.678  21.789  36.436  1.00  2.00      PROT
ATOM     63 CA    GLN     9      26.688  23.217  36.709  1.00  2.46      PROT
ATOM     64 C     GLN     9      25.696  23.932  35.795  1.00  2.00      PROT
ATOM     65 O     GLN     9      25.719  23.744  34.581  1.00  2.00      PROT
ATOM     66 CB    GLN     9      28.083  23.796  36.504  1.00  2.78      PROT
ATOM     67 CG    GLN     9      28.175  25.286  36.808  1.00  6.29      PROT
ATOM     68 CD    GLN     9      27.709  25.628  38.220  1.00  9.39      PROT
ATOM     69 OE1   GLN     9      28.198  25.063  39.198  1.00 12.04      PROT
ATOM     70 NE2   GLN     9      26.766  26.556  38.325  1.00 10.93      PROT
ATOM     79 N     LEU    10      24.831  24.738  36.400  1.00  2.00      PROT
ATOM     80 CA    LEU    10      23.885  25.557  35.665  1.00  2.37      PROT
ATOM     81 C     LEU    10      24.649  26.702  35.027  1.00  2.28      PROT
ATOM     82 O     LEU    10      25.310  27.463  35.717  1.00  2.01      PROT
ATOM     83 CB    LEU    10      22.802  26.092  36.605  1.00  2.26      PROT
ATOM     84 CG    LEU    10      21.740  26.995  35.965  1.00  2.58      PROT
ATOM     85 CD1   LEU    10      20.980  26.242  34.880  1.00  3.29      PROT
ATOM     86 CD2   LEU    10      20.784  27.505  37.034  1.00  2.73      PROT
ATOM     98 N     GLU    11      24.574  26.808  33.704  1.00  2.72      PROT
ATOM     99 CA    GLU    11      25.355  27.805  32.984  1.00  3.42      PROT
ATOM    100 C     GLU    11      24.485  28.985  32.570  1.00  3.46      PROT
ATOM    101 O     GLU    11      24.933  30.127  32.589  1.00  3.40      PROT
ATOM    102 CB    GLU    11      26.033  27.195  31.754  1.00  2.69      PROT
ATOM    103 CG    GLU    11      27.260  26.342  32.091  1.00  4.83      PROT
ATOM    104 CD    GLU    11      28.231  26.218  30.935  1.00  5.70      PROT
ATOM    105 OE1   GLU    11      27.872  26.620  29.809  1.00  5.87      PROT
ATOM    106 OE2   GLU    11      29.362  25.725  31.152  1.00  6.52      PROT
ATOM    113 N     LYS    12      23.252  28.691  32.174  1.00  4.39      PROT
ATOM    114 CA    LYS    12      22.299  29.734  31.805  1.00  5.12      PROT
ATOM    115 C     LYS    12      20.843  29.299  31.738  1.00  4.51      PROT
```

Figure 3 cont.

```
ATOM    116  O    LYS   12      20.546  28.114  31.665  1.00  3.98      PROT
ATOM    117  CB   LYS   12      22.741  30.493  30.553  1.00  6.06      PROT
ATOM    118  CG   LYS   12      22.824  29.545  29.343  1.00  0.00      PROT
ATOM    119  CD   LYS   12      23.272  30.219  28.049  1.00  0.00      PROT
ATOM    120  CE   LYS   12      24.744  30.506  28.031  1.00  0.00      PROT
ATOM    121  NZ   LYS   12      25.124  31.368  26.880  1.00  0.00      PROT
ATOM    135  N    VAL   13      19.944  30.277  31.807  1.00  3.72      PROT
ATOM    136  CA   VAL   13      18.508  30.017  31.824  1.00  3.81      PROT
ATOM    137  C    VAL   13      17.762  30.933  30.863  1.00  3.54      PROT
ATOM    138  O    VAL   13      18.056  32.131  30.769  1.00  3.40      PROT
ATOM    139  CB   VAL   13      17.926  30.203  33.253  1.00  4.18      PROT
ATOM    140  CG1  VAL   13      16.420  30.153  33.230  1.00  5.07      PROT
ATOM    141  CG2  VAL   13      18.472  29.147  34.209  1.00  3.49      PROT
ATOM    151  N    VAL   14      16.795  30.356  30.159  1.00  3.51      PROT
ATOM    152  CA   VAL   14      15.846  31.114  29.340  1.00  3.57      PROT
ATOM    153  C    VAL   14      14.448  30.857  29.893  1.00  2.90      PROT
ATOM    154  O    VAL   14      13.988  29.706  29.999  1.00  2.68      PROT
ATOM    155  CB   VAL   14      15.926  30.756  27.834  1.00  3.65      PROT
ATOM    156  CG1  VAL   14      15.019  31.687  26.988  1.00  4.58      PROT
ATOM    157  CG2  VAL   14      17.352  30.826  27.342  1.00  4.20      PROT
ATOM    167  N    ILE   15      13.789  31.945  30.266  1.00  2.11      PROT
ATOM    168  CA   ILE   15      12.480  31.891  30.869  1.00  2.32      PROT
ATOM    169  C    ILE   15      11.488  32.482  29.887  1.00  2.00      PROT
ATOM    170  O    ILE   15      11.596  33.652  29.520  1.00  2.00      PROT
ATOM    171  CB   ILE   15      12.447  32.687  32.197  1.00  2.00      PROT
ATOM    172  CG1  ILE   15      13.548  32.176  33.128  1.00  2.94      PROT
ATOM    173  CG2  ILE   15      11.058  32.605  32.856  1.00  2.63      PROT
ATOM    174  CD   ILE   15      13.825  33.060  34.295  1.00  3.09      PROT
ATOM    186  N    LEU   16      10.548  31.653  29.450  1.00  2.00      PROT
ATOM    187  CA   LEU   16       9.439  32.102  28.629  1.00  2.00      PROT
ATOM    188  C    LEU   16       8.204  32.170  29.504  1.00  2.00      PROT
ATOM    189  O    LEU   16       7.586  31.159  29.813  1.00  2.00      PROT
ATOM    190  CB   LEU   16       9.193  31.161  27.450  1.00  2.00      PROT
ATOM    191  CG   LEU   16       8.039  31.558  26.505  1.00  2.70      PROT
ATOM    192  CD1  LEU   16       8.204  32.958  25.898  1.00  2.00      PROT
ATOM    193  CD2  LEU   16       7.873  30.500  25.429  1.00  2.02      PROT
ATOM    205  N    SER   17       7.851  33.389  29.887  1.00  2.02      PROT
ATOM    206  CA   SER   17       6.840  33.601  30.897  1.00  2.08      PROT
ATOM    207  C    SER   17       5.592  34.235  30.330  1.00  2.37      PROT
ATOM    208  O    SER   17       5.668  35.118  29.476  1.00  3.14      PROT
ATOM    209  CB   SER   17       7.402  34.520  31.987  1.00  2.00      PROT
ATOM    210  OG   SER   17       6.447  34.740  33.005  1.00  2.68      PROT
ATOM    215  N    ARG   18       4.431  33.799  30.818  1.00  2.00      PROT
ATOM    216  CA   ARG   18       3.214  34.553  30.569  1.00  2.00      PROT
ATOM    217  C    ARG   18       3.221  35.825  31.419  1.00  2.00      PROT
ATOM    218  O    ARG   18       3.763  35.857  32.542  1.00  2.00      PROT
ATOM    219  CB   ARG   18       1.965  33.728  30.870  1.00  2.00      PROT
ATOM    220  CG   ARG   18       0.660  34.426  30.517  1.00  2.00      PROT
ATOM    221  CD   ARG   18      -0.511  33.466  30.647  1.00  2.00      PROT
ATOM    222  NE   ARG   18      -1.741  34.129  30.234  1.00  3.19      PROT
ATOM    223  CZ   ARG   18      -2.925  33.925  30.789  1.00  4.18      PROT
ATOM    224  NH1  ARG   18      -3.063  33.065  31.783  1.00  3.35      PROT
ATOM    225  NH2  ARG   18      -3.974  34.599  30.344  1.00  7.02      PROT
ATOM    239  N    HSD   19       2.620  36.870  30.857  1.00  2.00      PROT
ATOM    240  CA   HSD   19       2.293  38.099  31.594  1.00  2.00      PROT
ATOM    241  C    HSD   19       1.500  37.780  32.857  1.00  2.00      PROT
ATOM    242  O    HSD   19       0.937  36.681  32.983  1.00  2.00      PROT
ATOM    243  CB   HSD   19       1.503  39.067  30.692  1.00  2.00      PROT
ATOM    244  CG   HSD   19       0.192  38.524  30.208  1.00  2.00      PROT
ATOM    245  CD2  HSD   19      -0.036  38.193  28.883  1.00  2.84      PROT
ATOM    246  ND1  HSD   19      -0.966  38.269  30.860  1.00  2.00      PROT
ATOM    247  NE2  HSD   19      -1.266  37.730  28.751  1.00  2.00      PROT
ATOM    248  CE1  HSD   19      -1.848  37.750  29.939  1.00  2.04      PROT
ATOM    256  N    GLY   20       1.428  38.750  33.766  1.00  2.00      PROT
```

Figure 3 cont.

```
ATOM    257  CA   GLY    20       0.713  38.591  35.034  1.00  2.00      PROT
ATOM    258  C    GLY    20      -0.785  38.760  34.891  1.00  2.00      PROT
ATOM    259  O    GLY    20      -1.294  38.887  33.780  1.00  2.26      PROT
ATOM    263  N    VAL    21      -1.483  38.756  36.019  1.00  2.50      PROT
ATOM    264  CA   VAL    21      -2.945  38.897  36.064  1.00  3.01      PROT
ATOM    265  C    VAL    21      -3.369  40.196  35.402  1.00  3.16      PROT
ATOM    266  O    VAL    21      -2.797  41.267  35.654  1.00  3.58      PROT
ATOM    267  CB   VAL    21      -3.487  38.858  37.516  1.00  2.78      PROT
ATOM    268  CG1  VAL    21      -5.003  39.106  37.548  1.00  3.47      PROT
ATOM    269  CG2  VAL    21      -3.174  37.527  38.169  1.00  2.20      PROT
ATOM    279  N    ARG    22      -4.383  40.088  34.564  1.00  3.11      PROT
ATOM    280  CA   ARG    22      -4.814  41.201  33.748  1.00  4.21      PROT
ATOM    281  C    ARG    22      -6.333  41.241  33.667  1.00  3.73      PROT
ATOM    282  O    ARG    22      -6.991  40.232  33.881  1.00  3.14      PROT
ATOM    283  CB   ARG    22      -4.241  41.021  32.346  1.00  4.08      PROT
ATOM    284  CG   ARG    22      -4.698  39.735  31.718  1.00  6.73      PROT
ATOM    285  CD   ARG    22      -5.092  39.946  30.288  1.00 10.71      PROT
ATOM    286  NE   ARG    22      -4.715  38.779  29.526  1.00 16.61      PROT
ATOM    287  CZ   ARG    22      -5.500  37.751  29.239  1.00 17.99      PROT
ATOM    288  NH1  ARG    22      -6.774  37.726  29.628  1.00 19.11      PROT

ATOM    289  NH2  ARG    22      -4.991  36.748  28.531  1.00 19.82      PROT
ATOM    303  N    ALA    23      -6.873  42.417  33.353  1.00  4.55      PROT
ATOM    304  CA   ALA    23      -8.294  42.565  33.096  1.00  4.90      PROT
ATOM    305  C    ALA    23      -8.667  41.839  31.798  1.00  5.65      PROT
ATOM    306  O    ALA    23      -7.813  41.618  30.937  1.00  5.74      PROT
ATOM    307  CB   ALA    23      -8.675  44.068  33.048  1.00  4.90      PROT
ATOM    313  N    PRO    24      -9.927  41.394  31.668  1.00  6.59      PROT
ATOM    314  CA   PRO    24     -10.337  40.783  30.410  1.00  7.05      PROT
ATOM    315  C    PRO    24      -9.879  41.613  29.206  1.00  8.04      PROT
ATOM    316  O    PRO    24      -9.969  42.843  29.232  1.00  7.72      PROT
ATOM    317  CB   PRO    24     -11.859  40.796  30.510  1.00  7.08      PROT
ATOM    318  CG   PRO    24     -12.114  40.624  31.943  1.00  6.76      PROT
ATOM    319  CD   PRO    24     -11.032  41.418  32.642  1.00  6.35      PROT
ATOM    327  N    THR    25      -9.366  40.938  28.180  1.00  8.78      PROT
ATOM    328  CA   THR    25      -8.915  41.612  26.954  1.00  9.99      PROT
ATOM    329  C    THR    25     -10.104  42.297  26.257  1.00 10.25      PROT
ATOM    330  O    THR    25      -9.995  43.432  25.774  1.00 10.55      PROT
ATOM    331  CB   THR    25      -8.210  40.600  26.011  1.00 10.17      PROT
ATOM    332  OG1  THR    25      -7.092  40.008  26.700  1.00 12.82      PROT
ATOM    333  CG2  THR    25      -7.698  41.267  24.748  1.00 12.25      PROT
ATOM    340  N    LYS    26     -11.240  41.609  26.235  1.00  9.88      PROT
ATOM    341  CA   LYS    26     -12.457  42.142  25.633  1.00 10.27      PROT
ATOM    342  C    LYS    26     -13.667  41.729  26.452  1.00  9.40      PROT
ATOM    343  O    LYS    26     -13.638  40.722  27.164  1.00  8.76      PROT
ATOM    344  CB   LYS    26     -12.602  41.672  24.175  1.00 10.05      PROT
ATOM    345  CG   LYS    26     -12.540  40.155  23.989  1.00 12.65      PROT
ATOM    346  CD   LYS    26     -12.847  39.707  22.554  1.00 12.17      PROT
ATOM    347  CE   LYS    26     -12.136  40.561  21.511  1.00 15.65      PROT
ATOM    348  NZ   LYS    26     -12.445  40.105  20.119  1.00 18.10      PROT
ATOM    362  N    MET    27     -14.721  42.531  26.355  1.00  8.63      PROT
ATOM    363  CA   MET    27     -15.988  42.217  26.971  1.00  8.61      PROT
ATOM    364  C    MET    27     -17.044  42.491  25.899  1.00  7.95      PROT
ATOM    365  O    MET    27     -17.493  43.628  25.720  1.00  8.61      PROT
ATOM    366  CB   MET    27     -16.190  43.048  28.251  1.00  9.07      PROT
ATOM    367  CG   MET    27     -17.470  42.757  29.049  1.00 10.49      PROT
ATOM    368  SD   MET    27     -17.795  41.019  29.436  1.00 13.25      PROT
ATOM    369  CE   MET    27     -16.353  40.540  30.368  1.00  9.60      PROT
ATOM    379  N    THR    28     -17.391  41.430  25.171  1.00  6.47      PROT
ATOM    380  CA   THR    28     -18.244  41.501  23.991  1.00  5.05      PROT
ATOM    381  C    THR    28     -19.699  41.482  24.396  1.00  4.62      PROT
ATOM    382  O    THR    28     -20.027  41.144  25.544  1.00  3.85      PROT
ATOM    383  CB   THR    28     -18.001  40.298  23.044  1.00  5.05      PROT
ATOM    384  OG1  THR    28     -18.538  39.106  23.633  1.00  2.00      PROT
ATOM    385  CG2  THR    28     -16.532  40.103  22.782  1.00  4.28      PROT
```

Figure 3 cont.

```
ATOM    392  N    GLN    29     -20.576  41.823  23.449  1.00   4.28      PROT
ATOM    393  CA   GLN    29     -22.004  41.757  23.699  1.00   3.94      PROT
ATOM    394  C    GLN    29     -22.452  40.343  24.044  1.00   3.99      PROT
ATOM    395  O    GLN    29     -23.220  40.153  24.998  1.00   4.23      PROT
ATOM    396  CB   GLN    29     -22.827  42.329  22.528  1.00   4.43      PROT
ATOM    397  CG   GLN    29     -24.285  42.587  22.906  1.00   4.28      PROT
ATOM    398  CD   GLN    29     -24.421  43.540  24.083  1.00   5.08      PROT
ATOM    399  OE1  GLN    29     -23.819  44.608  24.094  1.00   5.80      PROT
ATOM    400  NE2  GLN    29     -25.211  43.152  25.084  1.00   6.12      PROT
ATOM    409  N    THR    30     -21.965  39.357  23.293  1.00   4.21      PROT
ATOM    410  CA   THR    30     -22.272  37.950  23.575  1.00   4.98      PROT
ATOM    411  C    THR    30     -21.914  37.579  25.023  1.00   4.96      PROT
ATOM    412  O    THR    30     -22.752  37.042  25.753  1.00   4.22      PROT
ATOM    413  CB   THR    30     -21.598  36.977  22.556  1.00   5.04      PROT
ATOM    414  OG1  THR    30     -22.127  37.214  21.244  1.00   7.16      PROT
ATOM    415  CG2  THR    30     -21.867  35.508  22.924  1.00   6.76      PROT
ATOM    422  N    MET    31     -20.685  37.893  25.434  1.00   5.01      PROT
ATOM    423  CA   MET    31     -20.223  37.644  26.806  1.00   5.86      PROT
ATOM    424  C    MET    31     -21.156  38.242  27.861  1.00   5.88      PROT
ATOM    425  O    MET    31     -21.374  37.649  28.918  1.00   5.89      PROT
ATOM    426  CB   MET    31     -18.802  38.175  27.003  1.00   5.35      PROT
ATOM    427  CG   MET    31     -17.722  37.353  26.301  1.00   5.61      PROT
ATOM    428  SD   MET    31     -16.176  38.271  26.202  1.00   8.17      PROT
ATOM    429  CE   MET    31     -15.303  37.353  24.959  1.00   7.03      PROT
ATOM    439  N    ARG    32     -21.709  39.413  27.567  1.00   6.15      PROT
ATOM    440  CA   ARG    32     -22.697  40.037  28.448  1.00   6.96      PROT
ATOM    441  C    ARG    32     -24.050  39.335  28.371  1.00   6.30      PROT
ATOM    442  O    ARG    32     -24.731  39.182  29.387  1.00   7.23      PROT
ATOM    443  CB   ARG    32     -22.850  41.531  28.134  1.00   6.82      PROT
ATOM    444  CG   ARG    32     -21.569  42.327  28.343  1.00   8.87      PROT
ATOM    445  CD   ARG    32     -21.859  43.739  28.824  1.00  13.26      PROT
ATOM    446  NE   ARG    32     -20.766  44.223  29.664  1.00  16.64      PROT
ATOM    447  CZ   ARG    32     -20.662  43.990  30.971  1.00  17.47      PROT
ATOM    448  NH1  ARG    32     -21.595  43.288  31.621  1.00  18.77      PROT
ATOM    449  NH2  ARG    32     -19.620  44.462  31.630  1.00  18.21      PROT
ATOM    463  N    ASP    33     -24.421  38.905  27.169  1.00   6.38      PROT
ATOM    464  CA   ASP    33     -25.746  38.347  26.876  1.00   5.81      PROT
ATOM    465  C    ASP    33     -25.989  36.949  27.479  1.00   5.40      PROT
ATOM    466  O    ASP    33     -27.126  36.612  27.826  1.00   5.43      PROT
ATOM    467  CB   ASP    33     -26.011  38.342  25.347  1.00   6.20      PROT
ATOM    468  CG   ASP    33     -26.242  39.753  24.765  1.00   7.59      PROT
ATOM    469  OD1  ASP    33     -26.339  40.733  25.534  1.00   7.92      PROT
ATOM    470  OD2  ASP    33     -26.318  39.884  23.519  1.00   8.53      PROT
ATOM    475  N    VAL    34     -24.927  36.154  27.626  1.00   4.41      PROT
ATOM    476  CA   VAL    34     -25.036  34.753  28.078  1.00   3.47      PROT
ATOM    477  C    VAL    34     -25.260  34.594  29.595  1.00   3.40      PROT
ATOM    478  O    VAL    34     -25.376  33.479  30.114  1.00   3.09      PROT
ATOM    479  CB   VAL    34     -23.822  33.908  27.624  1.00   3.48      PROT
ATOM    480  CG1  VAL    34     -23.711  33.915  26.100  1.00   3.25      PROT
ATOM    481  CG2  VAL    34     -22.522  34.396  28.279  1.00   3.10      PROT
ATOM    491  N    THR    35     -25.324  35.716  30.301  1.00   2.98      PROT
ATOM    492  CA   THR    35     -25.647  35.697  31.725  1.00   2.95      PROT
ATOM    493  C    THR    35     -26.552  36.865  32.107  1.00   3.14      PROT
ATOM    494  O    THR    35     -26.387  37.970  31.575  1.00   2.76      PROT
ATOM    495  CB   THR    35     -24.369  35.642  32.619  1.00   3.13      PROT
ATOM    496  OG1  THR    35     -24.735  35.672  34.009  1.00   2.29      PROT
ATOM    497  CG2  THR    35     -23.399  36.807  32.311  1.00   2.00      PROT
ATOM    504  N    PRO    36     -27.535  36.615  33.007  1.00   3.31      PROT
ATOM    505  CA   PRO    36     -28.334  37.697  33.587  1.00   3.59      PROT
ATOM    506  C    PRO    36     -27.536  38.491  34.631  1.00   4.01      PROT
ATOM    507  O    PRO    36     -27.977  39.566  35.064  1.00   4.34      PROT
ATOM    508  CB   PRO    36     -29.482  36.954  34.271  1.00   3.57      PROT
ATOM    509  CG   PRO    36     -28.889  35.651  34.661  1.00   3.53      PROT
ATOM    510  CD   PRO    36     -27.949  35.300  33.535  1.00   2.96      PROT
ATOM    518  N    HSD    37     -26.382  37.954  35.026  1.00   4.16      PROT
```

Figure 3 cont.

```
ATOM   519  CA   HSD  37     -25.505  38.598  36.006  1.00   4.65      PROT
ATOM   520  C    HSD  37     -24.622  39.659  35.350  1.00   4.84      PROT
ATOM   521  O    HSD  37     -24.291  39.562  34.170  1.00   4.87      PROT
ATOM   522  CB   HSD  37     -24.634  37.559  36.715  1.00   4.50      PROT
ATOM   523  CG   HSD  37     -25.398  36.399  37.276  1.00   6.78      PROT
ATOM   524  CD2  HSD  37     -25.232  35.108  36.820  1.00   7.57      PROT
ATOM   525  ND1  HSD  37     -26.330  36.334  38.257  1.00   7.61      PROT
ATOM   526  NE2  HSD  37     -26.021  34.297  37.502  1.00   7.73      PROT
ATOM   527  CE1  HSD  37     -26.699  35.014  38.380  1.00   8.20      PROT
ATOM   535  N    GLN  38     -24.256  40.670  36.128  1.00   4.87      PROT
ATOM   536  CA   GLN  38     -23.381  41.734  35.668  1.00   4.88      PROT
ATOM   537  C    GLN  38     -21.916  41.356  35.891  1.00   4.90      PROT
ATOM   538  O    GLN  38     -21.520  40.934  36.988  1.00   4.84      PROT
ATOM   539  CB   GLN  38     -23.711  43.042  36.379  1.00   5.48      PROT
ATOM   540  CG   GLN  38     -25.285  43.369  36.613  1.00   7.42      PROT
ATOM   541  CD   GLN  38     -26.017  42.762  37.806  1.00  10.27      PROT
ATOM   542  OE1  GLN  38     -25.592  41.745  38.384  1.00  11.02      PROT
ATOM   543  NE2  GLN  38     -27.142  43.387  38.178  1.00   8.29      PROT
ATOM   552  N    TRP  39     -21.123  41.484  34.832  1.00   4.56      PROT
ATOM   553  CA   TRP  39     -19.672  41.321  34.934  1.00   4.68      PROT
ATOM   554  C    TRP  39     -19.038  42.413  35.787  1.00   4.54      PROT
ATOM   555  O    TRP  39     -19.312  43.588  35.579  1.00   4.25      PROT
ATOM   556  CB   TRP  39     -19.032  41.288  33.551  1.00   4.76      PROT
ATOM   557  CG   TRP  39     -19.382  40.048  32.801  1.00   4.40      PROT
ATOM   558  CD1  TRP  39     -20.381  39.899  31.883  1.00   5.28      PROT
ATOM   559  CD2  TRP  39     -18.739  38.779  32.905  1.00   5.11      PROT
ATOM   560  NE1  TRP  39     -20.400  38.612  31.407  1.00   3.73      PROT
ATOM   561  CE2  TRP  39     -19.399  37.903  32.016  1.00   4.98      PROT
ATOM   562  CE3  TRP  39     -17.658  38.294  33.659  1.00   5.42      PROT
ATOM   563  CZ2  TRP  39     -19.019  36.567  31.863  1.00   5.75      PROT
ATOM   564  CZ3  TRP  39     -17.283  36.966  33.509  1.00   4.53      PROT
ATOM   565  CH2  TRP  39     -17.959  36.120  32.611  1.00   5.11      PROT
ATOM   576  N    PRO  40     -18.161  42.023  36.731  1.00   4.95      PROT
ATOM   577  CA   PRO  40     -17.560  42.985  37.660  1.00   5.49      PROT
ATOM   578  C    PRO  40     -16.574  43.922  36.956  1.00   5.93      PROT
ATOM   579  O    PRO  40     -15.876  43.501  36.026  1.00   5.78      PROT
ATOM   580  CB   PRO  40     -16.836  42.092  38.674  1.00   5.53      PROT
ATOM   581  CG   PRO  40     -16.553  40.826  37.950  1.00   6.07      PROT
ATOM   582  CD   PRO  40     -17.685  40.646  36.966  1.00   4.85      PROT
ATOM   590  N    GLU  41     -16.528  45.187  37.370  1.00   6.05      PROT
ATOM   591  CA   GLU  41     -15.529  46.093  36.811  1.00   7.01      PROT
ATOM   592  C    GLU  41     -14.141  45.863  37.381  1.00   5.93      PROT
ATOM   593  O    GLU  41     -13.960  45.625  38.569  1.00   6.33      PROT
ATOM   594  CB   GLU  41     -15.929  47.570  36.920  1.00   7.71      PROT
ATOM   595  CG   GLU  41     -16.406  48.192  35.585  1.00  11.21      PROT
ATOM   596  CD   GLU  41     -15.298  48.375  34.521  1.00  16.08      PROT
ATOM   597  OE1  GLU  41     -14.093  48.142  34.802  1.00  18.62      PROT
ATOM   598  OE2  GLU  41     -15.640  48.774  33.384  1.00  16.73      PROT
ATOM   605  N    TRP  42     -13.155  45.926  36.503  1.00   5.39      PROT
ATOM   606  CA   TRP  42     -11.772  45.799  36.915  1.00   4.35      PROT
ATOM   607  C    TRP  42     -11.177  47.175  37.202  1.00   4.25      PROT
ATOM   608  O    TRP  42     -11.600  48.166  36.613  1.00   3.94      PROT
ATOM   609  CB   TRP  42     -10.985  45.046  35.839  1.00   3.64      PROT
ATOM   610  CG   TRP  42     -11.207  43.564  35.894  1.00   3.85      PROT
ATOM   611  CD1  TRP  42     -12.371  42.888  35.604  1.00   3.07      PROT
ATOM   612  CD2  TRP  42     -10.253  42.569  36.276  1.00   2.05      PROT
ATOM   613  NE1  TRP  42     -12.183  41.540  35.779  1.00   2.00      PROT
ATOM   614  CE2  TRP  42     -10.900  41.316  36.198  1.00   2.03      PROT
ATOM   615  CE3  TRP  42      -8.907  42.615  36.674  1.00   2.96      PROT
ATOM   616  CZ2  TRP  42     -10.246  40.108  36.508  1.00   2.75      PROT
ATOM   617  CZ3  TRP  42      -8.264  41.430  36.982  1.00   3.10      PROT
ATOM   618  CH2  TRP  42      -8.935  40.188  36.895  1.00   3.42      PROT
ATOM   629  N    PRO  43     -10.198  47.240  38.122  1.00   4.47      PROT
ATOM   630  CA   PRO  43      -9.509  48.485  38.464  1.00   4.28      PROT
ATOM   631  C    PRO  43      -8.587  49.066  37.363  1.00   4.85      PROT
```

Figure 3 cont.

```
ATOM    632  O    PRO    43      -7.955  50.105  37.583  1.00  4.70      PROT
ATOM    633  CB   PRO    43      -8.689  48.095  39.707  1.00  4.40      PROT
ATOM    634  CG   PRO    43      -8.466  46.619  39.565  1.00  4.95      PROT
ATOM    635  CD   PRO    43      -9.697  46.090  38.906  1.00  3.52      PROT
ATOM    643  N    VAL    44      -8.490  48.415  36.197  1.00  5.39      PROT
ATOM    644  CA   VAL    44      -7.643  48.925  35.100  1.00  5.89      PROT
ATOM    645  C    VAL    44      -8.353  48.848  33.746  1.00  6.09      PROT
ATOM    646  O    VAL    44      -9.456  48.318  33.643  1.00  5.41      PROT
ATOM    647  CB   VAL    44      -6.259  48.194  34.987  1.00  6.61      PROT
ATOM    648  CG1  VAL    44      -6.442  46.711  34.658  1.00  6.04      PROT
ATOM    649  CG2  VAL    44      -5.401  48.401  36.260  1.00  6.72      PROT
ATOM    659  N    LYS    45      -7.691  49.372  32.722  1.00  5.96      PROT
ATOM    660  CA   LYS    45      -8.127  49.257  31.335  1.00  6.89      PROT
ATOM    661  C    LYS    45      -8.202  47.779  30.916  1.00  6.26      PROT
ATOM    662  O    LYS    45      -7.383  46.984  31.356  1.00  5.53      PROT
ATOM    663  CB   LYS    45      -7.112  50.003  30.462  1.00  7.49      PROT
ATOM    664  CG   LYS    45      -7.153  49.653  28.991  1.00 10.33      PROT
ATOM    665  CD   LYS    45      -8.228  50.429  28.255  1.00 13.76      PROT
ATOM    666  CE   LYS    45      -7.670  51.725  27.682  1.00 14.41      PROT
ATOM    667  NZ   LYS    45      -6.643  51.519  26.610  1.00 16.40      PROT
ATOM    681  N    LEU    46      -9.167  47.415  30.069  1.00  5.86      PROT
ATOM    682  CA   LEU    46      -9.227  46.057  29.508  1.00  6.20      PROT
ATOM    683  C    LEU    46      -7.867  45.636  28.913  1.00  5.80      PROT
ATOM    684  O    LEU    46      -7.253  46.393  28.187  1.00  5.53      PROT
ATOM    685  CB   LEU    46     -10.326  45.954  28.429  1.00  6.49      PROT
ATOM    686  CG   LEU    46     -11.801  46.115  28.807  1.00  7.72      PROT
ATOM    687  CD1  LEU    46     -12.637  46.121  27.542  1.00 12.17      PROT
ATOM    688  CD2  LEU    46     -12.280  45.022  29.759  1.00  9.52      PROT
ATOM    700  N    GLY    47      -7.387  44.453  29.279  1.00  5.97      PROT
ATOM    701  CA   GLY    47      -6.110  43.931  28.772  1.00  6.58      PROT
ATOM    702  C    GLY    47      -4.850  44.379  29.508  1.00  6.04      PROT
ATOM    703  O    GLY    47      -3.751  43.885  29.233  1.00  6.46      PROT
ATOM    707  N    TYR    48      -4.998  45.327  30.429  1.00  5.50      PROT
ATOM    708  CA   TYR    48      -3.864  45.799  31.238  1.00  4.86      PROT
ATOM    709  C    TYR    48      -3.594  44.874  32.405  1.00  4.19      PROT
ATOM    710  O    TYR    48      -4.528  44.289  32.980  1.00  3.87      PROT
ATOM    711  CB   TYR    48      -4.139  47.197  31.809  1.00  5.44      PROT
ATOM    712  CG   TYR    48      -3.805  48.358  30.889  1.00  6.31      PROT
ATOM    713  CD1  TYR    48      -3.853  48.220  29.507  1.00  6.51      PROT
ATOM    714  CD2  TYR    48      -3.483  49.612  31.419  1.00  6.97      PROT
ATOM    715  CE1  TYR    48      -3.555  49.280  28.667  1.00  7.62      PROT
ATOM    716  CE2  TYR    48      -3.196  50.688  30.587  1.00  7.42      PROT
ATOM    717  CZ   TYR    48      -3.232  50.505  29.211  1.00  7.57      PROT
ATOM    718  OH   TYR    48      -2.955  51.550  28.376  1.00  7.06      PROT
ATOM    727  N    ILE    49      -2.322  44.757  32.772  1.00  3.12      PROT
ATOM    728  CA   ILE    49      -1.942  44.106  34.024  1.00  2.56      PROT
ATOM    729  C    ILE    49      -2.464  44.959  35.199  1.00  2.39      PROT
ATOM    730  O    ILE    49      -2.527  46.198  35.127  1.00  2.00      PROT
ATOM    731  CB   ILE    49      -0.377  43.803  34.094  1.00  3.10      PROT
ATOM    732  CG1  ILE    49      -0.027  42.828  35.224  1.00  2.27      PROT
ATOM    733  CG2  ILE    49       0.447  45.082  34.192  1.00  3.29      PROT
ATOM    734  CD   ILE    49       1.423  42.284  35.162  1.00  2.61      PROT
ATOM    746  N    THR    50      -2.892  44.296  36.262  1.00  2.00      PROT
ATOM    747  CA   THR    50      -3.295  45.020  37.473  1.00  2.00      PROT
ATOM    748  C    THR    50      -2.071  45.240  38.382  1.00  2.00      PROT
ATOM    749  O    THR    50      -1.090  44.533  38.251  1.00  2.00      PROT
ATOM    750  CB   THR    50      -4.368  44.248  38.233  1.00  2.00      PROT
ATOM    751  OG1  THR    50      -3.824  42.998  38.652  1.00  3.05      PROT
ATOM    752  CG2  THR    50      -5.579  43.993  37.323  1.00  2.00      PROT
ATOM    759  N    PRO    51      -2.110  46.243  39.282  1.00  2.00      PROT
ATOM    760  CA   PRO    51      -1.003  46.327  40.259  1.00  2.00      PROT
ATOM    761  C    PRO    51      -0.765  45.009  41.041  1.00  2.00      PROT
ATOM    762  O    PRO    51       0.386  44.663  41.347  1.00  2.00      PROT
ATOM    763  CB   PRO    51      -1.443  47.452  41.210  1.00  2.38      PROT
ATOM    764  CG   PRO    51      -2.434  48.297  40.402  1.00  2.06      PROT
```

Figure 3 cont.

```
ATOM    765  CD  PRO    51      -3.081  47.347  39.414  1.00  2.26       PROT
ATOM    773  N   ARG    52      -1.839  44.298  41.371  1.00  2.00       PROT
ATOM    774  CA  ARG    52      -1.741  42.979  42.019  1.00  2.00       PROT
ATOM    775  C   ARG    52      -1.050  41.946  41.114  1.00  2.00       PROT
ATOM    776  O   ARG    52      -0.248  41.153  41.600  1.00  2.00       PROT
ATOM    777  CB  ARG    52      -3.124  42.489  42.437  1.00  2.00       PROT
ATOM    778  CG  ARG    52      -3.172  41.047  42.893  1.00  2.00       PROT
ATOM    779  CD  ARG    52      -4.387  40.796  43.732  1.00  5.06       PROT
ATOM    780  NE  ARG    52      -4.517  39.381  44.081  1.00  5.77       PROT
ATOM    781  CZ  ARG    52      -5.064  38.936  45.208  1.00  7.20       PROT
ATOM    782  NH1 ARG    52      -5.526  39.789  46.116  1.00  6.06       PROT
ATOM    783  NH2 ARG    52      -5.142  37.636  45.436  1.00  4.67       PROT
ATOM    797  N   GLY    53      -1.385  41.969  39.820  1.00  2.00       PROT
ATOM    798  CA  GLY    53      -0.705  41.181  38.781  1.00  2.00       PROT
ATOM    799  C   GLY    53       0.793  41.440  38.790  1.00  2.00       PROT
ATOM    800  O   GLY    53       1.584  40.507  38.746  1.00  2.00       PROT
ATOM    804  N   GLU    54       1.169  42.716  38.875  1.00  2.00       PROT
ATOM    805  CA  GLU    54       2.581  43.101  38.960  1.00  2.00       PROT
ATOM    806  C   GLU    54       3.253  42.571  40.232  1.00  2.00       PROT
ATOM    807  O   GLU    54       4.335  41.982  40.170  1.00  2.00       PROT
ATOM    808  CB  GLU    54       2.719  44.617  38.861  1.00  2.00       PROT
ATOM    809  CG  GLU    54       2.353  45.194  37.503  1.00  2.40       PROT
ATOM    810  CD  GLU    54       2.408  46.712  37.500  1.00  6.68       PROT
ATOM    811  OE1 GLU    54       1.503  47.353  38.065  1.00  7.39       PROT
ATOM    812  OE2 GLU    54       3.358  47.266  36.924  1.00 11.95       PROT
ATOM    819  N   HSD    55       2.607  42.764  41.376  1.00  2.00       PROT
ATOM    820  CA  HSD    55       3.110  42.239  42.645  1.00  2.00       PROT
ATOM    821  C   HSD    55       3.314  40.733  42.577  1.00  2.00       PROT
ATOM    822  O   HSD    55       4.327  40.214  43.035  1.00  2.00       PROT
ATOM    823  CB  HSD    55       2.166  42.566  43.815  1.00  2.00       PROT
ATOM    824  CG  HSD    55       2.642  42.027  45.128  1.00  2.00       PROT
ATOM    825  ND1 HSD    55       3.835  42.421  45.697  1.00  2.22       PROT
ATOM    826  CD2 HSD    55       2.107  41.109  45.972  1.00  2.00       PROT
ATOM    827  CE1 HSD    55       4.012  41.772  46.836  1.00  5.06       PROT
ATOM    828  NE2 HSD    55       2.980  40.968  47.024  1.00  4.14       PROT
ATOM    836  N   LEU    56       2.332  40.044  42.014  1.00  2.00       PROT
ATOM    837  CA  LEU    56       2.410  38.588  41.866  1.00  2.00       PROT
ATOM    838  C   LEU    56       3.604  38.145  41.027  1.00  2.00       PROT
ATOM    839  O   LEU    56       4.266  37.152  41.361  1.00  2.00       PROT
ATOM    840  CB  LEU    56       1.100  38.042  41.291  1.00  2.12       PROT
ATOM    841  CG  LEU    56      -0.031  38.012  42.328  1.00  2.16       PROT
ATOM    842  CD1 LEU    56      -1.378  37.761  41.657  1.00  2.32       PROT
ATOM    843  CD2 LEU    56       0.246  36.950  43.384  1.00  4.12       PROT
ATOM    855  N   ILE    57       3.850  38.863  39.924  1.00  2.00       PROT
ATOM    856  CA  ILE    57       5.031  38.643  39.076  1.00  2.00       PROT
ATOM    857  C   ILE    57       6.327  38.892  39.851  1.00  2.00       PROT
ATOM    858  O   ILE    57       7.291  38.124  39.745  1.00  2.00       PROT
ATOM    859  CB  ILE    57       5.018  39.526  37.783  1.00  2.00       PROT
ATOM    860  CG1 ILE    57       3.891  39.099  36.825  1.00  2.00       PROT
ATOM    861  CG2 ILE    57       6.343  39.378  36.979  1.00  2.30       PROT
ATOM    862  CD  ILE    57       3.863  37.606  36.469  1.00  2.00       PROT
ATOM    874  N   SER    58       6.350  39.962  40.639  1.00  2.00       PROT
ATOM    875  CA  SER    58       7.586  40.272  41.375  1.00  2.17       PROT
ATOM    876  C   SER    58       7.859  39.209  42.456  1.00  2.00       PROT
ATOM    877  O   SER    58       9.017  38.903  42.753  1.00  2.34       PROT
ATOM    878  CB  SER    58       7.568  41.694  41.930  1.00  2.12       PROT
ATOM    879  OG  SER    58       6.913  41.731  43.178  1.00  7.89       PROT
ATOM    884  N   LEU    59       6.800  38.625  43.012  1.00  2.00       PROT
ATOM    885  CA  LEU    59       6.953  37.478  43.923  1.00  2.00       PROT
ATOM    886  C   LEU    59       7.615  36.283  43.229  1.00  2.00       PROT
ATOM    887  O   LEU    59       8.485  35.642  43.809  1.00  2.00       PROT
ATOM    888  CB  LEU    59       5.617  37.078  44.559  1.00  2.00       PROT
ATOM    889  CG  LEU    59       4.969  38.048  45.563  1.00  2.14       PROT
ATOM    890  CD1 LEU    59       3.621  37.504  45.959  1.00  2.00       PROT
ATOM    891  CD2 LEU    59       5.830  38.326  46.795  1.00  4.95       PROT
```

Figure 3 cont.

```
ATOM    903  N    MET   60       7.215  36.016  41.982  1.00  2.00      PROT
ATOM    904  CA   MET   60       7.917  35.048  41.126  1.00  2.00      PROT
ATOM    905  C    MET   60       9.379  35.412  40.882  1.00  2.00      PROT
ATOM    906  O    MET   60      10.241  34.546  40.971  1.00  2.00      PROT
ATOM    907  CB   MET   60       7.224  34.858  39.766  1.00  2.29      PROT
ATOM    908  CG   MET   60       6.035  33.908  39.732  1.00  5.39      PROT
ATOM    909  SD   MET   60       6.233  32.152  40.171  1.00  9.67      PROT
ATOM    910  CE   MET   60       7.983  31.814  40.061  1.00  3.93      PROT
ATOM    920  N    GLY   61       9.656  36.682  40.573  1.00  2.00      PROT
ATOM    921  CA   GLY   61      11.042  37.153  40.404  1.00  2.00      PROT
ATOM    922  C    GLY   61      11.933  36.885  41.618  1.00  2.00      PROT
ATOM    923  O    GLY   61      13.102  36.514  41.481  1.00  2.00      PROT
ATOM    927  N    GLY   62      11.363  37.070  42.804  1.00  2.00      PROT
ATOM    928  CA   GLY   62      12.035  36.776  44.079  1.00  2.00      PROT
ATOM    929  C    GLY   62      12.343  35.297  44.225  1.00  2.00      PROT
ATOM    930  O    GLY   62      13.398  34.926  44.757  1.00  2.00      PROT
ATOM    934  N    PHE   63      11.433  34.453  43.732  1.00  2.16      PROT
ATOM    935  CA   PHE   63      11.653  33.014  43.740  1.00  2.22      PROT
ATOM    936  C    PHE   63      12.798  32.645  42.805  1.00  2.90      PROT
ATOM    937  O    PHE   63      13.683  31.877  43.190  1.00  2.46      PROT
ATOM    938  CB   PHE   63      10.380  32.211  43.420  1.00  2.94      PROT
ATOM    939  CG   PHE   63      10.628  30.726  43.333  1.00  3.29      PROT
ATOM    940  CD1  PHE   63      10.946  29.997  44.481  1.00  3.52      PROT
ATOM    941  CD2  PHE   63      10.621  30.077  42.112  1.00  4.03      PROT
ATOM    942  CE1  PHE   63      11.216  28.623  44.402  1.00  4.11      PROT
ATOM    943  CE2  PHE   63      10.880  28.709  42.038  1.00  5.69      PROT
ATOM    944  CZ   PHE   63      11.185  27.992  43.185  1.00  3.33      PROT
ATOM    954  N    TYR   64      12.772  33.196  41.582  1.00  3.92      PROT
ATOM    955  CA   TYR   64      13.862  33.040  40.618  1.00  4.54      PROT
ATOM    956  C    TYR   64      15.215  33.458  41.211  1.00  4.67      PROT
ATOM    957  O    TYR   64      16.191  32.715  41.112  1.00  4.47      PROT
ATOM    958  CB   TYR   64      13.571  33.809  39.322  1.00  5.31      PROT
ATOM    959  CG   TYR   64      12.500  33.169  38.454  1.00  6.16      PROT
ATOM    960  CD1  TYR   64      12.586  31.829  38.090  1.00  4.38      PROT
ATOM    961  CD2  TYR   64      11.420  33.911  37.984  1.00  6.59      PROT
ATOM    962  CE1  TYR   64      11.620  31.226  37.298  1.00  8.27      PROT
ATOM    963  CE2  TYR   64      10.440  33.318  37.175  1.00  6.92      PROT
ATOM    964  CZ   TYR   64      10.554  31.974  36.845  1.00  7.72      PROT
ATOM    965  OH   TYR   64       9.621  31.359  36.052  1.00 10.78      PROT
ATOM    974  N    ARG   65      15.248  34.624  41.843  1.00  4.87      PROT
ATOM    975  CA   ARG   65      16.456  35.143  42.517  1.00  5.61      PROT
ATOM    976  C    ARG   65      17.062  34.119  43.486  1.00  4.96      PROT
ATOM    977  O    ARG   65      18.225  33.752  43.349  1.00  5.21      PROT
ATOM    978  CB   ARG   65      16.160  36.480  43.219  1.00  6.01      PROT
ATOM    979  CG   ARG   65      17.154  36.839  44.348  1.00  6.81      PROT
ATOM    980  CD   ARG   65      16.951  38.249  44.886  1.00  7.76      PROT
ATOM    981  NE   ARG   65      17.598  39.186  43.975  1.00 14.22      PROT
ATOM    982  CZ   ARG   65      18.891  39.499  43.998  1.00 13.94      PROT
ATOM    983  NH1  ARG   65      19.697  38.986  44.915  1.00 17.72      PROT
ATOM    984  NH2  ARG   65      19.373  40.325  43.092  1.00 12.46      PROT
ATOM    998  N    GLU   66      16.272  33.638  44.440  1.00  4.36      PROT
ATOM    999  CA   GLU   66      16.756  32.632  45.390  1.00  4.71      PROT
ATOM   1000  C    GLU   66      17.236  31.352  44.726  1.00  4.38      PROT
ATOM   1001  O    GLU   66      18.277  30.811  45.099  1.00  3.86      PROT
ATOM   1002  CB   GLU   66      15.686  32.282  46.404  1.00  4.46      PROT
ATOM   1003  CG   GLU   66      15.453  33.333  47.420  1.00  6.83      PROT
ATOM   1004  CD   GLU   66      14.617  32.826  48.566  1.00  9.94      PROT
ATOM   1005  OE1  GLU   66      14.685  31.610  48.885  1.00  9.67      PROT
ATOM   1006  OE2  GLU   66      13.908  33.659  49.161  1.00 11.88      PROT
ATOM   1013  N    ARG   67      16.463  30.875  43.753  1.00  4.19      PROT
ATOM   1014  CA   ARG   67      16.790  29.654  43.037  1.00  5.20      PROT
ATOM   1015  C    ARG   67      18.107  29.795  42.273  1.00  4.98      PROT
ATOM   1016  O    ARG   67      18.955  28.901  42.327  1.00  5.04      PROT
ATOM   1017  CB   ARG   67      15.647  29.268  42.093  1.00  5.58      PROT
ATOM   1018  CG   ARG   67      15.784  27.907  41.470  1.00  9.20      PROT
```

Figure 3 cont.

```
ATOM   1019  CD   ARG    67      15.408  26.797  42.444  1.00 14.02      PROT
ATOM   1020  NE   ARG    67      15.480  25.489  41.807  1.00 18.33      PROT
ATOM   1021  CZ   ARG    67      16.416  24.571  42.050  1.00 19.85      PROT
ATOM   1022  NH1  ARG    67      16.380  23.417  41.404  1.00 21.89      PROT
ATOM   1023  NH2  ARG    67      17.384  24.799  42.930  1.00 21.56      PROT
ATOM   1037  N    PHE    68      18.284  30.920  41.584  1.00  4.63      PROT
ATOM   1038  CA   PHE    68      19.488  31.127  40.767  1.00  5.23      PROT
ATOM   1039  C    PHE    68      20.733  31.441  41.601  1.00  5.51      PROT
ATOM   1040  O    PHE    68      21.846  31.148  41.170  1.00  5.25      PROT
ATOM   1041  CB   PHE    68      19.254  32.180  39.681  1.00  5.29      PROT
ATOM   1042  CG   PHE    68      18.177  31.796  38.687  1.00  6.33      PROT
ATOM   1043  CD1  PHE    68      17.984  30.468  38.325  1.00  6.76      PROT
ATOM   1044  CD2  PHE    68      17.359  32.762  38.122  1.00  8.13      PROT
ATOM   1045  CE1  PHE    68      16.988  30.105  37.419  1.00  8.41      PROT
ATOM   1046  CE2  PHE    68      16.367  32.410  37.200  1.00  7.26      PROT
ATOM   1047  CZ   PHE    68      16.175  31.084  36.863  1.00  8.28      PROT
ATOM   1057  N    GLN    69      20.534  32.029  42.786  1.00  5.99      PROT
ATOM   1058  CA   GLN    69      21.608  32.186  43.781  1.00  7.65      PROT
ATOM   1059  C    GLN    69      22.065  30.830  44.329  1.00  7.80      PROT
ATOM   1060  O    GLN    69      23.263  30.588  44.460  1.00  7.84      PROT
ATOM   1061  CB   GLN    69      21.176  33.102  44.938  1.00  7.41      PROT
ATOM   1062  CG   GLN    69      21.119  34.611  44.609  1.00  8.87      PROT
ATOM   1063  CD   GLN    69      20.607  35.452  45.780  1.00  8.91      PROT
ATOM   1064  OE1  GLN    69      20.995  36.601  45.943  1.00 13.38      PROT
ATOM   1065  NE2  GLN    69      19.747  34.870  46.604  1.00 12.25      PROT
ATOM   1074  N    GLN    70      21.108  29.962  44.663  1.00  8.00      PROT
ATOM   1075  CA   GLN    70      21.395  28.595  45.135  1.00  8.76      PROT
ATOM   1076  C    GLN    70      22.240  27.755  44.157  1.00  8.73      PROT
ATOM   1077  O    GLN    70      23.143  27.015  44.567  1.00  8.76      PROT
ATOM   1078  CB   GLN    70      20.083  27.867  45.442  1.00  8.31      PROT
ATOM   1079  CG   GLN    70      20.252  26.470  46.050  1.00  9.36      PROT
ATOM   1080  CD   GLN    70      18.930  25.746  46.237  1.00  9.94      PROT
ATOM   1081  OE1  GLN    70      18.091  25.711  45.341  1.00 10.88      PROT
ATOM   1082  NE2  GLN    70      18.747  25.156  47.411  1.00 12.48      PROT
ATOM   1091  N    GLN    71      21.942  27.882  42.867  1.00  8.75      PROT
ATOM   1092  CA   GLN    71      22.617  27.111  41.821  1.00  9.45      PROT
ATOM   1093  C    GLN    71      23.888  27.808  41.281  1.00  9.61      PROT
ATOM   1094  O    GLN    71      24.543  27.307  40.369  1.00  9.03      PROT
ATOM   1095  CB   GLN    71      21.624  26.789  40.703  1.00  9.50      PROT
ATOM   1096  CG   GLN    71      20.393  26.046  41.214  1.00 10.91      PROT
ATOM   1097  CD   GLN    71      19.300  25.887  40.181  1.00 11.49      PROT
ATOM   1098  OE1  GLN    71      18.757  26.871  39.666  1.00 12.06      PROT
ATOM   1099  NE2  GLN    71      18.947  24.636  39.888  1.00 13.08      PROT
ATOM   1108  N    GLY    72      24.209  28.968  41.850  1.00 10.16      PROT
ATOM   1109  CA   GLY    72      25.478  29.663  41.591  1.00 11.22      PROT
ATOM   1110  C    GLY    72      25.479  30.584  40.393  1.00 11.79      PROT
ATOM   1111  O    GLY    72      26.537  31.079  39.979  1.00 11.92      PROT
ATOM   1115  N    LEU    73      24.291  30.823  39.843  1.00 11.69      PROT
ATOM   1116  CA   LEU    73      24.142  31.570  38.601  1.00 11.35      PROT
ATOM   1117  C    LEU    73      24.007  33.078  38.826  1.00 11.82      PROT
ATOM   1118  O    LEU    73      24.479  33.880  38.004  1.00 11.93      PROT
ATOM   1119  CB   LEU    73      22.953  31.015  37.804  1.00 11.17      PROT
ATOM   1120  CG   LEU    73      22.759  31.445  36.357  1.00 11.20      PROT
ATOM   1121  CD1  LEU    73      23.915  30.953  35.483  1.00 10.42      PROT
ATOM   1122  CD2  LEU    73      21.415  30.947  35.834  1.00 10.49      PROT
ATOM   1134  N    LEU    74      23.357  33.456  39.924  1.00 11.68      PROT
ATOM   1135  CA   LEU    74      23.375  34.831  40.410  1.00 12.06      PROT
ATOM   1136  C    LEU    74      24.196  34.951  41.685  1.00 12.50      PROT
ATOM   1137  O    LEU    74      24.223  34.028  42.498  1.00 11.85      PROT
ATOM   1138  CB   LEU    74      21.966  35.362  40.683  1.00 11.96      PROT
ATOM   1139  CG   LEU    74      21.078  35.821  39.522  1.00 13.15      PROT
ATOM   1140  CD1  LEU    74      19.703  36.195  40.049  1.00 13.13      PROT
ATOM   1141  CD2  LEU    74      21.673  36.999  38.763  1.00 14.79      PROT
ATOM   1153  N    PRO    75      24.840  36.113  41.871  1.00 13.04      PROT
ATOM   1154  CA   PRO    75      25.643  36.436  43.041  1.00 13.81      PROT
```

Figure 3 cont.

```
ATOM   1155  C    PRO  75      24.799  36.557  44.303  1.00 14.26      PROT
ATOM   1156  O    PRO  75      23.639  36.990  44.255  1.00 14.74      PROT
ATOM   1157  CB   PRO  75      26.084  37.990  42.829  1.00 17.17      PROT
ATOM   1158  CG   PRO  75      25.303  38.476  41.656  1.00 17.10      PROT
ATOM   1159  CD   PRO  75      25.013  37.256  40.851  1.00 16.76      PROT
ATOM   1167  N    LYS  76      25.381  36.143  45.422  1.00 14.55      PROT
ATOM   1168  CA   LYS  76      24.781  36.359  46.728  1.00 14.97      PROT
ATOM   1169  C    LYS  76      25.095  37.804  47.140  1.00 15.01      PROT
ATOM   1170  O    LYS  76      24.208  38.573  47.523  1.00 15.08      PROT
ATOM   1171  CB   LYS  76      25.369  35.379  47.751  1.00 15.25      PROT
ATOM   1172  CG   LYS  76      25.579  33.934  47.254  1.00 15.58      PROT
ATOM   1173  CD   LYS  76      24.390  33.027  47.535  1.00 15.07      PROT
ATOM   1174  CE   LYS  76      24.809  31.563  47.710  1.00 15.35      PROT
ATOM   1175  NZ   LYS  76      25.497  30.954  46.513  1.00 16.66      PROT
ATOM   1189  N    ASP  77      25.014  38.165  47.360  1.00 37.09      PROT
ATOM   1190  CA   ASP  77      24.883  39.549  47.761  1.00 37.81      PROT
ATOM   1191  C    ASP  77      25.035  40.380  46.498  1.00 37.73      PROT
ATOM   1192  O    ASP  77      25.566  39.895  45.494  1.00 37.70      PROT
ATOM   1193  CB   ASP  77      25.957  39.911  48.795  1.00 38.34      PROT
ATOM   1194  CG   ASP  77      25.588  41.130  49.632  1.00 39.50      PROT
ATOM   1195  OD1  ASP  77      24.509  41.730  49.403  1.00 41.09      PROT
ATOM   1196  OD2  ASP  77      26.389  41.488  50.524  1.00 41.62      PROT
ATOM   1201  N    ASN  78      24.553  41.619  46.538  1.00 37.41      PROT
ATOM   1202  CA   ASN  78      24.753  42.569  45.439  1.00 37.22      PROT
ATOM   1203  C    ASN  78      23.856  42.352  44.228  1.00 36.77      PROT
ATOM   1204  O    ASN  78      23.461  41.224  43.909  1.00 36.84      PROT
ATOM   1205  CB   ASN  78      26.223  42.612  44.987  1.00 37.57      PROT
ATOM   1206  CG   ASN  78      27.163  43.081  46.081  1.00 37.74      PROT
ATOM   1207  OD1  ASN  78      27.389  42.377  47.067  1.00 38.55      PROT
ATOM   1208  ND2  ASN  78      27.730  44.271  45.903  1.00 37.98      PROT
ATOM   1215  N    CYS  79      23.397  43.243  43.914  1.00 16.19      PROT
ATOM   1216  CA   CYS  79      22.832  43.532  42.605  1.00 16.26      PROT
ATOM   1217  C    CYS  79      23.597  42.791  41.510  1.00 16.22      PROT
ATOM   1218  O    CYS  79      24.836  42.753  41.526  1.00 16.10      PROT
ATOM   1219  CB   CYS  79      22.825  45.043  42.332  1.00 16.20      PROT
ATOM   1220  SG   CYS  79      21.462  45.965  43.104  1.00 17.58      PROT
ATOM   1225  N    PRO  80      22.865  42.200  40.548  1.00 16.04      PROT
ATOM   1226  CA   PRO  80      23.566  41.462  39.506  1.00 15.97      PROT
ATOM   1227  C    PRO  80      24.155  42.393  38.455  1.00 15.86      PROT
ATOM   1228  O    PRO  80      23.637  43.493  38.239  1.00 15.75      PROT
ATOM   1229  CB   PRO  80      22.472  40.599  38.877  1.00 15.93      PROT
ATOM   1230  CG   PRO  80      21.191  41.279  39.190  1.00 16.39      PROT
ATOM   1231  CD   PRO  80      21.401  42.197  40.358  1.00 15.83      PROT
ATOM   1239  N    THR  81      25.243  41.938  37.839  1.00 15.11      PROT
ATOM   1240  CA   THR  81      25.784  42.515  36.613  1.00 14.98      PROT
ATOM   1241  C    THR  81      24.648  42.736  35.604  1.00 14.03      PROT
ATOM   1242  O    THR  81      23.858  41.828  35.355  1.00 14.74      PROT
ATOM   1243  CB   THR  81      26.897  41.573  36.058  1.00 14.99      PROT
ATOM   1244  OG1  THR  81      28.173  42.023  36.521  1.00 16.45      PROT
ATOM   1245  CG2  THR  81      26.926  41.521  34.561  1.00 15.70      PROT
ATOM   1252  N    PRO  82      24.527  43.960  35.057  1.00 13.18      PROT
ATOM   1253  CA   PRO  82      23.515  44.236  34.026  1.00 12.07      PROT
ATOM   1254  C    PRO  82      23.628  43.344  32.792  1.00 11.01      PROT
ATOM   1255  O    PRO  82      22.628  43.098  32.114  1.00 10.90      PROT
ATOM   1256  CB   PRO  82      23.793  45.694  33.648  1.00 12.12      PROT
ATOM   1257  CG   PRO  82      24.421  46.277  34.890  1.00 13.06      PROT
ATOM   1258  CD   PRO  82      25.298  45.169  35.398  1.00 13.38      PROT
ATOM   1266  N    ASP  83      24.832  42.862  32.493  1.00  9.26      PROT
ATOM   1267  CA   ASP  83      25.009  41.969  31.354  1.00  8.37      PROT
ATOM   1268  C    ASP  83      24.413  40.588  31.665  1.00  7.22      PROT
ATOM   1269  O    ASP  83      23.980  39.870  30.765  1.00  7.05      PROT
ATOM   1270  CB   ASP  83      26.486  41.867  30.978  1.00  8.54      PROT
ATOM   1271  CG   ASP  83      27.001  43.100  30.241  1.00 10.63      PROT
ATOM   1272  OD1  ASP  83      26.186  43.945  29.808  1.00 12.62      PROT
ATOM   1273  OD2  ASP  83      28.234  43.224  30.096  1.00 12.07      PROT
```

Figure 3 cont.

```
ATOM   1278  N    ALA   84     24.370  40.253  32.953  1.00  6.02      PROT
ATOM   1279  CA   ALA   84     23.876  38.959  33.440  1.00  4.89      PROT
ATOM   1280  C    ALA   84     22.375  38.717  33.258  1.00  3.61      PROT
ATOM   1281  O    ALA   84     21.956  37.583  33.065  1.00  3.69      PROT
ATOM   1282  CB   ALA   84     24.267  38.775  34.910  1.00  4.25      PROT
ATOM   1288  N    VAL   85     21.561  39.766  33.347  1.00  3.41      PROT
ATOM   1289  CA   VAL   85     20.110  39.604  33.194  1.00  2.71      PROT
ATOM   1290  C    VAL   85     19.608  40.423  32.012  1.00  2.79      PROT
ATOM   1291  O    VAL   85     19.955  41.598  31.878  1.00  2.49      PROT
ATOM   1292  CB   VAL   85     19.338  40.014  34.489  1.00  3.07      PROT
ATOM   1293  CG1  VAL   85     17.851  39.679  34.358  1.00  2.00      PROT
ATOM   1294  CG2  VAL   85     19.945  39.324  35.722  1.00  3.73      PROT
ATOM   1304  N    TYR   86     18.774  39.812  31.171  1.00  2.33      PROT
ATOM   1305  CA   TYR   86     18.164  40.529  30.052  1.00  2.23      PROT
ATOM   1306  C    TYR   86     16.683  40.203  29.904  1.00  2.27      PROT
ATOM   1307  O    TYR   86     16.284  39.028  29.918  1.00  2.01      PROT
ATOM   1308  CB   TYR   86     18.935  40.205  28.765  1.00  2.41      PROT
ATOM   1309  CG   TYR   86     18.526  40.952  27.511  1.00  2.00      PROT
ATOM   1310  CD1  TYR   86     19.306  42.001  27.026  1.00  2.14      PROT
ATOM   1311  CD2  TYR   86     17.385  40.585  26.784  1.00  2.00      PROT
ATOM   1312  CE1  TYR   86     18.961  42.675  25.871  1.00  2.91      PROT
ATOM   1313  CE2  TYR   86     17.017  41.271  25.612  1.00  2.00      PROT
ATOM   1314  CZ   TYR   86     17.819  42.301  25.161  1.00  3.15      PROT
ATOM   1315  OH   TYR   86     17.505  42.982  24.012  1.00  2.57      PROT
ATOM   1324  N    VAL   87     15.859  41.240  29.763  1.00  2.00      PROT
ATOM   1325  CA   VAL   87     14.422  41.021  29.549  1.00  2.00      PROT
ATOM   1326  C    VAL   87     14.020  41.529  28.183  1.00  2.00      PROT
ATOM   1327  O    VAL   87     14.320  42.677  27.829  1.00  2.00      PROT
ATOM   1328  CB   VAL   87     13.552  41.734  30.617  1.00  2.00      PROT
ATOM   1329  CG1  VAL   87     12.060  41.591  30.302  1.00  2.00      PROT
ATOM   1330  CG2  VAL   87     13.889  41.243  32.021  1.00  2.00      PROT
ATOM   1340  N    TRP   88     13.382  40.652  27.413  1.00  2.00      PROT
ATOM   1341  CA   TRP   88     12.676  41.029  26.201  1.00  2.00      PROT
ATOM   1342  C    TRP   88     11.173  40.796  26.415  1.00  2.00      PROT
ATOM   1343  O    TRP   88     10.729  39.683  26.716  1.00  2.00      PROT
ATOM   1344  CB   TRP   88     13.196  40.275  24.971  1.00  2.00      PROT
ATOM   1345  CG   TRP   88     12.630  40.807  23.672  1.00  2.09      PROT
ATOM   1346  CD1  TRP   88     11.587  40.278  22.959  1.00  2.63      PROT
ATOM   1347  CD2  TRP   88     13.066  41.966  22.948  1.00  2.00      PROT
ATOM   1348  NE1  TRP   88     11.347  41.039  21.836  1.00  2.61      PROT
ATOM   1349  CE2  TRP   88     12.232  42.087  21.810  1.00  2.00      PROT
ATOM   1350  CE3  TRP   88     14.074  42.925  23.155  1.00  2.00      PROT
ATOM   1351  CZ2  TRP   88     12.391  43.111  20.866  1.00  2.62      PROT
ATOM   1352  CZ3  TRP   88     14.221  43.951  22.242  1.00  2.08      PROT
ATOM   1353  CH2  TRP   88     13.391  44.036  21.092  1.00  3.02      PROT
ATOM   1364  N    ALA   89     10.405  41.871  26.281  1.00  2.00      PROT
ATOM   1365  CA   ALA   89      8.974  41.845  26.500  1.00  2.00      PROT
ATOM   1366  C    ALA   89      8.268  42.148  25.197  1.00  2.00      PROT
ATOM   1367  O    ALA   89      8.772  42.938  24.375  1.00  2.00      PROT
ATOM   1368  CB   ALA   89      8.608  42.895  27.536  1.00  2.00      PROT
ATOM   1374  N    ASP   90      7.096  41.540  25.014  1.00  2.00      PROT
ATOM   1375  CA   ASP   90      6.230  41.890  23.905  1.00  2.00      PROT
ATOM   1376  C    ASP   90      5.762  43.321  24.123  1.00  2.00      PROT
ATOM   1377  O    ASP   90      5.960  43.903  25.201  1.00  2.00      PROT
ATOM   1378  CB   ASP   90      5.038  40.939  23.806  1.00  2.02      PROT
ATOM   1379  CG   ASP   90      4.386  40.927  22.419  1.00  3.26      PROT
ATOM   1380  OD1  ASP   90      4.904  41.530  21.427  1.00  2.00      PROT
ATOM   1381  OD2  ASP   90      3.366  40.234  22.305  1.00  4.44      PROT
ATOM   1386  N    VAL   91      5.145  43.884  23.089  1.00  2.00      PROT
ATOM   1387  CA   VAL   91      4.839  45.312  23.044  1.00  2.00      PROT
ATOM   1388  C    VAL   91      3.708  45.743  23.983  1.00  2.00      PROT
ATOM   1389  O    VAL   91      3.607  46.935  24.307  1.00  2.00      PROT
ATOM   1390  CB   VAL   91      4.491  45.759  21.610  1.00  2.00      PROT
ATOM   1391  CG1  VAL   91      5.703  45.611  20.703  1.00  2.00      PROT
ATOM   1392  CG2  VAL   91      3.283  44.988  21.063  1.00  2.00      PROT
```

Figure 3 cont.

```
ATOM   1402  N    ASP   92      2.865  44.784  24.380  1.00   2.00      PROT
ATOM   1403  CA   ASP   92      1.653  45.051  25.160  1.00   2.44      PROT
ATOM   1404  C    ASP   92      2.039  45.637  26.509  1.00   2.47      PROT
ATOM   1405  O    ASP   92      3.096  45.290  27.059  1.00   2.00      PROT
ATOM   1406  CB   ASP   92      0.830  43.773  25.409  1.00   2.85      PROT
ATOM   1407  CG   ASP   92      0.335  43.110  24.117  1.00   6.94      PROT
ATOM   1408  OD1  ASP   92     -0.731  43.495  23.587  1.00   7.72      PROT
ATOM   1409  OD2  ASP   92      1.008  42.172  23.644  1.00  11.14      PROT
ATOM   1414  N    GLN   93      1.177  46.489  27.064  1.00   2.72      PROT
ATOM   1415  CA   GLN   93      1.454  46.986  28.408  1.00   3.30      PROT
ATOM   1416  C    GLN   93      1.531  45.856  29.444  1.00   3.26      PROT
ATOM   1417  O    GLN   93      2.402  45.897  30.302  1.00   2.71      PROT
ATOM   1418  CB   GLN   93      0.587  48.198  28.820  1.00   5.15      PROT
ATOM   1419  CG   GLN   93     -0.668  48.007  29.653  1.00   5.19      PROT
ATOM   1420  CD   GLN   93     -0.479  47.599  31.121  1.00   4.49      PROT
ATOM   1421  OE1  GLN   93     -0.305  48.431  32.046  1.00   7.38      PROT
ATOM   1422  NE2  GLN   93     -0.602  46.329  31.346  1.00   2.00      PROT
ATOM   1431  N    ARG   94      0.674  44.833  29.320  1.00   2.89      PROT
ATOM   1432  CA   ARG   94      0.690  43.683  30.240  1.00   2.30      PROT
ATOM   1433  C    ARG   94      2.030  42.923  30.263  1.00   2.13      PROT
ATOM   1434  O    ARG   94      2.490  42.522  31.326  1.00   2.00      PROT
ATOM   1435  CB   ARG   94     -0.498  42.730  30.018  1.00   2.00      PROT
ATOM   1436  CG   ARG   94     -0.562  42.008  28.641  1.00   2.96      PROT
ATOM   1437  CD   ARG   94     -1.826  41.138  28.482  1.00   4.83      PROT
ATOM   1438  NE   ARG   94     -2.869  41.869  27.755  1.00  13.78      PROT
ATOM   1439  CZ   ARG   94     -3.314  41.610  26.528  1.00  13.85      PROT
ATOM   1440  NH1  ARG   94     -2.869  40.583  25.807  1.00  13.84      PROT
ATOM   1441  NH2  ARG   94     -4.249  42.395  26.022  1.00  17.68      PROT
ATOM   1455  N    THR   95      2.634  42.734  29.095  1.00   2.00      PROT
ATOM   1456  CA   THR   95      3.957  42.087  28.989  1.00   2.00      PROT
ATOM   1457  C    THR   95      5.125  42.993  29.397  1.00   2.00      PROT
ATOM   1458  O    THR   95      6.019  42.544  30.118  1.00   2.00      PROT
ATOM   1459  CB   THR   95      4.190  41.458  27.584  1.00   2.00      PROT
ATOM   1460  OG1  THR   95      3.868  42.402  26.560  1.00   2.00      PROT
ATOM   1461  CG2  THR   95      3.302  40.241  27.407  1.00   2.00      PROT
ATOM   1468  N    ARG   96      5.134  44.256  28.961  1.00   2.00      PROT
ATOM   1469  CA   ARG   96      6.208  45.173  29.375  1.00   2.00      PROT
ATOM   1470  C    ARG   96      6.265  45.331  30.900  1.00   2.00      PROT
ATOM   1471  O    ARG   96      7.342  45.239  31.498  1.00   2.00      PROT
ATOM   1472  CB   ARG   96      6.073  46.550  28.702  1.00   2.00      PROT
ATOM   1473  CG   ARG   96      6.334  46.523  27.195  1.00   2.00      PROT
ATOM   1474  CD   ARG   96      6.262  47.911  26.602  1.00   3.41      PROT
ATOM   1475  NE   ARG   96      4.897  48.358  26.337  1.00   2.27      PROT
ATOM   1476  CZ   ARG   96      4.238  49.279  27.044  1.00   3.34      PROT
ATOM   1477  NH1  ARG   96      4.789  49.871  28.093  1.00   2.00      PROT
ATOM   1478  NH2  ARG   96      3.011  49.609  26.691  1.00   4.75      PROT
ATOM   1492  N    LYS   97      5.097  45.561  31.510  1.00   2.00      PROT
ATOM   1493  CA   LYS   97      4.970  45.685  32.964  1.00   2.15      PROT
ATOM   1494  C    LYS   97      5.325  44.388  33.688  1.00   2.00      PROT
ATOM   1495  O    LYS   97      5.894  44.425  34.779  1.00   2.00      PROT
ATOM   1496  CB   LYS   97      3.566  46.151  33.373  1.00   2.09      PROT
ATOM   1497  CG   LYS   97      3.225  47.581  32.958  1.00   4.19      PROT
ATOM   1498  CD   LYS   97      3.935  48.612  33.816  1.00   9.00      PROT
ATOM   1499  CE   LYS   97      3.721  50.013  33.260  1.00  11.26      PROT
ATOM   1500  NZ   LYS   97      3.956  51.008  34.350  1.00  16.81      PROT
ATOM   1514  N    THR   98      5.047  43.251  33.058  1.00   2.00      PROT
ATOM   1515  CA   THR   98      5.477  41.952  33.602  1.00   2.10      PROT
ATOM   1516  C    THR   98      7.011  41.887  33.667  1.00   2.00      PROT
ATOM   1517  O    THR   98      7.574  41.520  34.691  1.00   2.00      PROT
ATOM   1518  CB   THR   98      4.894  40.779  32.802  1.00   2.41      PROT
ATOM   1519  OG1  THR   98      3.466  40.757  32.953  1.00   2.10      PROT
ATOM   1520  CG2  THR   98      5.480  39.437  33.283  1.00   4.45      PROT
ATOM   1527  N    GLY   99      7.669  42.268  32.571  1.00   2.00      PROT
ATOM   1528  CA   GLY   99      9.132  42.372  32.532  1.00   2.00      PROT
ATOM   1529  C    GLY   99      9.665  43.275  33.639  1.00   2.00      PROT
```

Figure 3 cont.

```
ATOM   1530 O    GLY  99   10.609  42.906  34.359  1.00  2.00       PROT
ATOM   1534 N    GLU  100   9.051  44.449  33.784  1.00  2.00       PROT
ATOM   1535 CA   GLU  100   9.460  45.396  34.826  1.00  2.05       PROT
ATOM   1536 C    GLU  100   9.293  44.767  36.213  1.00  2.00       PROT
ATOM   1537 O    GLU  100  10.219  44.802  37.024  1.00  2.00       PROT
ATOM   1538 CB   GLU  100   8.719  46.721  34.703  1.00  2.00       PROT
ATOM   1539 CG   GLU  100   9.125  47.507  33.444  1.00  3.36       PROT
ATOM   1540 CD   GLU  100   8.469  48.865  33.348  1.00  6.20       PROT
ATOM   1541 OE1  GLU  100   8.580  49.652  34.303  1.00 10.98       PROT
ATOM   1542 OE2  GLU  100   7.853  49.169  32.307  1.00 13.47       PROT
ATOM   1549 N    ALA  101   8.126  44.172  36.459  1.00  2.00       PROT
ATOM   1550 CA   ALA  101   7.860  43.482  37.745  1.00  2.00       PROT
ATOM   1551 C    ALA  101   8.811  42.304  38.036  1.00  2.00       PROT
ATOM   1552 O    ALA  101   9.177  42.083  39.194  1.00  2.00       PROT
ATOM   1553 CB   ALA  101   6.412  43.033  37.817  1.00  2.00       PROT
ATOM   1559 N    PHE  102   9.205  41.557  37.004  1.00  2.00       PROT
ATOM   1560 CA   PHE  102  10.183  40.463  37.165  1.00  2.00       PROT
ATOM   1561 C    PHE  102  11.506  41.008  37.708  1.00  2.00       PROT
ATOM   1562 O    PHE  102  12.078  40.461  38.651  1.00  2.00       PROT
ATOM   1563 CB   PHE  102  10.413  39.688  35.845  1.00  2.00       PROT
ATOM   1564 CG   PHE  102  11.708  38.891  35.801  1.00  2.00       PROT
ATOM   1565 CD1  PHE  102  11.805  37.638  36.417  1.00  2.31       PROT
ATOM   1566 CD2  PHE  102  12.813  39.379  35.108  1.00  2.00       PROT
ATOM   1567 CE1  PHE  102  12.992  36.895  36.380  1.00  2.00       PROT
ATOM   1568 CE2  PHE  102  14.001  38.658  35.062  1.00  2.98       PROT
ATOM   1569 CZ   PHE  102  14.090  37.405  35.677  1.00  2.00       PROT
ATOM   1579 N    LEU  103  11.959  42.112  37.119  1.00  2.00       PROT
ATOM   1580 CA   LEU  103  13.195  42.755  37.548  1.00  2.00       PROT
ATOM   1581 C    LEU  103  13.104  43.264  38.992  1.00  2.00       PROT
ATOM   1582 O    LEU  103  14.070  43.171  39.735  1.00  2.00       PROT
ATOM   1583 CB   LEU  103  13.620  43.855  36.559  1.00  2.00       PROT
ATOM   1584 CG   LEU  103  14.007  43.457  35.125  1.00  2.00       PROT
ATOM   1585 CD1  LEU  103  14.503  44.694  34.349  1.00  2.53       PROT
ATOM   1586 CD2  LEU  103  15.084  42.375  35.133  1.00  2.00       PROT
ATOM   1598 N    ALA  104  11.926  43.759  39.378  1.00  2.00       PROT
ATOM   1599 CA   ALA  104  11.671  44.317  40.709  1.00  2.00       PROT
ATOM   1600 C    ALA  104  11.822  43.270  41.789  1.00  2.00       PROT
ATOM   1601 O    ALA  104  12.226  43.575  42.930  1.00  2.00       PROT
ATOM   1602 CB   ALA  104  10.262  44.906  40.760  1.00  3.11       PROT
ATOM   1608 N    GLY  105  11.474  42.039  41.425  1.00  2.00       PROT
ATOM   1609 CA   GLY  105  11.554  40.915  42.325  1.00  2.35       PROT
ATOM   1610 C    GLY  105  12.865  40.164  42.272  1.00  2.19       PROT
ATOM   1611 O    GLY  105  13.355  39.725  43.304  1.00  2.00       PROT
ATOM   1615 N    LEU  106  13.426  40.001  41.070  1.00  2.74       PROT
ATOM   1616 CA   LEU  106  14.717  39.336  40.886  1.00  3.45       PROT
ATOM   1617 C    LEU  106  15.858  40.160  41.457  1.00  4.64       PROT
ATOM   1618 O    LEU  106  16.849  39.608  41.946  1.00  4.33       PROT
ATOM   1619 CB   LEU  106  14.997  39.092  39.396  1.00  3.80       PROT
ATOM   1620 CG   LEU  106  16.282  38.341  39.031  1.00  3.13       PROT
ATOM   1621 CD1  LEU  106  16.014  36.839  38.949  1.00  3.36       PROT
ATOM   1622 CD2  LEU  106  16.808  38.858  37.714  1.00  3.16       PROT
ATOM   1634 N    ALA  107  15.722  41.478  41.384  1.00  5.01       PROT
ATOM   1635 CA   ALA  107  16.807  42.366  41.747  1.00  6.45       PROT
ATOM   1636 C    ALA  107  16.269  43.689  42.271  1.00  6.90       PROT
ATOM   1637 O    ALA  107  16.396  44.715  41.605  1.00  6.73       PROT
ATOM   1638 CB   ALA  107  17.720  42.583  40.543  1.00  6.01       PROT
ATOM   1644 N    PRO  108  15.689  43.677  43.485  1.00  8.39       PROT
ATOM   1645 CA   PRO  108  15.052  44.872  44.037  1.00  9.44       PROT
ATOM   1646 C    PRO  108  16.064  45.979  44.282  1.00 10.34       PROT
ATOM   1647 O    PRO  108  17.180  45.706  44.720  1.00 10.41       PROT
ATOM   1648 CB   PRO  108  14.474  44.385  45.370  1.00  9.24       PROT
ATOM   1649 CG   PRO  108  14.475  42.901  45.280  1.00  9.66       PROT
ATOM   1650 CD   PRO  108  15.630  42.551  44.430  1.00  8.13       PROT
ATOM   1658 N    GLN  109  15.671  47.215  43.982  1.00 11.29       PROT
ATOM   1659 CA   GLN  109  16.546  48.387  44.132  1.00 12.67       PROT
```

Figure 3 cont.

```
ATOM   1660  C    GLN   109      17.826  48.298  43.287  1.00 12.75      PROT
ATOM   1661  O    GLN   109      18.837  48.922  43.619  1.00 13.13      PROT
ATOM   1662  CB   GLN   109      16.904  48.643  45.612  1.00 13.03      PROT
ATOM   1663  CG   GLN   109      15.785  48.393  46.633  1.00 15.35      PROT
ATOM   1664  CD   GLN   109      14.513  49.181  46.357  1.00 18.56      PROT
ATOM   1665  OE1  GLN   109      14.529  50.223  45.689  1.00 19.89      PROT
ATOM   1666  NE2  GLN   109      13.400  48.689  46.887  1.00 19.67      PROT
ATOM   1675  N    CYS   110      17.787  47.499  42.219  1.00 12.66      PROT
ATOM   1676  CA   CYS   110      18.857  47.466  41.238  1.00 12.25      PROT
ATOM   1677  C    CYS   110      18.376  48.198  39.993  1.00 11.96      PROT
ATOM   1678  O    CYS   110      17.204  48.084  39.605  1.00 11.75      PROT
ATOM   1679  CB   CYS   110      19.288  46.024  40.920  1.00 12.49      PROT
ATOM   1680  SG   CYS   110      19.778  45.068  42.410  1.00 13.69      PROT
ATOM   1685  N    ASP   111      19.278  48.957  39.381  1.00 11.33      PROT
ATOM   1686  CA   ASP   111      18.908  49.879  38.305  1.00 11.30      PROT
ATOM   1687  C    ASP   111      18.925  49.204  36.941  1.00 10.16      PROT
ATOM   1688  O    ASP   111      19.773  49.490  36.087  1.00 10.47      PROT
ATOM   1689  CB   ASP   111      19.822  51.102  38.317  1.00 12.10      PROT
ATOM   1690  CG   ASP   111      19.128  52.360  37.836  1.00 13.34      PROT
ATOM   1691  OD1  ASP   111      17.909  52.325  37.553  1.00 14.20      PROT
ATOM   1692  OD2  ASP   111      19.817  53.396  37.743  1.00 17.24      PROT
ATOM   1697  N    LEU   112      17.973  48.295  36.756  1.00  8.69      PROT
ATOM   1698  CA   LEU   112      17.854  47.508  35.546  1.00  6.78      PROT
ATOM   1699  C    LEU   112      16.579  47.909  34.798  1.00  5.58      PROT
ATOM   1700  O    LEU   112      15.632  48.421  35.394  1.00  5.83      PROT
ATOM   1701  CB   LEU   112      17.844  46.004  35.880  1.00  7.06      PROT
ATOM   1702  CG   LEU   112      19.012  45.458  36.725  1.00  7.52      PROT
ATOM   1703  CD1  LEU   112      20.331  45.536  35.970  1.00  5.79      PROT
ATOM   1704  CD2  LEU   112      18.757  44.036  37.212  1.00  6.06      PROT
ATOM   1716  N    ALA   113      16.579  47.672  33.496  1.00  3.63      PROT
ATOM   1717  CA   ALA   113      15.482  48.053  32.611  1.00  2.78      PROT
ATOM   1718  C    ALA   113      15.235  46.956  31.601  1.00  2.00      PROT
ATOM   1719  O    ALA   113      16.164  46.211  31.254  1.00  2.00      PROT
ATOM   1720  CB   ALA   113      15.807  49.371  31.894  1.00  2.36      PROT
ATOM   1726  N    ILE   114      13.993  46.878  31.120  1.00  2.00      PROT
ATOM   1727  CA   ILE   114      13.588  45.913  30.101  1.00  2.00      PROT
ATOM   1728  C    ILE   114      13.959  46.388  28.685  1.00  2.00      PROT
ATOM   1729  O    ILE   114      14.258  47.561  28.466  1.00  2.00      PROT
ATOM   1730  CB   ILE   114      12.059  45.592  30.175  1.00  2.00      PROT
ATOM   1731  CG1  ILE   114      11.209  46.783  29.701  1.00  2.00      PROT
ATOM   1732  CG2  ILE   114      11.676  45.154  31.607  1.00  2.00      PROT
ATOM   1733  CD   ILE   114       9.700  46.471  29.500  1.00  2.00      PROT
ATOM   1745  N    HSD   115      13.952  45.445  27.748  1.00  2.00      PROT
ATOM   1746  CA   HSD   115      14.074  45.727  26.333  1.00  2.00      PROT
ATOM   1747  C    HSD   115      12.756  45.349  25.659  1.00  2.00      PROT
ATOM   1748  O    HSD   115      12.042  44.448  26.126  1.00  2.00      PROT
ATOM   1749  CB   HSD   115      15.239  44.938  25.734  1.00  2.00      PROT
ATOM   1750  CG   HSD   115      16.579  45.398  26.216  1.00  2.00      PROT
ATOM   1751  ND1  HSD   115      17.142  44.954  27.390  1.00  2.04      PROT
ATOM   1752  CD2  HSD   115      17.449  46.293  25.699  1.00  2.00      PROT
ATOM   1753  CE1  HSD   115      18.312  45.540  27.565  1.00  2.00      PROT
ATOM   1754  NE2  HSD   115      18.526  46.349  26.546  1.00  2.21      PROT
ATOM   1762  N    HSD   116      12.425  46.047  24.577  1.00  2.00      PROT
ATOM   1763  CA   HSD   116      11.242  45.700  23.774  1.00  2.00      PROT
ATOM   1764  C    HSD   116      11.350  46.370  22.402  1.00  2.00      PROT
ATOM   1765  O    HSD   116      12.160  47.270  22.221  1.00  2.00      PROT
ATOM   1766  CB   HSD   116       9.911  46.038  24.503  1.00  2.00      PROT
ATOM   1767  CG   HSD   116       9.625  47.507  24.633  1.00  2.00      PROT
ATOM   1768  CD2  HSD   116       9.723  48.182  25.834  1.00  2.12      PROT
ATOM   1769  ND1  HSD   116       9.231  48.425  23.719  1.00  2.00      PROT
ATOM   1770  NE2  HSD   116       9.410  49.453  25.650  1.00  2.00      PROT
ATOM   1771  CE1  HSD   116       9.109  49.628  24.375  1.00  3.14      PROT
ATOM   1779  N    GLN   117      10.545  45.903  21.448  1.00  2.00      PROT
ATOM   1780  CA   GLN   117      10.493  46.478  20.108  1.00  2.44      PROT
ATOM   1781  C    GLN   117      10.198  47.973  20.207  1.00  2.94      PROT
```

Figure 3 cont.

```
ATOM   1782  O    GLN  117       9.301  48.385  20.950  1.00   2.56      PROT
ATOM   1783  CB   GLN  117       9.426  45.769  19.273  1.00   2.08      PROT
ATOM   1784  CG   GLN  117       9.236  46.301  17.870  1.00   3.58      PROT
ATOM   1785  CD   GLN  117       8.402  45.380  17.021  1.00   3.37      PROT
ATOM   1786  OE1  GLN  117       8.895  44.358  16.536  1.00   2.00      PROT
ATOM   1787  NE2  GLN  117       7.129  45.739  16.818  1.00   3.63      PROT
ATOM   1796  N    GLN  118      10.965  48.767  19.465  1.00   2.94      PROT
ATOM   1797  CA   GLN  118      10.839  50.231  19.471  1.00   4.36      PROT
ATOM   1798  C    GLN  118       9.416  50.735  19.236  1.00   4.23      PROT
ATOM   1799  O    GLN  118       8.923  51.585  19.982  1.00   4.27      PROT
ATOM   1800  CB   GLN  118      11.789  50.862  18.446  1.00   4.57      PROT
ATOM   1801  CG   GLN  118      13.234  51.016  18.915  1.00   7.90      PROT
ATOM   1802  CD   GLN  118      13.453  52.158  19.930  1.00  10.01      PROT
ATOM   1803  OE1  GLN  118      12.523  52.627  20.590  1.00  11.52      PROT
ATOM   1804  NE2  GLN  118      14.696  52.566  20.080  1.00  12.05      PROT
ATOM   1813  N    ASN  119       8.772  50.211  18.196  1.00   4.34      PROT
ATOM   1814  CA   ASN  119       7.373  50.532  17.873  1.00   3.91      PROT
ATOM   1815  C    ASN  119       6.407  49.544  18.509  1.00   3.28      PROT
ATOM   1816  O    ASN  119       6.314  48.391  18.077  1.00   2.33      PROT
ATOM   1817  CB   ASN  119       7.179  50.528  16.351  1.00   4.16      PROT
ATOM   1818  CG   ASN  119       5.887  51.197  15.910  1.00   5.24      PROT
ATOM   1819  OD1  ASN  119       4.809  50.875  16.391  1.00   7.69      PROT
ATOM   1820  ND2  ASN  119       5.994  52.111  14.960  1.00   6.10      PROT
ATOM   1827  N    THR  120       5.676  50.004  19.519  1.00   3.07      PROT
ATOM   1828  CA   THR  120       4.763  49.153  20.265  1.00   4.57      PROT
ATOM   1829  C    THR  120       3.377  49.154  19.610  1.00   5.02      PROT
ATOM   1830  O    THR  120       2.465  48.483  20.063  1.00   5.27      PROT
ATOM   1831  CB   THR  120       4.681  49.567  21.763  1.00   4.46      PROT
ATOM   1832  OG1  THR  120       4.106  50.875  21.874  1.00   3.87      PROT
ATOM   1833  CG2  THR  120       6.076  49.605  22.365  1.00   4.19      PROT
ATOM   1840  N    GLN  121       3.236  49.889  18.512  1.00   6.52      PROT
ATOM   1841  CA   GLN  121       1.939  49.972  17.849  1.00   7.59      PROT
ATOM   1842  C    GLN  121       1.860  48.936  16.726  1.00   7.88      PROT
ATOM   1843  O    GLN  121       0.851  48.841  16.015  1.00   9.07      PROT
ATOM   1844  CB   GLN  121       1.676  51.391  17.346  1.00   8.37      PROT
ATOM   1845  CG   GLN  121       1.798  52.482  18.423  1.00   9.82      PROT
ATOM   1846  CD   GLN  121       0.733  52.391  19.517  1.00  12.79      PROT
ATOM   1847  OE1  GLN  121      -0.348  51.841  19.311  1.00  14.41      PROT
ATOM   1848  NE2  GLN  121       1.047  52.935  20.687  1.00  12.67      PROT
ATOM   1857  N    GLN  122       2.939  48.167  16.576  1.00   7.18      PROT
ATOM   1858  CA   GLN  122       3.034  47.097  15.584  1.00   6.63      PROT
ATOM   1859  C    GLN  122       3.405  45.795  16.284  1.00   5.51      PROT
ATOM   1860  O    GLN  122       4.132  45.809  17.275  1.00   4.57      PROT
ATOM   1861  CB   GLN  122       4.093  47.423  14.530  1.00   6.79      PROT
ATOM   1862  CG   GLN  122       3.795  48.651  13.691  1.00   9.40      PROT
ATOM   1863  CD   GLN  122       4.278  48.506  12.277  1.00  12.32      PROT
ATOM   1864  OE1  GLN  122       4.437  47.391  11.776  1.00  14.95      PROT
ATOM   1865  NE2  GLN  122       4.502  49.636  11.605  1.00  13.56      PROT
ATOM   1874  N    ALA  123       2.901  44.674  15.769  1.00   4.39      PROT
ATOM   1875  CA   ALA  123       3.224  43.366  16.327  1.00   3.92      PROT
ATOM   1876  C    ALA  123       4.740  43.145  16.352  1.00   3.61      PROT
ATOM   1877  O    ALA  123       5.454  43.612  15.467  1.00   2.39      PROT
ATOM   1878  CB   ALA  123       2.537  42.258  15.528  1.00   4.62      PROT
ATOM   1884  N    ASP  124       5.228  42.477  17.393  1.00   3.00      PROT
ATOM   1885  CA   ASP  124       6.619  42.021  17.434  1.00   2.70      PROT
ATOM   1886  C    ASP  124       6.651  40.631  16.794  1.00   2.31      PROT
ATOM   1887  O    ASP  124       6.051  39.707  17.332  1.00   2.50      PROT
ATOM   1888  CB   ASP  124       7.107  41.954  18.901  1.00   3.22      PROT
ATOM   1889  CG   ASP  124       8.564  41.497  19.026  1.00   2.93      PROT
ATOM   1890  OD1  ASP  124       9.121  40.927  18.068  1.00   3.58      PROT
ATOM   1891  OD2  ASP  124       9.162  41.732  20.087  1.00   3.75      PROT
ATOM   1896  N    PRO  125       7.374  40.464  15.661  1.00   2.33      PROT
ATOM   1897  CA   PRO  125       7.386  39.193  14.934  1.00   2.64      PROT
ATOM   1898  C    PRO  125       7.921  38.001  15.738  1.00   2.17      PROT
ATOM   1899  O    PRO  125       7.657  36.859  15.389  1.00   2.28      PROT
```

Figure 3 cont.

```
ATOM   1900  CB   PRO   125       8.310   39.473   13.739  1.00   2.31      PROT
ATOM   1901  CG   PRO   125       9.151   40.596   14.144  1.00   3.16      PROT
ATOM   1902  CD   PRO   125       8.249   41.459   15.023  1.00   2.63      PROT
ATOM   1910  N    LEU   126       8.688   38.265   16.787  1.00   2.21      PROT
ATOM   1911  CA   LEU   126       9.104   37.200   17.718  1.00   2.06      PROT
ATOM   1912  C    LEU   126       7.920   36.492   18.387  1.00   2.03      PROT
ATOM   1913  O    LEU   126       7.925   35.268   18.552  1.00   2.00      PROT
ATOM   1914  CB   LEU   126      10.038   37.770   18.794  1.00   2.27      PROT
ATOM   1915  CG   LEU   126      10.662   36.746   19.750  1.00   2.85      PROT
ATOM   1916  CD1  LEU   126      11.671   35.870   19.025  1.00   4.52      PROT
ATOM   1917  CD2  LEU   126      11.314   37.451   20.921  1.00   2.00      PROT
ATOM   1929  N    PHE   127       6.900   37.264   18.760  1.00   2.00      PROT
ATOM   1930  CA   PHE   127       5.759   36.729   19.501  1.00   2.00      PROT
ATOM   1931  C    PHE   127       4.574   36.382   18.613  1.00   2.00      PROT
ATOM   1932  O    PHE   127       3.789   35.471   18.930  1.00   2.00      PROT
ATOM   1933  CB   PHE   127       5.296   37.743   20.543  1.00   2.00      PROT
ATOM   1934  CG   PHE   127       6.302   38.010   21.611  1.00   2.00      PROT
ATOM   1935  CD1  PHE   127       6.416   37.165   22.703  1.00   2.00      PROT
ATOM   1936  CD2  PHE   127       7.136   39.131   21.528  1.00   2.00      PROT
ATOM   1937  CE1  PHE   127       7.347   37.422   23.711  1.00   2.00      PROT
ATOM   1938  CE2  PHE   127       8.062   39.394   22.514  1.00   2.00      PROT
ATOM   1939  CZ   PHE   127       8.169   38.547   23.615  1.00   2.00      PROT
ATOM   1949  N    HSD   128       4.425   37.145   17.535  1.00   2.00      PROT
ATOM   1950  CA   HSD   128       3.300   37.005   16.619  1.00   2.00      PROT
ATOM   1951  C    HSD   128       3.764   37.146   15.166  1.00   2.00      PROT
ATOM   1952  O    HSD   128       3.434   38.139   14.501  1.00   2.69      PROT
ATOM   1953  CB   HSD   128       2.211   38.039   16.951  1.00   2.11      PROT
ATOM   1954  CG   HSD   128       1.713   37.969   18.362  1.00   3.31      PROT
ATOM   1955  ND1  HSD   128       2.150   38.822   19.354  1.00   5.46      PROT
ATOM   1956  CD2  HSD   128       0.811   37.144   18.947  1.00   4.58      PROT
ATOM   1957  CE1  HSD   128       1.531   38.530   20.487  1.00   3.86      PROT
ATOM   1958  NE2  HSD   128       0.717   37.513   20.265  1.00   5.27      PROT
ATOM   1966  N    PRO   129       4.529   36.153   14.661  1.00   2.00      PROT
ATOM   1967  CA   PRO   129       5.059   36.245   13.286  1.00   2.01      PROT
ATOM   1968  C    PRO   129       3.984   36.299   12.185  1.00   2.75      PROT
ATOM   1969  O    PRO   129       4.206   36.930   11.149  1.00   2.09      PROT
ATOM   1970  CB   PRO   129       5.925   34.991   13.139  1.00   2.40      PROT
ATOM   1971  CG   PRO   129       5.546   34.077   14.243  1.00   2.00      PROT
ATOM   1972  CD   PRO   129       4.969   34.923   15.347  1.00   2.00      PROT
ATOM   1980  N    VAL   130       2.845   35.647   12.427  1.00   3.60      PROT
ATOM   1981  CA   VAL   130       1.705   35.628   11.503  1.00   5.10      PROT
ATOM   1982  C    VAL   130       1.063   37.015   11.337  1.00   5.72      PROT
ATOM   1983  O    VAL   130       0.845   37.477   10.202  1.00   6.14      PROT
ATOM   1984  CB   VAL   130       0.636   34.575   11.950  1.00   4.93      PROT
ATOM   1985  CG1  VAL   130      -0.599   34.634   11.068  1.00   5.21      PROT
ATOM   1986  CG2  VAL   130       1.227   33.166   11.934  1.00   5.30      PROT
ATOM   1996  N    LYS   131       0.759   37.654   12.465  1.00   6.57      PROT
ATOM   1997  CA   LYS   131       0.211   39.013   12.512  1.00   7.61      PROT
ATOM   1998  C    LYS   131       1.188   40.012   11.887  1.00   7.65      PROT
ATOM   1999  O    LYS   131       0.798   40.825   11.037  1.00   7.82      PROT
ATOM   2000  CB   LYS   131      -0.130   39.391   13.965  1.00   7.17      PROT
ATOM   2001  CG   LYS   131      -0.973   40.667   14.132  1.00   8.64      PROT
ATOM   2002  CD   LYS   131      -2.306   40.720   13.426  1.00  13.01      PROT
ATOM   2003  CE   LYS   131      -2.930   42.115   13.438  1.00  13.65      PROT
ATOM   2004  NZ   LYS   131      -4.359   42.080   12.995  1.00  16.73      PROT
ATOM   2018  N    ALA   132       2.462   39.912   12.275  1.00   7.95      PROT
ATOM   2019  CA   ALA   132       3.525   40.770   11.735  1.00   8.15      PROT
ATOM   2020  C    ALA   132       3.842   40.533   10.252  1.00   8.44      PROT
ATOM   2021  O    ALA   132       4.630   41.273    9.657  1.00   8.27      PROT
ATOM   2022  CB   ALA   132       4.788   40.656   12.574  1.00   7.91      PROT
ATOM   2028  N    GLY   133       3.233   39.501    9.668  1.00   8.62      PROT
ATOM   2029  CA   GLY   133       3.329   39.246    8.231  1.00   8.97      PROT
ATOM   2030  C    GLY   133       4.598   38.549    7.783  1.00   9.39      PROT
ATOM   2031  O    GLY   133       5.050   38.748    6.654  1.00   9.35      PROT
ATOM   2035  N    ILE   134       5.180   37.738    8.660  1.00   9.31      PROT
```

Figure 3 cont.

```
ATOM   2036  CA   ILE   134       6.383  36.979   8.309  1.00   9.89      PROT
ATOM   2037  C    ILE   134       6.026  35.742   7.472  1.00   9.68      PROT
ATOM   2038  O    ILE   134       6.738  35.382   6.532  1.00   9.47      PROT
ATOM   2039  CB   ILE   134       7.207  36.616   9.578  1.00  10.04      PROT
ATOM   2040  CG1  ILE   134       7.846  37.888  10.139  1.00  10.17      PROT
ATOM   2041  CG2  ILE   134       8.280  35.569   9.283  1.00  10.44      PROT
ATOM   2042  CD   ILE   134       8.764  37.645  11.282  1.00  11.79      PROT
ATOM   2054  N    CYS   135       4.917  35.102   7.833  1.00   9.94      PROT
ATOM   2055  CA   CYS   135       4.417  33.938   7.110  1.00  10.07      PROT
ATOM   2056  C    CYS   135       2.909  33.848   7.291  1.00   9.95      PROT
ATOM   2057  O    CYS   135       2.328  34.526   8.155  1.00   9.01      PROT
ATOM   2058  CB   CYS   135       5.106  32.651   7.591  1.00  10.48      PROT
ATOM   2059  SG   CYS   135       4.902  32.261   9.378  1.00  11.84      PROT
ATOM   2064  N    SER   136       2.275  33.015   6.474  1.00   9.55      PROT
ATOM   2065  CA   SER   136       0.831  32.842   6.548  1.00   9.94      PROT
ATOM   2066  C    SER   136       0.457  31.367   6.544  1.00   9.52      PROT
ATOM   2067  O    SER   136       1.240  30.531   6.111  1.00   8.84      PROT
ATOM   2068  CB   SER   136       0.153  33.563   5.383  1.00   9.92      PROT
ATOM   2069  OG   SER   136      -1.148  33.971   5.756  1.00  12.83      PROT
ATOM   2074  N    MET   137      -0.731  31.055   7.053  1.00   9.86      PROT
ATOM   2075  CA   MET   137      -1.216  29.677   7.059  1.00   9.99      PROT
ATOM   2076  C    MET   137      -2.259  29.465   5.971  1.00   9.79      PROT
ATOM   2077  O    MET   137      -2.913  30.409   5.508  1.00   9.77      PROT
ATOM   2078  CB   MET   137      -1.790  29.295   8.421  1.00   9.87      PROT
ATOM   2079  CG   MET   137      -0.760  29.233   9.549  1.00  10.04      PROT
ATOM   2080  SD   MET   137      -1.523  28.727  11.094  1.00  10.76      PROT
ATOM   2081  CE   MET   137      -2.309  30.239  11.618  1.00  11.00      PROT
ATOM   2091  N    ASP   138      -2.405  28.215   5.558  1.00   9.73      PROT
ATOM   2092  CA   ASP   138      -3.364  27.877   4.519  1.00   9.45      PROT
ATOM   2093  C    ASP   138      -4.627  27.343   5.177  1.00   9.32      PROT
ATOM   2094  O    ASP   138      -4.572  26.367   5.920  1.00   8.95      PROT
ATOM   2095  CB   ASP   138      -2.774  26.845   3.574  1.00   9.57      PROT
ATOM   2096  CG   ASP   138      -3.754  26.407   2.524  1.00   9.74      PROT
ATOM   2097  OD1  ASP   138      -4.155  27.253   1.689  1.00   9.34      PROT
ATOM   2098  OD2  ASP   138      -4.131  25.220   2.555  1.00   9.76      PROT
ATOM   2103  N    LYS   139      -5.758  27.989   4.897  1.00   9.53      PROT
ATOM   2104  CA   LYS   139      -7.031  27.680   5.560  1.00   9.57      PROT
ATOM   2105  C    LYS   139      -7.378  26.190   5.552  1.00   9.23      PROT
ATOM   2106  O    LYS   139      -7.841  25.656   6.555  1.00   9.35      PROT
ATOM   2107  CB   LYS   139      -8.176  28.470   4.930  1.00  10.02      PROT
ATOM   2108  CG   LYS   139      -8.031  29.984   4.987  1.00  10.44      PROT
ATOM   2109  CD   LYS   139      -8.828  30.640   3.855  1.00  13.87      PROT
ATOM   2110  CE   LYS   139     -10.332  30.663   4.108  1.00  14.28      PROT
ATOM   2111  NZ   LYS   139     -11.024  31.459   3.053  1.00  14.34      PROT
ATOM   2125  N    SER   140      -7.152  25.532   4.420  1.00   8.74      PROT
ATOM   2126  CA   SER   140      -7.443  24.110   4.274  1.00   8.37      PROT
ATOM   2127  C    SER   140      -6.565  23.263   5.200  1.00   7.52      PROT
ATOM   2128  O    SER   140      -7.049  22.338   5.849  1.00   7.42      PROT
ATOM   2129  CB   SER   140      -7.255  23.676   2.822  1.00   8.29      PROT
ATOM   2130  OG   SER   140      -7.896  22.441   2.575  1.00  10.38      PROT
ATOM   2135  N    GLN   141      -5.276  23.589   5.247  1.00   6.55      PROT
ATOM   2136  CA   GLN   141      -4.333  22.890   6.111  1.00   6.00      PROT
ATOM   2137  C    GLN   141      -4.607  23.122   7.589  1.00   5.09      PROT
ATOM   2138  O    GLN   141      -4.299  22.254   8.413  1.00   4.98      PROT
ATOM   2139  CB   GLN   141      -2.893  23.273   5.786  1.00   6.20      PROT
ATOM   2140  CG   GLN   141      -2.382  22.657   4.501  1.00   7.20      PROT
ATOM   2141  CD   GLN   141      -1.135  21.824   4.724  1.00   9.60      PROT
ATOM   2142  OE1  GLN   141      -0.128  22.316   5.227  1.00  10.33      PROT
ATOM   2143  NE2  GLN   141      -1.198  20.551   4.344  1.00  10.78      PROT
ATOM   2152  N    VAL   142      -5.161  24.292   7.921  1.00   4.17      PROT
ATOM   2153  CA   VAL   142      -5.501  24.617   9.311  1.00   3.52      PROT
ATOM   2154  C    VAL   142      -6.674  23.758   9.764  1.00   3.88      PROT
ATOM   2155  O    VAL   142      -6.616  23.159  10.843  1.00   3.43      PROT
ATOM   2156  CB   VAL   142      -5.835  26.131   9.541  1.00   3.49      PROT
ATOM   2157  CG1  VAL   142      -6.237  26.383  11.012  1.00   2.00      PROT
```

Figure 3 cont.

```
ATOM   2158  CG2  VAL  142   -4.644  27.017   9.212  1.00   2.63      PROT
ATOM   2168  N    HSD  143   -7.723  23.690   8.934  1.00   4.22      PROT
ATOM   2169  CA   HSD  143   -8.906  22.894   9.247  1.00   5.30      PROT
ATOM   2170  C    HSD  143   -8.529  21.439   9.481  1.00   5.28      PROT
ATOM   2171  O    HSD  143   -8.915  20.857  10.484  1.00   5.56      PROT
ATOM   2172  CB   HSD  143   -9.975  22.986   8.153  1.00   6.01      PROT
ATOM   2173  CG   HSD  143  -10.923  24.134   8.316  1.00   8.21      PROT
ATOM   2174  CD2  HSD  143  -11.933  24.138   9.255  1.00  10.34      PROT
ATOM   2175  ND1  HSD  143  -11.031  25.303   7.641  1.00   9.85      PROT
ATOM   2176  NE2  HSD  143  -12.613  25.267   9.158  1.00  10.38      PROT
ATOM   2177  CE1  HSD  143  -12.084  25.993   8.191  1.00  10.32      PROT
ATOM   2185  N    ALA  144   -7.774  20.859   8.546  1.00   5.66      PROT
ATOM   2186  CA   ALA  144   -7.294  19.486   8.675  1.00   5.46      PROT
ATOM   2187  C    ALA  144   -6.507  19.236   9.976  1.00   5.51      PROT
ATOM   2188  O    ALA  144   -6.716  18.222  10.653  1.00   5.68      PROT
ATOM   2189  CB   ALA  144   -6.456  19.103   7.460  1.00   5.37      PROT
ATOM   2195  N    ALA  145   -5.606  20.152  10.327  1.00   5.35      PROT
ATOM   2196  CA   ALA  145   -4.727  19.951  11.491  1.00   5.18      PROT
ATOM   2197  C    ALA  145   -5.471  20.069  12.827  1.00   5.04      PROT
ATOM   2198  O    ALA  145   -5.232  19.286  13.755  1.00   4.55      PROT
ATOM   2199  CB   ALA  145   -3.563  20.905  11.438  1.00   5.49      PROT
ATOM   2205  N    VAL  146   -6.372  21.042  12.905  1.00   5.08      PROT
ATOM   2206  CA   VAL  146   -7.250  21.216  14.062  1.00   5.19      PROT
ATOM   2207  C    VAL  146   -8.130  19.963  14.279  1.00   5.61      PROT
ATOM   2208  O    VAL  146   -8.196  19.438  15.394  1.00   5.70      PROT
ATOM   2209  CB   VAL  146   -8.075  22.524  13.954  1.00   4.89      PROT
ATOM   2210  CG1  VAL  146   -9.089  22.624  15.075  1.00   5.89      PROT
ATOM   2211  CG2  VAL  146   -7.140  23.742  14.011  1.00   4.56      PROT
ATOM   2221  N    GLU  147   -8.767  19.473  13.213  1.00   5.93      PROT
ATOM   2222  CA   GLU  147   -9.564  18.236  13.283  1.00   6.70      PROT
ATOM   2223  C    GLU  147   -8.709  17.058  13.780  1.00   6.58      PROT
ATOM   2224  O    GLU  147   -9.144  16.279  14.635  1.00   6.68      PROT
ATOM   2225  CB   GLU  147  -10.196  17.898  11.923  1.00   6.31      PROT
ATOM   2226  CG   GLU  147  -10.981  16.576  11.915  1.00   7.34      PROT
ATOM   2227  CD   GLU  147  -11.758  16.311  10.623  1.00   7.06      PROT
ATOM   2228  OE1  GLU  147  -12.017  17.258   9.851  1.00   8.18      PROT
ATOM   2229  OE2  GLU  147  -12.122  15.139  10.382  1.00   8.64      PROT
ATOM   2236  N    LYS  148   -7.495  16.954  13.240  1.00   6.53      PROT
ATOM   2237  CA   LYS  148   -6.522  15.935  13.638  1.00   6.46      PROT
ATOM   2238  C    LYS  148   -6.164  16.002  15.130  1.00   6.29      PROT
ATOM   2239  O    LYS  148   -6.136  14.971  15.816  1.00   5.63      PROT
ATOM   2240  CB   LYS  148   -5.282  16.029  12.740  1.00   6.86      PROT
ATOM   2241  CG   LYS  148   -3.993  15.484  13.326  1.00   7.83      PROT
ATOM   2242  CD   LYS  148   -2.928  15.360  12.246  1.00  10.37      PROT
ATOM   2243  CE   LYS  148   -1.695  14.872  12.565  1.00  15.37      PROT
ATOM   2244  NZ   LYS  148   -1.339  14.689  13.999  1.00  16.10      PROT
ATOM   2258  N    GLN  149   -5.898  17.215  15.616  1.00   5.59      PROT
ATOM   2259  CA   GLN  149   -5.627  17.470  17.035  1.00   6.00      PROT
ATOM   2260  C    GLN  149   -6.813  17.139  17.943  1.00   6.22      PROT
ATOM   2261  O    GLN  149   -6.622  16.660  19.065  1.00   7.19      PROT
ATOM   2262  CB   GLN  149   -5.205  18.929  17.257  1.00   5.56      PROT
ATOM   2263  CG   GLN  149   -4.564  19.221  18.652  1.00   4.72      PROT
ATOM   2264  CD   GLN  149   -3.099  18.813  18.745  1.00   4.43      PROT
ATOM   2265  OE1  GLN  149   -2.509  18.331  17.773  1.00   4.32      PROT
ATOM   2266  NE2  GLN  149   -2.498  19.015  19.922  1.00   4.62      PROT
ATOM   2275  N    ALA  150   -8.024  17.443  17.480  1.00   6.27      PROT
ATOM   2276  CA   ALA  150   -9.243  17.157  18.245  1.00   6.03      PROT
ATOM   2277  C    ALA  150   -9.560  15.668  18.228  1.00   6.29      PROT
ATOM   2278  O    ALA  150  -10.169  15.153  19.164  1.00   6.24      PROT
ATOM   2279  CB   ALA  150  -10.421  17.954  17.694  1.00   6.22      PROT
ATOM   2285  N    GLY  151   -9.143  14.990  17.157  1.00   5.81      PROT
ATOM   2286  CA   GLY  151   -9.402  13.559  16.975  1.00   6.64      PROT
ATOM   2287  C    GLY  151  -10.811  13.275  16.492  1.00   6.92      PROT
ATOM   2288  O    GLY  151  -11.247  12.126  16.475  1.00   6.89      PROT
ATOM   2292  N    THR  152  -11.521  14.332  16.103  1.00   7.29      PROT
```

Figure 3 cont.

```
ATOM   2293  CA   THR   152    -12.926  14.251  15.709  1.00   8.38      PROT
ATOM   2294  C    THR   152    -13.325  15.562  15.010  1.00   8.07      PROT
ATOM   2295  O    THR   152    -12.725  16.603  15.280  1.00   8.24      PROT
ATOM   2296  CB   THR   152    -13.849  13.913  16.943  1.00   8.33      PROT
ATOM   2297  OG1  THR   152    -15.230  14.076  16.595  1.00   9.87      PROT
ATOM   2298  CG2  THR   152    -13.533  14.799  18.126  1.00   9.36      PROT
ATOM   2305  N    PRO   153    -14.313  15.519  14.090  1.00   8.15      PROT
ATOM   2306  CA   PRO   153    -14.776  16.768  13.475  1.00   8.02      PROT
ATOM   2307  C    PRO   153    -15.041  17.868  14.503  1.00   7.92      PROT
ATOM   2308  O    PRO   153    -15.646  17.615  15.544  1.00   7.36      PROT
ATOM   2309  CB   PRO   153    -16.080  16.346  12.789  1.00   7.99      PROT
ATOM   2310  CG   PRO   153    -15.826  14.939  12.403  1.00   8.33      PROT
ATOM   2311  CD   PRO   153    -15.040  14.353  13.546  1.00   7.92      PROT
ATOM   2319  N    ILE   154    -14.577  19.081  14.209  1.00   8.44      PROT
ATOM   2320  CA   ILE   154    -14.710  20.206  15.140  1.00   8.44      PROT
ATOM   2321  C    ILE   154    -16.167  20.581  15.384  1.00   8.05      PROT
ATOM   2322  O    ILE   154    -16.520  21.006  16.474  1.00   8.68      PROT
ATOM   2323  CB   ILE   154    -13.871  21.431  14.690  1.00   8.93      PROT
ATOM   2324  CG1  ILE   154    -12.375  21.109  14.799  1.00   9.95      PROT
ATOM   2325  CG2  ILE   154    -14.182  22.682  15.538  1.00   9.37      PROT
ATOM   2326  CD   ILE   154    -11.865  20.914  16.235  1.00  11.85      PROT
ATOM   2338  N    GLU   155    -17.016  20.378  14.383  1.00   7.69      PROT
ATOM   2339  CA   GLU   155    -18.447  20.647  14.512  1.00   7.38      PROT
ATOM   2340  C    GLU   155    -19.136  19.743  15.546  1.00   6.57      PROT
ATOM   2341  O    GLU   155    -20.213  20.071  16.050  1.00   6.19      PROT
ATOM   2342  CB   GLU   155    -19.143  20.595  13.144  1.00   7.87      PROT
ATOM   2343  CG   GLU   155    -18.531  19.606  12.143  1.00  10.89      PROT
ATOM   2344  CD   GLU   155    -17.323  20.179  11.397  1.00  13.73      PROT
ATOM   2345  OE1  GLU   155    -16.269  19.502  11.353  1.00  13.73      PROT
ATOM   2346  OE2  GLU   155    -17.425  21.306  10.858  1.00  16.15      PROT
ATOM   2353  N    THR   156    -18.486  18.631  15.876  1.00   5.93      PROT
ATOM   2354  CA   THR   156    -18.962  17.703  16.907  1.00   5.89      PROT
ATOM   2355  C    THR   156    -18.312  17.964  18.295  1.00   5.13      PROT
ATOM   2356  O    THR   156    -18.543  17.220  19.247  1.00   5.25      PROT
ATOM   2357  CB   THR   156    -18.718  16.225  16.475  1.00   5.87      PROT
ATOM   2358  OG1  THR   156    -18.913  16.074  15.056  1.00   7.17      PROT
ATOM   2359  CG2  THR   156    -19.678  15.278  17.194  1.00   7.44      PROT
ATOM   2366  N    LEU   157    -17.534  19.038  18.415  1.00   4.31      PROT
ATOM   2367  CA   LEU   157    -16.666  19.253  19.600  1.00   3.66      PROT
ATOM   2368  C    LEU   157    -17.397  19.304  20.947  1.00   3.43      PROT
ATOM   2369  O    LEU   157    -16.905  18.753  21.937  1.00   3.45      PROT
ATOM   2370  CB   LEU   157    -15.821  20.530  19.438  1.00   3.36      PROT
ATOM   2371  CG   LEU   157    -14.329  20.603  19.803  1.00   3.43      PROT
ATOM   2372  CD1  LEU   157    -13.963  21.977  20.359  1.00   2.00      PROT
ATOM   2373  CD2  LEU   157    -13.861  19.490  20.727  1.00   3.10      PROT
ATOM   2385  N    ASN   158    -18.542  19.980  20.982  1.00   3.12      PROT
ATOM   2386  CA   ASN   158    -19.342  20.151  22.202  1.00   3.97      PROT
ATOM   2387  C    ASN   158    -19.700  18.829  22.902  1.00   4.30      PROT
ATOM   2388  O    ASN   158    -19.862  18.788  24.118  1.00   4.18      PROT
ATOM   2389  CB   ASN   158    -20.639  20.908  21.895  1.00   3.81      PROT
ATOM   2390  CG   ASN   158    -20.408  22.370  21.535  1.00   3.63      PROT
ATOM   2391  OD1  ASN   158    -19.279  22.799  21.332  1.00   3.58      PROT
ATOM   2392  ND2  ASN   158    -21.494  23.136  21.443  1.00   4.72      PROT
ATOM   2399  N    GLN   159    -19.822  17.768  22.114  1.00   5.33      PROT
ATOM   2400  CA   GLN   159    -20.170  16.433  22.602  1.00   6.24      PROT
ATOM   2401  C    GLN   159    -19.059  15.755  23.419  1.00   6.65      PROT
ATOM   2402  O    GLN   159    -19.314  14.800  24.158  1.00   6.81      PROT
ATOM   2403  CB   GLN   159    -20.591  15.559  21.416  1.00   6.56      PROT
ATOM   2404  CG   GLN   159    -22.096  15.515  21.139  1.00   8.56      PROT
ATOM   2405  CD   GLN   159    -22.746  16.876  20.937  1.00  11.86      PROT
ATOM   2406  OE1  GLN   159    -22.254  17.717  20.183  1.00  13.25      PROT
ATOM   2407  NE2  GLN   159    -23.880  17.090  21.602  1.00  13.29      PROT
ATOM   2416  N    ARG   160    -17.830  16.242  23.273  1.00   7.14      PROT
ATOM   2417  CA   ARG   160    -16.711  15.818  24.111  1.00   8.01      PROT
ATOM   2418  C    ARG   160    -16.764  16.465  25.502  1.00   7.68      PROT
```

Figure 3 cont.

```
ATOM   2419  O    ARG   160     -16.123  15.979  26.441  1.00   7.37      PROT
ATOM   2420  CB   ARG   160     -15.373  16.181  23.453  1.00   8.27      PROT
ATOM   2421  CG   ARG   160     -15.246  15.827  21.965  1.00  11.38      PROT
ATOM   2422  CD   ARG   160     -14.541  14.504  21.769  1.00  14.83      PROT
ATOM   2423  NE   ARG   160     -15.476  13.385  21.709  1.00  17.77      PROT
ATOM   2424  CZ   ARG   160     -15.148  12.123  21.967  1.00  19.18      PROT
ATOM   2425  NH1  ARG   160     -13.904  11.808  22.316  1.00  20.08      PROT
ATOM   2426  NH2  ARG   160     -16.069  11.172  21.881  1.00  19.75      PROT
ATOM   2440  N    TYR   161     -17.532  17.551  25.631  1.00   7.10      PROT
ATOM   2441  CA   TYR   161     -17.459  18.408  26.825  1.00   6.58      PROT
ATOM   2442  C    TYR   161     -18.798  18.724  27.467  1.00   6.14      PROT
ATOM   2443  O    TYR   161     -18.976  19.788  28.051  1.00   5.81      PROT
ATOM   2444  CB   TYR   161     -16.721  19.705  26.490  1.00   6.67      PROT
ATOM   2445  CG   TYR   161     -15.309  19.448  26.072  1.00   6.84      PROT
ATOM   2446  CD1  TYR   161     -14.338  19.091  27.014  1.00   5.28      PROT
ATOM   2447  CD2  TYR   161     -14.943  19.512  24.727  1.00   5.67      PROT
ATOM   2448  CE1  TYR   161     -13.041  18.827  26.625  1.00   6.48      PROT
ATOM   2449  CE2  TYR   161     -13.652  19.255  24.333  1.00   7.24      PROT
ATOM   2450  CZ   TYR   161     -12.701  18.917  25.290  1.00   7.32      PROT
ATOM   2451  OH   TYR   161     -11.419  18.656  24.897  1.00   7.83      PROT
ATOM   2460  N    GLN   162     -19.722  17.773  27.387  1.00   5.85      PROT
ATOM   2461  CA   GLN   162     -21.103  17.980  27.825  1.00   5.64      PROT
ATOM   2462  C    GLN   162     -21.255  18.398  29.292  1.00   5.22      PROT
ATOM   2463  O    GLN   162     -21.957  19.365  29.590  1.00   4.79      PROT
ATOM   2464  CB   GLN   162     -21.957  16.746  27.494  1.00   6.07      PROT
ATOM   2465  CG   GLN   162     -22.276  16.628  26.002  1.00   7.29      PROT
ATOM   2466  CD   GLN   162     -23.093  17.804  25.489  1.00   9.89      PROT
ATOM   2467  OE1  GLN   162     -22.590  18.657  24.754  1.00  12.00      PROT
ATOM   2468  NE2  GLN   162     -24.355  17.868  25.897  1.00  10.47      PROT
ATOM   2477  N    ALA   163     -20.592  17.685  30.198  1.00   4.95      PROT
ATOM   2478  CA   ALA   163     -20.605  18.042  31.625  1.00   5.07      PROT
ATOM   2479  C    ALA   163     -19.969  19.422  31.924  1.00   4.84      PROT
ATOM   2480  O    ALA   163     -20.490  20.188  32.736  1.00   5.08      PROT
ATOM   2481  CB   ALA   163     -19.929  16.969  32.438  1.00   5.22      PROT
ATOM   2487  N    SER   164     -18.838  19.713  31.287  1.00   4.33      PROT
ATOM   2488  CA   SER   164     -18.154  21.010  31.434  1.00   3.93      PROT
ATOM   2489  C    SER   164     -18.985  22.178  30.925  1.00   3.60      PROT
ATOM   2490  O    SER   164     -18.942  23.293  31.471  1.00   3.72      PROT
ATOM   2491  CB   SER   164     -16.821  20.989  30.694  1.00   3.77      PROT
ATOM   2492  OG   SER   164     -15.851  20.224  31.389  1.00   5.27      PROT
ATOM   2497  N    LEU   165     -19.716  21.933  29.849  1.00   3.10      PROT
ATOM   2498  CA   LEU   165     -20.547  22.971  29.264  1.00   2.60      PROT
ATOM   2499  C    LEU   165     -21.775  23.160  30.129  1.00   2.63      PROT
ATOM   2500  O    LEU   165     -22.204  24.290  30.356  1.00   2.36      PROT
ATOM   2501  CB   LEU   165     -20.925  22.620  27.829  1.00   2.45      PROT
ATOM   2502  CG   LEU   165     -19.806  22.767  26.795  1.00   2.00      PROT
ATOM   2503  CD1  LEU   165     -20.337  22.399  25.426  1.00   2.00      PROT
ATOM   2504  CD2  LEU   165     -19.223  24.196  26.773  1.00   2.00      PROT
ATOM   2516  N    ALA   166     -22.312  22.046  30.630  1.00   2.33      PROT
ATOM   2517  CA   ALA   166     -23.439  22.076  31.557  1.00   2.66      PROT
ATOM   2518  C    ALA   166     -23.106  22.901  32.796  1.00   2.61      PROT
ATOM   2519  O    ALA   166     -23.896  23.766  33.191  1.00   2.92      PROT
ATOM   2520  CB   ALA   166     -23.869  20.664  31.951  1.00   2.37      PROT
ATOM   2526  N    LEU   167     -21.939  22.638  33.391  1.00   2.61      PROT
ATOM   2527  CA   LEU   167     -21.466  23.387  34.554  1.00   2.48      PROT
ATOM   2528  C    LEU   167     -21.286  24.885  34.247  1.00   2.24      PROT
ATOM   2529  O    LEU   167     -21.697  25.728  35.037  1.00   2.00      PROT
ATOM   2530  CB   LEU   167     -20.176  22.777  35.140  1.00   2.38      PROT
ATOM   2531  CG   LEU   167     -19.553  23.473  36.358  1.00   2.00      PROT
ATOM   2532  CD1  LEU   167     -20.461  23.405  37.608  1.00   2.51      PROT
ATOM   2533  CD2  LEU   167     -18.171  22.919  36.668  1.00   2.62      PROT
ATOM   2545  N    MET   168     -20.682  25.211  33.107  1.00   3.01      PROT
ATOM   2546  CA   MET   168     -20.564  26.619  32.676  1.00   3.63      PROT
ATOM   2547  C    MET   168     -21.944  27.282  32.546  1.00   3.83      PROT
ATOM   2548  O    MET   168     -22.129  28.438  32.944  1.00   3.71      PROT
```

Figure 3 cont.

```
ATOM   2549  CB   MET   168     -19.749  26.745  31.373  1.00   3.75      PROT
ATOM   2550  CG   MET   168     -19.644  28.174  30.811  1.00   4.17      PROT
ATOM   2551  SD   MET   168     -18.816  29.329  31.939  1.00   3.11      PROT
ATOM   2552  CE   MET   168     -17.096  28.868  31.742  1.00   4.61      PROT
ATOM   2562  N    SER   169     -22.910  26.543  32.011  1.00   4.54      PROT
ATOM   2563  CA   SER   169     -24.292  27.042  31.904  1.00   5.24      PROT
ATOM   2564  C    SER   169     -24.938  27.396  33.262  1.00   5.82      PROT
ATOM   2565  O    SER   169     -25.612  28.423  33.389  1.00   6.44      PROT
ATOM   2566  CB   SER   169     -25.168  26.060  31.133  1.00   5.03      PROT
ATOM   2567  OG   SER   169     -26.468  26.587  30.959  1.00   5.10      PROT
ATOM   2572  N    SER   170     -24.718  26.573  34.281  1.00   5.91      PROT
ATOM   2573  CA   SER   170     -25.290  26.880  35.593  1.00   6.38      PROT
ATOM   2574  C    SER   170     -24.539  28.012  36.315  1.00   5.95      PROT
ATOM   2575  O    SER   170     -25.172  28.857  36.944  1.00   5.72      PROT
ATOM   2576  CB   SER   170     -25.458  25.625  36.466  1.00   6.14      PROT
ATOM   2577  OG   SER   170     -24.233  24.956  36.660  1.00   8.41      PROT
ATOM   2582  N    VAL   171     -23.210  28.039  36.191  1.00   6.01      PROT
ATOM   2583  CA   VAL   171     -22.382  29.133  36.725  1.00   5.64      PROT
ATOM   2584  C    VAL   171     -22.877  30.487  36.186  1.00   5.62      PROT
ATOM   2585  O    VAL   171     -23.000  31.458  36.936  1.00   5.35      PROT
ATOM   2586  CB   VAL   171     -20.865  28.922  36.381  1.00   5.79      PROT
ATOM   2587  CG1  VAL   171     -20.043  30.193  36.611  1.00   5.78      PROT
ATOM   2588  CG2  VAL   171     -20.286  27.763  37.176  1.00   5.14      PROT
ATOM   2598  N    LEU   172     -23.180  30.522  34.887  1.00   5.18      PROT
ATOM   2599  CA   LEU   172     -23.710  31.704  34.212  1.00   5.27      PROT
ATOM   2600  C    LEU   172     -25.189  31.987  34.449  1.00   5.48      PROT
ATOM   2601  O    LEU   172     -25.627  33.110  34.219  1.00   5.62      PROT
ATOM   2602  CB   LEU   172     -23.521  31.582  32.693  1.00   5.01      PROT
ATOM   2603  CG   LEU   172     -22.105  31.635  32.103  1.00   5.33      PROT
ATOM   2604  CD1  LEU   172     -22.159  31.213  30.637  1.00   5.43      PROT
ATOM   2605  CD2  LEU   172     -21.481  33.006  32.269  1.00   5.50      PROT
ATOM   2617  N    ASP   173     -25.951  30.973  34.866  1.00   5.59      PROT
ATOM   2618  CA   ASP   173     -27.433  30.977  34.778  1.00   5.99      PROT
ATOM   2619  C    ASP   173     -27.895  31.308  33.352  1.00   5.68      PROT
ATOM   2620  O    ASP   173     -28.846  32.065  33.140  1.00   5.09      PROT
ATOM   2621  CB   ASP   173     -28.071  31.919  35.804  1.00   6.51      PROT
ATOM   2622  CG   ASP   173     -29.256  31.296  36.522  1.00   8.87      PROT
ATOM   2623  OD1  ASP   173     -30.077  30.601  35.878  1.00   9.09      PROT
ATOM   2624  OD2  ASP   173     -29.361  31.496  37.753  1.00  11.68      PROT
ATOM   2629  N    PHE   174     -27.201  30.721  32.380  1.00   5.67      PROT
ATOM   2630  CA   PHE   174     -27.473  30.922  30.952  1.00   6.15      PROT
ATOM   2631  C    PHE   174     -28.950  30.796  30.516  1.00   6.35      PROT
ATOM   2632  O    PHE   174     -29.393  31.549  29.638  1.00   6.68      PROT
ATOM   2633  CB   PHE   174     -26.561  30.002  30.126  1.00   5.77      PROT
ATOM   2634  CG   PHE   174     -26.868  29.994  28.656  1.00   5.76      PROT
ATOM   2635  CD1  PHE   174     -26.400  31.006  27.826  1.00   5.71      PROT
ATOM   2636  CD2  PHE   174     -27.621  28.963  28.099  1.00   5.78      PROT
ATOM   2637  CE1  PHE   174     -26.684  30.996  26.463  1.00   5.35      PROT
ATOM   2638  CE2  PHE   174     -27.913  28.949  26.733  1.00   6.26      PROT
ATOM   2639  CZ   PHE   174     -27.442  29.964  25.918  1.00   5.74      PROT
ATOM   2649  N    PRO   175     -29.712  29.846  31.104  1.00   6.82      PROT
ATOM   2650  CA   PRO   175     -31.141  29.704  30.769  1.00   7.25      PROT
ATOM   2651  C    PRO   175     -32.011  30.944  31.008  1.00   7.70      PROT
ATOM   2652  O    PRO   175     -33.022  31.122  30.323  1.00   7.59      PROT
ATOM   2653  CB   PRO   175     -31.592  28.584  31.708  1.00   6.97      PROT
ATOM   2654  CG   PRO   175     -30.378  27.788  31.922  1.00   6.58      PROT
ATOM   2655  CD   PRO   175     -29.312  28.812  32.078  1.00   6.49      PROT
ATOM   2663  N    LYS   176     -31.620  31.778  31.967  1.00   8.14      PROT
ATOM   2664  CA   LYS   176     -32.378  32.975  32.328  1.00   8.62      PROT
ATOM   2665  C    LYS   176     -31.738  34.247  31.768  1.00   8.84      PROT
ATOM   2666  O    LYS   176     -32.118  35.359  32.137  1.00   8.74      PROT
ATOM   2667  CB   LYS   176     -32.496  33.065  33.853  1.00   9.04      PROT
ATOM   2668  CG   LYS   176     -33.399  31.986  34.468  1.00   9.70      PROT
ATOM   2669  CD   LYS   176     -33.030  31.722  35.919  1.00  10.80      PROT
ATOM   2670  CE   LYS   176     -33.976  30.742  36.585  1.00  12.05      PROT
```

Figure 3 cont.

```
ATOM   2671 NZ   LYS   176    -35.322  31.314  36.898  1.00 12.42      PROT
ATOM   2685 N    SER   177    -30.772  34.067  30.874  1.00  8.39      PROT
ATOM   2686 CA   SER   177    -30.008  35.171  30.303  1.00  9.24      PROT
ATOM   2687 C    SER   177    -30.753  35.810  29.133  1.00  9.25      PROT
ATOM   2688 O    SER   177    -31.610  35.163  28.533  1.00  9.85      PROT
ATOM   2689 CB   SER   177    -28.651  34.660  29.819  1.00  8.59      PROT
ATOM   2690 OG   SER   177    -28.811  33.794  28.704  1.00  9.38      PROT
ATOM   2695 N    PRO   178    -30.452  37.092  28.831  1.00  9.58      PROT
ATOM   2696 CA   PRO   178    -30.905  37.764  27.610  1.00  9.76      PROT
ATOM   2697 C    PRO   178    -30.762  36.908  26.342  1.00 10.11      PROT
ATOM   2698 O    PRO   178    -31.660  36.926  25.487  1.00  9.94      PROT
ATOM   2699 CB   PRO   178    -29.999  38.991  27.544  1.00  9.85      PROT
ATOM   2700 CG   PRO   178    -29.756  39.327  28.978  1.00  9.78      PROT
ATOM   2701 CD   PRO   178    -29.684  38.009  29.698  1.00  9.59      PROT
ATOM   2709 N    TYR   179    -29.662  36.158  26.232  1.00 10.33      PROT
ATOM   2710 CA   TYR   179    -29.466  35.195  25.138  1.00 10.76      PROT
ATOM   2711 C    TYR   179    -30.584  34.154  25.110  1.00 10.92      PROT
ATOM   2712 O    TYR   179    -31.061  33.706  26.156  1.00 10.56      PROT
ATOM   2713 CB   TYR   179    -28.106  34.495  25.259  1.00 11.42      PROT
ATOM   2714 CG   TYR   179    -27.595  33.893  23.966  1.00 11.90      PROT
ATOM   2715 CD1  TYR   179    -26.733  34.610  23.136  1.00 12.65      PROT
ATOM   2716 CD2  TYR   179    -27.975  32.605  23.568  1.00 12.33      PROT
ATOM   2717 CE1  TYR   179    -26.266  34.065  21.948  1.00 13.68      PROT
ATOM   2718 CE2  TYR   179    -27.514  32.052  22.387  1.00 12.05      PROT
ATOM   2719 CZ   TYR   179    -26.666  32.786  21.580  1.00 13.14      PROT
ATOM   2720 OH   TYR   179    -26.205  32.236  20.410  1.00 13.39      PROT
ATOM   2729 N    CYS   180    -31.106  33.670  26.393  1.00  0.00      PROT
ATOM   2730 CA   CYS   180    -32.625  32.710  26.247  1.00  0.00      PROT
ATOM   2731 C    CYS   180    -33.851  33.571  25.960  1.00  0.00      PROT
ATOM   2732 O    CYS   180    -34.664  33.246  25.099  1.00  0.00      PROT
ATOM   2733 CB   CYS   180    -32.981  31.550  27.199  1.00  0.00      PROT
ATOM   2734 SG   CYS   180    -34.226  30.414  26.438  1.00  0.00      PROT
ATOM   2739 N    GLN   181    -34.012  34.723  26.636  1.00  0.00      PROT
ATOM   2740 CA   GLN   181    -35.190  35.564  26.459  1.00  0.00      PROT
ATOM   2741 C    GLN   181    -35.349  36.159  25.053  1.00  0.00      PROT
ATOM   2742 O    GLN   181    -36.462  36.400  24.594  1.00  0.00      PROT
ATOM   2743 CB   GLN   181    -35.244  36.676  27.541  1.00  0.00      PROT
ATOM   2744 CG   GLN   181    -35.447  36.125  28.977  1.00  0.00      PROT
ATOM   2745 CD   GLN   181    -36.842  35.513  29.159  1.00  0.00      PROT
ATOM   2746 OE1  GLN   181    -37.855  36.033  28.699  1.00  0.00      PROT
ATOM   2747 NE2  GLN   181    -36.918  34.371  29.881  1.00  0.00      PROT
ATOM   2756 N    GLN   182    -34.250  36.376  24.309  1.00  0.00      PROT
ATOM   2757 CA   GLN   182    -34.302  36.781  22.911  1.00  0.00      PROT
ATOM   2758 C    GLN   182    -34.071  35.622  21.937  1.00  0.00      PROT
ATOM   2759 O    GLN   182    -33.681  35.826  20.790  1.00  0.00      PROT
ATOM   2760 CB   GLN   182    -33.240  37.879  22.632  1.00  0.00      PROT
ATOM   2761 CG   GLN   182    -33.339  39.118  23.557  1.00  0.00      PROT
ATOM   2762 CD   GLN   182    -34.727  39.756  23.493  1.00  0.00      PROT
ATOM   2763 OE1  GLN   182    -35.166  40.266  22.465  1.00  0.00      PROT
ATOM   2764 NE2  GLN   182    -35.460  39.731  24.630  1.00  0.00      PROT
ATOM   2773 N    HSD   183    -34.301  34.360  22.345  1.00  2.18      PROT
ATOM   2774 CA   HSD   183    -33.937  33.212  21.530  1.00  2.18      PROT
ATOM   2775 C    HSD   183    -35.131  32.628  20.785  1.00  2.18      PROT
ATOM   2776 O    HSD   183    -35.956  31.918  21.355  1.00  2.18      PROT
ATOM   2777 CB   HSD   183    -33.272  32.129  22.414  1.00  2.18      PROT
ATOM   2778 CG   HSD   183    -32.290  31.235  21.708  1.00  2.18      PROT
ATOM   2779 ND1  HSD   183    -32.503  30.632  20.489  1.00  2.18      PROT
ATOM   2780 CD2  HSD   183    -31.045  30.848  22.096  1.00  2.18      PROT
ATOM   2781 CE1  HSD   183    -31.387  29.922  20.198  1.00  2.18      PROT
ATOM   2782 NE2  HSD   183    -30.480  30.020  21.145  1.00  2.18      PROT
ATOM   2790 N    ASN   184    -35.261  32.886  19.463  1.00  7.42      PROT
ATOM   2791 CA   ASN   184    -36.389  32.409  18.661  1.00  7.42      PROT
ATOM   2792 C    ASN   184    -36.373  30.908  18.340  1.00  7.42      PROT
ATOM   2793 O    ASN   184    -36.242  30.503  17.186  1.00  7.42      PROT
ATOM   2794 CB   ASN   184    -36.467  33.143  17.291  1.00  7.42      PROT
```

Figure 3 cont.

```
ATOM   2795  CG   ASN   184     -36.424  34.656  17.432  1.00  7.42      PROT
ATOM   2796  OD1  ASN   184     -35.478  35.300  16.983  1.00  7.42      PROT
ATOM   2797  ND2  ASN   184     -37.465  35.254  18.055  1.00  7.42      PROT
ATOM   2804  N    ILE   185     -36.528  30.035  19.350  1.00  9.23      PROT
ATOM   2805  CA   ILE   185     -36.596  28.597  19.160  1.00  9.23      PROT
ATOM   2806  C    ILE   185     -37.859  28.016  19.761  1.00  9.23      PROT
ATOM   2807  O    ILE   185     -38.264  28.323  20.875  1.00  9.23      PROT
ATOM   2808  CB   ILE   185     -35.390  27.832  19.713  1.00  9.23      PROT
ATOM   2809  CG1  ILE   185     -35.058  28.206  21.181  1.00  9.23      PROT
ATOM   2810  CG2  ILE   185     -34.216  28.060  18.735  1.00  9.23      PROT
ATOM   2811  CD   ILE   185     -33.898  27.391  21.763  1.00  9.23      PROT
ATOM   2823  N    GLY   186     -38.499  27.080  19.027  1.00  2.38      PROT
ATOM   2824  CA   GLY   186     -39.502  26.184  19.593  1.00  2.38      PROT
ATOM   2825  C    GLY   186     -38.841  24.905  20.038  1.00  2.38      PROT
ATOM   2826  O    GLY   186     -39.069  23.840  19.462  1.00  2.38      PROT
ATOM   2830  N    LYS   187     -37.958  25.004  21.043  1.00  0.00      PROT
ATOM   2831  CA   LYS   187     -37.185  23.937  21.652  1.00  0.00      PROT
ATOM   2832  C    LYS   187     -36.869  24.470  23.032  1.00  0.00      PROT
ATOM   2833  O    LYS   187     -37.276  25.581  23.360  1.00  0.00      PROT
ATOM   2834  CB   LYS   187     -35.833  23.619  20.932  1.00  0.00      PROT
ATOM   2835  CG   LYS   187     -35.926  23.091  19.487  1.00  0.00      PROT
ATOM   2836  CD   LYS   187     -36.552  21.686  19.415  1.00  0.00      PROT
ATOM   2837  CE   LYS   187     -37.039  21.248  18.031  1.00  0.00      PROT
ATOM   2838  NZ   LYS   187     -38.067  22.193  17.540  1.00  0.00      PROT
ATOM   2852  N    LEU   188     -36.128  23.720  23.869  1.00  0.00      PROT
ATOM   2853  CA   LEU   188     -35.630  24.256  25.120  1.00  0.00      PROT
ATOM   2854  C    LEU   188     -34.268  24.883  24.865  1.00  0.00      PROT
ATOM   2855  O    LEU   188     -33.491  24.376  24.064  1.00  0.00      PROT
ATOM   2856  CB   LEU   188     -35.478  23.145  26.195  1.00  0.00      PROT
ATOM   2857  CG   LEU   188     -36.794  22.443  26.593  1.00  0.00      PROT
ATOM   2858  CD1  LEU   188     -36.497  21.236  27.492  1.00  0.00      PROT
ATOM   2859  CD2  LEU   188     -37.768  23.393  27.308  1.00  0.00      PROT
ATOM   2871  N    CYS   189     -33.926  26.000  25.539  1.00  0.00      PROT
ATOM   2872  CA   CYS   189     -32.590  26.577  25.446  1.00  0.00      PROT
ATOM   2873  C    CYS   189     -31.562  25.706  26.148  1.00  0.00      PROT
ATOM   2874  O    CYS   189     -31.818  25.168  27.214  1.00  0.00      PROT
ATOM   2875  CB   CYS   189     -32.487  27.996  26.074  1.00  0.00      PROT
ATOM   2876  SG   CYS   189     -33.232  29.308  25.066  1.00  0.00      PROT
ATOM   2881  N    ASP   190     -30.386  25.569  25.528  1.00 12.56      PROT
ATOM   2882  CA   ASP   190     -29.248  24.757  25.939  1.00 12.21      PROT
ATOM   2883  C    ASP   190     -27.959  25.403  25.428  1.00 11.72      PROT
ATOM   2884  O    ASP   190     -27.870  25.765  24.253  1.00 11.77      PROT
ATOM   2885  CB   ASP   190     -29.403  23.330  25.393  1.00 12.34      PROT
ATOM   2886  CG   ASP   190     -28.337  22.380  25.912  1.00 12.95      PROT
ATOM   2887  OD1  ASP   190     -27.404  22.063  25.146  1.00 13.80      PROT
ATOM   2888  OD2  ASP   190     -28.431  21.955  27.081  1.00 11.81      PROT
ATOM   2893  N    PHE   191     -26.982  25.555  26.322  1.00 11.05      PROT
ATOM   2894  CA   PHE   191     -25.706  26.215  26.015  1.00 10.27      PROT
ATOM   2895  C    PHE   191     -24.959  25.548  24.861  1.00  9.72      PROT
ATOM   2896  O    PHE   191     -24.542  26.228  23.924  1.00  9.18      PROT
ATOM   2897  CB   PHE   191     -24.829  26.289  27.274  1.00 10.13      PROT
ATOM   2898  CG   PHE   191     -23.640  27.213  27.157  1.00 10.27      PROT
ATOM   2899  CD1  PHE   191     -23.804  28.597  27.154  1.00 10.30      PROT
ATOM   2900  CD2  PHE   191     -22.348  26.696  27.096  1.00 10.43      PROT
ATOM   2901  CE1  PHE   191     -22.702  29.449  27.075  1.00 10.91      PROT
ATOM   2902  CE2  PHE   191     -21.235  27.540  27.014  1.00 11.48      PROT
ATOM   2903  CZ   PHE   191     -21.412  28.921  26.998  1.00  9.94      PROT
ATOM   2913  N    SER   192     -24.815  24.223  24.930  1.00  9.46      PROT
ATOM   2914  CA   SER   192     -24.131  23.436  23.893  1.00  9.21      PROT
ATOM   2915  C    SER   192     -24.880  23.444  22.563  1.00  9.27      PROT
ATOM   2916  O    SER   192     -24.275  23.529  21.495  1.00  9.24      PROT
ATOM   2917  CB   SER   192     -23.934  21.989  24.354  1.00  9.47      PROT
ATOM   2918  OG   SER   192     -23.378  21.188  23.321  1.00  8.08      PROT
ATOM   2923  N    GLN   193     -26.202  23.360  22.653  1.00  9.49      PROT
ATOM   2924  CA   GLN   193     -27.092  23.303  21.502  1.00  9.52      PROT
```

Figure 3 cont.

```
ATOM   2925  C    GLN  193   -27.195  24.654  20.785  1.00   9.04      PROT
ATOM   2926  O    GLN  193   -27.181  24.709  19.558  1.00   9.14      PROT
ATOM   2927  CB   GLN  193   -28.457  22.825  21.982  1.00   9.57      PROT
ATOM   2928  CG   GLN  193   -29.647  23.182  21.128  1.00  10.55      PROT
ATOM   2929  CD   GLN  193   -30.935  22.613  21.694  1.00  11.20      PROT
ATOM   2930  OE1  GLN  193   -32.005  23.209  21.550  1.00  14.63      PROT
ATOM   2931  NE2  GLN  193   -30.840  21.452  22.344  1.00  12.34      PROT
ATOM   2940  N    ALA  194   -27.301  25.735  21.559  1.00   8.50      PROT
ATOM   2941  CA   ALA  194   -27.391  27.074  20.996  1.00   7.80      PROT
ATOM   2942  C    ALA  194   -26.127  27.433  20.227  1.00   7.21      PROT
ATOM   2943  O    ALA  194   -26.197  28.146  19.226  1.00   6.73      PROT
ATOM   2944  CB   ALA  194   -27.675  28.108  22.079  1.00   7.72      PROT
ATOM   2950  N    MET  195   -24.979  26.924  20.684  1.00   6.87      PROT
ATOM   2951  CA   MET  195   -23.696  27.304  20.096  1.00   6.66      PROT
ATOM   2952  C    MET  195   -22.779  26.143  19.711  1.00   5.61      PROT
ATOM   2953  O    MET  195   -21.802  25.870  20.409  1.00   5.29      PROT
ATOM   2954  CB   MET  195   -22.941  28.262  21.023  1.00   6.66      PROT
ATOM   2955  CG   MET  195   -23.713  29.499  21.397  1.00   7.00      PROT
ATOM   2956  SD   MET  195   -22.762  30.422  22.586  1.00   8.48      PROT
ATOM   2957  CE   MET  195   -23.955  30.565  23.909  1.00   9.43      PROT
ATOM   2967  N    PRO  196   -23.057  25.497  18.570  1.00   5.22      PROT
ATOM   2968  CA   PRO  196   -22.198  24.431  18.075  1.00   5.06      PROT
ATOM   2969  C    PRO  196   -20.785  24.943  17.807  1.00   4.80      PROT
ATOM   2970  O    PRO  196   -20.610  26.107  17.436  1.00   4.49      PROT
ATOM   2971  CB   PRO  196   -22.867  24.036  16.755  1.00   5.23      PROT
ATOM   2972  CG   PRO  196   -23.679  25.220  16.367  1.00   4.79      PROT
ATOM   2973  CD   PRO  196   -24.184  25.751  17.651  1.00   4.86      PROT
ATOM   2981  N    SER  197   -19.791  24.084  18.008  1.00   4.86      PROT
ATOM   2982  CA   SER  197   -18.403  24.426  17.709  1.00   4.96      PROT
ATOM   2983  C    SER  197   -18.147  24.561  16.195  1.00   5.23      PROT
ATOM   2984  O    SER  197   -18.730  23.836  15.384  1.00   5.02      PROT
ATOM   2985  CB   SER  197   -17.459  23.402  18.334  1.00   4.94      PROT
ATOM   2986  OG   SER  197   -17.338  23.580  19.736  1.00   4.42      PROT
ATOM   2991  N    ARG  198   -17.277  25.497  15.822  1.00   5.56      PROT
ATOM   2992  CA   ARG  198   -16.926  25.721  14.419  1.00   6.03      PROT
ATOM   2993  C    ARG  198   -15.565  26.417  14.323  1.00   6.32      PROT
ATOM   2994  O    ARG  198   -15.270  27.320  15.108  1.00   5.70      PROT
ATOM   2995  CB   ARG  198   -18.018  26.577  13.746  1.00   6.15      PROT
ATOM   2996  CG   ARG  198   -17.843  26.836  12.268  1.00   6.81      PROT
ATOM   2997  CD   ARG  198   -18.993  27.686  11.678  1.00   6.37      PROT
ATOM   2998  NE   ARG  198   -19.098  29.020  12.283  1.00   8.21      PROT
ATOM   2999  CZ   ARG  198   -18.392  30.085  11.908  1.00   7.33      PROT
ATOM   3000  NH1  ARG  198   -17.495  30.006  10.939  1.00   5.92      PROT
ATOM   3001  NH2  ARG  198   -18.577  31.242  12.518  1.00   9.37      PROT
ATOM   3015  N    LEU  199   -14.745  26.008  13.358  1.00   6.60      PROT
ATOM   3016  CA   LEU  199   -13.488  26.703  13.093  1.00   7.26      PROT
ATOM   3017  C    LEU  199   -13.694  27.820  12.067  1.00   7.72      PROT
ATOM   3018  O    LEU  199   -14.038  27.562  10.909  1.00   6.94      PROT
ATOM   3019  CB   LEU  199   -12.389  25.732  12.625  1.00   7.16      PROT
ATOM   3020  CG   LEU  199   -10.979  26.318  12.433  1.00   7.44      PROT
ATOM   3021  CD1  LEU  199   -10.368  26.730  13.750  1.00   9.05      PROT
ATOM   3022  CD2  LEU  199   -10.060  25.336  11.741  1.00   7.76      PROT
ATOM   3034  N    ALA  200   -13.489  29.057  12.509  1.00   8.41      PROT
ATOM   3035  CA   ALA  200   -13.617  30.228  11.644  1.00   9.34      PROT
ATOM   3036  C    ALA  200   -12.233  30.747  11.284  1.00  10.27      PROT
ATOM   3037  O    ALA  200   -11.423  31.026  12.164  1.00   9.85      PROT
ATOM   3038  CB   ALA  200   -14.434  31.309  12.335  1.00   8.51      PROT
ATOM   3044  N    ILE  201   -11.960  30.846   9.988  1.00  11.92      PROT
ATOM   3045  CA   ILE  201   -10.681  31.366   9.496  1.00  13.65      PROT
ATOM   3046  C    ILE  201   -10.920  32.530   8.531  1.00  14.75      PROT
ATOM   3047  O    ILE  201   -11.827  32.488   7.701  1.00  14.63      PROT
ATOM   3048  CB   ILE  201    -9.821  30.272   8.800  1.00  13.79      PROT
ATOM   3049  CG1  ILE  201    -9.842  28.961   9.596  1.00  14.01      PROT
ATOM   3050  CG2  ILE  201    -8.376  30.760   8.612  1.00  13.88      PROT
ATOM   3051  CD   ILE  201    -9.148  27.812   8.907  1.00  13.98      PROT
```

Figure 3 cont.

```
ATOM   3063  N    ASN   202     -10.091  33.560   8.647  1.00 16.40      PROT
ATOM   3064  CA   ASN   202     -10.227  34.757   7.833  1.00 17.93      PROT
ATOM   3065  C    ASN   202      -9.639  34.620   6.441  1.00 18.75      PROT
ATOM   3066  O    ASN   202      -8.990  33.623   6.108  1.00 18.41      PROT
ATOM   3067  CB   ASN   202      -9.545  35.942   8.518  1.00 18.43      PROT
ATOM   3068  CG   ASN   202      -8.028  35.913   8.363  1.00 19.42      PROT
ATOM   3069  OD1  ASN   202      -7.406  34.849   8.396  1.00 20.35      PROT
ATOM   3070  ND2  ASN   202      -7.432  37.084   8.192  1.00 20.23      PROT
ATOM   3077  N    ASP   203      -9.912  35.649   5.646  1.00 19.86      PROT
ATOM   3078  CA   ASP   203      -9.135  36.025   4.483  1.00 20.78      PROT
ATOM   3079  C    ASP   203      -7.971  36.858   5.052  1.00 21.20      PROT
ATOM   3080  O    ASP   203      -8.219  37.884   5.702  1.00 21.59      PROT
ATOM   3081  CB   ASP   203     -10.030  36.873   3.573  1.00 20.96      PROT
ATOM   3082  CG   ASP   203      -9.536  36.934   2.145  1.00 21.50      PROT
ATOM   3083  OD1  ASP   203     -10.169  36.298   1.271  1.00 22.64      PROT
ATOM   3084  OD2  ASP   203      -8.531  37.628   1.893  1.00 22.64      PROT
ATOM   3089  N    ASP   204      -6.710  36.454   4.852  1.00 21.50      PROT
ATOM   3090  CA   ASP   204      -6.286  35.387   3.931  1.00 21.87      PROT
ATOM   3091  C    ASP   204      -6.635  33.943   4.357  1.00 21.70      PROT
ATOM   3092  O    ASP   204      -7.484  33.329   3.710  1.00 21.69      PROT
ATOM   3093  CB   ASP   204      -4.792  35.536   3.577  1.00 22.16      PROT
ATOM   3094  CG   ASP   204      -4.464  36.883   2.924  1.00 22.96      PROT
ATOM   3095  OD1  ASP   204      -5.323  37.795   2.943  1.00 23.28      PROT
ATOM   3096  OD2  ASP   204      -3.338  37.027   2.393  1.00 22.93      PROT
ATOM   3101  N    GLY   205      -5.979  33.383   5.386  1.00 21.41      PROT
ATOM   3102  CA   GLY   205      -4.796  33.983   6.006  1.00 21.25      PROT
ATOM   3103  C    GLY   205      -4.483  33.847   7.488  1.00 21.01      PROT
ATOM   3104  O    GLY   205      -4.042  32.793   7.961  1.00 21.30      PROT
ATOM   3108  N    ASN   206      -4.713  34.935   8.219  1.00 20.47      PROT
ATOM   3109  CA   ASN   206      -3.939  35.243   9.418  1.00 19.96      PROT
ATOM   3110  C    ASN   206      -4.702  35.241  10.745  1.00 19.07      PROT
ATOM   3111  O    ASN   206      -4.105  35.433  11.802  1.00 19.05      PROT
ATOM   3112  CB   ASN   206      -3.227  36.594   9.217  1.00 20.29      PROT
ATOM   3113  CG   ASN   206      -2.662  36.763   7.806  1.00 21.25      PROT
ATOM   3114  OD1  ASN   206      -2.171  35.807   7.197  1.00 22.03      PROT
ATOM   3115  ND2  ASN   206      -2.728  37.989   7.281  1.00 21.50      PROT
ATOM   3122  N    LYS   207      -6.015  35.024  10.683  1.00 17.84      PROT
ATOM   3123  CA   LYS   207      -6.864  35.012  11.871  1.00 16.59      PROT
ATOM   3124  C    LYS   207      -7.659  33.715  11.949  1.00 15.36      PROT
ATOM   3125  O    LYS   207      -8.433  33.397  11.044  1.00 15.17      PROT
ATOM   3126  CB   LYS   207      -7.818  36.213  11.881  1.00 16.63      PROT
ATOM   3127  CG   LYS   207      -7.128  37.577  11.930  1.00 17.64      PROT
ATOM   3128  CD   LYS   207      -7.743  38.570  10.943  1.00 17.75      PROT
ATOM   3129  CE   LYS   207      -9.220  38.877  11.223  1.00 18.73      PROT
ATOM   3130  NZ   LYS   207      -9.747  39.911  10.276  1.00 18.65      PROT
ATOM   3144  N    VAL   208      -7.458  32.979  13.040  1.00 13.76      PROT
ATOM   3145  CA   VAL   208      -8.121  31.693  13.285  1.00 12.10      PROT
ATOM   3146  C    VAL   208      -8.801  31.730  14.662  1.00 11.30      PROT
ATOM   3147  O    VAL   208      -8.235  32.257  15.633  1.00 11.34      PROT
ATOM   3148  CB   VAL   208      -7.096  30.524  13.202  1.00 12.32      PROT
ATOM   3149  CG1  VAL   208      -7.716  29.204  13.626  1.00 11.62      PROT
ATOM   3150  CG2  VAL   208      -6.522  30.409  11.792  1.00 11.10      PROT
ATOM   3160  N    ALA   209     -10.022  31.202  14.750  1.00  9.53      PROT
ATOM   3161  CA   ALA   209     -10.725  31.152  16.034  1.00  8.69      PROT
ATOM   3162  C    ALA   209     -11.713  29.999  16.168  1.00  7.69      PROT
ATOM   3163  O    ALA   209     -12.354  29.600  15.202  1.00  7.52      PROT
ATOM   3164  CB   ALA   209     -11.419  32.481  16.324  1.00  8.81      PROT
ATOM   3170  N    LEU   210     -11.820  29.485  17.388  1.00  6.93      PROT
ATOM   3171  CA   LEU   210     -12.815  28.482  17.744  1.00  6.00      PROT
ATOM   3172  C    LEU   210     -14.104  29.162  18.178  1.00  5.69      PROT
ATOM   3173  O    LEU   210     -14.180  29.698  19.281  1.00  5.74      PROT
ATOM   3174  CB   LEU   210     -12.288  27.589  18.880  1.00  5.94      PROT
ATOM   3175  CG   LEU   210     -13.147  26.392  19.291  1.00  5.64      PROT
ATOM   3176  CD1  LEU   210     -13.227  25.363  18.175  1.00  3.02      PROT
ATOM   3177  CD2  LEU   210     -12.621  25.734  20.573  1.00  4.91      PROT
```

Figure 3 cont.

```
ATOM   3189 N    GLU   211     -15.105  29.155  17.302  1.00  5.20      PROT
ATOM   3190 CA   GLU   211     -16.412  29.735  17.615  1.00  4.60      PROT
ATOM   3191 C    GLU   211     -17.308  28.687  18.255  1.00  4.10      PROT
ATOM   3192 O    GLU   211     -17.154  27.498  17.987  1.00  3.35      PROT
ATOM   3193 CB   GLU   211     -17.095  30.274  16.351  1.00  4.35      PROT
ATOM   3194 CG   GLU   211     -16.283  31.280  15.535  1.00  4.28      PROT
ATOM   3195 CD   GLU   211     -16.023  32.603  16.224  1.00  6.19      PROT
ATOM   3196 OE1  GLU   211     -16.818  33.045  17.090  1.00  5.53      PROT
ATOM   3197 OE2  GLU   211     -14.993  33.224  15.882  1.00  8.01      PROT
ATOM   3204 N    GLY   212     -18.235  29.139  19.094  1.00  3.96      PROT
ATOM   3205 CA   GLY   212     -19.238  28.261  19.710  1.00  4.12      PROT
ATOM   3206 C    GLY   212     -19.048  28.106  21.212  1.00  3.93      PROT
ATOM   3207 O    GLY   212     -18.259  28.823  21.815  1.00  3.55      PROT
ATOM   3211 N    ALA   213     -19.758  27.138  21.795  1.00  3.67      PROT
ATOM   3212 CA   ALA   213     -19.830  26.940  23.245  1.00  3.61      PROT
ATOM   3213 C    ALA   213     -18.479  26.715  23.924  1.00  3.45      PROT
ATOM   3214 O    ALA   213     -18.224  27.277  24.977  1.00  3.73      PROT
ATOM   3215 CB   ALA   213     -20.789  25.798  23.577  1.00  3.67      PROT
ATOM   3221 N    VAL   214     -17.623  25.897  23.316  1.00  3.68      PROT
ATOM   3222 CA   VAL   214     -16.315  25.577  23.900  1.00  3.04      PROT
ATOM   3223 C    VAL   214     -15.366  26.773  23.830  1.00  3.14      PROT
ATOM   3224 O    VAL   214     -14.745  27.113  24.835  1.00  2.01      PROT
ATOM   3225 CB   VAL   214     -15.688  24.282  23.311  1.00  3.26      PROT
ATOM   3226 CG1  VAL   214     -14.237  24.121  23.770  1.00  2.07      PROT
ATOM   3227 CG2  VAL   214     -16.504  23.068  23.728  1.00  2.17      PROT
ATOM   3237 N    GLY   215     -15.273  27.417  22.663  1.00  2.68      PROT
ATOM   3238 CA   GLY   215     -14.533  28.686  22.543  1.00  2.77      PROT
ATOM   3239 C    GLY   215     -14.948  29.774  23.520  1.00  2.71      PROT
ATOM   3240 O    GLY   215     -14.120  30.280  24.310  1.00  3.18      PROT
ATOM   3244 N    LEU   216     -16.227  30.124  23.507  1.00  2.08      PROT
ATOM   3245 CA   LEU   216     -16.761  31.074  24.492  1.00  2.00      PROT
ATOM   3246 C    LEU   216     -16.479  30.690  25.960  1.00  2.00      PROT
ATOM   3247 O    LEU   216     -15.990  31.527  26.714  1.00  2.00      PROT
ATOM   3248 CB   LEU   216     -18.260  31.332  24.263  1.00  2.00      PROT
ATOM   3249 CG   LEU   216     -19.011  32.124  25.341  1.00  2.00      PROT
ATOM   3250 CD1  LEU   216     -18.481  33.538  25.449  1.00  2.00      PROT
ATOM   3251 CD2  LEU   216     -20.517  32.128  25.066  1.00  2.00      PROT
ATOM   3263 N    ALA   217     -16.774  29.444  26.344  1.00  2.00      PROT
ATOM   3264 CA   ALA   217     -16.570  28.970  27.722  1.00  2.00      PROT
ATOM   3265 C    ALA   217     -15.097  28.975  28.112  1.00  2.00      PROT
ATOM   3266 O    ALA   217     -14.762  29.300  29.241  1.00  2.00      PROT
ATOM   3267 CB   ALA   217     -17.205  27.575  27.956  1.00  2.00      PROT
ATOM   3273 N    SER   218     -14.213  28.648  27.175  1.00  2.00      PROT
ATOM   3274 CA   SER   218     -12.770  28.803  27.400  1.00  2.24      PROT
ATOM   3275 C    SER   218     -12.389  30.221  27.835  1.00  2.21      PROT
ATOM   3276 O    SER   218     -11.598  30.413  28.765  1.00  2.00      PROT
ATOM   3277 CB   SER   218     -11.978  28.424  26.148  1.00  2.00      PROT
ATOM   3278 OG   SER   218     -10.671  28.990  26.205  1.00  4.20      PROT
ATOM   3283 N    THR   219     -12.961  31.214  27.171  1.00  2.27      PROT
ATOM   3284 CA   THR   219     -12.681  32.616  27.512  1.00  2.60      PROT
ATOM   3285 C    THR   219     -13.228  32.946  28.896  1.00  2.43      PROT
ATOM   3286 O    THR   219     -12.505  33.479  29.746  1.00  2.00      PROT
ATOM   3287 CB   THR   219     -13.230  33.594  26.434  1.00  3.51      PROT
ATOM   3288 OG1  THR   219     -12.593  33.302  25.191  1.00  3.71      PROT
ATOM   3289 CG2  THR   219     -12.917  35.049  26.803  1.00  4.31      PROT
ATOM   3296 N    LEU   220     -14.497  32.610  29.125  1.00  2.00      PROT
ATOM   3297 CA   LEU   220     -15.148  32.885  30.421  1.00  2.00      PROT
ATOM   3298 C    LEU   220     -14.500  32.178  31.609  1.00  2.00      PROT
ATOM   3299 O    LEU   220     -14.370  32.765  32.686  1.00  2.00      PROT
ATOM   3300 CB   LEU   220     -16.643  32.552  30.356  1.00  2.00      PROT
ATOM   3301 CG   LEU   220     -17.466  33.197  29.228  1.00  2.00      PROT
ATOM   3302 CD1  LEU   220     -18.944  32.808  29.350  1.00  3.45      PROT
ATOM   3303 CD2  LEU   220     -17.293  34.714  29.118  1.00  2.74      PROT
ATOM   3315 N    ALA   221     -14.114  30.917  31.418  1.00  2.00      PROT
ATOM   3316 CA   ALA   221     -13.398  30.152  32.440  1.00  2.27      PROT
```

Figure 3 cont.

```
ATOM   3317  C    ALA   221    -12.080  30.795  32.844  1.00   2.17      PROT
ATOM   3318  O    ALA   221    -11.761  30.856  34.032  1.00   2.00      PROT
ATOM   3319  CB   ALA   221    -13.157  28.723  31.971  1.00   2.20      PROT
ATOM   3325  N    GLU   222    -11.303  31.230  31.853  1.00   2.19      PROT
ATOM   3326  CA   GLU   222    -10.080  32.012  32.098  1.00   2.98      PROT
ATOM   3327  C    GLU   222    -10.388  33.321  32.847  1.00   2.60      PROT
ATOM   3328  O    GLU   222     -9.652  33.719  33.752  1.00   2.00      PROT
ATOM   3329  CB   GLU   222     -9.340  32.272  30.776  1.00   3.21      PROT
ATOM   3330  CG   GLU   222     -8.064  33.120  30.876  1.00   6.23      PROT
ATOM   3331  CD   GLU   222     -6.966  32.461  31.693  1.00   8.38      PROT
ATOM   3332  OE1  GLU   222     -7.086  31.262  32.049  1.00   9.61      PROT
ATOM   3333  OE2  GLU   222     -5.982  33.165  32.006  1.00  10.00      PROT
ATOM   3340  N    ILE   223    -11.486  33.988  32.482  1.00   2.69      PROT
ATOM   3341  CA   ILE   223    -11.864  35.218  33.196  1.00   2.62      PROT
ATOM   3342  C    ILE   223    -12.137  34.930  34.687  1.00   2.26      PROT
ATOM   3343  O    ILE   223    -11.697  35.681  35.563  1.00   2.00      PROT
ATOM   3344  CB   ILE   223    -13.050  35.968  32.512  1.00   2.92      PROT
ATOM   3345  CG1  ILE   223    -12.628  36.483  31.118  1.00   2.45      PROT
ATOM   3346  CG2  ILE   223    -13.514  37.115  33.392  1.00   2.75      PROT
ATOM   3347  CD   ILE   223    -13.751  37.189  30.289  1.00   3.70      PROT
ATOM   3359  N    PHE   224    -12.838  33.836  34.974  1.00   2.54      PROT
ATOM   3360  CA   PHE   224    -13.080  33.440  36.373  1.00   2.24      PROT
ATOM   3361  C    PHE   224    -11.772  33.194  37.121  1.00   2.01      PROT
ATOM   3362  O    PHE   224    -11.586  33.693  38.226  1.00   2.00      PROT
ATOM   3363  CB   PHE   224    -13.958  32.184  36.463  1.00   2.01      PROT
ATOM   3364  CG   PHE   224    -15.309  32.330  35.820  1.00   2.00      PROT
ATOM   3365  CD1  PHE   224    -15.989  33.555  35.841  1.00   3.21      PROT
ATOM   3366  CD2  PHE   224    -15.923  31.233  35.224  1.00   2.00      PROT
ATOM   3367  CE1  PHE   224    -17.248  33.691  35.255  1.00   2.00      PROT
ATOM   3368  CE2  PHE   224    -17.188  31.353  34.643  1.00   2.00      PROT
ATOM   3369  CZ   PHE   224    -17.846  32.595  34.652  1.00   2.00      PROT
ATOM   3379  N    LEU   225    -10.866  32.425  36.522  1.00   2.00      PROT
ATOM   3380  CA   LEU   225     -9.564  32.178  37.155  1.00   2.44      PROT
ATOM   3381  C    LEU   225     -8.805  33.476  37.447  1.00   2.00      PROT
ATOM   3382  O    LEU   225     -8.200  33.612  38.513  1.00   2.01      PROT
ATOM   3383  CB   LEU   225     -8.723  31.211  36.318  1.00   3.03      PROT
ATOM   3384  CG   LEU   225     -7.435  30.746  36.995  1.00   4.44      PROT
ATOM   3385  CD1  LEU   225     -7.255  29.246  36.823  1.00   6.20      PROT
ATOM   3386  CD2  LEU   225     -6.248  31.526  36.427  1.00   6.69      PROT
ATOM   3398  N    LEU   226     -8.866  34.428  36.517  1.00   2.00      PROT
ATOM   3399  CA   LEU   226     -8.243  35.744  36.689  1.00   2.19      PROT
ATOM   3400  C    LEU   226     -8.901  36.583  37.799  1.00   2.16      PROT
ATOM   3401  O    LEU   226     -8.182  37.262  38.554  1.00   2.00      PROT
ATOM   3402  CB   LEU   226     -8.181  36.525  35.356  1.00   2.81      PROT
ATOM   3403  CG   LEU   226     -7.214  35.953  34.314  1.00   4.36      PROT
ATOM   3404  CD1  LEU   226     -7.327  36.609  32.916  1.00   5.59      PROT
ATOM   3405  CD2  LEU   226     -5.787  35.960  34.834  1.00   4.87      PROT
ATOM   3417  N    GLU   227    -10.240  36.542  37.881  1.00   2.00      PROT
ATOM   3418  CA   GLU   227    -10.997  37.156  38.996  1.00   2.26      PROT
ATOM   3419  C    GLU   227    -10.506  36.620  40.344  1.00   2.00      PROT
ATOM   3420  O    GLU   227    -10.355  37.374  41.307  1.00   2.00      PROT
ATOM   3421  CB   GLU   227    -12.502  36.888  38.881  1.00   2.48      PROT
ATOM   3422  CG   GLU   227    -13.241  37.635  37.750  1.00   3.00      PROT
ATOM   3423  CD   GLU   227    -14.688  37.182  37.552  1.00   3.47      PROT
ATOM   3424  OE1  GLU   227    -15.197  36.302  38.295  1.00   6.37      PROT
ATOM   3425  OE2  GLU   227    -15.343  37.723  36.639  1.00   5.01      PROT
ATOM   3432  N    HSD   228    -10.279  35.310  40.404  1.00   2.00      PROT
ATOM   3433  CA   HSD   228     -9.819  34.667  41.636  1.00   2.00      PROT
ATOM   3434  C    HSD   228     -8.358  35.016  41.918  1.00   2.00      PROT
ATOM   3435  O    HSD   228     -7.983  35.299  43.058  1.00   2.22      PROT
ATOM   3436  CB   HSD   228    -10.048  33.148  41.587  1.00   2.00      PROT
ATOM   3437  CG   HSD   228     -9.896  32.476  42.914  1.00   2.42      PROT
ATOM   3438  ND1  HSD   228     -8.758  31.787  43.270  1.00   5.23      PROT
ATOM   3439  CD2  HSD   228    -10.727  32.400  43.977  1.00   3.56      PROT
ATOM   3440  CE1  HSD   228     -8.896  31.310  44.491  1.00   2.61      PROT
```

Figure 3 cont.

```
ATOM   3441 NE2  HSD   228     -10.076  31.682  44.951  1.00  3.92       PROT
ATOM   3449 N    ALA   229      -7.537  35.030  40.874  1.00  2.00       PROT
ATOM   3450 CA   ALA   229      -6.139  35.425  41.010  1.00  2.00       PROT
ATOM   3451 C    ALA   229      -5.984  36.898  41.406  1.00  2.00       PROT
ATOM   3452 O    ALA   229      -5.009  37.272  42.068  1.00  2.04       PROT
ATOM   3453 CB   ALA   229      -5.386  35.120  39.713  1.00  2.00       PROT
ATOM   3459 N    GLN   230      -6.955  37.720  41.001  1.00  2.00       PROT
ATOM   3460 CA   GLN   230      -7.006  39.136  41.330  1.00  2.75       PROT
ATOM   3461 C    GLN   230      -7.536  39.348  42.749  1.00  3.94       PROT
ATOM   3462 O    GLN   230      -7.429  40.438  43.297  1.00  4.74       PROT
ATOM   3463 CB   GLN   230      -7.916  39.870  40.332  1.00  2.31       PROT
ATOM   3464 CG   GLN   230      -8.108  41.386  40.559  1.00  2.00       PROT
ATOM   3465 CD   GLN   230      -6.810  42.168  40.458  1.00  2.00       PROT
ATOM   3466 OE1  GLN   230      -5.813  41.669  39.956  1.00  2.00       PROT
ATOM   3467 NE2  GLN   230      -6.816  43.401  40.967  1.00  2.00       PROT
ATOM   3476 N    GLY   231      -8.134  38.306  43.312  1.00  4.89       PROT
ATOM   3477 CA   GLY   231      -8.737  38.364  44.628  1.00  7.20       PROT
ATOM   3478 C    GLY   231      -9.927  39.306  44.639  1.00  9.03       PROT
ATOM   3479 O    GLY   231     -10.097  40.079  45.582  1.00  9.60       PROT
ATOM   3483 N    MET   232     -10.731  39.253  43.577  1.00 10.20       PROT
ATOM   3484 CA   MET   232     -11.959  40.047  43.471  1.00 11.96       PROT
ATOM   3485 C    MET   232     -12.962  39.581  44.512  1.00 11.63       PROT
ATOM   3486 O    MET   232     -12.988  38.390  44.838  1.00 11.93       PROT
ATOM   3487 CB   MET   232     -12.618  39.882  42.106  1.00 11.55       PROT
ATOM   3488 CG   MET   232     -11.757  40.152  40.921  1.00 12.75       PROT
ATOM   3489 SD   MET   232     -12.629  41.223  39.789  1.00 16.78       PROT
ATOM   3490 CE   MET   232     -11.894  42.772  40.269  1.00 10.26       PROT
ATOM   3500 N    PRO   233     -13.829  40.501  44.990  1.00 11.66       PROT
ATOM   3501 CA   PRO   233     -14.789  40.142  46.037  1.00 11.78       PROT
ATOM   3502 C    PRO   233     -15.754  39.050  45.575  1.00 11.56       PROT
ATOM   3503 O    PRO   233     -16.091  38.161  46.352  1.00 12.02       PROT
ATOM   3504 CB   PRO   233     -15.530  41.460  46.325  1.00 11.48       PROT
ATOM   3505 CG   PRO   233     -15.285  42.330  45.170  1.00 11.93       PROT
ATOM   3506 CD   PRO   233     -13.983  41.902  44.550  1.00 11.61       PROT
ATOM   3514 N    LYS   234     -16.170  39.103  44.313  1.00 11.27       PROT
ATOM   3515 CA   LYS   234     -17.050  38.080  43.772  1.00 10.91       PROT
ATOM   3516 C    LYS   234     -16.482  37.446  42.514  1.00 10.37       PROT
ATOM   3517 O    LYS   234     -16.269  38.127  41.505  1.00  9.97       PROT
ATOM   3518 CB   LYS   234     -18.449  38.645  43.510  1.00 11.04       PROT
ATOM   3519 CG   LYS   234     -19.347  38.645  44.722  1.00 12.37       PROT
ATOM   3520 CD   LYS   234     -19.906  36.372  44.997  1.00 25.75       PROT
ATOM   3521 CE   LYS   234     -19.135  35.110  45.534  1.00 25.07       PROT
ATOM   3522 NZ   LYS   234     -17.572  34.857  45.362  1.00 21.97       PROT
ATOM   3536 N    VAL   235     -16.246  36.134  42.595  1.00  9.38       PROT
ATOM   3537 CA   VAL   235     -15.716  35.342  41.486  1.00  8.21       PROT
ATOM   3538 C    VAL   235     -16.846  34.497  40.899  1.00  7.50       PROT
ATOM   3539 O    VAL   235     -17.465  33.694  41.609  1.00  7.42       PROT
ATOM   3540 CB   VAL   235     -14.551  34.408  41.939  1.00  8.69       PROT
ATOM   3541 CG1  VAL   235     -13.375  35.217  42.485  1.00  8.22       PROT
ATOM   3542 CG2  VAL   235     -14.086  33.498  40.794  1.00  7.04       PROT
ATOM   3552 N    ALA   236     -17.124  34.685  39.607  1.00  6.92       PROT
ATOM   3553 CA   ALA   236     -18.181  33.936  38.922  1.00  6.04       PROT
ATOM   3554 C    ALA   236     -19.496  34.023  39.708  1.00  5.79       PROT
ATOM   3555 O    ALA   236     -20.252  33.044  39.791  1.00  4.79       PROT
ATOM   3556 CB   ALA   236     -17.772  32.488  38.737  1.00  6.17       PROT
ATOM   3562 N    TRP   237     -19.732  35.199  40.298  1.00  5.43       PROT
ATOM   3563 CA   TRP   237     -20.937  35.516  41.077  1.00  5.65       PROT
ATOM   3564 C    TRP   237     -21.211  34.542  42.234  1.00  5.73       PROT
ATOM   3565 O    TRP   237     -22.372  34.272  42.569  1.00  5.65       PROT
ATOM   3566 CB   TRP   237     -22.167  35.674  40.163  1.00  5.62       PROT
ATOM   3567 CG   TRP   237     -21.862  36.503  38.966  1.00  6.72       PROT
ATOM   3568 CD1  TRP   237     -21.827  37.865  38.894  1.00  6.98       PROT
ATOM   3569 CD2  TRP   237     -21.492  36.020  37.679  1.00  6.01       PROT
ATOM   3570 NE1  TRP   237     -21.478  38.260  37.632  1.00  7.13       PROT
ATOM   3571 CE2  TRP   237     -21.265  37.147  36.861  1.00  8.16       PROT
```

Figure 3 cont.

```
ATOM   3572 CE3  TRP   237     -21.344  34.743  37.128  1.00  6.02      PROT
ATOM   3573 CZ2  TRP   237     -20.888  37.036  35.523  1.00  6.55      PROT
ATOM   3574 CZ3  TRP   237     -20.963  34.632  35.800  1.00  6.46      PROT
ATOM   3575 CH2  TRP   237     -20.741  35.771  35.013  1.00  6.77      PROT
ATOM   3586 N    GLY   238     -20.132  34.025  42.824  1.00  5.45      PROT
ATOM   3587 CA   GLY   238     -20.202  33.083  43.937  1.00  5.24      PROT
ATOM   3588 C    GLY   238     -20.454  31.628  43.569  1.00  5.65      PROT
ATOM   3589 O    GLY   238     -20.635  30.802  44.457  1.00  5.14      PROT
ATOM   3593 N    ASN   239     -20.406  31.300  42.274  1.00  5.32      PROT
ATOM   3594 CA   ASN   239     -20.907  30.004  41.781  1.00  5.87      PROT
ATOM   3595 C    ASN   239     -19.907  28.871  41.576  1.00  5.69      PROT
ATOM   3596 O    ASN   239     -20.310  27.760  41.224  1.00  5.93      PROT
ATOM   3597 CB   ASN   239     -21.740  30.185  40.505  1.00  5.58      PROT
ATOM   3598 CG   ASN   239     -23.035  30.930  40.758  1.00  6.11      PROT
ATOM   3599 OD1  ASN   239     -23.612  30.838  41.837  1.00  6.78      PROT
ATOM   3600 ND2  ASN   239     -23.502  31.667  39.758  1.00  6.62      PROT
ATOM   3607 N    ILE   240     -18.621  29.148  41.781  1.00  6.14      PROT
ATOM   3608 CA   ILE   240     -17.601  28.102  41.786  1.00  6.09      PROT
ATOM   3609 C    ILE   240     -17.274  27.779  43.246  1.00  6.58      PROT
ATOM   3610 O    ILE   240     -16.827  28.640  44.007  1.00  7.29      PROT
ATOM   3611 CB   ILE   240     -16.305  28.489  41.011  1.00  5.88      PROT
ATOM   3612 CG1  ILE   240     -16.632  29.054  39.622  1.00  5.79      PROT
ATOM   3613 CG2  ILE   240     -15.399  27.274  40.885  1.00  5.36      PROT
ATOM   3614 CD   ILE   240     -15.421  29.613  38.881  1.00  5.45      PROT
ATOM   3626 N    HSD   241     -17.519  26.535  43.633  1.00  7.26      PROT
ATOM   3627 CA   HSD   241     -17.391  26.132  45.025  1.00  7.62      PROT
ATOM   3628 C    HSD   241     -16.229  25.180  45.269  1.00  7.39      PROT
ATOM   3629 O    HSD   241     -15.580  25.249  46.311  1.00  7.30      PROT
ATOM   3630 CB   HSD   241     -18.698  25.503  45.515  1.00  8.36      PROT
ATOM   3631 CG   HSD   241     -19.873  26.430  45.460  1.00  9.94      PROT
ATOM   3632 ND1  HSD   241     -20.845  26.347  44.486  1.00 11.72      PROT
ATOM   3633 CD2  HSD   241     -20.226  27.465  46.258  1.00 11.00      PROT
ATOM   3634 CE1  HSD   241     -21.752  27.287  44.691  1.00 11.28      PROT
ATOM   3635 NE2  HSD   241     -21.394  27.983  45.755  1.00 12.05      PROT
ATOM   3643 N    THR   242     -15.974  24.291  44.314  1.00  6.92      PROT
ATOM   3644 CA   THR   242     -15.038  23.191  44.536  1.00  7.02      PROT
ATOM   3645 C    THR   242     -13.886  23.156  43.542  1.00  6.93      PROT
ATOM   3646 O    THR   242     -13.983  23.695  42.445  1.00  7.23      PROT
ATOM   3647 CB   THR   242     -15.742  21.809  44.527  1.00  6.55      PROT
ATOM   3648 OG1  THR   242     -16.076  21.444  43.184  1.00  5.56      PROT
ATOM   3649 CG2  THR   242     -16.995  21.820  45.392  1.00  7.90      PROT
ATOM   3656 N    GLU   243     -12.800  22.503  43.944  1.00  7.08      PROT
ATOM   3657 CA   GLU   243     -11.680  22.226  43.053  1.00  6.85      PROT
ATOM   3658 C    GLU   243     -12.163  21.463  41.821  1.00  6.38      PROT
ATOM   3659 O    GLU   243     -11.759  21.761  40.692  1.00  5.51      PROT
ATOM   3660 CB   GLU   243     -10.615  21.420  43.790  1.00  7.39      PROT
ATOM   3661 CG   GLU   243      -9.663  20.676  42.867  1.00  8.63      PROT
ATOM   3662 CD   GLU   243      -8.704  19.809  43.633  1.00  9.49      PROT
ATOM   3663 OE1  GLU   243      -8.930  18.588  43.691  1.00  7.97      PROT
ATOM   3664 OE2  GLU   243      -7.741  20.362  44.199  1.00 11.16      PROT
ATOM   3671 N    GLN   244     -13.041  20.485  42.042  1.00  5.14      PROT
ATOM   3672 CA   GLN   244     -13.617  19.717  40.945  1.00  4.68      PROT
ATOM   3673 C    GLN   244     -14.289  20.612  39.881  1.00  3.99      PROT
ATOM   3674 O    GLN   244     -14.139  20.367  38.676  1.00  3.31      PROT
ATOM   3675 CB   GLN   244     -14.603  18.674  41.474  1.00  4.41      PROT
ATOM   3676 CG   GLN   244     -15.122  17.733  40.401  1.00  4.63      PROT
ATOM   3677 CD   GLN   244     -15.468  16.262  40.731  1.00 10.22      PROT
ATOM   3678 OE1  GLN   244     -16.675  16.076  40.539  1.00 13.93      PROT
ATOM   3679 NE2  GLN   244     -14.680  15.348  41.318  1.00 14.14      PROT
ATOM   3688 N    GLN   245     -15.005  21.642  40.339  1.00  3.48      PROT
ATOM   3689 CA   GLN   245     -15.657  22.621  39.457  1.00  3.56      PROT
ATOM   3690 C    GLN   245     -14.659  23.525  38.753  1.00  3.07      PROT
ATOM   3691 O    GLN   245     -14.855  23.872  37.589  1.00  2.89      PROT
ATOM   3692 CB   GLN   245     -16.657  23.484  40.231  1.00  3.63      PROT
ATOM   3693 CG   GLN   245     -17.995  22.813  40.438  1.00  5.02      PROT
```

Figure 3 cont.

```
ATOM   3694 CD   GLN  245   -18.810  23.415  41.566  1.00  6.61      PROT
ATOM   3695 OE1  GLN  245   -18.346  24.271  42.313  1.00  7.00      PROT
ATOM   3696 NE2  GLN  245   -20.043  22.953  41.694  1.00  8.44      PROT
ATOM   3705 N    TRP  246   -13.593  23.911  39.454  1.00  2.79      PROT
ATOM   3706 CA   TRP  246   -12.538  24.684  38.822  1.00  2.54      PROT
ATOM   3707 C    TRP  246   -11.933  23.891  37.670  1.00  2.35      PROT
ATOM   3708 O    TRP  246   -11.725  24.435  36.580  1.00  2.00      PROT
ATOM   3709 CB   TRP  246   -11.442  25.067  39.808  1.00  2.58      PROT
ATOM   3710 CG   TRP  246   -11.695  26.339  40.537  1.00  3.39      PROT
ATOM   3711 CD1  TRP  246   -11.934  26.476  41.869  1.00  2.69      PROT
ATOM   3712 CD2  TRP  246   -11.712  27.665  39.982  1.00  3.44      PROT
ATOM   3713 NE1  TRP  246   -12.107  27.803  42.182  1.00  6.09      PROT
ATOM   3714 CE2  TRP  246   -11.981  28.553  41.039  1.00  2.93      PROT
ATOM   3715 CE3  TRP  246   -11.548  28.182  38.684  1.00  2.71      PROT
ATOM   3716 CZ2  TRP  246   -12.077  29.946  40.851  1.00  3.81      PROT
ATOM   3717 CZ3  TRP  246   -11.654  29.557  38.493  1.00  2.47      PROT
ATOM   3718 CH2  TRP  246   -11.913  30.423  39.569  1.00  2.84      PROT
ATOM   3729 N    ASN  247   -11.662  22.608  37.919  1.00  2.00      PROT
ATOM   3730 CA   ASN  247   -10.992  21.769  36.939  1.00  2.50      PROT
ATOM   3731 C    ASN  247   -11.885  21.575  35.705  1.00  2.01      PROT
ATOM   3732 O    ASN  247   -11.417  21.678  34.580  1.00  2.60      PROT
ATOM   3733 CB   ASN  247   -10.610  20.409  37.549  1.00  2.50      PROT
ATOM   3734 CG   ASN  247    -9.361  20.473  38.426  1.00  3.92      PROT
ATOM   3735 OD1  ASN  247    -8.663  21.484  38.483  1.00  7.36      PROT
ATOM   3736 ND2  ASN  247    -9.073  19.376  39.107  1.00  5.56      PROT
ATOM   3743 N    SER  248   -13.168  21.322  35.945  1.00  2.00      PROT
ATOM   3744 CA   SER  248   -14.171  21.135  34.884  1.00  2.06      PROT
ATOM   3745 C    SER  248   -14.284  22.357  33.948  1.00  2.10      PROT
ATOM   3746 O    SER  248   -14.343  22.199  32.722  1.00  2.30      PROT
ATOM   3747 CB   SER  248   -15.531  20.749  35.506  1.00  2.00      PROT
ATOM   3748 OG   SER  248   -16.535  20.480  34.533  1.00  2.40      PROT
ATOM   3753 N    LEU  249   -14.305  23.562  34.526  1.00  2.00      PROT
ATOM   3754 CA   LEU  249   -14.346  24.807  33.744  1.00  2.00      PROT
ATOM   3755 C    LEU  249   -13.064  25.020  32.953  1.00  2.00      PROT
ATOM   3756 O    LEU  249   -13.111  25.269  31.748  1.00  2.00      PROT
ATOM   3757 CB   LEU  249   -14.632  26.027  34.636  1.00  2.00      PROT
ATOM   3758 CG   LEU  249   -16.038  26.035  35.252  1.00  2.37      PROT
ATOM   3759 CD1  LEU  249   -16.198  27.198  36.223  1.00  3.63      PROT
ATOM   3760 CD2  LEU  249   -17.132  26.089  34.188  1.00  2.00      PROT
ATOM   3772 N    LEU  250   -11.920  24.892  33.620  1.00  2.00      PROT
ATOM   3773 CA   LEU  250   -10.636  25.116  32.948  1.00  2.51      PROT
ATOM   3774 C    LEU  250   -10.289  24.056  31.914  1.00  2.05      PROT
ATOM   3775 O    LEU  250    -9.466  24.302  31.051  1.00  2.35      PROT
ATOM   3776 CB   LEU  250    -9.491  25.289  33.948  1.00  2.33      PROT
ATOM   3777 CG   LEU  250    -9.173  26.716  34.416  1.00  3.60      PROT
ATOM   3778 CD1  LEU  250   -10.329  27.303  35.221  1.00  4.29      PROT
ATOM   3779 CD2  LEU  250    -8.798  27.642  33.220  1.00  3.17      PROT
ATOM   3791 N    LYS  251   -10.907  22.879  32.012  1.00  2.55      PROT
ATOM   3792 CA   LYS  251   -10.734  21.842  31.000  1.00  3.10      PROT
ATOM   3793 C    LYS  251   -11.104  22.384  29.606  1.00  2.88      PROT
ATOM   3794 O    LYS  251   -10.428  22.094  28.615  1.00  2.97      PROT
ATOM   3795 CB   LYS  251   -11.572  20.603  31.356  1.00  3.79      PROT
ATOM   3796 CG   LYS  251   -11.673  19.566  30.242  1.00  5.55      PROT
ATOM   3797 CD   LYS  251   -11.927  18.159  30.794  1.00  8.54      PROT
ATOM   3798 CE   LYS  251   -13.399  17.823  30.804  1.00 10.50      PROT
ATOM   3799 NZ   LYS  251   -13.602  16.364  31.026  1.00 11.77      PROT
ATOM   3813 N    LEU  252   -12.156  23.193  29.550  1.00  2.97      PROT
ATOM   3814 CA   LEU  252   -12.601  23.835  28.305  1.00  2.99      PROT
ATOM   3815 C    LEU  252   -11.526  24.770  27.746  1.00  2.76      PROT
ATOM   3816 O    LEU  252   -11.266  24.788  26.541  1.00  2.86      PROT
ATOM   3817 CB   LEU  252   -13.902  24.604  28.547  1.00  3.15      PROT
ATOM   3818 CG   LEU  252   -15.136  23.760  28.905  1.00  4.13      PROT
ATOM   3819 CD1  LEU  252   -16.194  24.614  29.604  1.00  4.74      PROT
ATOM   3820 CD2  LEU  252   -15.729  23.040  27.684  1.00  4.65      PROT
ATOM   3832 N    HSD  253   -10.894  25.523  28.644  1.00  2.58      PROT
```

Figure 3 cont.

```
ATOM   3833 CA   HSD   253     -9.837  26.448  28.295  1.00  2.90      PROT
ATOM   3834 C    HSD   253     -8.571  25.751  27.804  1.00  2.67      PROT
ATOM   3835 O    HSD   253     -7.992  26.162  26.795  1.00  3.21      PROT
ATOM   3836 CB   HSD   253     -9.535  27.358  29.486  1.00  2.97      PROT
ATOM   3837 CG   HSD   253     -8.384  28.284  29.275  1.00  4.58      PROT
ATOM   3838 ND1  HSD   253     -8.518  29.510  28.658  1.00  4.97      PROT
ATOM   3839 CD2  HSD   253     -7.088  28.197  29.660  1.00  5.22      PROT
ATOM   3840 CE1  HSD   253     -7.353  30.131  28.661  1.00  4.54      PROT
ATOM   3841 NE2  HSD   253     -6.467  29.352  29.253  1.00  5.30      PROT
ATOM   3849 N    ASN   254     -8.119  24.728  28.526  1.00  2.59      PROT
ATOM   3850 CA   ASN   254     -6.945  23.951  28.085  1.00  2.44      PROT
ATOM   3851 C    ASN   254     -7.183  23.231  26.753  1.00  2.45      PROT
ATOM   3852 O    ASN   254     -6.258  23.092  25.957  1.00  2.24      PROT
ATOM   3853 CB   ASN   254     -6.494  22.938  29.147  1.00  2.25      PROT
ATOM   3854 CG   ASN   254     -6.059  23.595  30.451  1.00  2.51      PROT
ATOM   3855 OD1  ASN   254     -5.449  24.666  30.468  1.00  2.78      PROT
ATOM   3856 ND2  ASN   254     -6.381  22.950  31.545  1.00  2.76      PROT
ATOM   3863 N    ALA   255     -8.424  22.795  26.515  1.00  2.46      PROT
ATOM   3864 CA   ALA   255     -8.804  22.166  25.241  1.00  2.81      PROT
ATOM   3865 C    ALA   255     -8.711  23.154  24.094  1.00  2.85      PROT
ATOM   3866 O    ALA   255     -8.199  22.827  23.022  1.00  2.52      PROT
ATOM   3867 CB   ALA   255    -10.226  21.598  25.313  1.00  2.00      PROT
ATOM   3873 N    GLN   256     -9.244  24.348  24.325  1.00  3.13      PROT
ATOM   3874 CA   GLN   256     -9.235  25.401  23.319  1.00  3.86      PROT
ATOM   3875 C    GLN   256     -7.810  25.750  22.926  1.00  3.34      PROT
ATOM   3876 O    GLN   256     -7.515  25.912  21.745  1.00  3.84      PROT
ATOM   3877 CB   GLN   256     -9.993  26.632  23.806  1.00  3.76      PROT
ATOM   3878 CG   GLN   256    -10.183  27.719  22.733  1.00  6.52      PROT
ATOM   3879 CD   GLN   256     -9.205  28.876  22.876  1.00 11.10      PROT
ATOM   3880 OE1  GLN   256     -8.494  29.220  21.932  1.00 14.66      PROT
ATOM   3881 NE2  GLN   256     -9.173  29.488  24.056  1.00 12.60      PROT
ATOM   3890 N    PHE   257     -6.935  25.845  23.930  1.00  3.08      PROT
ATOM   3891 CA   PHE   257     -5.518  26.084  23.721  1.00  2.83      PROT
ATOM   3892 C    PHE   257     -4.771  24.969  23.008  1.00  2.45      PROT
ATOM   3893 O    PHE   257     -3.906  25.230  22.174  1.00  2.54      PROT
ATOM   3894 CB   PHE   257     -4.855  26.494  25.039  1.00  2.41      PROT
ATOM   3895 CG   PHE   257     -4.897  27.976  25.237  1.00  3.23      PROT
ATOM   3896 CD1  PHE   257     -3.770  28.738  25.008  1.00  4.55      PROT
ATOM   3897 CD2  PHE   257     -6.107  28.616  25.515  1.00  3.03      PROT
ATOM   3898 CE1  PHE   257     -3.817  30.124  25.133  1.00  5.36      PROT
ATOM   3899 CE2  PHE   257     -6.167  30.009  25.620  1.00  4.80      PROT
ATOM   3900 CZ   PHE   257     -5.014  30.752  25.439  1.00  4.29      PROT
ATOM   3910 N    ASP   258     -5.121  23.730  23.311  1.00  2.85      PROT
ATOM   3911 CA   ASP   258     -4.570  22.589  22.579  1.00  4.03      PROT
ATOM   3912 C    ASP   258     -4.880  22.692  21.075  1.00  3.31      PROT
ATOM   3913 O    ASP   258     -3.986  22.584  20.226  1.00  3.35      PROT
ATOM   3914 CB   ASP   258     -5.115  21.274  23.150  1.00  4.59      PROT
ATOM   3915 CG   ASP   258     -4.447  20.053  22.553  1.00  6.92      PROT
ATOM   3916 OD1  ASP   258     -3.209  20.056  22.409  1.00  9.90      PROT
ATOM   3917 OD2  ASP   258     -5.162  19.078  22.225  1.00 11.03      PROT
ATOM   3922 N    LEU   259     -6.148  22.924  20.758  1.00  2.92      PROT
ATOM   3923 CA   LEU   259     -6.580  23.011  19.367  1.00  3.06      PROT
ATOM   3924 C    LEU   259     -6.055  24.234  18.626  1.00  2.87      PROT
ATOM   3925 O    LEU   259     -5.609  24.119  17.474  1.00  3.56      PROT
ATOM   3926 CB   LEU   259     -8.112  22.937  19.257  1.00  3.04      PROT
ATOM   3927 CG   LEU   259     -8.817  21.754  19.914  1.00  3.29      PROT
ATOM   3928 CD1  LEU   259    -10.326  21.901  19.742  1.00  3.83      PROT
ATOM   3929 CD2  LEU   259     -8.321  20.431  19.354  1.00  4.84      PROT
ATOM   3941 N    MET   260     -6.103  25.395  19.269  1.00  2.39      PROT
ATOM   3942 CA   MET   260     -5.763  26.644  18.596  1.00  2.81      PROT
ATOM   3943 C    MET   260     -4.295  27.024  18.631  1.00  2.51      PROT
ATOM   3944 O    MET   260     -3.841  27.749  17.753  1.00  2.00      PROT
ATOM   3945 CB   MET   260     -6.606  27.814  19.116  1.00  3.54      PROT
ATOM   3946 CG   MET   260     -8.101  27.734  18.825  1.00  6.15      PROT
ATOM   3947 SD   MET   260     -8.492  27.539  17.081  1.00 12.80      PROT
```

Figure 3 cont.

```
ATOM   3948  CE   MET   260     -8.804  25.805  17.030  1.00  6.34      PROT
ATOM   3958  N    SER   261     -3.564  26.561  19.643  1.00  2.88      PROT
ATOM   3959  CA   SER   261     -2.160  26.953  19.822  1.00  3.70      PROT
ATOM   3960  C    SER   261     -1.148  25.796  19.846  1.00  3.64      PROT
ATOM   3961  O    SER   261      0.011  25.985  19.461  1.00  4.13      PROT
ATOM   3962  CB   SER   261     -1.992  27.824  21.077  1.00  3.66      PROT
ATOM   3963  OG   SER   261     -2.516  29.135  20.896  1.00  5.70      PROT
ATOM   3968  N    ARG   262     -1.557  24.620  20.314  1.00  3.67      PROT
ATOM   3969  CA   ARG   262     -0.639  23.462  20.327  1.00  3.94      PROT
ATOM   3970  C    ARG   262     -0.604  22.654  19.023  1.00  3.73      PROT
ATOM   3971  O    ARG   262      0.438  22.107  18.667  1.00  4.26      PROT
ATOM   3972  CB   ARG   262     -0.888  22.543  21.524  1.00  4.18      PROT
ATOM   3973  CG   ARG   262     -0.745  23.236  22.898  1.00  4.84      PROT
ATOM   3974  CD   ARG   262     -0.292  22.260  23.997  1.00 10.03      PROT
ATOM   3975  NE   ARG   262     -0.792  20.943  23.708  1.00 14.21      PROT
ATOM   3976  CZ   ARG   262     -0.066  19.869  23.412  1.00 14.65      PROT
ATOM   3977  NH1  ARG   262      1.267  19.870  23.435  1.00 14.69      PROT
ATOM   3978  NH2  ARG   262     -0.711  18.769  23.119  1.00 11.65      PROT
ATOM   3992  N    THR   263     -1.734  22.583  18.319  1.00  3.54      PROT
ATOM   3993  CA   THR   263     -1.814  21.914  17.000  1.00  3.69      PROT
ATOM   3994  C    THR   263     -0.519  22.219  16.229  1.00  4.08      PROT
ATOM   3995  O    THR   263     -0.251  23.385  15.956  1.00  4.64      PROT
ATOM   3996  CB   THR   263     -3.055  22.424  16.222  1.00  3.39      PROT
ATOM   3997  OG1  THR   263     -4.248  22.049  16.921  1.00  2.35      PROT
ATOM   3998  CG2  THR   263     -3.114  21.874  14.797  1.00  3.17      PROT
ATOM   4005  N    PRO   264      0.309  21.186  15.917  1.00  4.83      PROT
ATOM   4006  CA   PRO   264      1.659  21.420  15.365  1.00  4.72      PROT
ATOM   4007  C    PRO   264      1.762  22.345  14.132  1.00  4.77      PROT
ATOM   4008  O    PRO   264      2.674  23.182  14.070  1.00  3.58      PROT
ATOM   4009  CB   PRO   264      2.159  20.007  15.042  1.00  5.63      PROT
ATOM   4010  CG   PRO   264      1.429  19.138  16.011  1.00  5.68      PROT
ATOM   4011  CD   PRO   264      0.057  19.746  16.113  1.00  5.12      PROT
ATOM   4019  N    TYR   265      0.844  22.199  13.175  1.00  3.82      PROT
ATOM   4020  CA   TYR   265      0.781  23.105  12.023  1.00  4.05      PROT
ATOM   4021  C    TYR   265      0.718  24.599  12.414  1.00  3.79      PROT
ATOM   4022  O    TYR   265      1.449  25.427  11.855  1.00  3.58      PROT
ATOM   4023  CB   TYR   265     -0.400  22.738  11.118  1.00  4.47      PROT
ATOM   4024  CG   TYR   265     -0.499  23.596   9.882  1.00  5.56      PROT
ATOM   4025  CD1  TYR   265      0.337  23.371   8.795  1.00  5.47      PROT
ATOM   4026  CD2  TYR   265     -1.414  24.651   9.809  1.00  6.44      PROT
ATOM   4027  CE1  TYR   265      0.262  24.163   7.661  1.00  7.13      PROT
ATOM   4028  CE2  TYR   265     -1.494  25.456   8.671  1.00  6.49      PROT
ATOM   4029  CZ   TYR   265     -0.648  25.201   7.604  1.00  6.04      PROT
ATOM   4030  OH   TYR   265     -0.711  25.971   6.467  1.00  6.52      PROT
ATOM   4039  N    ILE   266     -0.162  24.925  13.358  1.00  2.90      PROT
ATOM   4040  CA   ILE   266     -0.330  26.292  13.854  1.00  3.39      PROT
ATOM   4041  C    ILE   266      0.845  26.698  14.751  1.00  2.97      PROT
ATOM   4042  O    ILE   266      1.326  27.828  14.680  1.00  2.90      PROT
ATOM   4043  CB   ILE   266     -1.665  26.453  14.640  1.00  3.05      PROT
ATOM   4044  CG1  ILE   266     -2.862  26.215  13.715  1.00  3.33      PROT
ATOM   4045  CG2  ILE   266     -1.742  27.830  15.357  1.00  3.59      PROT
ATOM   4046  CD   ILE   266     -4.173  25.893  14.426  1.00  3.45      PROT
ATOM   4058  N    ALA   267      1.306  25.756  15.568  1.00  2.97      PROT
ATOM   4059  CA   ALA   267      2.349  26.012  16.559  1.00  3.39      PROT
ATOM   4060  C    ALA   267      3.663  26.407  15.888  1.00  2.90      PROT
ATOM   4061  O    ALA   267      4.327  27.328  16.326  1.00  2.80      PROT
ATOM   4062  CB   ALA   267      2.532  24.794  17.476  1.00  2.96      PROT
ATOM   4068  N    LYS   268      4.019  25.736  14.803  1.00  2.85      PROT
ATOM   4069  CA   LYS   268      5.275  26.063  14.107  1.00  2.85      PROT
ATOM   4070  C    LYS   268      5.215  27.404  13.358  1.00  2.70      PROT
ATOM   4071  O    LYS   268      6.228  28.096  13.238  1.00  2.43      PROT
ATOM   4072  CB   LYS   268      5.715  24.921  13.176  1.00  3.42      PROT
ATOM   4073  CG   LYS   268      4.764  24.660  12.027  1.00  3.26      PROT
ATOM   4074  CD   LYS   268      5.248  23.549  11.110  1.00  3.56      PROT
ATOM   4075  CE   LYS   268      4.415  23.511   9.852  1.00  4.15      PROT
```

Figure 3 cont.

```
ATOM   4076 NZ   LYS 268      4.621  22.242   9.118 1.00  6.09      PROT
ATOM   4090 N    HSD 269      4.034  27.763  12.857 1.00  2.47      PROT
ATOM   4091 CA   HSD 269      3.842  29.035  12.149 1.00  2.69      PROT
ATOM   4092 C    HSD 269      3.918  30.241  13.084 1.00  2.81      PROT
ATOM   4093 O    HSD 269      4.331  31.330  12.686 1.00  3.29      PROT
ATOM   4094 CB   HSD 269      2.505  29.040  11.407 1.00  2.64      PROT
ATOM   4095 CG   HSD 269      2.556  28.327  10.092 1.00  3.35      PROT
ATOM   4096 ND1  HSD 269      2.302  26.981   9.973 1.00  4.72      PROT
ATOM   4097 CD2  HSD 269      2.838  28.769   8.845 1.00  4.80      PROT
ATOM   4098 CE1  HSD 269      2.429  26.620   8.708 1.00  3.86      PROT
ATOM   4099 NE2  HSD 269      2.751  27.688   8.003 1.00  4.94      PROT
ATOM   4107 N    ASN 270      3.518  30.017  14.323 1.00  2.44      PROT
ATOM   4108 CA   ASN 270      3.454  31.044  15.348 1.00  3.16      PROT
ATOM   4109 C    ASN 270      4.638  30.998  16.310 1.00  2.45      PROT
ATOM   4110 O    ASN 270      5.032  32.025  16.879 1.00  2.07      PROT
ATOM   4111 CB   ASN 270      2.151  30.893  16.130 1.00  3.29      PROT
ATOM   4112 CG   ASN 270      0.974  31.496  15.405 1.00  7.11      PROT
ATOM   4113 OD1  ASN 270      0.936  32.704  15.166 1.00 11.82      PROT
ATOM   4114 ND2  ASN 270      0.012  30.658  15.029 1.00  9.68      PROT
ATOM   4121 N    GLY 271      5.202  29.809  16.492 1.00  2.29      PROT
ATOM   4122 CA   GLY 271      6.252  29.630  17.496 1.00  2.63      PROT
ATOM   4123 C    GLY 271      7.681  29.495  17.002 1.00  2.72      PROT
ATOM   4124 O    GLY 271      8.595  29.448  17.811 1.00  3.41      PROT
ATOM   4128 N    THR 272      7.886  29.414  15.689 1.00  2.65      PROT
ATOM   4129 CA   THR 272      9.251  29.259  15.132 1.00  2.53      PROT
ATOM   4130 C    THR 272     10.297  30.309  15.591 1.00  2.84      PROT
ATOM   4131 O    THR 272     11.384  29.917  16.034 1.00  2.14      PROT
ATOM   4132 CB   THR 272      9.249  29.055  13.590 1.00  2.64      PROT
ATOM   4133 OG1  THR 272      8.799  27.726  13.293 1.00  2.00      PROT
ATOM   4134 CG2  THR 272     10.645  29.253  12.985 1.00  2.16      PROT
ATOM   4141 N    PRO 273      9.989  31.631  15.472 1.00  3.18      PROT
ATOM   4142 CA   PRO 273     10.929  32.638  15.991 1.00  3.00      PROT
ATOM   4143 C    PRO 273     11.329  32.458  17.462 1.00  2.64      PROT
ATOM   4144 O    PRO 273     12.507  32.575  17.798 1.00  2.00      PROT
ATOM   4145 CB   PRO 273     10.169  33.962  15.802 1.00  3.45      PROT
ATOM   4146 CG   PRO 273      9.256  33.692  14.650 1.00  3.72      PROT
ATOM   4147 CD   PRO 273      8.820  32.263  14.828 1.00  2.86      PROT
ATOM   4155 N    LEU 274     10.357  32.181  18.328 1.00  2.00      PROT
ATOM   4156 CA   LEU 274     10.648  31.979  19.741 1.00  2.18      PROT
ATOM   4157 C    LEU 274     11.519  30.756  20.008 1.00  2.00      PROT
ATOM   4158 O    LEU 274     12.508  30.854  20.743 1.00  2.00      PROT
ATOM   4159 CB   LEU 274      9.358  31.929  20.577 1.00  2.00      PROT
ATOM   4160 CG   LEU 274      8.883  33.271  21.139 1.00  4.76      PROT
ATOM   4161 CD1  LEU 274      9.874  33.724  22.199 1.00  3.36      PROT
ATOM   4162 CD2  LEU 274      7.508  33.114  21.742 1.00  6.75      PROT
ATOM   4174 N    LEU 275     11.167  29.627  19.389 1.00  2.00      PROT
ATOM   4175 CA   LEU 275     11.944  28.385  19.522 1.00  2.41      PROT
ATOM   4176 C    LEU 275     13.389  28.541  19.063 1.00  2.73      PROT
ATOM   4177 O    LEU 275     14.313  28.171  19.780 1.00  2.88      PROT
ATOM   4178 CB   LEU 275     11.278  27.193  18.813 1.00  2.00      PROT
ATOM   4179 CG   LEU 275     11.895  25.814  19.118 1.00  2.08      PROT
ATOM   4180 CD1  LEU 275     11.847  25.446  20.605 1.00  2.23      PROT
ATOM   4181 CD2  LEU 275     11.316  24.665  18.251 1.00  2.25      PROT
ATOM   4193 N    GLN 276     13.564  29.102  17.868 1.00  3.17      PROT
ATOM   4194 CA   GLN 276     14.880  29.446  17.356 1.00  3.37      PROT
ATOM   4195 C    GLN 276     15.669  30.367  18.308 1.00  2.83      PROT
ATOM   4196 O    GLN 276     16.851  30.145  18.549 1.00  2.23      PROT
ATOM   4197 CB   GLN 276     14.752  30.018  15.935 1.00  3.63      PROT
ATOM   4198 CG   GLN 276     14.378  28.934  14.893 1.00  5.11      PROT
ATOM   4199 CD   GLN 276     14.282  29.439  13.459 1.00  4.81      PROT
ATOM   4200 OE1  GLN 276     14.054  30.624  13.213 1.00  5.03      PROT
ATOM   4201 NE2  GLN 276     14.433  28.519  12.498 1.00  5.08      PROT
ATOM   4210 N    THR 277     15.001  31.365  18.886 1.00  3.09      PROT
ATOM   4211 CA   THR 277     15.631  32.260  19.863 1.00  2.65      PROT
ATOM   4212 C    THR 277     16.013  31.550  21.175 1.00  2.25      PROT
```

Figure 3 cont.

```
ATOM   4213  O    THR  277      17.114  31.744  21.707  1.00  2.00      PROT
ATOM   4214  CB   THR  277      14.730  33.470  20.152  1.00  3.05      PROT
ATOM   4215  OG1  THR  277      14.626  34.265  18.968  1.00  4.88      PROT
ATOM   4216  CG2  THR  277      15.294  34.323  21.300  1.00  3.24      PROT
ATOM   4223  N    ILE  278      15.099  30.744  21.700  1.00  2.00      PROT
ATOM   4224  CA   ILE  278      15.406  29.926  22.870  1.00  2.16      PROT
ATOM   4225  C    ILE  278      16.604  28.996  22.591  1.00  2.00      PROT
ATOM   4226  O    ILE  278      17.609  29.043  23.309  1.00  2.00      PROT
ATOM   4227  CB   ILE  278      14.158  29.181  23.390  1.00  2.52      PROT
ATOM   4228  CG1  ILE  278      13.157  30.209  23.944  1.00  2.00      PROT
ATOM   4229  CG2  ILE  278      14.528  28.187  24.479  1.00  2.43      PROT
ATOM   4230  CD   ILE  278      11.727  29.683  24.176  1.00  3.75      PROT
ATOM   4242  N    ALA  279      16.502  28.202  21.522  1.00  2.00      PROT
ATOM   4243  CA   ALA  279      17.579  27.295  21.106  1.00  2.00      PROT
ATOM   4244  C    ALA  279      18.930  28.001  21.117  1.00  2.00      PROT
ATOM   4245  O    ALA  279      19.892  27.511  21.709  1.00  2.00      PROT
ATOM   4246  CB   ALA  279      17.288  26.716  19.716  1.00  2.00      PROT
ATOM   4252  N    HSD  280      18.985  29.164  20.480  1.00  2.25      PROT
ATOM   4253  CA   HSD  280      20.245  29.874  20.276  1.00  2.27      PROT
ATOM   4254  C    HSD  280      20.811  30.381  21.605  1.00  2.65      PROT
ATOM   4255  O    HSD  280      22.013  30.268  21.833  1.00  2.02      PROT
ATOM   4256  CB   HSD  280      20.075  31.031  19.289  1.00  2.01      PROT
ATOM   4257  CG   HSD  280      21.357  31.735  18.962  1.00  2.59      PROT
ATOM   4258  ND1  HSD  280      21.757  32.886  19.606  1.00  2.93      PROT
ATOM   4259  CD2  HSD  280      22.342  31.437  18.083  1.00  3.83      PROT
ATOM   4260  CE1  HSD  280      22.924  33.275  19.128  1.00  4.17      PROT
ATOM   4261  NE2  HSD  280      23.301  32.414  18.200  1.00  2.85      PROT
ATOM   4269  N    ALA  281      19.950  30.920  22.478  1.00  2.95      PROT
ATOM   4270  CA   ALA  281      20.386  31.358  23.816  1.00  3.63      PROT
ATOM   4271  C    ALA  281      20.961  30.195  24.639  1.00  4.19      PROT
ATOM   4272  O    ALA  281      21.894  30.380  25.434  1.00  4.36      PROT
ATOM   4273  CB   ALA  281      19.230  32.050  24.571  1.00  3.83      PROT
ATOM   4279  N    LEU  282      20.433  28.989  24.416  1.00  5.08      PROT
ATOM   4280  CA   LEU  282      20.901  27.788  25.118  1.00  5.36      PROT
ATOM   4281  C    LEU  282      22.222  27.248  24.557  1.00  6.17      PROT
ATOM   4282  O    LEU  282      22.823  26.347  25.148  1.00  5.73      PROT
ATOM   4283  CB   LEU  282      19.822  26.691  25.152  1.00  4.36      PROT
ATOM   4284  CG   LEU  282      18.509  26.990  25.897  1.00  3.91      PROT
ATOM   4285  CD1  LEU  282      17.408  26.015  25.496  1.00  3.34      PROT
ATOM   4286  CD2  LEU  282      18.709  27.002  27.423  1.00  2.18      PROT
ATOM   4298  N    GLY  283      22.652  27.784  23.411  1.00  7.22      PROT
ATOM   4299  CA   GLY  283      23.939  27.422  22.822  1.00  8.72      PROT
ATOM   4300  C    GLY  283      23.892  26.605  21.538  1.00  9.89      PROT
ATOM   4301  O    GLY  283      24.921  26.129  21.082  1.00  9.62      PROT
ATOM   4305  N    SER  284      22.703  26.454  20.953  1.00 11.20      PROT
ATOM   4306  CA   SER  284      22.541  25.737  19.690  1.00 12.67      PROT
ATOM   4307  C    SER  284      23.257  26.428  18.528  1.00 13.73      PROT
ATOM   4308  O    SER  284      23.248  27.657  18.426  1.00 13.58      PROT
ATOM   4309  CB   SER  284      21.059  25.569  19.357  1.00 12.83      PROT
ATOM   4310  OG   SER  284      20.422  24.728  20.304  1.00 13.58      PROT
ATOM   4315  N    ASN  285      23.851  25.625  17.644  1.00 14.88      PROT
ATOM   4316  CA   ASN  285      24.564  26.133  16.462  1.00 16.45      PROT
ATOM   4317  C    ASN  285      23.593  26.578  15.364  1.00 17.15      PROT
ATOM   4318  O    ASN  285      23.823  26.368  14.169  1.00 17.28      PROT
ATOM   4319  CB   ASN  285      25.549  25.080  15.934  1.00 16.75      PROT
ATOM   4320  CG   ASN  285      26.471  25.623  14.847  1.00 17.57      PROT
ATOM   4321  OD1  ASN  285      26.633  25.003  13.790  1.00 20.17      PROT
ATOM   4322  ND2  ASN  285      27.076  26.782  15.099  1.00 18.07      PROT
ATOM   4329  N    ILE  286      22.499  27.186  15.802  1.00 17.97      PROT
ATOM   4330  CA   ILE  286      21.437  27.676  14.942  1.00 19.06      PROT
ATOM   4331  C    ILE  286      21.742  29.138  14.578  1.00 19.26      PROT
ATOM   4332  O    ILE  286      22.673  29.737  15.129  1.00 19.67      PROT
ATOM   4333  CB   ILE  286      20.076  27.529  15.688  1.00 19.19      PROT
ATOM   4334  CG1  ILE  286      18.926  27.256  14.714  1.00 20.03      PROT
ATOM   4335  CG2  ILE  286      19.820  28.715  16.628  1.00 19.40      PROT
```

Figure 3 cont.

```
ATOM   4336  CD   ILE   286      17.630  26.813  15.403  1.00 19.77      PROT
ATOM   4348  N    THR   287      20.995  29.692  13.624  1.00 19.35      PROT
ATOM   4349  CA   THR   287      21.047  31.123  13.329  1.00 19.22      PROT
ATOM   4350  C    THR   287      19.748  31.752  13.838  1.00 18.84      PROT
ATOM   4351  O    THR   287      18.662  31.212  13.616  1.00 19.08      PROT
ATOM   4352  CB   THR   287      21.240  31.394  11.810  1.00 19.37      PROT
ATOM   4353  OG1  THR   287      22.487  30.837  11.375  1.00 20.03      PROT
ATOM   4354  CG2  THR   287      21.235  32.894  11.505  1.00 19.77      PROT
ATOM   4361  N    SER   288      19.862  32.871  14.550  1.00 18.17      PROT
ATOM   4362  CA   SER   288      18.680  33.597  15.016  1.00 17.36      PROT
ATOM   4363  C    SER   288      18.910  35.096  15.127  1.00 16.63      PROT
ATOM   4364  O    SER   288      19.949  35.540  15.623  1.00 16.86      PROT
ATOM   4365  CB   SER   288      18.190  33.059  16.364  1.00 17.31      PROT
ATOM   4366  OG   SER   288      16.940  33.645  16.693  1.00 17.47      PROT
ATOM   4371  N    ARG   289      17.916  35.864  14.688  1.00 15.58      PROT
ATOM   4372  CA   ARG   289      17.969  37.319  14.761  1.00 14.97      PROT
ATOM   4373  C    ARG   289      18.319  37.790  16.171  1.00 14.04      PROT
ATOM   4374  O    ARG   289      17.614  37.459  17.134  1.00 13.54      PROT
ATOM   4375  CB   ARG   289      16.660  37.945  14.282  1.00 15.14      PROT
ATOM   4376  CG   ARG   289      16.754  39.458  14.097  1.00 17.07      PROT
ATOM   4377  CD   ARG   289      16.049  39.907  12.837  1.00 18.64      PROT
ATOM   4378  NE   ARG   289      14.655  40.279  13.072  1.00 19.63      PROT
ATOM   4379  CZ   ARG   289      13.718  40.287  12.127  1.00 20.16      PROT
ATOM   4380  NH1  ARG   289      14.014  39.924  10.886  1.00 19.78      PROT
ATOM   4381  NH2  ARG   289      12.477  40.647  12.421  1.00 19.88      PROT
ATOM   4395  N    PRO   290      19.423  38.550  16.291  1.00 12.91      PROT
ATOM   4396  CA   PRO   290      19.926  39.014  17.583  1.00 12.31      PROT
ATOM   4397  C    PRO   290      18.932  39.900  18.338  1.00 11.14      PROT
ATOM   4398  O    PRO   290      18.254  40.727  17.739  1.00 11.04      PROT
ATOM   4399  CB   PRO   290      21.181  39.816  17.208  1.00 12.08      PROT
ATOM   4400  CG   PRO   290      21.573  39.315  15.835  1.00 12.40      PROT
ATOM   4401  CD   PRO   290      20.272  39.015  15.172  1.00 13.25      PROT
ATOM   4409  N    LEU   291      18.820  39.693  19.644  1.00 10.51      PROT
ATOM   4410  CA   LEU   291      18.121  40.643  20.498  1.00  9.58      PROT
ATOM   4411  C    LEU   291      19.108  41.784  20.679  1.00  9.24      PROT
ATOM   4412  O    LEU   291      20.286  41.524  20.916  1.00  8.85      PROT
ATOM   4413  CB   LEU   291      17.760  40.016  21.847  1.00  9.67      PROT
ATOM   4414  CG   LEU   291      16.668  38.937  21.819  1.00  9.62      PROT
ATOM   4415  CD1  LEU   291      15.330  39.536  21.423  1.00  9.83      PROT
ATOM   4416  CD2  LEU   291      16.576  38.239  23.165  1.00  9.61      PROT
ATOM   4428  N    PRO   292      18.650  43.042  20.536  1.00  8.92      PROT
ATOM   4429  CA   PRO   292      19.614  44.143  20.551  1.00  9.07      PROT
ATOM   4430  C    PRO   292      20.261  44.282  21.919  1.00  9.08      PROT
ATOM   4431  O    PRO   292      19.574  44.194  22.937  1.00  8.65      PROT
ATOM   4432  CB   PRO   292      18.748  45.375  20.247  1.00  9.48      PROT
ATOM   4433  CG   PRO   292      17.371  44.990  20.716  1.00  9.59      PROT
ATOM   4434  CD   PRO   292      17.265  43.518  20.377  1.00  8.83      PROT
ATOM   4442  N    ASP   293      21.577  44.471  21.942  1.00  9.25      PROT
ATOM   4443  CA   ASP   293      22.268  44.887  23.157  1.00  9.55      PROT
ATOM   4444  C    ASP   293      22.326  43.814  24.241  1.00  9.31      PROT
ATOM   4445  O    ASP   293      22.404  44.142  25.433  1.00  9.87      PROT
ATOM   4446  CB   ASP   293      21.581  46.138  23.724  1.00 10.30      PROT
ATOM   4447  CG   ASP   293      22.559  47.147  24.229  1.00 12.60      PROT
ATOM   4448  OD1  ASP   293      22.788  48.150  23.509  1.00 16.51      PROT
ATOM   4449  OD2  ASP   293      23.116  46.930  25.324  1.00 13.71      PROT
ATOM   4454  N    ILE   294      22.253  42.549  23.834  1.00  7.89      PROT
ATOM   4455  CA   ILE   294      22.397  41.426  24.752  1.00  7.00      PROT
ATOM   4456  C    ILE   294      23.883  41.048  24.851  1.00  7.00      PROT
ATOM   4457  O    ILE   294      24.620  41.100  23.855  1.00  7.24      PROT
ATOM   4458  CB   ILE   294      21.473  40.217  24.373  1.00  6.93      PROT
ATOM   4459  CG1  ILE   294      21.364  39.222  25.542  1.00  5.67      PROT
ATOM   4460  CG2  ILE   294      21.923  39.541  23.043  1.00  6.07      PROT
ATOM   4461  CD   ILE   294      20.236  38.197  25.417  1.00  6.23      PROT
ATOM   4473  N    SER   295      24.330  40.736  26.062  1.00  6.66      PROT
ATOM   4474  CA   SER   295      25.726  40.403  26.309  1.00  7.30      PROT
```

Figure 3 cont.

```
ATOM   4475  C    SER   295      25.961  38.930  26.006  1.00  7.52       PROT
ATOM   4476  O    SER   295      25.103  38.107  26.307  1.00  6.84       PROT
ATOM   4477  CB   SER   295      26.078  40.699  27.767  1.00  7.35       PROT
ATOM   4478  OG   SER   295      27.393  40.273  28.071  1.00  7.94       PROT
ATOM   4483  N    PRO   296      27.116  38.587  25.385  1.00  8.12       PROT
ATOM   4484  CA   PRO   296      27.460  37.159  25.286  1.00  8.38       PROT
ATOM   4485  C    PRO   296      27.607  36.486  26.651  1.00  8.43       PROT
ATOM   4486  O    PRO   296      27.472  35.263  26.753  1.00  9.10       PROT
ATOM   4487  CB   PRO   296      28.792  37.147  24.512  1.00  8.72       PROT
ATOM   4488  CG   PRO   296      29.289  38.545  24.523  1.00  8.24       PROT
ATOM   4489  CD   PRO   296      28.106  39.449  24.710  1.00  8.34       PROT
ATOM   4497  N    ASP   297      27.853  37.284  27.686  1.00  8.51       PROT
ATOM   4498  CA   ASP   297      27.945  36.795  29.062  1.00  8.73       PROT
ATOM   4499  C    ASP   297      26.585  36.738  29.781  1.00  8.19       PROT
ATOM   4500  O    ASP   297      26.539  36.603  31.002  1.00  8.75       PROT
ATOM   4501  CB   ASP   297      28.932  37.653  29.869  1.00  9.14       PROT
ATOM   4502  CG   ASP   297      30.382  37.489  29.399  1.00 10.18       PROT
ATOM   4503  OD1  ASP   297      30.736  36.412  28.878  1.00 12.04       PROT
ATOM   4504  OD2  ASP   297      31.173  38.445  29.559  1.00 12.86       PROT
ATOM   4509  N    ASN   298      25.488  36.834  29.027  1.00  7.52       PROT
ATOM   4510  CA   ASN   298      24.145  36.730  29.611  1.00  7.12       PROT
ATOM   4511  C    ASN   298      23.885  35.373  30.256  1.00  7.01       PROT
ATOM   4512  O    ASN   298      24.176  34.318  29.664  1.00  7.09       PROT
ATOM   4513  CB   ASN   298      23.055  37.040  28.580  1.00  6.85       PROT
ATOM   4514  CG   ASN   298      21.672  37.156  29.206  1.00  6.67       PROT
ATOM   4515  OD1  ASN   298      21.378  38.114  29.924  1.00  5.83       PROT
ATOM   4516  ND2  ASN   298      20.831  36.161  28.966  1.00  4.59       PROT
ATOM   4523  N    LYS   299      23.319  35.415  31.456  1.00  6.21       PROT
ATOM   4524  CA   LYS   299      23.036  34.216  32.232  1.00  6.05       PROT
ATOM   4525  C    LYS   299      21.547  33.920  32.360  1.00  4.84       PROT
ATOM   4526  O    LYS   299      21.143  32.747  32.471  1.00  4.89       PROT
ATOM   4527  CB   LYS   299      23.689  34.319  33.605  1.00  6.57       PROT
ATOM   4528  CG   LYS   299      25.174  34.024  33.567  1.00  8.71       PROT
ATOM   4529  CD   LYS   299      25.897  34.510  34.806  1.00 12.22       PROT
ATOM   4530  CE   LYS   299      27.410  34.481  34.568  1.00 13.87       PROT
ATOM   4531  NZ   LYS   299      27.913  33.118  34.226  1.00 15.49       PROT
ATOM   4545  N    ILE   300      20.745  34.982  32.344  1.00  3.36       PROT
ATOM   4546  CA   ILE   300      19.298  34.898  32.517  1.00  2.90       PROT
ATOM   4547  C    ILE   300      18.609  35.727  31.435  1.00  2.00       PROT
ATOM   4548  O    ILE   300      18.752  36.953  31.376  1.00  2.00       PROT
ATOM   4549  CB   ILE   300      18.843  35.410  33.915  1.00  3.14       PROT
ATOM   4550  CG1  ILE   300      19.515  34.625  35.041  1.00  3.01       PROT
ATOM   4551  CG2  ILE   300      17.302  35.314  34.070  1.00  3.93       PROT
ATOM   4552  CD   ILE   300      19.359  35.289  36.405  1.00  3.25       PROT
ATOM   4564  N    LEU   301      17.878  35.046  30.567  1.00  2.00       PROT
ATOM   4565  CA   LEU   301      17.060  35.712  29.574  1.00  2.00       PROT
ATOM   4566  C    LEU   301      15.595  35.484  29.918  1.00  2.00       PROT
ATOM   4567  O    LEU   301      15.104  34.346  29.897  1.00  2.47       PROT
ATOM   4568  CB   LEU   301      17.364  35.187  28.164  1.00  2.00       PROT
ATOM   4569  CG   LEU   301      16.419  35.594  27.022  1.00  2.00       PROT
ATOM   4570  CD1  LEU   301      16.352  37.118  26.832  1.00  2.00       PROT
ATOM   4571  CD2  LEU   301      16.886  34.942  25.714  1.00  2.00       PROT
ATOM   4583  N    PHE   302      14.896  36.573  30.196  1.00  2.00       PROT
ATOM   4584  CA   PHE   302      13.482  36.510  30.554  1.00  2.00       PROT
ATOM   4585  C    PHE   302      12.693  37.095  29.385  1.00  2.00       PROT
ATOM   4586  O    PHE   302      12.940  38.232  28.943  1.00  2.00       PROT
ATOM   4587  CB   PHE   302      13.254  37.306  31.836  1.00  2.00       PROT
ATOM   4588  CG   PHE   302      11.838  37.255  32.377  1.00  2.00       PROT
ATOM   4589  CD1  PHE   302      11.450  36.249  33.260  1.00  2.00       PROT
ATOM   4590  CD2  PHE   302      10.904  38.238  32.031  1.00  2.00       PROT
ATOM   4591  CE1  PHE   302      10.133  36.232  33.791  1.00  2.00       PROT
ATOM   4592  CE2  PHE   302       9.602  38.223  32.546  1.00  2.02       PROT
ATOM   4593  CZ   PHE   302       9.212  37.222  33.423  1.00  2.00       PROT
ATOM   4603  N    ILE   303      11.787  36.289  28.859  1.00  2.00       PROT
ATOM   4604  CA   ILE   303      10.968  36.669  27.711  1.00  2.00       PROT
```

Figure 3 cont.

```
ATOM   4605  C    ILE   303       9.525  36.740  28.173  1.00  2.09      PROT
ATOM   4606  O    ILE   303       8.948  35.735  28.580  1.00  2.11      PROT
ATOM   4607  CB   ILE   303      11.127  35.680  26.520  1.00  2.00      PROT
ATOM   4608  CG1  ILE   303      12.608  35.569  26.126  1.00  2.05      PROT
ATOM   4609  CG2  ILE   303      10.279  36.164  25.335  1.00  2.00      PROT
ATOM   4610  CD   ILE   303      12.954  34.372  25.220  1.00  2.00      PROT
ATOM   4622  N    ALA   304       8.974  37.950  28.152  1.00  2.18      PROT
ATOM   4623  CA   ALA   304       7.620  38.216  28.607  1.00  2.00      PROT
ATOM   4624  C    ALA   304       6.622  38.205  27.435  1.00  2.00      PROT
ATOM   4625  O    ALA   304       6.603  39.091  26.574  1.00  2.00      PROT
ATOM   4626  CB   ALA   304       7.563  39.531  29.389  1.00  2.00      PROT
ATOM   4632  N    GLY   305       5.825  37.146  27.402  1.00  2.00      PROT
ATOM   4633  CA   GLY   305       4.877  36.939  26.334  1.00  2.00      PROT
ATOM   4634  C    GLY   305       3.564  36.441  26.895  1.00  2.00      PROT
ATOM   4635  O    GLY   305       3.122  36.901  27.948  1.00  2.00      PROT
ATOM   4639  N    HSD   306       2.962  35.486  26.190  1.00  2.01      PROT
ATOM   4640  CA   HSD   306       1.574  35.092  26.416  1.00  2.90      PROT
ATOM   4641  C    HSD   306       1.423  33.575  26.539  1.00  2.82      PROT
ATOM   4642  O    HSD   306       2.328  32.824  26.165  1.00  2.86      PROT
ATOM   4643  CB   HSD   306       0.718  35.598  25.249  1.00  2.49      PROT
ATOM   4644  CG   HSD   306       0.874  37.070  24.999  1.00  4.73      PROT
ATOM   4645  CD2  HSD   306       1.849  37.583  24.168  1.00  6.93      PROT
ATOM   4646  ND1  HSD   306       0.209  38.134  25.498  1.00  4.07      PROT
ATOM   4647  NE2  HSD   306       1.760  38.900  24.147  1.00  3.76      PROT
ATOM   4648  CE1  HSD   306       0.772  39.258  24.944  1.00  7.37      PROT
ATOM   4656  N    ASP   307       0.265  33.155  27.041  1.00  2.72      PROT
ATOM   4657  CA   ASP   307      -0.140  31.756  27.089  1.00  3.01      PROT
ATOM   4658  C    ASP   307      -0.082  31.060  25.727  1.00  2.89      PROT
ATOM   4659  O    ASP   307       0.321  29.896  25.649  1.00  2.00      PROT
ATOM   4660  CB   ASP   307      -1.525  31.583  27.749  1.00  3.25      PROT
ATOM   4661  CG   ASP   307      -2.620  32.532  27.208  1.00  5.23      PROT
ATOM   4662  OD1  ASP   307      -2.523  33.095  26.084  1.00  5.17      PROT
ATOM   4663  OD2  ASP   307      -3.643  32.653  27.929  1.00  4.48      PROT
ATOM   4668  N    THR   308      -0.470  31.787  24.670  1.00  2.32      PROT
ATOM   4669  CA   THR   308      -0.437  31.279  23.291  1.00  2.85      PROT
ATOM   4670  C    THR   308       1.009  30.906  22.887  1.00  2.42      PROT
ATOM   4671  O    THR   308       1.244  29.875  22.261  1.00  2.00      PROT
ATOM   4672  CB   THR   308      -1.025  32.302  22.273  1.00  3.37      PROT
ATOM   4673  OG1  THR   308      -0.182  33.457  22.222  1.00  5.53      PROT
ATOM   4674  CG2  THR   308      -2.449  32.770  22.670  1.00  3.89      PROT
ATOM   4681  N    ASN   309       1.965  31.764  23.241  1.00  2.00      PROT
ATOM   4682  CA   ASN   309       3.389  31.466  23.045  1.00  2.00      PROT
ATOM   4683  C    ASN   309       3.846  30.191  23.759  1.00  2.00      PROT
ATOM   4684  O    ASN   309       4.525  29.372  23.173  1.00  2.00      PROT
ATOM   4685  CB   ASN   309       4.264  32.651  23.473  1.00  2.00      PROT
ATOM   4686  CG   ASN   309       3.951  33.923  22.683  1.00  2.82      PROT
ATOM   4687  OD1  ASN   309       4.090  33.972  21.456  1.00  5.77      PROT
ATOM   4688  ND2  ASN   309       3.552  34.948  23.383  1.00  2.00      PROT
ATOM   4695  N    ILE   310       3.452  30.008  25.019  1.00  2.00      PROT
ATOM   4696  CA   ILE   310       3.858  28.802  25.753  1.00  2.00      PROT
ATOM   4697  C    ILE   310       3.242  27.561  25.114  1.00  2.00      PROT
ATOM   4698  O    ILE   310       3.902  26.538  24.973  1.00  2.00      PROT
ATOM   4699  CB   ILE   310       3.535  28.917  27.276  1.00  2.00      PROT
ATOM   4700  CG1  ILE   310       4.489  29.946  27.922  1.00  2.00      PROT
ATOM   4701  CG2  ILE   310       3.608  27.555  27.997  1.00  2.00      PROT
ATOM   4702  CD   ILE   310       4.078  30.387  29.287  1.00  4.61      PROT
ATOM   4714  N    ALA   311       1.977  27.668  24.732  1.00  2.00      PROT
ATOM   4715  CA   ALA   311       1.289  26.577  24.052  1.00  2.00      PROT
ATOM   4716  C    ALA   311       1.960  26.246  22.714  1.00  2.00      PROT
ATOM   4717  O    ALA   311       2.153  25.082  22.421  1.00  2.00      PROT
ATOM   4718  CB   ALA   311      -0.176  26.907  23.865  1.00  2.00      PROT
ATOM   4724  N    ASN   312       2.314  27.264  21.921  1.00  2.00      PROT
ATOM   4725  CA   ASN   312       3.052  27.050  20.663  1.00  2.00      PROT
ATOM   4726  C    ASN   312       4.351  26.265  20.881  1.00  2.00      PROT
ATOM   4727  O    ASN   312       4.607  25.280  20.191  1.00  2.00      PROT
```

Figure 3 cont.

```
ATOM   4728  CB   ASN  312      3.385  28.366  19.947  1.00  2.00      PROT
ATOM   4729  CG   ASN  312      2.162  29.133  19.482  1.00  2.00      PROT
ATOM   4730  OD1  ASN  312      1.107  28.570  19.212  1.00  4.60      PROT
ATOM   4731  ND2  ASN  312      2.309  30.438  19.378  1.00  2.13      PROT
ATOM   4738  N    ILE  313      5.168  26.715  21.835  1.00  2.00      PROT
ATOM   4739  CA   ILE  313      6.433  26.028  22.162  1.00  2.05      PROT
ATOM   4740  C    ILE  313      6.184  24.579  22.595  1.00  2.22      PROT
ATOM   4741  O    ILE  313      6.874  23.662  22.136  1.00  2.00      PROT
ATOM   4742  CB   ILE  313      7.277  26.802  23.214  1.00  2.59      PROT
ATOM   4743  CG1  ILE  313      7.717  28.170  22.671  1.00  3.03      PROT
ATOM   4744  CG2  ILE  313      8.493  25.951  23.702  1.00  2.26      PROT
ATOM   4745  CD   ILE  313      8.462  28.122  21.348  1.00  3.79      PROT
ATOM   4757  N    SER  314      5.177  24.379  23.444  1.00  3.00      PROT
ATOM   4758  CA   SER  314      4.796  23.037  23.892  1.00  3.34      PROT
ATOM   4759  C    SER  314      4.359  22.133  22.730  1.00  2.90      PROT
ATOM   4760  O    SER  314      4.749  20.976  22.670  1.00  2.00      PROT
ATOM   4761  CB   SER  314      3.693  23.108  24.952  1.00  4.25      PROT
ATOM   4762  OG   SER  314      2.461  23.528  24.397  1.00  8.68      PROT
ATOM   4767  N    GLY  315      3.544  22.677  21.831  1.00  2.41      PROT
ATOM   4768  CA   GLY  315      3.064  21.949  20.663  1.00  2.92      PROT
ATOM   4769  C    GLY  315      4.249  21.493  19.850  1.00  3.15      PROT
ATOM   4770  O    GLY  315      4.341  20.319  19.504  1.00  3.00      PROT
ATOM   4774  N    MET  316      5.162  22.426  19.578  1.00  3.27      PROT
ATOM   4775  CA   MET  316      6.360  22.175  18.762  1.00  4.05      PROT
ATOM   4776  C    MET  316      7.281  21.084  19.317  1.00  4.30      PROT
ATOM   4777  O    MET  316      7.769  20.248  18.564  1.00  4.51      PROT
ATOM   4778  CB   MET  316      7.161  23.466  18.560  1.00  3.25      PROT
ATOM   4779  CG   MET  316      6.468  24.519  17.703  1.00  4.72      PROT
ATOM   4780  SD   MET  316      7.483  25.988  17.390  1.00  5.18      PROT
ATOM   4781  CE   MET  316      8.508  25.414  16.043  1.00  5.78      PROT
ATOM   4791  N    LEU  317      7.518  21.112  20.630  1.00  4.39      PROT
ATOM   4792  CA   LEU  317      8.387  20.139  21.295  1.00  4.30      PROT
ATOM   4793  C    LEU  317      7.601  18.953  21.862  1.00  4.20      PROT
ATOM   4794  O    LEU  317      8.173  18.053  22.498  1.00  3.42      PROT
ATOM   4795  CB   LEU  317      9.181  20.825  22.413  1.00  4.11      PROT
ATOM   4796  CG   LEU  317     10.209  21.906  22.072  1.00  4.48      PROT
ATOM   4797  CD1  LEU  317     10.573  22.683  23.320  1.00  3.44      PROT
ATOM   4798  CD2  LEU  317     11.475  21.335  21.423  1.00  4.85      PROT
ATOM   4810  N    GLY  318      6.286  18.974  21.640  1.00  4.25      PROT
ATOM   4811  CA   GLY  318      5.385  17.911  22.089  1.00  5.16      PROT
ATOM   4812  C    GLY  318      5.388  17.687  23.591  1.00  5.33      PROT
ATOM   4813  O    GLY  318      5.188  16.560  24.056  1.00  5.23      PROT
ATOM   4817  N    MET  319      5.636  18.760  24.340  1.00  5.23      PROT
ATOM   4818  CA   MET  319      5.641  18.704  25.792  1.00  5.78      PROT
ATOM   4819  C    MET  319      4.233  18.908  26.303  1.00  5.67      PROT
ATOM   4820  O    MET  319      3.516  19.776  25.823  1.00  5.41      PROT
ATOM   4821  CB   MET  319      6.554  19.775  26.382  1.00  5.89      PROT
ATOM   4822  CG   MET  319      8.022  19.570  26.066  1.00  6.35      PROT
ATOM   4823  SD   MET  319      9.054  20.829  26.826  1.00  6.72      PROT
ATOM   4824  CE   MET  319      8.272  22.359  26.304  1.00  6.72      PROT
ATOM   4834  N    THR  320      3.826  18.077  27.255  1.00  5.01      PROT
ATOM   4835  CA   THR  320      2.518  18.238  27.884  1.00  5.22      PROT
ATOM   4836  C    THR  320      2.705  18.174  29.392  1.00  4.53      PROT
ATOM   4837  O    THR  320      3.755  17.739  29.870  1.00  4.49      PROT
ATOM   4838  CB   THR  320      1.502  17.178  27.410  1.00  5.50      PROT
ATOM   4839  OG1  THR  320      2.006  15.862  27.683  1.00  6.37      PROT
ATOM   4840  CG2  THR  320      1.224  17.315  25.912  1.00  6.03      PROT
ATOM   4847  N    TRP  321      1.695  18.613  30.129  1.00  3.83      PROT
ATOM   4848  CA   TRP  321      1.779  18.677  31.568  1.00  4.01      PROT
ATOM   4849  C    TRP  321      0.425  18.980  32.189  1.00  4.34      PROT
ATOM   4850  O    TRP  321     -0.502  19.424  31.513  1.00  3.81      PROT
ATOM   4851  CB   TRP  321      2.812  19.733  32.019  1.00  3.03      PROT
ATOM   4852  CG   TRP  321      2.493  21.161  31.601  1.00  3.26      PROT
ATOM   4853  CD1  TRP  321      1.600  22.007  32.196  1.00  2.00      PROT
ATOM   4854  CD2  TRP  321      3.097  21.906  30.528  1.00  2.02      PROT
```

Figure 3 cont.

```
ATOM   4855  NE1  TRP  321     1.592  23.217  31.555  1.00  2.00      PROT
ATOM   4856  CE2  TRP  321     2.484  23.181  30.515  1.00  2.00      PROT
ATOM   4857  CE3  TRP  321     4.058  21.605  29.548  1.00  2.00      PROT
ATOM   4858  CZ2  TRP  321     2.831  24.174  29.588  1.00  2.00      PROT
ATOM   4859  CZ3  TRP  321     4.396  22.587  28.620  1.00  2.00      PROT
ATOM   4860  CH2  TRP  321     3.788  23.861  28.651  1.00  2.89      PROT
ATOM   4871  N    THR  322     0.352  18.732  33.488  1.00  4.69      PROT
ATOM   4872  CA   THR  322    -0.745  19.169  34.340  1.00  5.92      PROT
ATOM   4873  C    THR  322    -0.082  19.783  35.567  1.00  5.32      PROT
ATOM   4874  O    THR  322     0.986  19.326  36.003  1.00  5.04      PROT
ATOM   4875  CB   THR  322    -1.726  18.000  34.706  1.00  6.24      PROT
ATOM   4876  OG1  THR  322    -2.847  18.515  35.440  1.00  7.87      PROT
ATOM   4877  CG2  THR  322    -1.053  16.913  35.526  1.00  7.29      PROT
ATOM   4884  N    LEU  323    -0.688  20.832  36.112  1.00  4.77      PROT
ATOM   4885  CA   LEU  323    -0.066  21.544  37.222  1.00  4.61      PROT
ATOM   4886  C    LEU  323    -0.847  21.309  38.504  1.00  4.74      PROT
ATOM   4887  O    LEU  323    -1.984  21.761  38.613  1.00  5.05      PROT
ATOM   4888  CB   LEU  323     0.026  23.040  36.919  1.00  3.76      PROT
ATOM   4889  CG   LEU  323     0.633  23.438  35.572  1.00  3.83      PROT
ATOM   4890  CD1  LEU  323     0.529  24.955  35.396  1.00  3.97      PROT
ATOM   4891  CD2  LEU  323     2.086  22.960  35.431  1.00  3.24      PROT
ATOM   4903  N    PRO  324    -0.257  20.559  39.461  1.00  5.15      PROT
ATOM   4904  CA   PRO  324    -0.859  20.425  40.787  1.00  5.43      PROT
ATOM   4905  C    PRO  324    -1.269  21.771  41.385  1.00  5.45      PROT
ATOM   4906  O    PRO  324    -0.454  22.705  41.466  1.00  5.97      PROT
ATOM   4907  CB   PRO  324     0.254  19.760  41.613  1.00  5.87      PROT
ATOM   4908  CG   PRO  324     0.980  18.928  40.620  1.00  5.37      PROT
ATOM   4909  CD   PRO  324     0.975  19.754  39.344  1.00  5.31      PROT
ATOM   4917  N    GLY  325    -2.546  21.882  41.738  1.00  4.92      PROT
ATOM   4918  CA   GLY  325    -3.059  23.084  42.389  1.00  5.21      PROT
ATOM   4919  C    GLY  325    -3.357  24.265  41.475  1.00  4.78      PROT
ATOM   4920  O    GLY  325    -3.784  25.304  41.953  1.00  5.22      PROT
ATOM   4924  N    GLN  326    -3.146  24.094  40.169  1.00  4.76      PROT
ATOM   4925  CA   GLN  326    -3.353  25.140  39.184  1.00  3.97      PROT
ATOM   4926  C    GLN  326    -4.088  24.571  37.960  1.00  4.48      PROT
ATOM   4927  O    GLN  326    -3.447  23.985  37.073  1.00  4.16      PROT
ATOM   4928  CB   GLN  326    -2.001  25.775  38.810  1.00  4.15      PROT
ATOM   4929  CG   GLN  326    -2.030  26.872  37.752  1.00  3.12      PROT
ATOM   4930  CD   GLN  326    -2.969  28.029  38.081  1.00  2.39      PROT
ATOM   4931  OE1  GLN  326    -2.605  28.969  38.800  1.00  3.42      PROT
ATOM   4932  NE2  GLN  326    -4.158  27.985  37.522  1.00  2.00      PROT
ATOM   4941  N    PRO  327    -5.433  24.731  37.921  1.00  4.21      PROT
ATOM   4942  CA   PRO  327    -6.269  24.234  36.839  1.00  4.49      PROT
ATOM   4943  C    PRO  327    -5.943  24.786  35.439  1.00  3.59      PROT
ATOM   4944  O    PRO  327    -6.208  24.104  34.472  1.00  3.93      PROT
ATOM   4945  CB   PRO  327    -7.683  24.643  37.267  1.00  4.40      PROT
ATOM   4946  CG   PRO  327    -7.520  25.726  38.215  1.00  5.15      PROT
ATOM   4947  CD   PRO  327    -6.247  25.423  38.943  1.00  5.18      PROT
ATOM   4955  N    ASP  328    -5.376  25.998  35.339  1.00  3.56      PROT
ATOM   4956  CA   ASP  328    -4.942  26.566  34.058  1.00  3.17      PROT
ATOM   4957  C    ASP  328    -3.544  26.032  33.763  1.00  3.26      PROT
ATOM   4958  O    ASP  328    -2.631  26.208  34.575  1.00  3.41      PROT
ATOM   4959  CB   ASP  328    -4.937  28.120  34.104  1.00  3.03      PROT
ATOM   4960  CG   ASP  328    -4.693  28.783  32.734  1.00  4.77      PROT
ATOM   4961  OD1  ASP  328    -4.506  28.081  31.724  1.00  4.72      PROT
ATOM   4962  OD2  ASP  328    -4.724  30.044  32.657  1.00  5.52      PROT
ATOM   4967  N    ASN  329    -3.398  25.351  32.625  1.00  3.26      PROT
ATOM   4968  CA   ASN  329    -2.104  24.839  32.168  1.00  4.54      PROT
ATOM   4969  C    ASN  329    -1.113  25.933  31.780  1.00  4.26      PROT
ATOM   4970  O    ASN  329     0.106  25.695  31.734  1.00  4.93      PROT
ATOM   4971  CB   ASN  329    -2.285  23.928  30.944  1.00  4.27      PROT
ATOM   4972  CG   ASN  329    -2.903  22.574  31.284  1.00  6.01      PROT
ATOM   4973  OD1  ASN  329    -3.054  22.213  32.447  1.00  6.63      PROT
ATOM   4974  ND2  ASN  329    -3.259  21.810  30.241  1.00  6.33      PROT
ATOM   4981  N    THR  330    -1.641  27.112  31.457  1.00  3.79      PROT
```

Figure 3 cont.

```
ATOM   4982  CA   THR   330      -0.808   28.282   31.137  1.00   3.65      PROT
ATOM   4983  C    THR   330      -1.210   29.481   31.997  1.00   2.93      PROT
ATOM   4984  O    THR   330      -1.678   30.503   31.471  1.00   2.00      PROT
ATOM   4985  CB   THR   330      -0.887   28.655   29.626  1.00   3.63      PROT
ATOM   4986  OG1  THR   330      -2.240   28.583   29.177  1.00   3.40      PROT
ATOM   4987  CG2  THR   330      -0.018   27.722   28.773  1.00   7.14      PROT
ATOM   4994  N    PRO   331      -1.004   29.382   33.329  1.00   2.60      PROT
ATOM   4995  CA   PRO   331      -1.559   30.397   34.203  1.00   3.12      PROT
ATOM   4996  C    PRO   331      -0.751   31.699   34.116  1.00   2.86      PROT
ATOM   4997  O    PRO   331       0.368   31.685   33.568  1.00   2.71      PROT
ATOM   4998  CB   PRO   331      -1.407   29.760   35.594  1.00   2.95      PROT
ATOM   4999  CG   PRO   331      -0.153   28.989   35.483  1.00   2.89      PROT
ATOM   5000  CD   PRO   331      -0.219   28.391   34.096  1.00   3.08      PROT
ATOM   5008  N    PRO   332      -1.319   32.817   34.622  1.00   3.75      PROT
ATOM   5009  CA   PRO   332      -0.616   34.107   34.737  1.00   3.67      PROT
ATOM   5010  C    PRO   332       0.665   33.998   35.550  1.00   3.37      PROT
ATOM   5011  O    PRO   332       0.658   33.484   36.693  1.00   3.50      PROT
ATOM   5012  CB   PRO   332      -1.608   35.003   35.477  1.00   4.18      PROT
ATOM   5013  CG   PRO   332      -2.632   34.074   36.042  1.00   5.00      PROT
ATOM   5014  CD   PRO   332      -2.697   32.908   35.132  1.00   3.74      PROT
ATOM   5022  N    GLY   333       1.755   34.381   34.956  1.00   2.28      PROT
ATOM   5023  CA   GLY   333       3.076   34.313   35.520  1.00   2.91      PROT
ATOM   5024  C    GLY   333       3.683   32.921   35.423  1.00   2.99      PROT
ATOM   5025  O    GLY   333       4.791   32.721   35.906  1.00   3.97      PROT
ATOM   5029  N    GLY   334       2.960   31.965   34.837  1.00   2.83      PROT
ATOM   5030  CA   GLY   334       3.486   30.616   34.583  1.00   2.33      PROT
ATOM   5031  C    GLY   334       4.519   30.738   33.484  1.00   2.69      PROT
ATOM   5032  O    GLY   334       4.343   31.540   32.588  1.00   2.36      PROT
ATOM   5036  N    ALA   335       5.613   29.991   33.594  1.00   2.62      PROT
ATOM   5037  CA   ALA   335       6.730   30.111   32.662  1.00   3.34      PROT
ATOM   5038  C    ALA   335       7.379   28.773   32.364  1.00   3.69      PROT
ATOM   5039  O    ALA   335       7.595   27.945   33.268  1.00   4.06      PROT
ATOM   5040  CB   ALA   335       7.783   31.093   33.210  1.00   3.15      PROT
ATOM   5046  N    LEU   336       7.734   28.592   31.095  1.00   4.32      PROT
ATOM   5047  CA   LEU   336       8.668   27.550   30.667  1.00   4.62      PROT
ATOM   5048  C    LEU   336      10.112   27.992   30.943  1.00   4.82      PROT
ATOM   5049  O    LEU   336      10.581   29.035   30.427  1.00   3.97      PROT
ATOM   5050  CB   LEU   336       8.487   27.274   29.174  1.00   4.66      PROT
ATOM   5051  CG   LEU   336       7.858   26.018   28.576  1.00   6.34      PROT
ATOM   5052  CD1  LEU   336       6.997   25.205   29.544  1.00   6.16      PROT
ATOM   5053  CD2  LEU   336       7.132   26.350   27.236  1.00   5.88      PROT
ATOM   5065  N    VAL   337      10.812   27.196   31.750  1.00   3.62      PROT
ATOM   5066  CA   VAL   337      12.170   27.524   32.177  1.00   3.27      PROT
ATOM   5067  C    VAL   337      13.123   26.521   31.550  1.00   3.62      PROT
ATOM   5068  O    VAL   337      13.118   25.339   31.910  1.00   3.55      PROT
ATOM   5069  CB   VAL   337      12.286   27.585   33.734  1.00   3.42      PROT
ATOM   5070  CG1  VAL   337      13.702   27.977   34.189  1.00   2.20      PROT
ATOM   5071  CG2  VAL   337      11.302   28.589   34.295  1.00   3.28      PROT
ATOM   5081  N    PHE   338      13.893   27.003   30.572  1.00   3.31      PROT
ATOM   5082  CA   PHE   338      14.894   26.213   29.886  1.00   4.21      PROT
ATOM   5083  C    PHE   338      16.239   26.483   30.544  1.00   4.44      PROT
ATOM   5084  O    PHE   338      16.661   27.633   30.691  1.00   4.06      PROT
ATOM   5085  CB   PHE   338      14.970   26.580   28.402  1.00   3.55      PROT
ATOM   5086  CG   PHE   338      13.682   26.364   27.641  1.00   4.01      PROT
ATOM   5087  CD1  PHE   338      13.530   25.256   26.819  1.00   5.16      PROT
ATOM   5088  CD2  PHE   338      12.633   27.281   27.736  1.00   4.22      PROT
ATOM   5089  CE1  PHE   338      12.334   25.043   26.098  1.00   6.41      PROT
ATOM   5090  CE2  PHE   338      11.441   27.086   27.024  1.00   3.64      PROT
ATOM   5091  CZ   PHE   338      11.294   25.968   26.208  1.00   4.82      PROT
ATOM   5101  N    GLU   339      16.907   25.421   30.944  1.00   4.45      PROT
ATOM   5102  CA   GLU   339      18.198   25.554   31.610  1.00   5.01      PROT
ATOM   5103  C    GLU   339      19.276   24.840   30.808  1.00   4.78      PROT
ATOM   5104  O    GLU   339      19.076   23.695   30.411  1.00   4.66      PROT
ATOM   5105  CB   GLU   339      18.119   24.951   33.004  1.00   5.11      PROT
ATOM   5106  CG   GLU   339      17.179   25.691   33.935  1.00   7.82      PROT
```

Figure 3 cont.

```
ATOM   5107  CD   GLU  339      16.869  24.916  35.197  1.00 12.08      PROT
ATOM   5108  OE1  GLU  339      17.199  23.712  35.272  1.00 14.47      PROT
ATOM   5109  OE2  GLU  339      16.300  25.518  36.125  1.00 13.95      PROT
ATOM   5116  N    ARG  340      20.400  25.522  30.578  1.00  4.68      PROT
ATOM   5117  CA   ARG  340      21.614  24.910  30.021  1.00  5.03      PROT
ATOM   5118  C    ARG  340      22.499  24.410  31.164  1.00  4.37      PROT
ATOM   5119  O    ARG  340      22.935  25.193  32.022  1.00  3.21      PROT
ATOM   5120  CB   ARG  340      22.388  25.893  29.133  1.00  4.96      PROT
ATOM   5121  CG   ARG  340      23.591  25.300  28.391  1.00  7.01      PROT
ATOM   5122  CD   ARG  340      24.611  26.383  27.962  1.00  7.29      PROT
ATOM   5123  NE   ARG  340      25.515  25.927  26.893  1.00 12.53      PROT
ATOM   5124  CZ   ARG  340      26.723  25.398  27.081  1.00 14.36      PROT
ATOM   5125  NH1  ARG  340      27.204  25.238  28.300  1.00 17.14      PROT
ATOM   5126  NH2  ARG  340      27.465  25.026  26.048  1.00 15.00      PROT
ATOM   5140  N    TRP  341      22.737  23.096  31.174  1.00  3.97      PROT
ATOM   5141  CA   TRP  341      23.539  22.439  32.202  1.00  4.09      PROT
ATOM   5142  C    TRP  341      24.771  21.841  31.559  1.00  4.50      PROT
ATOM   5143  O    TRP  341      24.704  21.367  30.423  1.00  4.22      PROT
ATOM   5144  CB   TRP  341      22.742  21.316  32.880  1.00  4.51      PROT
ATOM   5145  CG   TRP  341      21.699  21.773  33.856  1.00  3.65      PROT
ATOM   5146  CD1  TRP  341      20.376  22.013  33.593  1.00  4.03      PROT
ATOM   5147  CD2  TRP  341      21.885  22.034  35.252  1.00  4.22      PROT
ATOM   5148  NE1  TRP  341      19.735  22.408  34.739  1.00  3.92      PROT
ATOM   5149  CE2  TRP  341      20.637  22.430  35.771  1.00  3.81      PROT
ATOM   5150  CE3  TRP  341      22.989  21.969  36.121  1.00  3.62      PROT
ATOM   5151  CZ2  TRP  341      20.457  22.769  37.119  1.00  4.76      PROT
ATOM   5152  CZ3  TRP  341      22.810  22.295  37.453  1.00  4.50      PROT
ATOM   5153  CH2  TRP  341      21.554  22.696  37.940  1.00  4.15      PROT
ATOM   5164  N    VAL  342      25.898  21.875  32.271  1.00  4.71      PROT
ATOM   5165  CA   VAL  342      27.070  21.083  31.887  1.00  5.12      PROT
ATOM   5166  C    VAL  342      27.494  20.129  32.996  1.00  4.93      PROT
ATOM   5167  O    VAL  342      27.492  20.489  34.177  1.00  5.09      PROT
ATOM   5168  CB   VAL  342      28.289  21.943  31.422  1.00  5.51      PROT
ATOM   5169  CG1  VAL  342      28.807  22.845  32.553  1.00  6.56      PROT
ATOM   5170  CG2  VAL  342      27.923  22.760  30.202  1.00  6.74      PROT
ATOM   5180  N    ASP  343      27.870  18.912  32.612  1.00  4.45      PROT
ATOM   5181  CA   ASP  343      28.392  17.949  33.572  1.00  4.24      PROT
ATOM   5182  C    ASP  343      29.908  18.082  33.748  1.00  4.62      PROT
ATOM   5183  O    ASP  343      30.526  18.997  33.192  1.00  4.72      PROT
ATOM   5184  CB   ASP  343      28.005  16.516  33.174  1.00  3.93      PROT
ATOM   5185  CG   ASP  343      28.683  16.036  31.889  1.00  2.84      PROT
ATOM   5186  OD1  ASP  343      29.624  16.682  31.383  1.00  2.00      PROT
ATOM   5187  OD2  ASP  343      28.265  14.974  31.385  1.00  3.69      PROT
ATOM   5192  N    ASN  344      30.458  17.157  34.540  1.00  4.90      PROT
ATOM   5193  CA   ASN  344      31.889  16.876  34.747  1.00  5.40      PROT
ATOM   5194  C    ASN  344      32.784  17.068  33.519  1.00  5.27      PROT
ATOM   5195  O    ASN  344      33.895  17.606  33.617  1.00  5.66      PROT
ATOM   5196  CB   ASN  344      32.001  15.396  35.166  1.00  5.75      PROT
ATOM   5197  CG   ASN  344      32.744  15.197  36.464  1.00  7.06      PROT
ATOM   5198  OD1  ASN  344      33.976  15.180  36.498  1.00 11.04      PROT
ATOM   5199  ND2  ASN  344      31.998  14.997  37.541  1.00  8.19      PROT
ATOM   5206  N    ALA  345      32.308  16.592  32.372  1.00  4.45      PROT
ATOM   5207  CA   ALA  345      33.108  16.536  31.151  1.00  4.03      PROT
ATOM   5208  C    ALA  345      32.771  17.660  30.178  1.00  3.98      PROT
ATOM   5209  O    ALA  345      33.197  17.636  29.016  1.00  4.09      PROT
ATOM   5210  CB   ALA  345      32.924  15.185  30.479  1.00  4.00      PROT
ATOM   5216  N    GLY  346      31.995  18.635  30.644  1.00  3.89      PROT
ATOM   5217  CA   GLY  346      31.622  19.773  29.821  1.00  3.87      PROT
ATOM   5218  C    GLY  346      30.577  19.464  28.766  1.00  4.15      PROT
ATOM   5219  O    GLY  346      30.397  20.244  27.822  1.00  4.56      PROT
ATOM   5223  N    LYS  347      29.882  18.336  28.912  1.00  3.35      PROT
ATOM   5224  CA   LYS  347      28.781  18.033  28.006  1.00  3.39      PROT
ATOM   5225  C    LYS  347      27.571  18.878  28.390  1.00  2.53      PROT
ATOM   5226  O    LYS  347      27.125  18.820  29.536  1.00  2.10      PROT
ATOM   5227  CB   LYS  347      28.430  16.541  28.007  1.00  3.15      PROT
```

Figure 3 cont.

```
ATOM   5228  CG   LYS  347     27.350  16.179  26.982  1.00  3.71        PROT
ATOM   5229  CD   LYS  347     27.065  14.686  26.935  1.00  4.66        PROT
ATOM   5230  CE   LYS  347     25.818  14.395  26.080  1.00  7.37        PROT
ATOM   5231  NZ   LYS  347     26.052  14.673  24.628  1.00  7.31        PROT
ATOM   5245  N    PRO  348     27.054  19.684  27.439  1.00  2.45        PROT
ATOM   5246  CA   PRO  348     25.890  20.527  27.717  1.00  2.33        PROT
ATOM   5247  C    PRO  348     24.558  19.793  27.532  1.00  2.32        PROT
ATOM   5248  O    PRO  348     24.384  19.019  26.577  1.00  2.07        PROT
ATOM   5249  CB   PRO  348     26.029  21.666  26.705  1.00  2.65        PROT
ATOM   5250  CG   PRO  348     26.777  21.056  25.545  1.00  2.31        PROT
ATOM   5251  CD   PRO  348     27.540  19.852  26.056  1.00  2.61        PROT
ATOM   5259  N    TYR  349     23.646  20.040  28.465  1.00  2.47        PROT
ATOM   5260  CA   TYR  349     22.294  19.502  28.436  1.00  2.44        PROT
ATOM   5261  C    TYR  349     21.291  20.640  28.547  1.00  2.33        PROT
ATOM   5262  O    TYR  349     21.630  21.753  28.990  1.00  2.00        PROT
ATOM   5263  CB   TYR  349     22.063  18.546  29.604  1.00  3.09        PROT
ATOM   5264  CG   TYR  349     23.063  17.426  29.735  1.00  4.05        PROT
ATOM   5265  CD1  TYR  349     22.768  16.156  29.257  1.00  4.11        PROT
ATOM   5266  CD2  TYR  349     24.293  17.629  30.357  1.00  4.33        PROT
ATOM   5267  CE1  TYR  349     23.678  15.118  29.376  1.00  5.80        PROT
ATOM   5268  CE2  TYR  349     25.212  16.596  30.482  1.00  4.72        PROT
ATOM   5269  CZ   TYR  349     24.895  15.342  29.988  1.00  5.06        PROT
ATOM   5270  OH   TYR  349     25.785  14.304  30.108  1.00  4.73        PROT
ATOM   5279  N    VAL  350     20.063  20.336  28.131  1.00  2.28        PROT
ATOM   5280  CA   VAL  350     18.900  21.165  28.329  1.00  2.90        PROT
ATOM   5281  C    VAL  350     17.926  20.446  29.261  1.00  3.29        PROT
ATOM   5282  O    VAL  350     17.685  19.239  29.148  1.00  3.46        PROT
ATOM   5283  CB   VAL  350     18.191  21.529  26.994  1.00  3.06        PROT
ATOM   5284  CG1  VAL  350     16.988  22.418  27.254  1.00  2.59        PROT
ATOM   5285  CG2  VAL  350     19.157  22.243  26.037  1.00  3.35        PROT
ATOM   5295  N    SER  351     17.392  21.208  30.195  1.00  3.62        PROT
ATOM   5296  CA   SER  351     16.367  20.751  31.102  1.00  4.47        PROT
ATOM   5297  C    SER  351     15.225  21.750  30.974  1.00  4.38        PROT
ATOM   5298  O    SER  351     15.465  22.947  30.789  1.00  4.62        PROT
ATOM   5299  CB   SER  351     16.914  20.760  32.528  1.00  4.82        PROT
ATOM   5300  OG   SER  351     16.158  19.889  33.349  1.00  7.33        PROT
ATOM   5305  N    VAL  352     13.989  21.272  31.062  1.00  4.04        PROT
ATOM   5306  CA   VAL  352     12.833  22.160  30.969  1.00  3.57        PROT
ATOM   5307  C    VAL  352     11.847  21.916  32.097  1.00  3.71        PROT
ATOM   5308  O    VAL  352     11.451  20.780  32.373  1.00  3.29        PROT
ATOM   5309  CB   VAL  352     12.084  22.035  29.624  1.00  3.51        PROT
ATOM   5310  CG1  VAL  352     11.158  23.215  29.448  1.00  2.69        PROT
ATOM   5311  CG2  VAL  352     13.058  21.942  28.462  1.00  2.63        PROT
ATOM   5321  N    ASN  353     11.471  23.006  32.751  1.00  3.66        PROT
ATOM   5322  CA   ASN  353     10.466  22.979  33.788  1.00  4.40        PROT
ATOM   5323  C    ASN  353      9.326  23.943  33.530  1.00  4.77        PROT
ATOM   5324  O    ASN  353      9.546  25.045  32.997  1.00  4.84        PROT
ATOM   5325  CB   ASN  353     11.095  23.315  35.131  1.00  4.68        PROT
ATOM   5326  CG   ASN  353     12.036  22.242  35.613  1.00  6.13        PROT
ATOM   5327  OD1  ASN  353     13.196  22.183  35.199  1.00  9.71        PROT
ATOM   5328  ND2  ASN  353     11.554  21.404  36.523  1.00  6.41        PROT
ATOM   5335  N    MET  354      8.121  23.551  33.941  1.00  4.16        PROT
ATOM   5336  CA   MET  354      7.034  24.521  34.035  1.00  4.54        PROT
ATOM   5337  C    MET  354      6.885  25.013  35.470  1.00  4.11        PROT
ATOM   5338  O    MET  354      6.540  24.262  36.374  1.00  3.99        PROT
ATOM   5339  CB   MET  354      5.717  23.973  33.484  1.00  4.79        PROT
ATOM   5340  CG   MET  354      4.601  25.003  33.467  1.00  6.37        PROT
ATOM   5341  SD   MET  354      4.799  26.307  32.235  1.00  9.36        PROT
ATOM   5342  CE   MET  354      3.182  27.060  32.386  1.00  7.20        PROT
ATOM   5352  N    VAL  355      7.160  26.296  35.657  1.00  4.58        PROT
ATOM   5353  CA   VAL  355      7.235  26.917  36.977  1.00  4.86        PROT
ATOM   5354  C    VAL  355      6.042  27.849  37.104  1.00  4.85        PROT
ATOM   5355  O    VAL  355      5.778  28.631  36.196  1.00  5.49        PROT
ATOM   5356  CB   VAL  355      8.566  27.699  37.132  1.00  5.10        PROT
ATOM   5357  CG1  VAL  355      8.686  28.303  38.516  1.00  5.69        PROT
```

Figure 3 cont.

```
ATOM   5358  CG2  VAL  355     9.766  26.762  36.859  1.00  6.13      PROT
ATOM   5368  N    TYR  356     5.326  27.780  38.224  1.00  4.58      PROT
ATOM   5369  CA   TYR  356     4.031  28.448  38.314  1.00  3.94      PROT
ATOM   5370  C    TYR  356     3.638  28.697  39.759  1.00  3.64      PROT
ATOM   5371  O    TYR  356     4.162  28.053  40.678  1.00  4.24      PROT
ATOM   5372  CB   TYR  356     2.952  27.586  37.619  1.00  3.46      PROT
ATOM   5373  CG   TYR  356     2.690  26.299  38.360  1.00  2.83      PROT
ATOM   5374  CD1  TYR  356     3.535  25.204  38.204  1.00  3.31      PROT
ATOM   5375  CD2  TYR  356     1.615  26.187  39.239  1.00  3.22      PROT
ATOM   5376  CE1  TYR  356     3.314  24.037  38.889  1.00  3.12      PROT
ATOM   5377  CE2  TYR  356     1.384  25.029  39.940  1.00  2.03      PROT
ATOM   5378  CZ   TYR  356     2.243  23.957  39.766  1.00  4.66      PROT
ATOM   5379  OH   TYR  356     2.036  22.797  40.458  1.00  3.09      PROT
ATOM   5388  N    GLN  357     2.731  29.645  39.954  1.00  2.58      PROT
ATOM   5389  CA   GLN  357     2.007  29.792  41.222  1.00  2.57      PROT
ATOM   5390  C    GLN  357     0.717  28.962  41.186  1.00  2.10      PROT
ATOM   5391  O    GLN  357    -0.037  29.034  40.221  1.00  2.00      PROT
ATOM   5392  CB   GLN  357     1.687  31.267  41.486  1.00  2.00      PROT
ATOM   5393  CG   GLN  357     2.910  32.094  41.953  1.00  3.39      PROT
ATOM   5394  CD   GLN  357     2.903  33.536  41.467  1.00  2.38      PROT
ATOM   5395  OE1  GLN  357     3.076  34.478  42.261  1.00  4.96      PROT
ATOM   5396  NE2  GLN  357     2.702  33.724  40.172  1.00  2.00      PROT
ATOM   5405  N    THR  358     0.478  28.168  42.234  1.00  2.00      PROT
ATOM   5406  CA   THR  358    -0.805  27.477  42.393  1.00  2.02      PROT
ATOM   5407  C    THR  358    -1.901  28.516  42.437  1.00  2.14      PROT
ATOM   5408  O    THR  358    -1.620  29.707  42.630  1.00  2.00      PROT
ATOM   5409  CB   THR  358    -0.880  26.640  43.687  1.00  2.00      PROT
ATOM   5410  OG1  THR  358    -0.745  27.498  44.827  1.00  2.00      PROT
ATOM   5411  CG2  THR  358     0.203  25.585  43.701  1.00  2.00      PROT
ATOM   5418  N    LEU  359    -3.144  28.092  42.240  1.00  2.55      PROT
ATOM   5419  CA   LEU  359    -4.249  29.050  42.275  1.00  3.53      PROT
ATOM   5420  C    LEU  359    -4.381  29.698  43.665  1.00  3.50      PROT
ATOM   5421  O    LEU  359    -4.680  30.903  43.775  1.00  3.18      PROT
ATOM   5422  CB   LEU  359    -5.558  28.415  41.773  1.00  3.89      PROT
ATOM   5423  CG   LEU  359    -6.808  29.286  41.563  1.00  3.74      PROT
ATOM   5424  CD1  LEU  359    -6.588  30.456  40.600  1.00  3.16      PROT
ATOM   5425  CD2  LEU  359    -7.991  28.401  41.128  1.00  4.92      PROT
ATOM   5437  N    ALA  360    -4.129  28.915  44.717  1.00  2.90      PROT
ATOM   5438  CA   ALA  360    -4.097  29.457  46.076  1.00  3.11      PROT
ATOM   5439  C    ALA  360    -2.933  30.430  46.300  1.00  2.80      PROT
ATOM   5440  O    ALA  360    -3.097  31.424  46.996  1.00  3.30      PROT
ATOM   5441  CB   ALA  360    -4.108  28.338  47.139  1.00  3.28      PROT
ATOM   5447  N    GLN  361    -1.770  30.172  45.703  1.00  3.29      PROT
ATOM   5448  CA   GLN  361    -0.639  31.106  45.810  1.00  3.37      PROT
ATOM   5449  C    GLN  361    -0.935  32.486  45.191  1.00  3.34      PROT
ATOM   5450  O    GLN  361    -0.459  33.509  45.677  1.00  3.39      PROT
ATOM   5451  CB   GLN  361     0.638  30.500  45.224  1.00  3.24      PROT
ATOM   5452  CG   GLN  361     1.375  29.589  46.208  1.00  3.85      PROT
ATOM   5453  CD   GLN  361     2.460  28.749  45.555  1.00  3.80      PROT
ATOM   5454  OE1  GLN  361     2.389  28.433  44.365  1.00  2.00      PROT
ATOM   5455  NE2  GLN  361     3.486  28.402  46.332  1.00  4.40      PROT
ATOM   5464  N    LEU  362    -1.729  32.495  44.127  1.00  3.01      PROT
ATOM   5465  CA   LEU  362    -2.152  33.731  43.473  1.00  3.73      PROT
ATOM   5466  C    LEU  362    -3.194  34.452  44.298  1.00  3.56      PROT
ATOM   5467  O    LEU  362    -3.110  35.661  44.484  1.00  3.77      PROT
ATOM   5468  CB   LEU  362    -2.739  33.437  42.095  1.00  3.02      PROT
ATOM   5469  CG   LEU  362    -1.761  32.931  41.045  1.00  4.31      PROT
ATOM   5470  CD1  LEU  362    -2.539  32.458  39.851  1.00  3.00      PROT
ATOM   5471  CD2  LEU  362    -0.758  34.040  40.678  1.00  3.22      PROT
ATOM   5483  N    HSD  363    -4.177  33.703  44.785  1.00  3.82      PROT
ATOM   5484  CA   HSD  363    -5.260  34.283  45.584  1.00  4.30      PROT
ATOM   5485  C    HSD  363    -4.730  34.839  46.899  1.00  4.44      PROT
ATOM   5486  O    HSD  363    -5.135  35.915  47.338  1.00  4.87      PROT
ATOM   5487  CB   HSD  363    -6.363  33.254  45.837  1.00  4.13      PROT
ATOM   5488  CG   HSD  363    -7.626  33.843  46.387  1.00  5.46      PROT
```

Figure 3 cont.

```
ATOM   5489  ND1  HSD   363      -8.036   33.643   47.690  1.00   7.86      PROT
ATOM   5490  CD2  HSD   363      -8.564   34.634   45.814  1.00   4.16      PROT
ATOM   5491  CE1  HSD   363      -9.178   34.275   47.890  1.00   7.35      PROT
ATOM   5492  NE2  HSD   363      -9.520   34.881   46.766  1.00   7.63      PROT
ATOM   5500  N    ASP   364      -3.799   34.109   47.505  1.00   4.67      PROT
ATOM   5501  CA   ASP   364      -3.238   34.475   48.783  1.00   4.76      PROT
ATOM   5502  C    ASP   364      -2.037   35.420   48.662  1.00   4.40      PROT
ATOM   5503  O    ASP   364      -1.551   35.928   49.667  1.00   4.17      PROT
ATOM   5504  CB   ASP   364      -2.856   33.208   49.580  1.00   5.41      PROT
ATOM   5505  CG   ASP   364      -4.054   32.287   49.837  1.00   7.09      PROT
ATOM   5506  OD1  ASP   364      -5.207   32.692   49.573  1.00   8.62      PROT
ATOM   5507  OD2  ASP   364      -3.840   31.140   50.281  1.00   9.49      PROT
ATOM   5512  N    GLN   365      -1.587   35.664   47.436  1.00   4.26      PROT
ATOM   5513  CA   GLN   365      -0.345   36.403   47.165  1.00   3.68      PROT
ATOM   5514  C    GLN   365       0.809   35.861   48.021  1.00   2.79      PROT
ATOM   5515  O    GLN   365       1.556   36.622   48.620  1.00   2.38      PROT
ATOM   5516  CB   GLN   365      -0.538   37.917   47.360  1.00   3.68      PROT
ATOM   5517  CG   GLN   365      -1.497   38.582   46.378  1.00   5.70      PROT
ATOM   5518  CD   GLN   365      -1.630   40.074   46.651  1.00   6.77      PROT
ATOM   5519  OE1  GLN   365      -2.239   40.491   47.649  1.00  10.89      PROT
ATOM   5520  NE2  GLN   365      -1.040   40.880   45.789  1.00   9.97      PROT
ATOM   5529  N    ALA   366       0.938   34.535   48.058  1.00   2.21      PROT
ATOM   5530  CA   ALA   366       1.917   33.853   48.910  1.00   2.51      PROT
ATOM   5531  C    ALA   366       3.365   34.199   48.557  1.00   2.38      PROT
ATOM   5532  O    ALA   366       3.724   34.194   47.372  1.00   2.00      PROT
ATOM   5533  CB   ALA   366       1.712   32.347   48.843  1.00   2.00      PROT
ATOM   5539  N    PRO   367       4.190   34.527   49.577  1.00   2.89      PROT
ATOM   5540  CA   PRO   367       5.641   34.702   49.376  1.00   3.01      PROT
ATOM   5541  C    PRO   367       6.263   33.411   48.830  1.00   3.62      PROT
ATOM   5542  O    PRO   367       5.872   32.308   49.231  1.00   4.09      PROT
ATOM   5543  CB   PRO   367       6.153   35.017   50.791  1.00   3.66      PROT
ATOM   5544  CG   PRO   367       4.979   35.617   51.474  1.00   3.72      PROT
ATOM   5545  CD   PRO   367       3.816   34.796   50.980  1.00   2.86      PROT
ATOM   5553  N    LEU   368       7.178   33.550   47.875  1.00   3.23      PROT
ATOM   5554  CA   LEU   368       7.784   32.406   47.219  1.00   3.42      PROT
ATOM   5555  C    LEU   368       9.275   32.358   47.529  1.00   3.81      PROT
ATOM   5556  O    LEU   368      10.034   33.263   47.149  1.00   4.15      PROT
ATOM   5557  CB   LEU   368       7.535   32.450   45.706  1.00   2.79      PROT
ATOM   5558  CG   LEU   368       6.082   32.498   45.215  1.00   2.23      PROT
ATOM   5559  CD1  LEU   368       6.096   32.595   43.692  1.00   2.00      PROT
ATOM   5560  CD2  LEU   368       5.253   31.289   45.674  1.00   2.00      PROT
ATOM   5572  N    THR   369       9.677   31.300   48.229  1.00   3.36      PROT
ATOM   5573  CA   THR   369      11.042   31.162   48.740  1.00   3.13      PROT
ATOM   5574  C    THR   369      11.492   29.717   48.552  1.00   2.98      PROT
ATOM   5575  O    THR   369      10.683   28.881   48.258  1.00   3.03      PROT
ATOM   5576  CB   THR   369      11.084   31.448   50.247  1.00   2.50      PROT
ATOM   5577  OG1  THR   369      10.268   30.486   50.919  1.00   3.94      PROT
ATOM   5578  CG2  THR   369      10.583   32.865   50.577  1.00   2.02      PROT
ATOM   5585  N    LEU   370      12.778   29.419   48.753  1.00   3.81      PROT
ATOM   5586  CA   LEU   370      13.272   28.034   48.642  1.00   4.43      PROT
ATOM   5587  C    LEU   370      12.571   27.065   49.603  1.00   4.26      PROT
ATOM   5588  O    LEU   370      12.352   25.891   49.282  1.00   4.08      PROT
ATOM   5589  CB   LEU   370      14.786   27.993   48.855  1.00   5.24      PROT
ATOM   5590  CG   LEU   370      15.698   27.988   47.614  1.00   6.30      PROT
ATOM   5591  CD1  LEU   370      17.010   28.658   47.960  1.00   8.65      PROT
ATOM   5592  CD2  LEU   370      15.075   28.601   46.351  1.00   9.02      PROT
ATOM   5604  N    GLN   371      12.203   27.571   50.775  1.00   4.01      PROT
ATOM   5605  CA   GLN   371      11.481   26.774   51.753  1.00   4.81      PROT
ATOM   5606  C    GLN   371       9.999   26.714   51.444  1.00   4.40      PROT
ATOM   5607  O    GLN   371       9.319   25.751   51.820  1.00   4.04      PROT
ATOM   5608  CB   GLN   371      11.724   27.304   53.172  1.00   5.32      PROT
ATOM   5609  CG   GLN   371      13.171   27.165   53.648  1.00   8.93      PROT
ATOM   5610  CD   GLN   371      13.546   25.747   54.110  1.00  13.11      PROT
ATOM   5611  OE1  GLN   371      13.183   24.746   53.482  1.00  16.05      PROT
ATOM   5612  NE2  GLN   371      14.291   25.667   55.208  1.00  14.54      PROT
```

Figure 3 cont.

```
ATOM   5621 N    HSD 372      9.498  27.737  50.753  1.00  3.76      PROT
ATOM   5622 CA   HSD 372      8.087  27.785  50.388  1.00  4.03      PROT
ATOM   5623 C    HSD 372      7.926  28.118  48.899  1.00  3.57      PROT
ATOM   5624 O    HSD 372      7.416  29.181  48.548  1.00  3.41      PROT
ATOM   5625 CB   HSD 372      7.358  28.792  51.297  1.00  3.91      PROT
ATOM   5626 CG   HSD 372      7.399  28.419  52.747  1.00  4.12      PROT
ATOM   5627 ND1  HSD 372      8.234  29.032  53.655  1.00  2.79      PROT
ATOM   5628 CD2  HSD 372      6.737  27.460  53.437  1.00  3.90      PROT
ATOM   5629 CE1  HSD 372      8.068  28.487  54.844  1.00  2.96      PROT
ATOM   5630 NE2  HSD 372      7.171  27.526  54.737  1.00  4.03      PROT
ATOM   5638 N    PRO 373      8.346  27.188  48.013  1.00  3.63      PROT
ATOM   5639 CA   PRO 373      8.498  27.508  46.590  1.00  3.77      PROT
ATOM   5640 C    PRO 373      7.228  27.606  45.754  1.00  3.68      PROT
ATOM   5641 O    PRO 373      6.155  27.148  46.159  1.00  3.95      PROT
ATOM   5642 CB   PRO 373      9.347  26.345  46.068  1.00  3.52      PROT
ATOM   5643 CG   PRO 373      9.013  25.223  46.944  1.00  4.08      PROT
ATOM   5644 CD   PRO 373      8.712  25.785  48.296  1.00  3.70      PROT
ATOM   5652 N    ALA 374      7.390  28.172  44.565  1.00  3.31      PROT
ATOM   5653 CA   ALA 374      6.408  28.044  43.516  1.00  3.58      PROT
ATOM   5654 C    ALA 374      6.358  26.580  43.084  1.00  4.02      PROT
ATOM   5655 O    ALA 374      7.326  25.821  43.266  1.00  4.05      PROT
ATOM   5656 CB   ALA 374      6.775  28.936  42.339  1.00  4.40      PROT
ATOM   5662 N    GLY 375      5.203  26.174  42.575  1.00  4.07      PROT
ATOM   5663 CA   GLY 375      5.072  24.922  41.860  1.00  4.15      PROT
ATOM   5664 C    GLY 375      6.081  24.790  40.732  1.00  4.33      PROT
ATOM   5665 O    GLY 375      6.528  25.782  40.127  1.00  2.99      PROT
ATOM   5669 N    SER 376      6.443  23.550  40.438  1.00  4.62      PROT
ATOM   5670 CA   SER 376      7.384  23.267  39.372  1.00  5.54      PROT
ATOM   5671 C    SER 376      7.186  21.843  38.873  1.00  6.07      PROT
ATOM   5672 O    SER 376      7.109  20.919  39.678  1.00  6.63      PROT
ATOM   5673 CB   SER 376      8.819  23.479  39.885  1.00  5.74      PROT
ATOM   5674 OG   SER 376      9.754  23.504  38.814  1.00  7.31      PROT
ATOM   5679 N    VAL 377      7.098  21.677  37.553  1.00  6.61      PROT
ATOM   5680 CA   VAL 377      6.932  20.362  36.912  1.00  6.56      PROT
ATOM   5681 C    VAL 377      8.084  20.149  35.932  1.00  6.45      PROT
ATOM   5682 O    VAL 377      8.270  20.926  34.989  1.00  6.91      PROT
ATOM   5683 CB   VAL 377      5.538  20.214  36.195  1.00  6.43      PROT
ATOM   5684 CG1  VAL 377      5.432  18.880  35.398  1.00  7.12      PROT
ATOM   5685 CG2  VAL 377      4.398  20.318  37.194  1.00  6.19      PROT
ATOM   5695 N    ARG 378      8.869  19.107  36.181  1.00  5.91      PROT
ATOM   5696 CA   ARG 378      9.923  18.676  35.268  1.00  6.08      PROT
ATOM   5697 C    ARG 378      9.319  18.088  33.985  1.00  5.72      PROT
ATOM   5698 O    ARG 378      8.396  17.260  34.055  1.00  5.14      PROT
ATOM   5699 CB   ARG 378     10.796  17.622  35.958  1.00  6.73      PROT
ATOM   5700 CG   ARG 378     12.109  17.390  35.267  1.00  9.58      PROT
ATOM   5701 CD   ARG 378     13.187  18.281  35.836  1.00 14.74      PROT
ATOM   5702 NE   ARG 378     14.408  18.145  35.057  1.00 17.47      PROT
ATOM   5703 CZ   ARG 378     15.622  18.010  35.578  1.00 18.90      PROT
ATOM   5704 NH1  ARG 378     15.794  17.986  36.891  1.00 21.63      PROT
ATOM   5705 NH2  ARG 378     16.664  17.886  34.776  1.00 18.67      PROT
ATOM   5719 N    LEU 379      9.835  18.491  32.822  1.00  5.29      PROT
ATOM   5720 CA   LEU 379      9.181  18.131  31.547  1.00  5.79      PROT
ATOM   5721 C    LEU 379      9.942  17.157  30.644  1.00  5.88      PROT
ATOM   5722 O    LEU 379     11.123  17.357  30.356  1.00  6.76      PROT
ATOM   5723 CB   LEU 379      8.800  19.389  30.750  1.00  5.56      PROT
ATOM   5724 CG   LEU 379      7.840  20.425  31.366  1.00  6.20      PROT
ATOM   5725 CD1  LEU 379      7.630  21.578  30.402  1.00  6.28      PROT
ATOM   5726 CD2  LEU 379      6.497  19.784  31.728  1.00  5.49      PROT
ATOM   5738 N    ASN 380      9.243  16.120  30.191  1.00  5.81      PROT
ATOM   5739 CA   ASN 380      9.754  15.207  29.167  1.00  6.00      PROT
ATOM   5740 C    ASN 380      9.602  15.835  27.791  1.00  6.11      PROT
ATOM   5741 O    ASN 380      8.587  16.467  27.494  1.00  6.05      PROT
ATOM   5742 CB   ASN 380      9.011  13.857  29.191  1.00  5.83      PROT
ATOM   5743 CG   ASN 380      9.539  12.866  28.147  1.00  5.84      PROT
ATOM   5744 OD1  ASN 380      8.851  12.518  27.174  1.00  4.68      PROT
```

Figure 3 cont.

```
ATOM   5745 ND2  ASN   380     10.764  12.412  28.344  1.00  5.73      PROT
ATOM   5752 N    ILE   381     10.638  15.684  26.976  1.00  5.95      PROT
ATOM   5753 CA   ILE   381     10.571  16.031  25.561  1.00  6.63      PROT
ATOM   5754 C    ILE   381     10.528  14.693  24.801  1.00  6.61      PROT
ATOM   5755 O    ILE   381     11.562  14.064  24.641  1.00  6.72      PROT
ATOM   5756 CB   ILE   381     11.794  16.915  25.147  1.00  6.28      PROT
ATOM   5757 CG1  ILE   381     11.793  18.251  25.915  1.00  6.46      PROT
ATOM   5758 CG2  ILE   381     11.828  17.159  23.627  1.00  6.84      PROT
ATOM   5759 CD   ILE   381     13.184  18.806  26.214  1.00  5.79      PROT
ATOM   5771 N    PRO   382      9.330  14.249  24.340  1.00  7.23      PROT
ATOM   5772 CA   PRO   382      9.205  12.900  23.738  1.00  7.48      PROT
ATOM   5773 C    PRO   382     10.175  12.652  22.580  1.00  7.62      PROT
ATOM   5774 O    PRO   382     10.711  11.551  22.451  1.00  7.64      PROT
ATOM   5775 CB   PRO   382      7.751  12.854  23.243  1.00  7.39      PROT
ATOM   5776 CG   PRO   382      7.037  13.871  24.093  1.00  8.31      PROT
ATOM   5777 CD   PRO   382      8.043  14.964  24.347  1.00  6.99      PROT
ATOM   5785 N    GLY   383     10.418  13.675  21.769  1.00  7.96      PROT
ATOM   5786 CA   GLY   383     11.341  13.567  20.639  1.00  8.59      PROT
ATOM   5787 C    GLY   383     12.773  13.268  21.044  1.00  8.98      PROT
ATOM   5788 O    GLY   383     13.519  12.665  20.282  1.00  9.10      PROT
ATOM   5792 N    CYS   384     13.153  13.699  22.245  1.00  9.77      PROT
ATOM   5793 CA   CYS   384     14.500  13.468  22.759  1.00  9.74      PROT
ATOM   5794 C    CYS   384     14.618  12.042  23.295  1.00  9.29      PROT
ATOM   5795 O    CYS   384     14.267  11.760  24.446  1.00  9.55      PROT
ATOM   5796 CB   CYS   384     14.865  14.492  23.827  1.00 10.14      PROT
ATOM   5797 SG   CYS   384     16.611  14.411  24.285  1.00 11.38      PROT
ATOM   5802 N    SER   385     15.101  11.153  22.434  1.00  8.38      PROT
ATOM   5803 CA   SER   385     15.206   9.721  22.730  1.00  8.15      PROT
ATOM   5804 C    SER   385     16.287   9.392  23.757  1.00  7.30      PROT
ATOM   5805 O    SER   385     16.230   8.355  24.419  1.00  6.87      PROT
ATOM   5806 CB   SER   385     15.459   8.933  21.446  1.00  7.99      PROT
ATOM   5807 OG   SER   385     14.250   8.710  20.746  1.00 10.17      PROT
ATOM   5812 N    ASP   386     17.271  10.278  23.878  1.00  6.44      PROT
ATOM   5813 CA   ASP   386     18.367  10.067  24.820  1.00  5.92      PROT
ATOM   5814 C    ASP   386     18.277  10.955  26.071  1.00  5.20      PROT
ATOM   5815 O    ASP   386     19.275  11.156  26.765  1.00  4.61      PROT
ATOM   5816 CB   ASP   386     19.731  10.180  24.115  1.00  6.01      PROT
ATOM   5817 CG   ASP   386     19.822  11.379  23.173  1.00  6.66      PROT
ATOM   5818 OD1  ASP   386     18.944  12.263  23.208  1.00  7.37      PROT
ATOM   5819 OD2  ASP   386     20.790  11.435  22.388  1.00  7.73      PROT
ATOM   5824 N    GLN   387     17.076  11.469  26.361  1.00  4.84      PROT
ATOM   5825 CA   GLN   387     16.821  12.229  27.590  1.00  4.68      PROT
ATOM   5826 C    GLN   387     16.988  11.301  28.791  1.00  4.74      PROT
ATOM   5827 O    GLN   387     16.480  10.173  28.790  1.00  4.93      PROT
ATOM   5828 CB   GLN   387     15.421  12.871  27.578  1.00  4.41      PROT
ATOM   5829 CG   GLN   387     15.208  13.954  28.659  1.00  4.24      PROT
ATOM   5830 CD   GLN   387     13.846  14.669  28.562  1.00  4.94      PROT
ATOM   5831 OE1  GLN   387     12.965  14.260  27.808  1.00  4.19      PROT
ATOM   5832 NE2  GLN   387     13.677  15.739  29.344  1.00  5.87      PROT
ATOM   5841 N    THR   388     17.728  11.763  29.795  1.00  4.48      PROT
ATOM   5842 CA   THR   388     18.066  10.947  30.963  1.00  4.71      PROT
ATOM   5843 C    THR   388     16.843  10.764  31.870  1.00  5.00      PROT
ATOM   5844 O    THR   388     15.926  11.590  31.826  1.00  4.77      PROT
ATOM   5845 CB   THR   388     19.215  11.588  31.771  1.00  4.92      PROT
ATOM   5846 OG1  THR   388     18.774  12.854  32.284  1.00  4.89      PROT
ATOM   5847 CG2  THR   388     20.441  11.796  30.898  1.00  4.53      PROT
ATOM   5854 N    PRO   389     16.810   9.678  32.682  1.00  5.07      PROT
ATOM   5855 CA   PRO   389     15.705   9.510  33.637  1.00  5.23      PROT
ATOM   5856 C    PRO   389     15.464  10.712  34.556  1.00  5.19      PROT
ATOM   5857 O    PRO   389     14.327  10.937  34.974  1.00  5.28      PROT
ATOM   5858 CB   PRO   389     16.123   8.276  34.441  1.00  5.17      PROT
ATOM   5859 CG   PRO   389     16.951   7.501  33.485  1.00  5.57      PROT
ATOM   5860 CD   PRO   389     17.740   8.536  32.741  1.00  5.08      PROT
ATOM   5868 N    ASP   390     16.511  11.488  34.845  1.00  5.01      PROT
ATOM   5869 CA   ASP   390     16.349  12.715  35.620  1.00  5.06      PROT
```

Figure 3 cont.

```
ATOM   5870  C    ASP   390      16.107  13.981  34.779  1.00  4.87      PROT
ATOM   5871  O    ASP   390      16.172  15.091  35.303  1.00  5.02      PROT
ATOM   5872  CB   ASP   390      17.498  12.912  36.628  1.00  5.76      PROT
ATOM   5873  CG   ASP   390      18.867  12.656  36.031  1.00  5.29      PROT
ATOM   5874  OD1  ASP   390      19.835  12.632  36.808  1.00  5.95      PROT
ATOM   5875  OD2  ASP   390      18.982  12.459  34.803  1.00  7.08      PROT
ATOM   5880  N    GLY   391      15.830  13.808  33.484  1.00  4.08      PROT
ATOM   5881  CA   GLY   391      15.252  14.876  32.654  1.00  3.89      PROT
ATOM   5882  C    GLY   391      16.194  15.745  31.831  1.00  3.62      PROT
ATOM   5883  O    GLY   391      15.782  16.781  31.315  1.00  3.66      PROT
ATOM   5887  N    TYR   392      17.446  15.322  31.687  1.00  3.83      PROT
ATOM   5888  CA   TYR   392      18.433  16.088  30.926  1.00  4.36      PROT
ATOM   5889  C    TYR   392      18.512  15.652  29.461  1.00  4.81      PROT
ATOM   5890  O    TYR   392      18.803  14.490  29.148  1.00  3.99      PROT
ATOM   5891  CB   TYR   392      19.810  16.061  31.618  1.00  4.00      PROT
ATOM   5892  CG   TYR   392      19.763  16.650  33.013  1.00  4.79      PROT
ATOM   5893  CD1  TYR   392      19.632  15.830  34.135  1.00  5.38      PROT
ATOM   5894  CD2  TYR   392      19.804  18.038  33.208  1.00  3.59      PROT
ATOM   5895  CE1  TYR   392      19.572  16.378  35.425  1.00  5.47      PROT
ATOM   5896  CE2  TYR   392      19.739  18.585  34.478  1.00  5.43      PROT
ATOM   5897  CZ   TYR   392      19.623  17.752  35.580  1.00  4.30      PROT
ATOM   5898  OH   TYR   392      19.554  18.318  36.828  1.00  6.19      PROT
ATOM   5907  N    CYS   393      18.215  16.604  28.579  1.00  5.83      PROT
ATOM   5908  CA   CYS   393      18.265  16.413  27.140  1.00  5.86      PROT
ATOM   5909  C    CYS   393      19.594  16.941  26.582  1.00  5.26      PROT
ATOM   5910  O    CYS   393      19.868  18.141  26.678  1.00  5.55      PROT
ATOM   5911  CB   CYS   393      17.078  17.140  26.485  1.00  6.12      PROT
ATOM   5912  SG   CYS   393      17.124  17.179  24.676  1.00  9.15      PROT
ATOM   5917  N    PRO   394      20.427  16.056  25.999  1.00  4.67      PROT
ATOM   5918  CA   PRO   394      21.677  16.517  25.383  1.00  4.67      PROT
ATOM   5919  C    PRO   394      21.414  17.734  24.474  1.00  4.20      PROT
ATOM   5920  O    PRO   394      20.415  17.751  23.762  1.00  4.43      PROT
ATOM   5921  CB   PRO   394      22.128  15.307  24.561  1.00  4.74      PROT
ATOM   5922  CG   PRO   394      21.544  14.139  25.252  1.00  4.83      PROT
ATOM   5923  CD   PRO   394      20.242  14.596  25.859  1.00  4.62      PROT
ATOM   5931  N    LEU   395      22.272  18.753  24.526  1.00  3.97      PROT
ATOM   5932  CA   LEU   395      22.039  19.979  23.751  1.00  3.62      PROT
ATOM   5933  C    LEU   395      22.063  19.707  22.247  1.00  3.96      PROT
ATOM   5934  O    LEU   395      21.242  20.248  21.495  1.00  3.43      PROT
ATOM   5935  CB   LEU   395      23.037  21.092  24.118  1.00  3.07      PROT
ATOM   5936  CG   LEU   395      23.038  22.367  23.249  1.00  3.92      PROT
ATOM   5937  CD1  LEU   395      21.669  23.083  23.230  1.00  2.70      PROT
ATOM   5938  CD2  LEU   395      24.134  23.334  23.680  1.00  2.81      PROT
ATOM   5950  N    SER   396      22.999  18.859  21.820  1.00  4.70      PROT
ATOM   5951  CA   SER   396      23.127  18.506  20.409  1.00  5.32      PROT
ATOM   5952  C    SER   396      21.857  17.839  19.869  1.00  5.80      PROT
ATOM   5953  O    SER   396      21.424  18.145  18.754  1.00  6.19      PROT
ATOM   5954  CB   SER   396      24.386  17.669  20.152  1.00  5.48      PROT
ATOM   5955  OG   SER   396      24.523  16.613  21.085  1.00  5.87      PROT
ATOM   5960  N    THR   397      21.253  16.954  20.664  1.00  6.11      PROT
ATOM   5961  CA   THR   397      19.929  16.396  20.349  1.00  6.16      PROT
ATOM   5962  C    THR   397      18.835  17.457  20.370  1.00  6.05      PROT
ATOM   5963  O    THR   397      17.970  17.471  19.493  1.00  6.21      PROT
ATOM   5964  CB   THR   397      19.506  15.270  21.321  1.00  6.31      PROT
ATOM   5965  OG1  THR   397      20.538  14.287  21.405  1.00  4.48      PROT
ATOM   5966  CG2  THR   397      18.211  14.594  20.836  1.00  7.29      PROT
ATOM   5973  N    PHE   398      18.857  18.329  21.380  1.00  5.82      PROT
ATOM   5974  CA   PHE   398      17.885  19.415  21.465  1.00  5.36      PROT
ATOM   5975  C    PHE   398      17.907  20.276  20.200  1.00  5.41      PROT
ATOM   5976  O    PHE   398      16.845  20.576  19.663  1.00  5.23      PROT
ATOM   5977  CB   PHE   398      18.082  20.264  22.734  1.00  5.11      PROT
ATOM   5978  CG   PHE   398      16.976  21.270  22.981  1.00  4.66      PROT
ATOM   5979  CD1  PHE   398      15.787  20.891  23.599  1.00  3.01      PROT
ATOM   5980  CD2  PHE   398      17.143  22.599  22.623  1.00  5.20      PROT
ATOM   5981  CE1  PHE   398      14.769  21.825  23.833  1.00  4.07      PROT
```

Figure 3 cont.

```
ATOM   5982 CE2  PHE   398      16.148  23.543  22.861  1.00  5.56       PROT
ATOM   5983 CZ   PHE   398      14.949  23.154  23.462  1.00  4.23       PROT
ATOM   5993 N    SER   399      19.106  20.634  19.726  1.00  5.44       PROT
ATOM   5994 CA   SER   399      19.283  21.418  18.489  1.00  6.55       PROT
ATOM   5995 C    SER   399      18.640  20.758  17.263  1.00  6.95       PROT
ATOM   5996 O    SER   399      18.081  21.440  16.401  1.00  6.93       PROT
ATOM   5997 CB   SER   399      20.769  21.646  18.176  1.00  6.34       PROT
ATOM   5998 OG   SER   399      21.512  22.043  19.308  1.00  7.08       PROT
ATOM   6003 N    ARG   400      18.751  19.433  17.186  1.00  7.76       PROT
ATOM   6004 CA   ARG   400      18.214  18.661  16.068  1.00  8.83       PROT
ATOM   6005 C    ARG   400      16.701  18.664  16.079  1.00  9.30       PROT
ATOM   6006 O    ARG   400      16.073  18.776  15.024  1.00  9.29       PROT
ATOM   6007 CB   ARG   400      18.710  17.206  16.104  1.00  8.97       PROT
ATOM   6008 CG   ARG   400      20.199  17.037  16.328  1.00 10.18       PROT
ATOM   6009 CD   ARG   400      21.027  17.679  15.220  1.00 13.32       PROT
ATOM   6010 NE   ARG   400      20.692  17.123  13.912  1.00 14.23       PROT
ATOM   6011 CZ   ARG   400      21.390  16.180  13.285  1.00 15.63       PROT
ATOM   6012 NH1  ARG   400      22.488  15.672  13.832  1.00 17.67       PROT
ATOM   6013 NH2  ARG   400      20.991  15.751  12.098  1.00 15.05       PROT
ATOM   6027 N    LEU   401      16.124  18.527  17.276  1.00 10.33       PROT
ATOM   6028 CA   LEU   401      14.673  18.522  17.441  1.00 11.29       PROT
ATOM   6029 C    LEU   401      14.067  19.845  17.021  1.00 12.10       PROT
ATOM   6030 O    LEU   401      13.060  19.874  16.304  1.00 12.54       PROT
ATOM   6031 CB   LEU   401      14.264  18.163  18.876  1.00 11.30       PROT
ATOM   6032 CG   LEU   401      13.529  16.825  19.065  1.00 12.19       PROT
ATOM   6033 CD1  LEU   401      14.360  15.644  18.565  1.00 12.72       PROT
ATOM   6034 CD2  LEU   401      12.160  16.834  18.376  1.00 11.84       PROT
ATOM   6046 N    VAL   402      14.700  20.934  17.451  1.00 12.70       PROT
ATOM   6047 CA   VAL   402      14.286  22.276  17.052  1.00 13.12       PROT
ATOM   6048 C    VAL   402      14.356  22.433  15.525  1.00 13.49       PROT
ATOM   6049 O    VAL   402      13.367  22.797  14.889  1.00 12.87       PROT
ATOM   6050 CB   VAL   402      15.133  23.351  17.774  1.00 13.15       PROT
ATOM   6051 CG1  VAL   402      14.949  24.725  17.144  1.00 12.99       PROT
ATOM   6052 CG2  VAL   402      14.795  23.371  19.264  1.00 12.46       PROT
ATOM   6062 N    SER   403      15.521  22.136  14.952  1.00 14.58       PROT
ATOM   6063 CA   SER   403      15.744  22.259  13.510  1.00 15.62       PROT
ATOM   6064 C    SER   403      14.692  21.497  12.699  1.00 16.00       PROT
ATOM   6065 O    SER   403      14.274  21.960  11.639  1.00 16.66       PROT
ATOM   6066 CB   SER   403      17.155  21.818  13.143  1.00 16.07       PROT
ATOM   6067 OG   SER   403      18.167  22.481  13.874  1.00  0.00       PROT
ATOM   6072 N    HSD   404      14.243  20.355  13.219  1.00 16.33       PROT
ATOM   6073 CA   HSD   404      13.199  19.565  12.556  1.00 16.95       PROT
ATOM   6074 C    HSD   404      11.779  20.086  12.804  1.00 16.52       PROT
ATOM   6075 O    HSD   404      10.880  19.816  12.011  1.00 16.60       PROT
ATOM   6076 CB   HSD   404      13.289  18.082  12.944  1.00 17.22       PROT
ATOM   6077 CG   HSD   404      14.525  17.393  12.447  1.00 19.47       PROT
ATOM   6078 ND1  HSD   404      15.230  16.488  13.215  1.00 21.57       PROT
ATOM   6079 CD2  HSD   404      15.176  17.469  11.261  1.00 21.25       PROT
ATOM   6080 CE1  HSD   404      16.264  16.039  12.523  1.00 22.36       PROT
ATOM   6081 NE2  HSD   404      16.256  16.620  11.336  1.00 22.83       PROT
ATOM   6089 N    SER   405      11.584  20.835  13.891  1.00 16.43       PROT
ATOM   6090 CA   SER   405      10.254  21.321  14.281  1.00 16.43       PROT
ATOM   6091 C    SER   405       9.863  22.657  13.645  1.00 16.09       PROT
ATOM   6092 O    SER   405       8.696  22.894  13.353  1.00 16.13       PROT
ATOM   6093 CB   SER   405      10.148  21.423  15.808  1.00 16.58       PROT
ATOM   6094 OG   SER   405      10.437  20.169  16.410  1.00 16.84       PROT
ATOM   6099 N    VAL   406      10.844  23.528  13.450  1.00 16.25       PROT
ATOM   6100 CA   VAL   406      10.600  24.863  12.918  1.00 16.19       PROT
ATOM   6101 C    VAL   406      10.041  24.858  11.490  1.00 16.52       PROT
ATOM   6102 O    VAL   406      10.262  23.911  10.717  1.00 15.71       PROT
ATOM   6103 CB   VAL   406      11.873  25.758  13.009  1.00 16.37       PROT
ATOM   6104 CG1  VAL   406      12.234  26.015  14.480  1.00 15.56       PROT
ATOM   6105 CG2  VAL   406      13.045  25.135  12.261  1.00 16.53       PROT
ATOM   6115 N    GLU   407       9.274  25.901  11.179  1.00 16.52       PROT
ATOM   6116 CA   GLU   407       8.867  26.200   9.816  1.00 16.87       PROT
```

Figure 3 cont.

```
ATOM   6117  C    GLU   407       9.839  27.246   9.246  1.00 17.18      PROT
ATOM   6118  O    GLU   407       9.886  28.380   9.738  1.00 17.41      PROT
ATOM   6119  CB   GLU   407       7.412  26.703   9.792  1.00 16.59      PROT
ATOM   6120  CG   GLU   407       6.890  27.167   8.411  1.00 16.45      PROT
ATOM   6121  CD   GLU   407       7.009  26.095   7.330  1.00 16.08      PROT
ATOM   6122  OE1  GLU   407       6.531  24.961   7.542  1.00 15.69      PROT
ATOM   6123  OE2  GLU   407       7.591  26.393   6.267  1.00 16.92      PROT
ATOM   6130  N    PRO   408      10.627  26.866   8.213  1.00 17.40      PROT
ATOM   6131  CA   PRO   408      11.598  27.764   7.568  1.00 17.31      PROT
ATOM   6132  C    PRO   408      11.019  29.086   7.050  1.00 17.08      PROT
ATOM   6133  O    PRO   408      11.693  30.112   7.124  1.00 16.93      PROT
ATOM   6134  CB   PRO   408      12.130  26.925   6.394  1.00 17.55      PROT
ATOM   6135  CG   PRO   408      11.932  25.522   6.815  1.00 17.56      PROT
ATOM   6136  CD   PRO   408      10.650  25.522   7.603  1.00 17.68      PROT
ATOM   6144  N    ALA   409       9.792  29.059   6.535  1.00 17.22      PROT
ATOM   6145  CA   ALA   409       9.133  30.265   6.022  1.00 17.67      PROT
ATOM   6146  C    ALA   409       8.824  31.282   7.124  1.00 17.95      PROT
ATOM   6147  O    ALA   409       8.596  32.456   6.834  1.00 18.07      PROT
ATOM   6148  CB   ALA   409       7.857  29.900   5.271  1.00 17.40      PROT
ATOM   6154  N    CYS   410       8.808  30.817   8.375  1.00 18.41      PROT
ATOM   6155  CA   CYS   410       8.511  31.667   9.535  1.00 18.68      PROT
ATOM   6156  C    CYS   410       9.747  32.035  10.351  1.00 19.34      PROT
ATOM   6157  O    CYS   410       9.622  32.549  11.463  1.00 19.62      PROT
ATOM   6158  CB   CYS   410       7.464  31.010  10.436  1.00 18.18      PROT
ATOM   6159  SG   CYS   410       5.961  30.531   9.586  1.00 17.28      PROT
ATOM   6164  N    GLN   411      10.929  31.774   9.798  1.00 20.10      PROT
ATOM   6165  CA   GLN   411      12.186  32.186  10.410  1.00 21.33      PROT
ATOM   6166  C    GLN   411      12.343  33.699  10.335  1.00 21.81      PROT
ATOM   6167  O    GLN   411      11.879  34.330   9.385  1.00 21.94      PROT
ATOM   6168  CB   GLN   411      13.372  31.533   9.699  1.00 21.35      PROT
ATOM   6169  CG   GLN   411      13.505  30.036   9.901  1.00 21.83      PROT
ATOM   6170  CD   GLN   411      14.706  29.462   9.168  1.00 22.12      PROT
ATOM   6171  OE1  GLN   411      14.681  29.291   7.946  1.00 23.89      PROT
ATOM   6172  NE2  GLN   411      15.769  29.161   9.913  1.00 22.55      PROT
ATOM   6181  N    LEU   412      12.985  34.269  11.351  1.00 22.23      PROT
ATOM   6182  CA   LEU   412      13.408  35.664  11.332  1.00 23.01      PROT
ATOM   6183  C    LEU   412      14.792  35.752  10.702  1.00 23.67      PROT
ATOM   6184  O    LEU   412      15.744  35.167  11.224  1.00 24.29      PROT
ATOM   6185  CB   LEU   412      13.453  36.243  12.754  1.00 22.85      PROT
ATOM   6186  CG   LEU   412      12.241  37.017  13.278  1.00 22.57      PROT
ATOM   6187  CD1  LEU   412      10.969  36.233  13.090  1.00 20.93      PROT
ATOM   6188  CD2  LEU   412      12.417  37.398  14.742  1.00 22.61      PROT
ATOM   6200  N    PRO   413      14.913  36.467   9.573  1.00 24.50      PROT
ATOM   6201  CA   PRO   413      13.866  37.110   8.773  1.00 24.96      PROT
ATOM   6202  C    PRO   413      13.308  36.203   7.670  1.00 25.63      PROT
ATOM   6203  O    PRO   413      13.784  35.041   7.563  1.00  0.00      PROT
ATOM   6204  CB   PRO   413      14.606  38.303   8.145  1.00 25.21      PROT
ATOM   6205  CG   PRO   413      16.079  38.179   8.604  1.00 24.70      PROT
ATOM   6206  CD   PRO   413      16.240  36.765   9.014  1.00 24.53      PROT
END
ATOM   6276  OH2  TIP3    1      -3.872  26.428  28.319  1.00  5.13      XWAT
ATOM   6279  OH2  TIP3    2      19.235  31.249  47.659  1.00  7.39      XWAT
ATOM   6282  OH2  TIP3    4      -7.692  42.917  44.597  1.00 17.68      XWAT
ATOM   6285  OH2  TIP3    5     -23.906  40.436  31.657  1.00 10.85      XWAT
ATOM   6288  OH2  TIP3    6      -3.436  35.420  25.094  1.00 16.60      XWAT
ATOM   6291  OH2  TIP3    7      -4.285  20.702  37.937  1.00 13.56      XWAT
ATOM   6294  OH2  TIP3    8       6.238  18.126  39.958  1.00 34.49      XWAT
ATOM   6297  OH2  TIP3    9      -4.338  26.003  44.389  1.00  2.00      XWAT
ATOM   6300  OH2  TIP3   10      17.982  53.263  34.418  1.00 22.49      XWAT
ATOM   6303  OH2  TIP3   11     -15.336  45.435  40.866  1.00 24.08      XWAT
ATOM   6306  OH2  TIP3   12      -6.579  30.229  48.903  1.00  9.21      XWAT
ATOM   6309  OH2  TIP3   13     -24.617  39.602  20.934  1.00 16.28      XWAT
ATOM   6312  OH2  TIP3   14       5.228  44.028  12.852  1.00 11.14      XWAT
ATOM   6315  OH2  TIP3   15      16.987  43.790  30.477  1.00  2.00      XWAT
ATOM   6318  OH2  TIP3   16     -36.889  26.833  26.995  1.00 19.97      XWAT
```

Figure 3 cont.

```
ATOM   6321 OH2  TIP3    17       2.594   31.821   38.110  1.00  2.00      XWAT
ATOM   6324 OH2  TIP3    18       8.773   43.753   21.839  1.00  2.00      XWAT
ATOM   6327 OH2  TIP3    19       7.471   32.852   17.803  1.00  3.87      XWAT
ATOM   6330 OH2  TIP3    20       3.475   41.387   19.104  1.00  3.12      XWAT
ATOM   6333 OH2  TIP3    21      -8.051   51.464   41.465  1.00 31.31      XWAT
ATOM   6336 OH2  TIP3    22      13.604   18.554   31.108  1.00  2.85      XWAT
ATOM   6339 OH2  TIP3    23      -3.028   22.234   35.106  1.00  2.00      XWAT
ATOM   6342 OH2  TIP3    24       1.275   29.082    3.627  1.00 30.13      XWAT
ATOM   6345 OH2  TIP3    25      15.270   51.303   36.584  1.00 18.00      XWAT
ATOM   6348 OH2  TIP3    26      -6.265   44.031   24.876  1.00 23.60      XWAT
ATOM   6351 OH2  TIP3    27       1.627   35.581   38.617  1.00  2.00      XWAT
ATOM   6354 OH2  TIP3    29       8.932   35.977   46.472  1.00  4.06      XWAT
ATOM   6357 OH2  TIP3    30       2.500   33.893   44.957  1.00  2.00      XWAT
ATOM   6360 OH2  TIP3    31       7.257   34.269   35.602  1.00  6.65      XWAT
ATOM   6363 OH2  TIP3    32      -2.565   56.534   31.192  1.00  8.52      XWAT
ATOM   6366 OH2  TIP3    33      11.674   31.203   53.645  1.00 34.76      XWAT
ATOM   6369 OH2  TIP3    34      -4.341   29.841   16.524  1.00 19.11      XWAT
ATOM   6372 OH2  TIP3    35       1.964   33.926   17.971  1.00 11.95      XWAT
ATOM   6375 OH2  TIP3    36      -2.660   18.756   29.302  1.00 22.93      XWAT
ATOM   6378 OH2  TIP3    37      12.179   11.731   26.347  1.00 14.01      XWAT
ATOM   6381 OH2  TIP3    38     -17.095   31.454   43.045  1.00 11.14      XWAT
ATOM   6384 OH2  TIP3    39      -0.485   29.218   49.383  1.00 26.91      XWAT
ATOM   6387 OH2  TIP3    41       0.388   15.294   30.657  1.00 25.38      XWAT
ATOM   6390 OH2  TIP3    42      -0.754   35.930   21.602  1.00 14.70      XWAT
ATOM   6393 OH2  TIP3    43      30.751   22.813   27.685  1.00 21.61      XWAT
ATOM   6396 OH2  TIP3    44       0.034   36.216   15.196  1.00 15.47      XWAT
ATOM   6399 OH2  TIP3    45       4.915   31.645   19.808  1.00  2.00      XWAT
ATOM   6402 OH2  TIP3    46       0.519   36.968    7.747  1.00 11.79      XWAT
ATOM   6405 OH2  TIP3    47       1.766   30.262   31.734  1.00  2.00      XWAT
ATOM   6408 OH2  TIP3    48      30.537   43.971   43.066  1.00 50.80      XWAT
ATOM   6411 OH2  TIP3    50      -1.358   30.272   18.762  1.00  7.06      XWAT
ATOM   6414 OH2  TIP3    51      -1.917   40.015   21.194  1.00 32.76      XWAT
ATOM   6417 OH2  TIP3    52     -17.005   17.710   30.167  1.00 10.08      XWAT
ATOM   6420 OH2  TIP3    53      22.832   45.965   39.049  1.00 27.83      XWAT
ATOM   6423 OH2  TIP3    54     -27.895   25.164   29.213  1.00 10.74      XWAT
ATOM   6426 OH2  TIP3    55       0.457   38.134   38.089  1.00  2.00      XWAT
ATOM   6429 OH2  TIP3    56      27.614   44.494   33.182  1.00 18.11      XWAT
ATOM   6432 OH2  TIP3    58      22.048   39.345   42.697  1.00 20.36      XWAT
ATOM   6435 OH2  TIP3    59       4.963   26.085   48.456  1.00 17.72      XWAT
ATOM   6438 OH2  TIP3    60     -22.589   25.968   40.936  1.00 19.68      XWAT
ATOM   6441 OH2  TIP3    61     -31.306   25.064   29.720  1.00 27.75      XWAT
ATOM   6444 OH2  TIP3    62      -1.660   48.684   35.094  1.00 19.22      XWAT
ATOM   6447 OH2  TIP3    63      -4.788   42.529   17.037  1.00 30.85      XWAT
ATOM   6450 OH2  TIP3    64      -3.544   16.729   22.218  1.00 16.97      XWAT
ATOM   6453 OH2  TIP3    65     -26.106   31.745   38.820  1.00 22.55      XWAT
ATOM   6456 OH2  TIP3    67       3.952   21.585   41.813  1.00 10.93      XWAT
ATOM   6459 OH2  TIP3    68     -19.846   33.120   16.435  1.00  6.34      XWAT
ATOM   6462 OH2  TIP3    69      -8.752   40.793   21.738  1.00 38.90      XWAT
ATOM   6465 OH2  TIP3    70     -11.460   47.040   32.436  1.00 11.07      XWAT
ATOM   6468 OH2  TIP3    71      -3.054   17.405   26.050  1.00 42.00      XWAT
ATOM   6471 OH2  TIP3    72     -13.347   18.079   37.333  1.00 15.39      XWAT
ATOM   6474 OH2  TIP3    73      -4.140   30.490   29.711  1.00  2.00      XWAT
ATOM   6477 OH2  TIP3    74     -18.238   44.937   33.599  1.00 20.78      XWAT
ATOM   6480 OH2  TIP3    76      27.325   13.037   33.206  1.00  9.29      XWAT
ATOM   6483 OH2  TIP3    77      -4.034   22.356   26.702  1.00 30.41      XWAT
ATOM   6486 OH2  TIP3    78     -14.602   37.028   17.414  1.00 21.94      XWAT
ATOM   6489 OH2  TIP3    80      14.572   33.851   52.173  1.00 18.48      XWAT
ATOM   6492 OH2  TIP3    81     -20.846   22.901   44.865  1.00 46.27      XWAT
ATOM   6495 OH2  TIP3    82     -14.181   39.792   35.249  1.00  6.94      XWAT
ATOM   6498 OH2  TIP3    83       3.039   52.630   13.502  1.00 24.18      XWAT
ATOM   6501 OH2  TIP3    86      -4.365   55.903   33.584  1.00 49.46      XWAT
ATOM   6504 OH2  TIP3    87     -26.511   23.171   33.162  1.00 14.13      XWAT
ATOM   6507 OH2  TIP3    88     -23.934   20.144   27.983  1.00 10.91      XWAT
ATOM   6510 OH2  TIP3    89       7.808   49.733   29.658  1.00 12.68      XWAT
ATOM   6513 OH2  TIP3    90       5.993   16.030   28.077  1.00 13.56      XWAT
```

Figure 3 cont.

```
ATOM   6516  OH2  TIP3    91    -34.683  29.557  29.250  1.00 18.92      XWAT
ATOM   6519  OH2  TIP3    92     14.499  50.037  39.004  1.00 17.43      XWAT
ATOM   6522  OH2  TIP3    94     27.474  20.025  41.171  1.00 22.72      XWAT
ATOM   6525  OH2  TIP3    95     -9.521  20.837   5.122  1.00 26.03      XWAT
ATOM   6528  OH2  TIP3    96     10.644  43.991  45.229  1.00 34.20      XWAT
ATOM   6531  OH2  TIP3    97     19.673  46.568  45.681  1.00 22.99      XWAT
ATOM   6534  OH2  TIP3    98     -6.934  15.771   9.570  1.00  2.00      XWAT
ATOM   6537  OH2  TIP3    99    -34.305  25.894  30.628  1.00 33.79      XWAT
ATOM   6540  OH2  TIP3   102      8.909  37.371  48.431  1.00 20.01      XWAT
ATOM   6543  OH2  TIP3   103     25.420  17.781  24.053  1.00 14.21      XWAT
ATOM   6546  OH2  TIP3   104     -5.648  19.701  27.080  1.00 30.94      XWAT
ATOM   6549  OH2  TIP3   106     19.471  48.314  50.752  1.00 31.75      XWAT
ATOM   6552  OH2  TIP3   107    -15.487  31.506  46.327  1.00 34.41      XWAT
ATOM   6555  OH2  TIP3   108    -36.738  30.101  32.179  1.00 38.94      XWAT
ATOM   6558  OH2  TIP3   109    -11.179  17.086  38.913  1.00 18.15      XWAT
ATOM   6561  OH2  TIP3   110    -25.214  22.785  28.115  1.00 25.10      XWAT
ATOM   6564  OH2  TIP3   111      7.243  38.052  49.987  1.00 20.59      XWAT
ATOM   6567  OH2  TIP3   112    -10.404  18.789   7.035  1.00 43.30      XWAT
ATOM   6570  OH2  TIP3   113    -20.034  22.773  48.104  1.00 47.65      XWAT
ATOM   6573  OH2  TIP3   114    -27.218  19.793  28.995  1.00 27.43      XWAT
ATOM   6576  OH2  TIP3   115    -24.538  16.997  30.259  1.00 32.60      XWAT
ATOM   6579  OH2  TIP3   116     30.246  23.359  39.158  1.00 10.67      XWAT
ATOM   6582  OH2  TIP3   118     12.424  46.054  48.210  1.00 46.05      XWAT
ATOM   6585  OH2  TIP3   121     -1.281  47.033  25.727  1.00 14.74      XWAT
ATOM   6588  OH2  TIP3   123     -6.586  21.421  34.879  1.00 23.63      XWAT
ATOM   6591  OH2  TIP3   124    -16.531  27.349   9.704  1.00 12.22      XWAT
ATOM   6594  OH2  TIP3   126     12.221  49.090  32.006  1.00  5.05      XWAT
ATOM   6597  OH2  TIP3   127     -7.897  31.181  18.670  1.00 17.92      XWAT
ATOM   6600  OH2  TIP3   129    -13.867  28.591  44.834  1.00 15.14      XWAT
ATOM   6603  OH2  TIP3   130     -1.782  45.132  27.802  1.00  2.00      XWAT
ATOM   6606  OH2  TIP3   131    -15.595  41.881  34.028  1.00 10.51      XWAT
ATOM   6609  OH2  TIP3   132      6.298  16.138  30.868  1.00  6.49      XWAT
ATOM   6612  OH2  TIP3   133     11.512  47.236  37.606  1.00  2.00      XWAT
ATOM   6615  OH2  TIP3   134     19.286  46.897  32.557  1.00 12.95      XWAT
ATOM   6618  OH2  TIP3   135      0.742  51.629  31.304  1.00 11.59      XWAT
ATOM   6621  OH2  TIP3   136     -4.689  32.032  19.571  1.00 25.48      XWAT
ATOM   6624  OH2  TIP3   137     31.574  16.202  26.472  1.00 30.19      XWAT
ATOM   6627  OH2  TIP3   138     -0.787  26.277  47.192  1.00 11.50      XWAT
ATOM   6630  OH2  TIP3   140     -9.298  44.508  42.115  1.00 14.23      XWAT
ATOM   6633  OH2  TIP3   141     16.666  48.886  28.032  1.00  4.97      XWAT
ATOM   6636  OH2  TIP3   142    -10.378  18.463  22.500  1.00 13.44      XWAT
ATOM   6639  OH2  TIP3   144      2.471  39.135  49.063  1.00  4.79      XWAT
ATOM   6642  OH2  TIP3   146     -8.932  19.766  28.575  1.00 10.19      XWAT
ATOM   6645  OH2  TIP3   147      8.960  52.000  26.374  1.00  6.77      XWAT
ATOM   6648  OH2  TIP3   148    -20.203  45.043  25.034  1.00 13.56      XWAT
ATOM   6651  OH2  TIP3   149      7.339  23.005  44.668  1.00 21.49      XWAT
ATOM   6654  OH2  TIP3   150      2.056  46.463  42.157  1.00  5.58      XWAT
ATOM   6657  OH2  TIP3   151    -20.167  21.284  18.362  1.00  3.46      XWAT
ATOM   6660  OH2  TIP3   153     -5.961  33.846  27.750  1.00 23.52      XWAT
ATOM   6663  OH2  TIP3   154    -17.904  24.775   9.675  1.00 19.85      XWAT
ATOM   6666  OH2  TIP3   155     15.834  45.800  38.877  1.00  5.85      XWAT
ATOM   6669  OH2  TIP3   156     12.144  12.644  30.966  1.00 25.76      XWAT
ATOM   6672  OH2  TIP3   157     14.678  36.773  17.184  1.00 19.22      XWAT
ATOM   6675  OH2  TIP3   158     10.044  48.744  15.900  1.00  7.82      XWAT
ATOM   6678  OH2  TIP3   159    -20.447  28.488  16.163  1.00 18.20      XWAT
ATOM   6681  OH2  TIP3   160     -0.818  19.485  12.845  1.00  4.65      XWAT
ATOM   6684  OH2  TIP3   162      2.211  16.727  34.304  1.00  9.36      XWAT
ATOM   6687  OH2  TIP3   163    -13.231  19.447  11.529  1.00 14.57      XWAT
ATOM   6690  OH2  TIP3   165      5.818  44.236  44.472  1.00  8.37      XWAT
ATOM   6693  OH2  TIP3   166     -2.133  27.178  49.829  1.00 36.92      XWAT
ATOM   6696  OH2  TIP3   167      0.356  40.575  50.390  1.00 14.90      XWAT
ATOM   6699  OH2  TIP3   168     18.838  48.456  29.679  1.00  3.36      XWAT
ATOM   6702  OH2  TIP3   169      6.046  45.172  41.025  1.00 12.76      XWAT
ATOM   6705  OH2  TIP3   170      7.146  46.493  39.067  1.00  3.87      XWAT
ATOM   6708  OH2  TIP3   171     -1.185  43.464  45.752  1.00 14.81      XWAT
```

Figure 3 cont.

```
ATOM   6711  OH2  TIP3  172    -28.499  22.997  16.753  1.00 29.73      XWAT
ATOM   6714  OH2  TIP3  173     -7.665  18.904  23.197  1.00 22.44      XWAT
ATOM   6717  OH2  TIP3  175    -16.670  25.977  20.457  1.00  2.00      XWAT
ATOM   6720  OH2  TIP3  176      4.855  16.351  33.003  1.00 22.98      XWAT
ATOM   6723  OH2  TIP3  178     -7.681  20.427  32.270  1.00 36.55      XWAT
ATOM   6726  OH2  TIP3  180     28.558  31.447  41.569  1.00 14.65      XWAT
ATOM   6729  OH2  TIP3  181     12.783  48.008  35.551  1.00  7.97      XWAT
ATOM   6732  OH2  TIP3  182     -4.556  20.016  33.170  1.00 11.49      XWAT
ATOM   6735  OH2  TIP3  183     -4.759  45.391  41.506  1.00  2.00      XWAT
ATOM   6738  OH2  TIP3  184    -27.103  40.457  30.822  1.00 10.55      XWAT
ATOM   6741  OH2  TIP3  185     -4.549  46.166  26.507  1.00 24.95      XWAT
ATOM   6744  OH2  TIP3  186    -21.132  23.788  13.743  1.00 20.95      XWAT
ATOM   6747  OH2  TIP3  187     -5.074  44.959  44.622  1.00 13.48      XWAT
ATOM   6750  OH2  TIP3  188    -19.351  14.781  26.745  1.00  8.84      XWAT
ATOM   6753  OH2  TIP3  189     26.364  39.235  38.443  1.00 20.41      XWAT
ATOM   6756  OH2  TIP3  190    -20.159  31.629  14.171  1.00 10.67      XWAT
ATOM   6759  OH2  TIP3  191     32.998  17.064  39.436  1.00  2.00      XWAT
ATOM   6762  OH2  TIP3  192    -15.539  45.997  31.794  1.00 23.45      XWAT
ATOM   6765  OH2  TIP3  193      5.674  46.420  36.745  1.00  2.00      XWAT
ATOM   6768  OH2  TIP3  194    -13.733  10.283  15.149  1.00 30.03      XWAT
ATOM   6771  OH2  TIP3  195    -14.451  45.075  24.982  1.00 12.08      XWAT
ATOM   6774  OH2  TIP3  196     13.881  30.053  51.927  1.00  5.72      XWAT
ATOM   6777  OH2  TIP3  198      7.109  31.694  36.151  1.00 11.31      XWAT
ATOM   6780  OH2  TIP3  199     -9.531  13.810  13.314  1.00 18.42      XWAT
ATOM   6783  OH2  TIP3  200    -24.408  29.511  17.439  1.00  9.70      XWAT
ATOM   6786  OH2  TIP3  201    -15.380  24.117  11.361  1.00  9.69      XWAT
ATOM   6789  OH2  TIP3  202    -16.234  47.171  27.156  1.00 14.70      XWAT
ATOM   6792  OH2  TIP3  203     19.601  44.019  30.049  1.00  6.62      XWAT
ATOM   6795  OH2  TIP3  204    -27.869  25.450  33.153  1.00  9.51      XWAT
ATOM   6798  OH2  TIP3  205    -11.449  16.320  21.174  1.00 20.73      XWAT
ATOM   6801  OH2  TIP3  206     -4.001  14.317  19.529  1.00 34.99      XWAT
ATOM   6804  OH2  TIP3  207    -11.053  14.430  23.403  1.00 30.27      XWAT
END
```

HAFNIA PHYTASE

CROSS-REFERENCE TO RELATED APPLICATIONS

This application is a divisional of U.S. application Ser. No. 12/055,694 filed on Mar. 26, 2008, now U.S. Pat. No. 7,923,232, which claims priority or the benefit under 35 U.S.C. 119 of European application no. EP07104870.6 filed Mar. 26, 2007 and U.S. provisional application No. 60/908,705 filed Mar. 29, 2007, the contents of which are fully incorporated herein by reference.

SEQUENCE LISTING AND DEPOSITED MICROORGANISMS

Sequence Listing

The present application contains a computer readable form of a sequence listing. The contents of the computer readable form are fully incorporated herein by reference.

Deposit of Biological Material

A phytase producing bacterial strain was isolated from Danish soil. The strain was demonstrated to produce a phytase with acidic pH optimum and high thermostability. The strain was identified as *Hafnia alvei* and it was deposited on Mar. 21, 2007, under the terms of the Budapest Treaty with Deutsche Sammlung von Mikroorganismen and Zellkulturen (DSMZ) and given the following accession number:

| Deposit | Accession Number | Date of Deposit |
| --- | --- | --- |
| *Hafnia alvei* NN020125 | DSM 19197 | Mar. 21, 2007 |

FIELD OF THE INVENTION

The present invention relates to isolated polypeptides having phytase activity and isolated polynucleotides encoding the polypeptides. The polypeptides are related to a phytase derived from *Hafnia alvei*, the amino acid sequence of which is shown in the appended sequence listing as SEQ ID NO: 10. The invention also relates to nucleic acid constructs, vectors, and host cells comprising the polynucleotides as well as methods for producing and using the polypeptides, in particular within animal feed.

BACKGROUND OF THE INVENTION

Phytases are well-known enzymes, as are the advantages of adding them to foodstuffs for animals, including humans. Phytases have been isolated from very many sources, including a number of fungal and bacterial strains.

It is an object of the present invention to provide alternative polypeptides having phytase activity and polynucleotides encoding the polypeptides. The polypeptides of the invention are preferably of amended, more preferably improved, properties, for example of a different substrate specificity, of a higher specific activity, of an increased stability (such as acid-stability, heat-stability, and/or protease stability, in particular pepsin stability), of an altered pH optimum (such as a lower, or higher pH optimum) and/or of an improved performance in animal feed (such as an improved release and/or degradation of phytate).

SUMMARY OF THE INVENTION

The present invention relates to polypeptides having phytase activity, selected from the group consisting of: (a) a polypeptide having an amino acid sequence which has at least 75% identity with (i) amino acids 1 to 413 of SEQ ID NO: 10, and/or (ii) the mature polypeptide part of SEQ ID NO: 10; (b) a variant comprising a deletion, insertion, and/or conservative substitution of one or more amino acids of (i) amino acids 1 to 413 of SEQ ID NO: 10, and/or (ii) the mature polypeptide part of SEQ ID NO: 10; and/or (c) a fragment of (i) amino acids 1 to 413 of SEQ ID NO: 10, and/or (ii) the mature polypeptide part of SEQ ID NO: 10.

The invention also relates to isolated polynucleotides encoding a polypeptide having phytase activity, selected from the group consisting of: (a) a polynucleotide encoding a polypeptide having an amino acid sequence which has at least 75% identity with amino acids 1 to 413 of SEQ ID NO: 10; and (b) a polynucleotide having at least 75% identity with nucleotides 100 to 1338 of SEQ ID NO: 9.

The invention also relates to nucleic acid constructs, recombinant expression vectors, and recombinant host cells comprising the polynucleotides.

The invention also relates to methods for producing such polypeptides having phytase activity comprising (a) cultivating a recombinant host cell comprising a nucleic acid construct comprising a polynucleotide encoding the polypeptide under conditions conducive for production of the polypeptide; and (b) recovering the polypeptide.

The invention further relates to a nucleic acid construct comprising a gene encoding a protein operably linked to a nucleotide sequence encoding a signal peptide consisting of (i) nucleotides 1 to 99 of SEQ ID NO: 11.

The invention also relates to methods of using the phytases of the invention in animal feed, as well as animal feed and animal feed additive compositions containing the polypeptides.

The invention also relates to methods of using the phytases of the invention in producing a fermentation product, such as, e.g., ethanol, beer, wine, wherein the fermentation is carried out in the presence of a phytase of the present invention.

The present invention relates to methods for treating proteins, including vegetable proteins, with the phytases of the present invention.

BRIEF DESCRIPTION OF THE FIGURES

FIG. 3 shows the Appendix of the structural coordinates for the solved crystal three dimensional structure of the *Hafnia alvei* phytase.

DEFINITIONS

Figure 1:
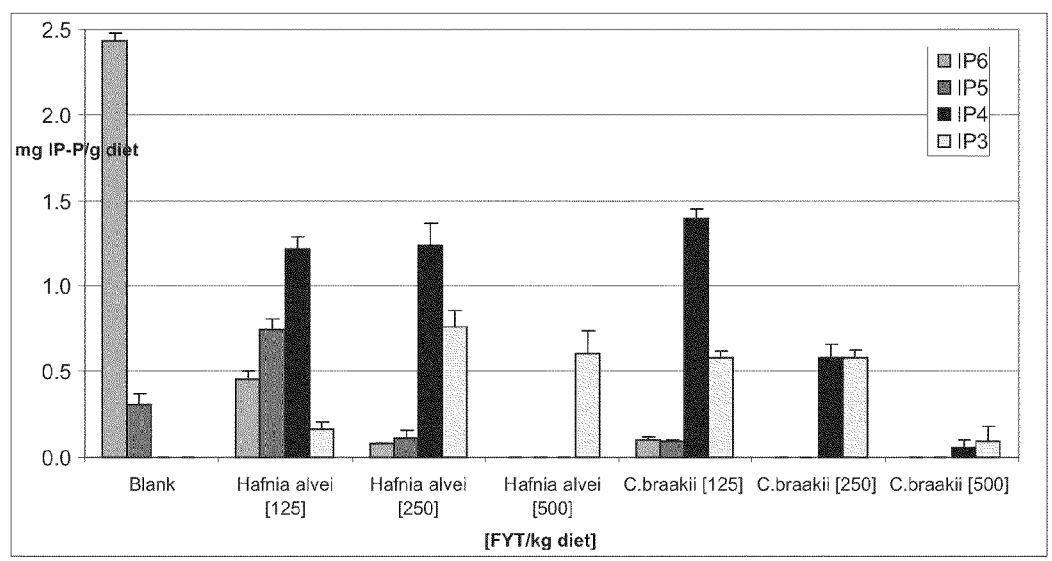
FIG. 1 shows the residual inositol-phosphate bound phosphorous after in vitro incubation in a comparison between the *Hafnia alvei* phytase and a *Citrobacter braakii* phytase dosed from 125 to 500 FYT/kg Feed.

Phytase activity: In the present context a polypeptide having phytase activity (a phytase) is an enzyme which catalyzes the hydrolysis of phytate (myo-inositol hexakisphosphate) to (1) myo-inositol and/or (2) mono-, di-, tri-, tetra- and/or penta-phosphates thereof and (3) inorganic phosphate.

The ENZYME site at the internet (www.expasy.ch/enzyme/) is a repository of information relative to the nomenclature of enzymes. It is primarily based on the recommendations of the Nomenclature Committee of the International Union of Biochemistry and Molecular Biology (IUB-MB)

and it describes each type of characterized enzyme for which an EC (Enzyme Commission) number has been provided (Bairoch A. The ENZYME database, 2000, Nucleic Acids Res 28:304-305). See also the handbook Enzyme Nomenclature from NC-IUBMB, 1992).

According to the ENZYME site, three different types of phytases are known: A 3-phytase (myo-inositol hexaphosphate 3-phosphohydrolase, EC 3.1.3.8), a 6-phytase (myo-inositol hexaphosphate 6-phosphohydrolase, EC 3.1.3.26), and a 5-phytase (EC 3.1.3.72). For the purposes of the present invention, all types are included in the definition of phytase.

In a particular embodiment, the phytases of the invention belong to the family of acid histidine phosphatases, which includes the *Escherichia coli* pH 2.5 acid phosphatase (gene appA) as well as fungal phytases such as *Aspergillus awamorii* phytases A and B (EC: 3.1.3.8) (gene phyA and phyB). The histidine acid phosphatases share two regions of sequence similarity, each centered around a conserved histidine residue. These two histidines seem to be involved in the enzymes' catalytic mechanism. The first histidine is located in the N-terminal section and forms a phosphor-histidine intermediate while the second is located in the C-terminal section and possibly acts as proton donor.

In a further particular embodiment, the phytases of the invention have a conserved active site motif, viz. R-H-G-X-R-X-P, wherein X designates any amino acid (see amino acids 18 to 24 of the mature phytase shown in SEQ ID NO: 10).

For the purposes of the present invention the phytase activity is determined in the unit of FYT, one FYT being the amount of enzyme that liberates 1 micro-mol inorganic orthophosphate per min. under the following conditions: pH 5.5; temperature 37° C.; substrate: sodium phytate ($C_6H_6O_{24}P_6Na_{12}$) in a concentration of 0.0050 mol/l. Suitable phytase assays are the FYT and FTU assays described in Example 1 of WO 00/20569. FTU is for determining phytase activity in feed and premix. Phytase activity may also be determined using the phytase assays of the examples herein.

pH optimum: The pH-optimum of a polypeptide of the invention is determined by incubating the phytase at various pH-values, using a substrate in a pre-determined concentration and a fixed incubation temperature. The pH-optimum is then determined from a graphical representation of phytase activity versus pH. In a particular embodiment, the FYT assay is used, viz. the substrate is 5 mM sodium phytate, the reaction temperature 37° C., and the activity is determined in FYT units at various pH-values, as done in the examples below. In another particular embodiment, the phytase assay of any one of the examples is used. A relatively low pH-optimum means a pH-optimum below pH 5.0, for example below pH 4.5, 4.0, 3.5, 3.0, 2.5, or even below 2.0. A relatively high pH-optimum means a pH-optimum above pH 5.0, for example above pH 5.5, 6.0, 6.5, 7.0, 7.5, 8.0, 8.5, or even above 9.0.

Isolated polypeptide: The term "isolated polypeptide" as used herein refers to a polypeptide which is at least 20% pure, preferably at least 40% pure, more preferably at least 60% pure, even more preferably at least 80% pure, most preferably at least 90% pure, and even most preferably at least 95% pure, as determined by SDS-PAGE.

Substantially pure polypeptide: The term "substantially pure polypeptide" denotes herein a polypeptide preparation which contains at most 10%, preferably at most 8%, more preferably at most 6%, more preferably at most 5%, more preferably at most 4%, at most 3%, even more preferably at most 2%, most preferably at most 1%, and even most preferably at most 0.5% by weight of other polypeptide material with which it is natively associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation.

The polypeptides of the present invention are preferably in a substantially pure form. In particular, it is preferred that the polypeptides are in "essentially pure form", i.e., that the polypeptide preparation is essentially free of other polypeptide material with which it is natively associated. This can be accomplished, for example, by preparing the polypeptide by means of well-known recombinant methods or by classical purification methods.

Herein, the term "substantially pure polypeptide" is synonymous with the terms "isolated polypeptide" and "polypeptide in isolated form."

Identity: The relatedness between two amino acid sequences or between two nucleotide sequences is described by the parameter "identity".

For purposes of the present invention, the degree of identity between two amino acid sequences, as well as the degree of identity between two nucleotide sequences, is determined by the program "align" which is a Needleman-Wunsch alignment (i.e. global alignment), useful for both protein and DNA alignments. The default scoring matrix BLOSUM50 and the default identity matrix are used for protein and DNA alignments respectively. The penalty for the first residue in a gap is −12 for proteins and −16 for DNA. While the penalties for additional residues in a gap are −2 for proteins and −4 for DNA.

"Align" is part of the FASTA package version v20u6 (see W. R. Pearson and D. J. Lipman (1988), "Improved Tools for Biological Sequence Analysis", PNAS 85:2444-2448, and W. R. Pearson (1990) "Rapid and Sensitive Sequence Comparison with FASTP and FASTA," Methods in Enzymology 183: 63-98). FASTA protein alignments use the Smith-Waterman algorithm with no limitation on gap size (see "Smith-Waterman algorithm", T. F. Smith and M. S. Waterman (1981) J. Mol. Biol. 147:195-197).

The Needleman-Wunsch algorithm is described in Needleman, S. B. and Wunsch, C. D., (1970), Journal of Molecular Biology, 48: 443-453, and the align program by Myers and W. Miller in "Optimal Alignments in Linear Space" CABIOS (computer applications in the biosciences) (1988) 4:11-17.

The degree of identity between the target (or sample, or test) sequence and a specified sequence (e.g. amino acids 1 to 413 of the mature phytase shown in SEQ ID NO: 10) may also be determined as follows: The sequences are aligned using the program "align." The number of perfect matches ("N-perfect-match") in the alignment is determined (a perfect match means same amino acid residue in same position of the alignment, usually designated with a "I" in the alignment). The length of the specified sequence (the number of amino acid residues) is determined ("N-specified", in the example mentioned above=413). The degree of identity is calculated as the ratio between "N-perfect-match" and "N-specified" (for conversion to percentage identity, multiply by 100).

In an alternative embodiment, the degree of identity between a target (or sample, or test) sequence and the specified sequence (e.g. amino acids 1 to 413 of SEQ ID NO: 10) is determined as follows: The two sequences are aligned using the program "align." The number of perfect matches ("N-perfect-match") in the alignment is determined (a perfect match means same amino acid residue in same position of the alignment, usually designated with a "I" in the alignment).

The common length of the two aligned sequences is also determined, viz. the total number of amino acids in the overlapping part of the alignment ("N-overlap"). The degree of identity is calculated as the ratio between "N-perfect-match" and "N-overlap" (for conversion to percentage identity, multiply by 100). In one embodiment, N-overlap includes trailing and leading gaps created by the alignment, if any. In another embodiment, N-overlap excludes trailing and leading gaps created by the alignment, if any.

In another alternative embodiment, the degree of identity between a target (or sample, or test) sequence and a specified sequence (e.g. amino acids 1 to 413 of SEQ ID NO: 10) is determined as follows: The sequences are aligned using the program "align." The number of perfect matches ("N-perfect-match") in the alignment is determined (a perfect match means same amino acid residue in same position of the alignment, usually designated with a "I" in the alignment). The length of the target sequence (the number of amino acid residues) is determined ("N-target"). The degree of identity is calculated as the ratio between "N-perfect-match" and "N-target" (for conversion to percentage identity, multiply by 100).

Preferably, the overlap is at least 20% of the specified sequence ("N-overlap" as defined above, divided by the number of the amino acids in the specified sequence ("N-specified"), and multiplied by 100), more preferably at least 25%, 30%, 35%, 40%, 45%, 50%, 55%, 60%, 65%, 70%, 75%, 80%, 85%, 90%, or at least 95%. This means that at least 20% (preferably 25-95%) of the amino acids of the specified sequence end up being included in the overlap, when the sample sequence is aligned to the specified sequence.

In the alternative, the overlap is at least 20% of the target (or sample, or test) sequence ("N-overlap" as defined above, divided by "N-target" as defined above, and multiplied by 100), more preferably at least 25%, 30%, 35%, 40%, 45%, 50%, 55%, 60%, 65%, 70%, 75%, 80%, 85%, 90%, or at least 95%. This means that at least 20% (preferably 25-95%) of the amino acids of the target sequence end up being included in the overlap, when aligned against the specified sequence).

Polypeptide Fragment: The term "polypeptide fragment" is defined herein as a polypeptide having one or more amino acids deleted from the amino and/or carboxyl terminus of the mature peptide part of the specified sequence, e.g. SEQ ID NO: 10, or a homologous sequence thereof, wherein the fragment has phytase activity. In particular embodiments, the fragment contains at least 350, 360, 370, 380, 390, 400, 405, or at least 410 amino acid residues.

Subsequence: The term "subsequence" is defined herein as a nucleotide sequence having one or more nucleotides deleted from the 5' and/or 3' end of the mature peptide encoding part of the specified sequence, e.g. SEQ ID NO: 9, or a homologous sequence thereof, wherein the subsequence encodes a polypeptide fragment having phytase activity. In particular embodiments, the subsequence contains at least 1050, 1080, 1110, 1140, 1170, 1200, 1215, 1230, 1245, 1260, 1275, 1290, 1305, 1320, or at least 1335 nucleotides.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99% pure, and even most preferably at least 99.5% pure by weight. The polynucleotides of the present invention are preferably in a substantially pure form. In particular, it is preferred that the polynucleotides disclosed herein are in "essentially pure form", i.e., that the polynucleotide preparation is essentially free of other polynucleotide material with which it is natively associated. Herein, the term "substantially pure polynucleotide" is synonymous with the terms "isolated polynucleotide" and "polynucleotide in isolated form." The polynucleotides may be of genomic, cDNA, RNA, semisynthetic, synthetic origin, or any combinations thereof.

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature. The term nucleic acid construct is synonymous with the term "expression cassette" when the nucleic acid construct contains the control sequences required for expression of a coding sequence of the present invention.

Control sequence: The term "control sequences" is defined herein to include all components, which are necessary or advantageous for the expression of a polynucleotide encoding a polypeptide of the present invention. Each control sequence may be native or foreign to the nucleotide sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG. The coding sequence may a DNA, cDNA, or recombinant nucleotide sequence.

Mature polypeptide part: When used herein the terms "mature polypeptide part" or "mature peptide part" refer to that part of the polypeptide which is secreted by a cell which contains, as part of its genetic equipment, a polynucleotide encoding the polypeptide. In other words, the mature polypeptide part refers to that part of the polypeptide which remains after the signal peptide part is cleaved off once it has fulfilled its function of directing the encoded polypeptide into the cell's secretory pathway. The predicted signal peptide part of SEQ ID NO: 10 is amino acids −33 to −1 thereof, which means that the predicted mature polypeptide part of SEQ ID NO: 10 corresponds to amino acids 1 to 413 thereof. However, a slight variation may occur from host cell to host cell, and therefore the expression mature polypeptide part is preferred.

Mature polypeptide encoding part: When used herein the term "mature polypeptide encoding part" or "mature polypeptide coding sequence" refers to that part of the polynucleotide encoding the polypeptide which encodes the mature polypeptide part. For example, for SEQ ID NO: 9, the predicted mature polypeptide encoding part corresponds to nucleotides 100 to 1338 (encoding amino acids 1 to 413 of SEQ ID NO: 10).

Expression: The term "expression" includes any step involved in the production of the polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the invention, and which is operably linked to additional nucleotides that provide for its expression.

Host cell: The term "host cell", as used herein, includes any cell type which is susceptible to transformation, transfection, transduction, and the like with a nucleic acid construct comprising a polynucleotide of the present invention.

Modification: The term "modification" means herein any chemical modification of the specified polypeptide, e.g. the polypeptide consisting of the amino acids 1 to 413 of SEQ ID NO: 10, as well as genetic manipulation of the DNA encoding that polypeptide. The modification(s) can be substitution(s), deletion(s) and/or insertions(s) of the amino acid(s) as well as replacement(s) of amino acid side chain(s).

Artificial variant: When used herein, the term "artificial variant" means a polypeptide having phytase activity produced by an organism expressing a modified nucleotide sequence of mature phytase encoding part of SEQ ID NO: 9. The modified nucleotide sequence is obtained through human intervention by modification of the mature phytase encoding part of the nucleotide sequence disclosed in SEQ ID NO: 9.

DETAILED DESCRIPTION OF THE INVENTION

Polypeptides having Phytase Activity

In a first aspect, the present invention relates to isolated polypeptides having phytase activity and having an amino acid sequence which has a degree of identity to amino acids 1 to 413 of SEQ ID NO: 10 (i.e., the mature polypeptide) of at least 75%.

In particular embodiments, the degree of identity is at least 76%, 77%, 78%, 79%, 80%, 81%, 82%, 83%, 84%, 85%, 86%, 87%, 88%, 89%, 90%, 91%, 92%, 93%, 94%, 95%, 96%, 96.5%, 97%, 97.5%, 98%, 98.5%, 98.7%, 98.8%, 98.9%, 99%, 99.0%, 99.1%, 99.2%, 99.3%, 99.4%, 99.5%, 99.6%, 99.7%, 99.8%, or at least 99.9%, which have phytase activity (hereinafter "homologous polypeptides").

In other particular embodiments, the homologous polypeptides have an amino acid sequence which differs by 20, 19, 18, 17, 16, 15, 14, 13, 12, 11, 10, 9, 8, 7, 6, 5, 4, 3, 2, or 1 amino acid from amino acids 1 to 413 of SEQ ID NO: 10.

In particular embodiments, the polypeptide of the present invention comprises the mature part of the amino acid sequence of SEQ ID NO: 10, or is an allelic variant thereof; or a fragment thereof that has phytase activity. In still further particular embodiments, the polypeptide comprises amino acids 1 to 413 of SEQ ID NO: 10, or an allelic variant thereof; or a fragment thereof that has phytase activity.

In a second aspect, the present invention relates to isolated polypeptides having phytase activity which are encoded by polynucleotides which hybridize under at least medium, preferably medium, stringency conditions with (i) nucleotides 100 to 1338 of SEQ ID NO: 9, (ii) the mature polypeptide encoding part of SEQ ID NO: 9, and/or (iii) a complementary strand of any one of (i), and (ii), and/or (iv) a subsequence of (i), (ii), or (iii) (J. Sambrook, E. F. Fritsch, and T. Maniatus, 1989, Molecular Cloning, A Laboratory Manual, 2d edition, Cold Spring Harbor, N.Y). A subsequence of SEQ ID NO: 9 contains at least 100 contiguous nucleotides or preferably at least 200 contiguous nucleotides. Moreover, the subsequence may encode a polypeptide fragment which has phytase activity.

In particular embodiments, the hybridization takes place under at least medium-high, at least high, or at least very high stringency conditions; preferably under medium-high, high, or very high stringency conditions.

In alternative embodiments, the hybridization is conducted under very low, or low stringency conditions.

The nucleotide sequence of SEQ ID NO: 9, or a subsequence thereof, as well as the amino acid sequence of SEQ ID NO: 10, or a fragment thereof, may be used to design a nucleic acid probe to identify and clone DNA encoding polypeptides having phytase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes which are at least 600 nucleotides, at least preferably at least 700 nucleotides, more preferably at least 800 nucleotides, or most preferably at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA library prepared from such other organisms may, therefore, be screened for DNA which hybridizes with the probes described above and which encodes a polypeptide having phytase activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO: 9, or a subsequence thereof, the carrier material is used in a Southern blot.

For purposes of the present invention, hybridization indicates that the nucleotide sequence hybridizes to a labeled nucleic acid probe corresponding to the nucleotide sequence shown in SEQ ID NO: 9, the complementary strand thereof, or a subsequence thereof, under very low to very high stringency conditions. Molecules to which the nucleic acid probe hybridizes under these conditions can be detected using X-ray film.

In a particular embodiment, the nucleic acid probe is any one of SEQ ID NOs: 1-8. In another particular embodiment, the nucleic acid probe is the complementary strand of nucleotides 100 to 450, nucleotides 450 to 900, or nucleotides 900 to 1338 of SEQ ID NO: 9. In a further particular embodiment, the nucleic acid probe is a polynucleotide sequence which encodes the mature part of the polypeptide of SEQ ID NO: 10, or a subsequence thereof. In a still further particular embodiment, the nucleic acid probe is SEQ ID NO: 9, in particular any one of the mature polypeptide coding regions thereof.

For long probes of at least 100 nucleotides in length, very low to very high stringency conditions are defined as prehybridization and hybridization at 42° C. in 5×SSPE, 0.3% SDS, 200 microgram/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, Proceedings of the National Academy of Sciences USA 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

Under salt-containing hybridization conditions, the effective $T_m$ is what controls the degree of identity required between the probe and the filter bound DNA for successful hybridization. The effective $T_m$ may be determined using the formula below to determine the degree of identity required for two DNAs to hybridize under various stringency conditions.

$$\text{Effective } T_m = 81.5 + 16.6(\log M[\text{Na}^+]) + 0.41(\% \, G+C) - 0.72(\% \text{ formamide})$$

(See ndsu.nodak.edu/instruct/mcclean/plsc731/dna/dna6.htm)

"G+C" designates the content of nucleotides G and T in the probe. For medium stringency, for example, the formamide is 35% and the Na$^+$ concentration for 5×SSPE is 0.75 M.

In one aspect, the present invention relates to isolated polypeptides having phytase activity, and the following physicochemical properties (as analyzed on the substantially pure polypeptides):
(i) a high specific activity, such as a specific activity on phytate of at least 50% of the specific activity of *E. coli* appA (SPTREMBL:Q8GN88), the specific activity being preferably measured in the units of FYT per mg phytase enzyme protein;
(ii) acid-stability; such as
  (a) at least 60%, preferably at least 65%, at least 70%, or at least 75%, residual activity after incubation over night at 37° C. in glycine/hydrochloric acid buffer pH 2.2, relative to the residual activity after incubation over night at 37° C. in HEPES buffer pH 7.0;
  (b) at least 80%, preferably at least 85%, at least 90%, or at least 95%, residual activity after incubation over night at 37° C. in glycine/hydrochloric acid buffer pH 3.0, relative to the residual activity after incubation over night at 37° C. in HEPES buffer pH 7.0; and/or
  (c) a residual phytase activity after 2 hours incubation at a temperature of 25, 30, 35, or 37° C., preferably 37° C., and a pH of 2.2, 2.4, 2.5, 2.6, 2.8, 3.0, 3.2, 3.4, or 3.5, preferably glycine/hydrochloric acid buffers of pH 2.2, or 3.0, of at least 50%, compared to the residual activity of *E. coli* appA (SPTREMBL:Q8GN88);
(iii) heat-stability, such as a residual phytase activity after 0.5, 1, 1.5, or 2 hours, preferably 0.5 hours, of incubation at a pH of 5.5 and a temperature of 55, 60, 65, 70, 75, 80, 85 or 95° C., preferably 70° C., of at least 50%, compared to the residual activity of *E. coli* appA (SPTREMBL:Q8GN88).

In the alternative, Differential Scanning Calorimetry (DSC) measurements may be used to determine the denaturation temperature, Td, of the purified phytase protein. The Td is indicative of the heat-stability of the protein: The higher the Td, the higher the heat-stability. DSC measurements may be performed at various pH values, e.g. using the VP-DSC from Micro Cal. Scans are performed at a constant scan rate of 1.5° C./min from 20-90° C. Preferred pH values are 4.0 and 5.5, preferably 4.0. Before running the DSC, the phytases are desalted, e.g. using NAP-5 columns (Pharmacia) equilibrated in appropriate buffers (e.g. 25 mM sodium acetate pH 4.0; 0.1M sodium acetate, pH 5.5). Data-handling is performed using the MicroCal Origin software (version 4.10), and the denaturation temperature, Td (also called the melting temperature, Tm) is defined as the temperature at the apex of the peak in the thermogram;
(iv) protease-stability, such as a residual phytase activity after 0.5, 1, 1.5, or 2 hours, preferably 1 hour, incubation at a temperature of 20, 25, 30, 35, or 37° C., preferably 37° C., and a pH of 5.5, in the presence of 0.1 mg/ml pepsin, of at least 50%, compared to the residual activity of *E. coli* appA (SPTREMBL:Q8GN88); and/or
(v) a pH-optimum below pH 5.0, for example below pH 4.5, 4.0, 3.5, 3.0, 2.5, or even below 2.0, determined using the FYT assay, and/or using the assay of Example 4, as described hereinbefore.

In particular embodiments of aspect (i) above, the specific activity is at least 60, 70, 80, 90, 100, 110, 120, 130, 140, or at least 150% of the specific activity of *E. coli* appA. In particular embodiments of each of aspects (ii) to (iv) above, the residual activity is at least 60, 70, 80, 90, 100, 110, 120, 130, 140, or at least 150% of the residual activity of *E. coli* appA.

In a fifth aspect, the activity of the enzyme of the invention, at pH 5.0 and 37° C., measured on the substrate pNP-phosphate is less than 11% of the activity of the enzyme measured on the substrate phytate. Preferably, the ratio is less than 10%, 9%, 8%, 7%, 6%, or less than 5%. The ratio of pNP to phytate hydrolysis is indicative of the true phytase nature of the enzyme. A high ratio of activity on pNP relative to activity on phytate may indicate that the enzyme in question is a phosphatase with relatively low substrate specificity, whereas a low ratio indicates that this is an enzyme more specifically accepting phytate as a substrate.

In a sixth aspect, the phytase of the invention has a higher release of phosphorous (P) in an in vitro model, as compared to the phytase from *Peniophora lycii*, preferably at least 110% thereof, more preferably at least 120%, 130%, or at least 140% thereof. In one embodiment, the phytase of the invention, dosed 0.25 FYT/g feed, releases at least 150% phosphorous (P), relative to the phosphorous released by the phytase from *Peniophora lycii*, also dosed 0.25 FYT/g feed, in the in vitro model. Preferably, the release is at least 155%, 160%, 165%, 170%, 175%, or at least 180%. In another embodiment, the phytase of the invention, dosed 0.75 FYT/g feed, releases at least 150% phosphorous (P), relative to the phosphorous released by the phytase from *Peniophora lycii*, also dosed 0.75 FYT/g feed, in the in vitro model. Preferably, the release is at least 155%, 160%, 165%, 170%, 175%, 180%, 185%, or at least 190%.

In a seventh aspect, the phytase of the invention has a residual activity following incubation at 37° C. and in a 0.1 M Glycine/HCl buffer, pH 2.0, for 4 hours of at least 20%, as compared to the activity at time, t=0, the activity (and the residual activity) being assayed at 37° C. and pH 5.5 on 1% (w/v) Na-phytate, using a 0.25 M Na-acetate buffer pH 5.5, buffer blind subtracted. In preferred embodiments, the residual activity is at least 25%, 30%, 35%, 40%, 45%, 50%, 55%, 60%, 65%, 70%, 75%, or at least 80%. In another embodiment, the phytase of the invention has a residual activity following incubation at 37° C. and in a 0.1M Glycine/HCl buffer, pH 2.5, for 1 day (24 hours) of at least 20%, as compared to the activity at time, t=0, the activity (and the residual activity) being assayed at 37° C. and pH 5.5 on 1% (w/v) Na-phytate, using a 0.25 M Na-acetate buffer pH 5.5, buffer blind subtracted. In preferred embodiments, the residual activity is at least 25%, 30%, 35%, 40%, 45%, 50%, 55%, 60%, 65%, 70%, 75%, or at least 80%.

In an eighth aspect, the present invention relates to artificial variants comprising a conservative substitution, deletion, and/or insertion of one or more amino acids of SEQ ID NO: 10, or the mature polypeptide thereof. An insertion can be inside the molecule, and/or at the N- and/or C-terminal end of the molecule in which case it is also designated extension. Preferably, amino acid changes are of a minor nature, that is conservative amino acid substitutions; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain—in other words: Changes that do not significantly affect the folding and/or activity of the protein.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine).

Other examples of conservative substitutions are substitutions of the 20 standard amino acids with non-standard amino acids (such as 4-hydroxyproline, 6-N-methyl lysine, 2-aminoisobutyric acid, isovaline, and alpha-methyl serine). Conservative substitutions may also include a substitution into amino acids that are not encoded by the genetic code, and unnatural amino acids. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in the parent polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for biological activity (i.e., phytase activity) to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309:59-64. The identities of essential amino acids can also be inferred from analysis of identities with polypeptides which are related to a polypeptide according to the invention.

Single or multiple amino acid substitutions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al., 1991, Biochem. 30:10832-10837; U.S. Pat. No. 5,223,409; WO 92/06204), and region-directed mutagenesis (Derbyshire et al., 1986, Gene 46:145; Ner et al., 1988, DNA 7:127).

Mutagenesis/shuffling methods can be combined with high-throughput, automated screening methods to detect activity of cloned, mutagenized polypeptides expressed by host cells. Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

The total number of amino acid substitutions (preferably conservative substitutions), deletions and/or insertions in the sequence of amino acids 1 to 413 of SEQ ID NO: 10 is at most 10, preferably at most 9, more preferably at most 8, more preferably at most 7, more preferably at most 6, more preferably at most 5, more preferably at most 4, even more preferably at most 3, most preferably at most 2, and even most preferably 1.

The total number of amino acid substitutions, deletions and/or insertions of amino acids 1 to 413 of SEQ ID NO: 10 is 10, preferably 9, more preferably 8, more preferably 7, more preferably at most 6, more preferably at most 5, more preferably 4, even more preferably 3, most preferably 2, and even most preferably 1. In the alternative, the total number of amino acid substitutions (preferably conservative substitutions), deletions and/or insertions in the sequence of amino acids 1 to 413 of SEQ ID NO: 10 is at most 50, 45, 40, 35, 30, 25, 20, 19, 18, 17, 16, 15, 14, 13, 12, or at most 11.

In a specific embodiment, the polypeptide of the invention is a low-allergenic variant, designed to invoke a reduced immunological response when exposed to animals, including man. The term immunological response is to be understood as any reaction by the immune system of an animal exposed to the polypeptide. One type of immunological response is an allergic response leading to increased levels of IgE in the exposed animal. Low-allergenic variants may be prepared using techniques known in the art. For example the polypeptide may be conjugated with polymer moieties shielding portions or epitopes of the polypeptide involved in an immunological response. Conjugation with polymers may involve in vitro chemical coupling of polymer to the polypeptide, e.g. as described in WO 96/17929, WO 98/30682, WO 98/35026, and/or WO 99/00489. Conjugation may in addition or alternatively thereto involve in vivo coupling of polymers to the polypeptide. Such conjugation may be achieved by genetic engineering of the nucleotide sequence encoding the polypeptide, inserting consensus sequences encoding additional glycosylation sites in the polypeptide and expressing the polypeptide in a host capable of glycosylating the polypeptide, see e.g. WO 00/26354. Another way of providing low-allergenic variants is genetic engineering of the nucleotide sequence encoding the polypeptide so as to cause the polypeptide to self-oligomerize, effecting that polypeptide monomers may shield the epitopes of other polypeptide monomers and thereby lowering the antigenicity of the oligomers. Such products and their preparation is described e.g. in WO96/16177. Epitopes involved in an immunological response may be identified by various methods such as the phage display method described in WO 00/26230 and WO 01/83559, or the random approach described in EP 561907. Once an epitope has been identified, its amino acid sequence may be altered to produce altered immunological properties of the polypeptide by known gene manipulation techniques such as site directed mutagenesis (see e.g. WO 00/26230, WO 00/26354 and/or WO 00/22103) and/or conjugation of a polymer may be done in sufficient proximity to the epitope for the polymer to shield the epitope.

Three Dimensional Structure of a *Hafnia alvei* Phytase

The three-dimensional structure of a *Hafnia alvei* phytase (amino acids 1 to 413 of SEQ ID NO:10) is provided in the Appendix. The structure was solved in accordance with the principles for x-ray crystallographic methods, for example, as given in X-Ray Structure Determinations, Stout, G. K. and Jensen, L. H., John Wiley and Sons, Inc. NY 1989. The structural coordinates for the solved crystal structure of *Hafnia alvei* phytase are given in standard PDB format (Protein Database Bank, Brookhaven National Laboratory, Brookhaven, Conn.) as set forth in the Appendix. It is to be understood that the Appendix forms part of the present application. The Appendix provides the coordinates of the heavy atoms, excluding the hydrogen atoms. The first three residues of the enzyme were not visible in the crystal structure as well as the amino acid residues between amino acids 180 and 189. However, the structure between 180 and 189 was built using modelling combining the homology modelling (see, for example, Marti-Renom et al., 2000) program NEST from the JACKAL package (wiki.c2b2.columbia.edu/honiglab_public/index.php/Software:Jackal) and the simulation software called CHARMm (//accelrys.com/products/scitegic/component-collections/charmm.html).

Sources of Polypeptides Having Phytase Activity

A polypeptide of the present invention may be obtained from microorganisms of any genus. For purposes of the present invention, the term "obtained from" as used herein in connection with a given source shall mean that the polypeptide encoded by a nucleotide sequence is produced by the source or by a strain in which the nucleotide sequence from the source has been inserted. In a preferred aspect, the polypeptide obtained from a given source is secreted extracellularly.

A polypeptide of the present invention may be a bacterial polypeptide. For example, the polypeptide may be a gram positive bacterial polypeptide such as a *Bacillus* polypeptide, or a *Streptomyces* polypeptide; or a gram negative bacterial polypeptide, e.g., an *Escherichia coli, Yersinia, Klebsiella, Citrobacter*, or a *Pseudomonas* polypeptide. In a particular embodiment, the polypeptide is derived from Proteobacteria, such as Gammaproteobacteria, for example Enterobacteriales, such as Enterobacteriaceae.

In a particular aspect, the polypeptide derived from Enterobacteriaceae is a *Hafnia* polypeptide, such as a *Hafnia alvei* species polypeptide.

A polypeptide of the present invention may also be a fungal polypeptide, such as a yeast polypeptide or a filamentous fungal polypeptide.

Strains of the above microorganisms are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The polynucleotide may then be obtained by similarly screening a genomic or cDNA library of another microorganism. Once a polynucleotide sequence encoding a polypeptide has been detected with the probe(s), the polynucleotide can be isolated or cloned by utilizing techniques which are well known to those of ordinary skill in the art (see, e.g., Sambrook et al., 1989, supra).

Polypeptides of the present invention also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Polynucleotides

The present invention also relates to isolated polynucleotides having a nucleotide sequence which encodes a polypeptide of the present invention. In a preferred aspect, the nucleotide sequence is set forth in SEQ ID NO: 9. In another preferred aspect, the nucleotide sequence is the mature polypeptide coding region of SEQ ID NO: 9. The present invention also encompasses nucleotide sequences which encode a polypeptide having the amino acid sequence of SEQ ID NO: 10, or the mature polypeptides thereof, which differ from SEQ ID NO: 9, by virtue of the degeneracy of the genetic code. The present invention also relates to subsequences of SEQ ID NO: 9, which encode fragments of SEQ ID NO: 10, that have phytase activity.

The present invention also relates to mutant polunucleotides comprising at least one mutation in the mature polypeptide coding sequence of any one of SEQ ID NO: 9, in which the mutant nucleotide sequence encodes a polypeptide which consists of amino acids 1 to 413 of SEQ ID NO: 10.

The techniques used to isolate or clone a polynucleotide encoding a polypeptide are known in the art and include isolation from genomic DNA, preparation from cDNA, or a combination thereof. The cloning of the polynucleotides of the present invention from such genomic DNA can be effected, e.g., by using the well known polymerase chain reaction (PCR) or antibody screening of expression libraries to detect cloned DNA fragments with shared structural features. See, e.g., Innis et al., 1990, PCR: A Guide to Methods and Application, Academic Press, New York. Other nucleic acid amplification procedures such as ligase chain reaction (LCR), ligated activated transcription (LAT) and nucleotide sequence-based amplification (NASBA) may be used. The polynucleotides may be cloned from a strain of Hafnia, or another or related organism and thus, for example, may be an allelic or species variant of the polypeptide encoding region of the nucleotide sequence.

The present invention also relates to polynucleotides having nucleotide sequences which have a degree of identity to the mature polypeptide coding sequence of SEQ ID NO: 9 (i.e., nucleotides 100 to 1338) of at least 75%, and which encode a polypeptide having phytase activity. In particular embodiments, the degree of identity is at least In particular embodiments, the degree of identity is at least 76%, 77%, 78%, 79%, 80%, 81%, 82%, 83%, 84%, 85%, 86%, 87%, 88%, 89%, 90%, 91%, 92%, 93%, 94%, 95%, 96%, 96.5%, 97%, 97.5%, 98%, 98.5%, 98.7%, 98.8%, 98.9%, 99%, 99.0%, 99.1%, 99.2%, 99.3%, 99.4%, 99.5%, 99.6%, 99.7%, 99.8%, or at least 99.9%. In alternative embodiments, the degree of identity is at least 75%, 80%, 85%, 90%, 94, 97, 98, 98.0, 98.1, 98.2, or at least 98.3%.

Modification of a nucleotide sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., artificial variants that differ in specific activity, thermostability, pH-optimum, or the like. The variant sequence may be constructed on the basis of the nucleotide sequence presented as the polypeptide encoding region of SEQ ID NO: 9, e.g., a subsequence thereof, and/or by introduction of nucleotide substitutions which do not give rise to another amino acid sequence of the polypeptide encoded by the nucleotide sequence, but which correspond to the codon usage of the host organism intended for production of the polypeptide, or by introduction of nucleotide substitutions which may give rise to a different amino acid sequence. For a general description of nucleotide substitution, see, e.g., Ford et al., 1991, Protein Expression and Purification 2: 95-107.

It will be apparent to those skilled in the art that such substitutions can be made outside the regions critical to the function of the molecule and still result in an active polypeptide. Amino acid residues essential to the activity of the polypeptide encoded by an isolated polynucleotide of the invention, and therefore preferably not subject to substitution, may be identified according to procedures known in the art, such as site-directed mutagenesis or alanine-scanning mutagenesis (see, e.g., Cunningham and Wells, 1989, Science 244: 1081-1085). In the latter technique, mutations are introduced at every positively charged residue in the molecule, and the resultant mutant molecules are tested for phytase activity to identify amino acid residues that are critical to the activity of the molecule. Sites of substrate-polypeptide interaction can also be determined by analysis of the three-dimensional structure as determined by such techniques as nuclear magnetic resonance analysis, crystallography or photoaffinity labelling (see, e.g., de Vos et al., 1992, Science 255: 306-312; Smith et al., 1992, Journal of Molecular Biology 224: 899-904; Wlodaver et al., 1992, FEBS Letters 309: 59-64).

The present invention also relates to isolated polynucleotides encoding a polypeptide of the present invention, which hybridize under medium stringency conditions, more preferably medium-high stringency conditions, even more preferably high stringency conditions, and most preferably very high stringency conditions with (i) nucleotides 100 to 1338 of SEQ ID NO: 9, (ii) the mature polypeptide encoding part of SEQ ID NO: 9, and/or (iii) a complementary strand of any one of (i), and/or (ii); or allelic variants and subsequences thereof (Sambrook et al., 1989, supra), as defined herein. In alternative embodiments the hybridization is conducted under very low, or low, stringency conditions.

The present invention also relates to isolated polynucleotides obtained, or obtainable, by (a) hybridizing a population of DNA under very low, low, medium, medium-high, high, or very high stringency conditions with (i) nucleotides 100 to 1338 of SEQ ID NO: 9, (ii) the mature polypeptide encoding part of SEQ ID NO: 9, and/or (iii) a complementary strand of any one of (i), and/or (ii); and (b) isolating the hybridizing polynucleotide, which encodes a polypeptide having phytase activity.

Nucleic Acid Constructs

The present invention also relates to nucleic acid constructs comprising an isolated polynucleotide of the present invention operably linked to one or more control sequences which direct the expression of the coding sequence in a suitable host cell under conditions compatible with the control sequences.

An isolated polynucleotide encoding a polypeptide of the present invention may be manipulated in a variety of ways to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence which is recognized by a host cell for expression of a polynucleotide encoding a polypeptide of the present invention. The promoter sequence contains transcriptional control sequences which mediate the expression of the polypeptide. The promoter may be any nucleotide sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM),

*Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, Proceedings of the National Academy of Sciences USA 75: 3727-3731), as well as the tac promoter (DeBoer et al., 1983, Proceedings of the National Academy of Sciences USA 80: 21-25). Further promoters are described in "Useful proteins from recombinant bacteria" in Scientific American, 1980, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Daria (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1,ADH2/GAP), *Saccharomyces cerevisiae* triose phosphate isomerase (TPI), *Saccharomyces cerevisiae* metallothionine (CUP1), *Saccharomyces cerevisiae* 3-phosphoglycerate kinase, and *Pichia pastoris* alcohol oxidase (AOX1). Other useful promoters for yeast host cells are described by Romanos et al., 1992, Yeast 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleotide sequence encoding the polypeptide. Any leader sequence that is functional in the host cell of choice may be used in the present invention.

The control sequence may also be a suitable leader sequence, a nontranslated region of an mRNA which is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, Molecular Cellular Biology 15: 5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleotide sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, Microbiological Reviews 57: 109-137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra, and by Xiong et al in Journal of Applied Microbiology 2005, 98, 418-428.

In a preferred aspect, the signal peptide coding region is nucleotides 1 to 99 of SEQ ID NO: 9, which encode amino acids 1 to 33 of SEQ ID NO: 10. In another preferred aspect, the signal peptide coding region is nucleotides 1 to 81 of SEQ ID NO: 11, which encode amino acids 1 to 27 of SEQ ID NO: 12.

The control sequence may also be a propeptide coding region that codes for an amino acid sequence positioned at the amino terminus of a polypeptide. The resultant polypeptide is known as a propolypeptide or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification.

Expression Vectors

The present invention also relates to recombinant expression vectors comprising a polynucleotide of the present invention, a promoter, and transcriptional and translational stop signals. The various nucleic acids and control sequences described above may be joined together to produce a recombinant expression vector which may include one or more convenient restriction sites to allow for insertion or substitution of the nucleotide sequence encoding the polypeptide at such sites. Alternatively, a nucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like.

A conditionally essential gene may function as a non-antibiotic selectable marker. Non-limiting examples of bacterial conditionally essential non-antibiotic selectable markers are the dal genes from *Bacillus subtilis*, *Bacillus licheniformis*, or other Bacilli, that are only essential when the bacterium is cultivated in the absence of D-alanine. Also the genes encoding enzymes involved in the turnover of UDP-galactose can function as conditionally essential markers in a cell when the cell is grown in the presence of galactose or grown in a medium which gives rise to the presence of galactose. Non-limiting examples of such genes are those from *B. subtilis* or *B. licheniformis* encoding UTP-dependent phosphorylase (EC 2.7.7.10), UDP-glucose-dependent uridylyltransferase (EC 2.7.7.12), or UDP-galactose epimerase (EC 5.1.3.2). Also a xylose isomerase gene such as xylA, of Bacilli can be used as selectable markers in cells grown in minimal medium with xylose as sole carbon source. The genes necessary for utilizing gluconate, gntK, and gntP can also be used as selectable markers in cells grown in minimal medium with gluconate as sole carbon source. Other examples of conditionally essential genes are known in the art. Antibiotic selectable markers confer antibiotic resistance to such antibiotics as ampicillin, kanamycin, chloramphenicol, erythromycin, tetracycline, neomycin, hygromycin or methotrexate.

Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity with the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication which functions in a cell. The term "origin of replication" or "plasmid replicator" is defined herein as a nucleotide sequence that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, Gene 98:61-67; Cullen et al., 1987, Nucleic Acids Research 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into the host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention, which are advantageously used in the recombinant production of the polypeptides. A vector comprising a polynucleotide of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote.

Useful unicellular microorganisms are bacterial cells such as gram positive bacteria including, but not limited to, a *Bacillus* cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis,* and *Bacillus thuringiensis*; or a *Streptomyces* cell, e.g., *Streptomyces lividans* and *Streptomyces murinus*, or gram negative bacteria such as *E. coli* and *Pseudomonas* sp. In a preferred aspect, the bacterial host cell is a *Bacillus lentus, Bacillus licheniformis, Bacillus stearothermophilus,* or *Bacillus subtilis* cell. In another preferred aspect, the *Bacillus* cell is an alkalophilic *Bacillus*.

The introduction of a vector into a bacterial host cell may, for instance, be effected by protoplast transformation (see, e.g., Chang and Cohen, 1979, Molecular General Genetics 168: 111-115), using competent cells (see, e.g., Young and Spizizin, 1961, Journal of Bacteriology 81: 823-829, or Dubnau and Davidoff-Abelson, 1971, Journal of Molecular Biology 56: 209-221), electroporation (see, e.g., Shigekawa and Dower, 1988, Biotechniques 6: 742-751), or conjugation (see, e.g., Koehler and Thorne, 1987, Journal of Bacteriology 169: 5771-5278).

The host cell may also be a eukaryote, such as a mammalian, insect, plant, or fungal cell.

In a preferred aspect, the host cell is a fungal cell. "Fungi" as used herein includes the phyla Ascomycota, Basidiomycota, Chytridiomycota, and Zygomycota (as defined by Hawksworth et al., In, Ainsworth and Bisby's Dictionary of The Fungi, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, F. A., Passmore, S. M., and Davenport, R. R., eds, Soc. App. Bacteriol. Symposium Series No. 9, 1980).

In an even more preferred aspect, the yeast host cell is a *Candida, Hansenula, Kluyveromyces, Pichia, Saccharomyces, Schizosaccharomyces,* or *Yarrowia* cell.

In a most preferred aspect, the yeast host cell is a *Pichia pastoris, Pichia methanolica, Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium, Aspergillus, Aureobasidium, Bjerkandera, Ceriporiopsis, Coprinus, Coriolus, Cryptococcus, Filobasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

In a most preferred aspect, the filamentous fungal host cell is an *Aspergillus awamori, Aspergillus fumigatus, Aspergillus foetidus, Aspergillus japonicus, Aspergillus nidulans, Aspergillus niger* or *Aspergillus oryzae* cell. In another most preferred aspect, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides,* or *Fusarium venenatum* cell. In another most preferred aspect, the filamentous fungal host cell is a *Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa,* or *Ceriporiopsis subvermispora, Coprinus cinereus, Coriolus hirsutus, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* strain cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, Proceedings of the National Academy of Sciences USA 81: 1470-1474. Suitable methods for transforming *Fusarium* species are described by Malardier et al., 1989, Gene 78: 147-156, and WO 96/00787. Yeast may be transformed using the procedures described by Becker and Guarente, In Abelson, J. N. and Simon, M. I., editors, Guide to Yeast Genetics and Molecular Biology, Methods in Enzymology, Volume 194, pp 182-187, Academic Press, Inc., New York; Ito et al., 1983, Journal of Bacteriology 153: 163; and Hinnen et al., 1978, Proceedings of the National Academy of Sciences USA 75: 1920.

Methods of Production

The present invention also relates to methods for producing a polypeptide of the present invention, comprising (a) cultivating a cell, which in its wild-type form is capable of producing the polypeptide, under conditions conducive for production of the polypeptide; and (b) recovering the polypeptide. Preferably, the cell is of the genus *Hafnia*, and more preferably *Hafnia alvei*.

The present invention also relates to methods for producing a polypeptide of the present invention, comprising (a) cultivating a host cell under conditions conducive for production of the polypeptide; and (b) recovering the polypeptide.

The present invention also relates to methods for producing a polypeptide of the present invention, comprising (a) cultivating a host cell under conditions conducive for production of the polypeptide, wherein the host cell comprises a mutant nucleotide sequence having at least one mutation in the mature polypeptide coding region of any one of SEQ ID NO: 9, wherein the mutant nucleotide sequence encodes a polypeptide which consists of amino acids 1 to 413 of SEQ ID NO: 10, and (b) recovering the polypeptide.

In the production methods of the present invention, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of a polypeptide product, or disappearance of an polypeptide substrate. For example, an polypeptide assay may be used to determine the activity of the polypeptide as described herein.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, J.-C. Janson and Lars Ryden, editors, VCH Publishers, New York, 1989).

Transgenic Plants

The present invention also relates to a transgenic plant, plant part, or plant cell which has been transformed with a nucleotide sequence encoding a polypeptide having phytase activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

In a particular embodiment, the polypeptide is targeted to the endosperm storage vacuoles in seeds. This can be obtained by synthesizing it as a precursor with a suitable signal peptide, see Horvath et al in PNAS, Feb. 15, 2000, vol. 97, no. 4, p. 1914-1919.

The transgenic plant can be dicotyledonous (a dicot) or monocotyledonous (a monocot) or engineered variants thereof. Examples of monocot plants are grasses, such as meadow grass (blue grass, *Poa*), forage grass such as *Festuca*, *Lolium*, temperate grass, such as *Agrostis*, and cereals, e.g., wheat, oats, rye, barley, rice, sorghum, triticale (stabilized hybrid of wheat (*Triticum*) and rye (*Secale*), and maize (corn). Examples of dicot plants are tobacco, legumes, such as sunflower (*Helianthus*), cotton (*Gossypium*), lupins, potato, sugar beet, pea, bean and soybean, and cruciferous plants (family Brassicaceae), such as cauliflower, rape seed, and the closely related model organism *Arabidopsis thaliana*. Low-phytate plants as described e.g. in U.S. Pat. No. 5,689,054 and U.S. Pat. No. 6,111,168 are examples of engineered plants.

Examples of plant parts are stem, callus, leaves, root, fruits, seeds, and tubers, as well as the individual tissues comprising these parts, e.g. epidermis, mesophyll, parenchyma, vascular tissues, meristems. Also specific plant cell compartments, such as chloroplast, apoplast, mitochondria, vacuole, peroxisomes, and cytoplasm are considered to be a plant part. Furthermore, any plant cell, whatever the tissue origin, is considered to be a plant part. Likewise, plant parts such as specific tissues and cells isolated to facilitate the utilisation of the invention are also considered plant parts, e.g. embryos, endosperms, aleurone and seed coats.

Also included within the scope of the present invention are the progeny of such plants, plant parts and plant cells.

The transgenic plant or plant cell expressing a polypeptide of the present invention may be constructed in accordance with methods known in the art. Briefly, the plant or plant cell is constructed by incorporating one or more expression constructs encoding a polypeptide of the present invention into the plant host genome and propagating the resulting modified plant or plant cell into a transgenic plant or plant cell.

Conveniently, the expression construct is a nucleic acid construct which comprises a nucleic acid sequence encoding a polypeptide of the present invention operably linked with appropriate regulatory sequences required for expression of the nucleic acid sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences are determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific cell compartment, tissue or plant part such as seeds or leaves. Regulatory sequences are, for example, described by Tague et al., 1988, Plant Physiology 86: 506.

For constitutive expression, the following promoters may be used: The 35S-CaMV promoter (Franck et al., 1980, Cell 21: 285-294), the maize ubiquitin 1 (Christensen A H, Sharrock R A and Quail 1992. Maize polyubiquitin genes: structure, thermal perturbation of expression and transcript splicing, and promoter activity following transfer to protoplasts by electroporation), or the rice actin 1 promoter (Plant Mo. Biol. 18, 675-689.; Zhang W, McElroy D. and Wu R 1991, Analysis of rice Act1 5' region activity in transgenic rice plants. Plant Cell 3, 1155-1165). Organ-specific promoters may be, for example, a promoter from storage sink tissues such as seeds, potato tubers, and fruits (Edwards & Coruzzi, 1990, Ann. Rev. Genet. 24: 275-303), or from metabolic sink tissues such as meristems (Ito et al., 1994, Plant Mol. Biol. 24: 863-878), a seed specific promoter such as the glutelin, prolamin, globulin, or albumin promoter from rice (Wu et al., 1998, Plant and Cell Physiology 39: 885-889), a *Vicia faba* promoter from the legumin B4 and the unknown seed protein gene from *Vicia faba* (Conrad et al., 1998, Journal of Plant Physiology 152: 708-711), a promoter from a seed oil body protein (Chen et al., 1998, Plant and Cell Physiology 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, Plant Physiology 102: 991-1000, the chlorella virus adenine methyltransferase gene promoter (Mitra and Higgins, 1994, Plant Molecular Biology 26: 85-93), or the aldP gene promoter from rice (Kagaya et al., 1995, Molecular and General Genetics 248: 668-674), or a wound inducible promoter such as the potato pin2 promoter (Xu et al., 1993, Plant Molecular Biology 22: 573-588). Likewise, the promoter may be inducible by abiotic treatments such as temperature, drought or alterations in salinity or inducible by exogenously applied substances that activate the promoter, e.g. ethanol, oestrogens, plant hormones like ethylene, abscisic acid, gibberellic acid, and/or heavy metals.

A promoter enhancer element may also be used to achieve higher expression of the polypeptide in the plant. For instance, the promoter enhancer element may be an intron which is placed between the promoter and the nucleotide sequence encoding a polypeptide of the present invention. For instance, Xu et al., 1993, supra disclose the use of the first intron of the rice actin 1 gene to enhance expression.

Still further, the codon usage may be optimized for the plant species in question to improve expression (see Horvath et al referred to above).

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, Science 244: 1293; Potrykus, 1990, Bio/Technology 8: 535; Shimamoto et al., 1989, Nature 338: 274).

Presently, *Agrobacterium tumefaciens*-mediated gene transfer is the method of choice for generating transgenic dicots (for a review, see Hooykas and Schilperoort, 1992, Plant Molecular Biology 19: 15-38), and it can also be used for transforming monocots, although other transformation methods are more often used for these plants. Presently, the method of choice for generating transgenic monocots, supplementing the *Agrobacterium* approach, is particle bombardment (microscopic gold or tungsten particles coated with the transforming DNA) of embryonic calli or developing embryos (Christou, 1992, Plant Journal 2: 275-281; Shimamoto, 1994, Current Opinion Biotechnology 5: 158-162; Vasil et al., 1992, Bio/Technology 10: 667-674). An alternative method for transformation of monocots is based on protoplast transformation as described by Omirulleh et al., 1993, Plant Molecular Biology 21: 415-428.

Following transformation, the transformants having incorporated therein the expression construct are selected and regenerated into whole plants according to methods well-known in the art. Often the transformation procedure is designed for the selective elimination of selection genes either during regeneration or in the following generations by using e.g. co-transformation with two separate T-DNA constructs or site specific excision of the selection gene by a specific recombinase.

The present invention also relates to methods for producing a polypeptide of the present invention comprising (a) cultivating a transgenic plant or a plant cell comprising a nucleic acid sequence encoding a polypeptide having phytase activity of the present invention under conditions conducive for production of the polypeptide; and (b) recovering the polypeptide.

Transgenic Animals

The present invention also relates to a transgenic, non-human animal and products or elements thereof, examples of which are body fluids such as milk and blood, organs, flesh, and animal cells. Techniques for expressing proteins, e.g. in mammalian cells, are known in the art, see e.g. the handbook Protein Expression: A Practical Approach, Higgins and Hames (eds), Oxford University Press (1999), and the three other handbooks in this series relating to Gene Transcription, RNA processing, and Post-translational Processing. Generally speaking, to prepare a transgenic animal, selected cells of a selected animal are transformed with a nucleic acid sequence encoding a polypeptide having phytase activity of the present invention so as to express and produce the polypeptide. The polypeptide may be recovered from the animal, e.g. from the milk of female animals, or the polypeptide may be expressed to the benefit of the animal itself, e.g. to assist the animal's digestion. Examples of animals are mentioned below in the section headed Animal Feed.

To produce a transgenic animal with a view to recovering the polypeptide from the milk of the animal, a gene encoding the polypeptide may be inserted into the fertilized eggs of an animal in question, e.g. by use of a transgene expression vector which comprises a suitable milk protein promoter, and the gene encoding the polypeptide. The transgene expression vector is is microinjected into fertilized eggs, and preferably permanently integrated into the chromosome. Once the egg begins to grow and divide, the potential embryo is implanted into a surrogate mother, and animals carrying the transgene are identified. The resulting animal can then be multiplied by conventional breeding. The polypeptide may be purified from the animal's milk, see e.g. Meade, H. M. et al (1999): Expression of recombinant proteins in the milk of transgenic animals, Gene expression systems: Using nature for the art of expression. J. M. Fernandez and J. P. Hoeffler (eds.), Academic Press.

In the alternative, in order to produce a transgenic non-human animal that carries in the genome of its somatic and/or germ cells a nucleic acid sequence including a heterologous transgene construct including a transgene encoding the polypeptide, the transgene may be operably linked to a first regulatory sequence for salivary gland specific expression of the polypeptide, as disclosed in WO 00/064247.

Compositions and Uses

In still further aspects, the present invention relates to compositions comprising a polypeptide of the present invention, as well as methods of using these.

The polypeptide compositions may be prepared in accordance with methods known in the art and may be in the form of a liquid or a dry composition. For instance, the polypeptide composition may be in the form of granulates or microgranulates. The polypeptide to be included in the composition may be stabilized in accordance with methods known in the art.

The phytase of the invention can be used for degradation, in any industrial context, of, for example, phytate, phytic acid, and/or the mono-, di-, tri-, tetra- and/or penta-phosphates of myo-inositol. It is well known that the phosphate moieties of these compounds chelates divalent and trivalent cations such as metal ions, i.a. the nutritionally essential ions of calcium, iron, zinc and magnesium as well as the trace minerals manganese, copper and molybdenum. Besides, the phytic acid also to a certain extent binds proteins by electrostatic interaction.

Accordingly, preferred uses of the polypeptides of the invention are in animal feed preparations (including human food) or in additives for such preparations.

In a particular embodiment, the polypeptide of the invention can be used for improving the nutritional value of an animal feed. Non-limiting examples of improving the nutritional value of animal feed (including human food), are: Improving feed digestibility; promoting growth of the animal; improving feed utilization; improving bio-availability of proteins; increasing the level of digestible phosphate; improving the release and/or degradation of phytate; improving bio-availability of trace minerals; improving bio-availability of macro minerals; eliminating the need for adding supplemental phosphate, trace minerals, and/or macro minerals; and/or improving egg shell quality. The nutritional value of the feed is therefore increased, and the growth rate and/or weight gain and/or feed conversion (i.e. the weight of ingested feed relative to weight gain) of the animal may be improved.

Furthermore, the polypeptide of the invention can be used for reducing phytate level of manure.

Animals, Animal Feed, and Animal Feed Additives

The term animal includes all animals, including human beings. Examples of animals are non-ruminants, and ruminants. Ruminant animals include, for example, animals such as sheep, goats, horses, and cattle, e.g. beef cattle, cows, and young calves. In a particular embodiment, the animal is a non-ruminant animal. Non-ruminant animals include monogastric animals, e.g. pigs or swine (including, but not limited to, piglets, growing pigs, and sows); poultry such as turkeys, ducks and chicken (including but not limited to broiler chicks, layers); young calves; and fish (including but not limited to salmon, trout, tilapia, catfish and carps; and crustaceans (including but not limited to shrimps and prawns).

The term feed or feed composition means any compound, preparation, mixture, or composition suitable for, or intended for intake by an animal.

In the use according to the invention the polypeptide can be fed to the animal before, after, or simultaneously with the diet. The latter is preferred.

In a particular embodiment, the polypeptide, in the form in which it is added to the feed, or when being included in a feed additive, is substantially pure. In a particular embodiment it is well-defined. The term "well-defined" means that the phytase preparation is at least 50% pure as determined by Size-exclusion chromatography (see Example 12 of WO 01/58275). In other particular embodiments the phytase preparation is at least 60, 70, 80, 85, 88, 90, 92, 94, or at least 95% pure as determined by this method.

A substantially pure, and/or well-defined polypeptide preparation is advantageous. For instance, it is much easier to dose correctly to the feed a polypeptide that is essentially free from interfering or contaminating other polypeptides. The term dose correctly refers in particular to the objective of obtaining consistent and constant results, and the capability of optimising dosage based upon the desired effect.

For the use in animal feed, however, the phytase polypeptide of the invention need not be that pure; it may e.g. include other polypeptides, in which case it could be termed a phytase preparation.

The phytase preparation can be (a) added directly to the feed (or used directly in a treatment process of proteins), or (b) it can be used in the production of one or more intermediate compositions such as feed additives or premixes that is subsequently added to the feed (or used in a treatment process). The degree of purity described above refers to the purity of the original polypeptide preparation, whether used according to (a) or (b) above.

Polypeptide preparations with purities of this order of magnitude are in particular obtainable using recombinant methods of production, whereas they are not so easily obtained and also subject to a much higher batch-to-batch variation when the polypeptide is produced by traditional fermentation methods.

Such polypeptide preparation may of course be mixed with other polypeptides.

The polypeptide can be added to the feed in any form, be it as a relatively pure polypeptide, or in admixture with other components intended for addition to animal feed, i.e., in the form of animal feed additives, such as the so-called pre-mixes for animal feed.

In a further aspect the present invention relates to compositions for use in animal feed, such as animal feed, and animal feed additives, e.g. premixes.

Apart from the polypeptide of the invention, the animal feed additives of the invention contain at least one fat-soluble vitamin, and/or at least one water soluble vitamin, and/or at least one trace mineral. The feed additive may also contain at least one macro mineral.

Further, optional, feed-additive ingredients are colouring agents, e.g. carotenoids such as beta-carotene, astaxanthin, and lutein; aroma compounds; stabilisers; antimicrobial peptides; polyunsaturated fatty acids; reactive oxygen generating species; and/or at least one other polypeptide selected from amongst phytase (EC 3.1.3.8 or 3.1.3.26); xylanase (EC 3.2.1.8); galactanase (EC 3.2.1.89); alpha-galactosidase (EC 3.2.1.22); protease (EC 3.4.-.-), phospholipase A1 (EC 3.1.1.32); phospholipase A2 (EC 3.1.1.4); lysophospholipase (EC 3.1.1.5); phospholipase C (3.1.4.3); phospholipase D (EC 3.1.4.4); amylase such as, for example, alpha-amylase (EC 3.2.1.1); and/or beta-glucanase (EC 3.2.1.4 or EC 3.2.1.6).

In a particular embodiment these other polypeptides are well-defined (as defined above for phytase preparations).

In a particularly preferred embodiment, the phytase of the invention having a relatively low pH-optimum is combined with at least one phytase having a higher pH-optimum. Preferred examples of phytases of higher pH-optimum are *Bacillus* phytases, such as the phytases from *Bacillus licheniformis* and *Bacillus subtilis*, as well as derivatives, variants, or fragments thereof having phytase activity.

The phytase of the invention may also be combined with other phytases, for example ascomycete phytases such as *Aspergillus* phytases, for example derived from *Aspergillus ficuum, Aspergillus niger*, or *Aspergillus awamori*; or basidiomycete phytases, for example derived from *Peniophora lycii, Agrocybe pediades, Trametes pubescens*, or *Paxillus involutus*; or derivatives, fragments or variants thereof which have phytase activity.

Thus, in preferred embodiments of the use in animal feed of the invention, and in preferred embodiments of the animal feed additive and the animal feed of the invention, the phytase of the invention is combined with such phytases.

The above-mentioned ascomycete and basidiomycete phytases, in particular the RONOZYME P phytase derived from *Peniophora lycii* as well as derivatives, variants, and fragments thereof, may also be combined with *Bacillus* phytases, in particular the *B. licheniformis* phytase as well as with a derivative, fragment or variant thereof, in particular for animal feed purposes.

Examples of antimicrobial peptides (AMP's) are CAP18, Leucocin A, Tritrpticin, Protegrin-1, Thanatin, Defensin, Lactoferrin, Lactoferricin, and Ovispirin such as Novispirin (Robert Lehrer, 2000), Plectasins, and Statins, including the compounds and polypeptides disclosed in WO 03/044049 and WO 03/048148, as well as variants or fragments of the above that retain antimicrobial activity.

Examples of antifungal polypeptides (AFP's) are the *Aspergillus giganteus*, and *Aspergillus niger* peptides, as well as variants and fragments thereof which retain antifungal activity, as disclosed in WO 94/01459 and WO 02/090384.

Examples of polyunsaturated fatty acids are C18, C20 and C22 polyunsaturated fatty acids, such as arachidonic acid, docosohexaenoic acid, eicosapentaenoic acid and gamma-linoleic acid.

Examples of reactive oxygen generating species are chemicals such as perborate, persulphate, or percarbonate; and polypeptides such as an oxidase, an oxygenase or a synthetase.

Usally fat- and water-soluble vitamins, as well as trace minerals form part of a so-called premix intended for addition to the feed, whereas macro minerals are usually separately added to the feed. Either of these composition types, when enriched with a polypeptide of the invention, is an animal feed additive of the invention.

In a particular embodiment, the animal feed additive of the invention is intended for being included (or prescribed as having to be included) in animal diets or feed at levels of 0.01 to 10.0%; more particularly 0.05 to 5.0%; or 0.2 to 1.0% (% meaning g additive per 100 g feed). This is so in particular for premixes.

The following are non-exclusive lists of examples of these components:

Examples of fat-soluble vitamins are vitamin A, vitamin D3, vitamin E, and vitamin K, e.g. vitamin K3.

Examples of water-soluble vitamins are vitamin B12, biotin and choline, vitamin B1, vitamin B2, vitamin B6, niacin, folic acid and panthothenate, e.g. Ca-D-panthothenate.

Examples of trace minerals are manganese, zinc, iron, copper, iodine, selenium, and cobalt.

Examples of macro minerals are calcium, phosphorus and sodium.

The nutritional requirements of these components (exemplified with poultry and piglets/pigs) are listed in Table A of WO 01/58275. Nutritional requirement means that these components should be provided in the diet in the concentrations indicated.

In the alternative, the animal feed additive of the invention comprises at least one of the individual components specified in Table A of WO 01/58275. At least one means either of, one or more of, one, or two, or three, or four and so forth up to all thirteen, or up to all fifteen individual components. More specifically, this at least one individual component is included in the additive of the invention in such an amount as to provide an in-feed-concentration within the range indicated in column four, or column five, or column six of Table A.

The present invention also relates to animal feed compositions. Animal feed compositions or diets have a relatively high content of protein. Poultry and pig diets can be characterised as indicated in Table B of WO 01/58275, columns 2-3. Fish diets can be characterised as indicated in column 4 of this Table B. Furthermore such fish diets usually have a crude fat content of 200-310 g/kg.

WO 01/58275 corresponds to U.S. Ser. No. 09/779,334 which is hereby incorporated by reference.

An animal feed composition according to the invention has a crude protein content of 50-800 g/kg, and furthermore comprises at least one polypeptide as claimed herein.

Furthermore, or in the alternative (to the crude protein content indicated above), the animal feed composition of the invention has a content of metabolisable energy of 10-30 MJ/kg; and/or a content of calcium of 0.1-200 g/kg; and/or a content of available phosphorus of 0.1-200 g/kg; and/or a content of methionine of 0.1-100 g/kg; and/or a content of methionine plus cysteine of 0.1-150 g/kg; and/or a content of lysine of 0.5-50 g/kg.

In particular embodiments, the content of metabolisable energy, crude protein, calcium, phosphorus, methionine, methionine plus cysteine, and/or lysine is within any one of ranges 2, 3, 4 or 5 in Table B of WO 01/58275 (R. 2-5).

Crude protein is calculated as nitrogen (N) multiplied by a factor 6.25, i.e. Crude protein (g/kg)=N (g/kg)×6.25. The nitrogen content is determined by the Kjeldahl method (A.O.A.C., 1984, Official Methods of Analysis 14th ed., Association of Official Analytical Chemists, Washington D.C.).

Metabolisable energy can be calculated on the basis of the NRC publication Nutrient requirements in swine, ninth revised edition 1988, subcommittee on swine nutrition, committee on animal nutrition, board of agriculture, national research council. National Academy Press, Washington, D.C., pp. 2-6, and the European Table of Energy Values for Poultry Feed-stuffs, Spelderholt centre for poultry research and extension, 7361 DA Beekbergen, The Netherlands. Grafisch bedrijf Ponsen & looijen by, Wageningen. ISBN 90-71463-12-5.

The dietary content of calcium, available phosphorus and amino acids in complete animal diets is calculated on the basis of feed tables such as Veevoedertabel 1997, gegevens over chemische samenstelling, verteerbaarheid en voederwaarde van voedermiddelen, Central Veevoederbureau, Runderweg 6, 8219 pk Lelystad. ISBN 90-72839-13-7.

In a particular embodiment, the animal feed composition of the invention contains at least one protein. The protein may be an animal protein, such as meat and bone meal, and/or fish meal; or it may be a vegetable protein. The term vegetable proteins as used herein refers to any compound, composition, preparation or mixture that includes at least one protein derived from or originating from a vegetable, including modified proteins and protein-derivatives. In particular embodiments, the protein content of the vegetable proteins is at least 10, 20, 30, 40, 50, or 60% (w/w).

Vegetable proteins may be derived from vegetable protein sources, such as legumes and cereals, for example materials from plants of the families Fabaceae (Leguminosae), Cruciferaceae, Chenopodiaceae, and Poaceae, such as soy bean meal, lupin meal and rapeseed meal.

In a particular embodiment, the vegetable protein source is material from one or more plants of the family Fabaceae, e.g. soybean, lupine, pea, or bean.

In another particular embodiment, the vegetable protein source is material from one or more plants of the family Chenopodiaceae, e.g. beet, sugar beet, spinach or quinoa.

Other examples of vegetable protein sources are rapeseed, sunflower seed, cotton seed, and cabbage.

Soybean is a preferred vegetable protein source.

Other examples of vegetable protein sources are cereals such as barley, wheat, rye, oat, maize (corn), rice, triticale, and sorghum.

In still further particular embodiments, the animal feed composition of the invention contains 0-80% maize; and/or 0-80% sorghum; and/or 0-70% wheat; and/or 0-70% Barley; and/or 0-30% oats; and/or 0-40% soybean meal; and/or 0-25% fish meal; and/or 0-25% meat and bone meal; and/or 0-20% whey.

Animal diets can e.g. be manufactured as mash feed (non pelleted) or pelleted feed. Typically, the milled feed-stuffs are mixed and sufficient amounts of essential vitamins and minerals are added according to the specifications for the species in question. Polypeptides can be added as solid or liquid polypeptide formulations. For example, a solid polypeptide formulation is typically added before or during the mixing step; and a liquid polypeptide preparation is typically added after the pelleting step. The polypeptide may also be incorporated in a feed additive or premix.

The final polypeptide concentration in the diet is within the range of 0.01-200 mg polypeptide protein per kg diet, for example in the range of 0.1-10 mg/kg animal diet (typical dosage is in the range of 250 to 2000 FYT/kg animal diet).

The phytase of the invention should of course be applied in an effective amount, i.e. in an amount adequate for improving solubilisation and/or improving nutritional value of feed. It is at present contemplated that the polypeptide is administered in one or more of the following amounts (dosage ranges): 0.01-200; 0.01-100; 0.5-100; 1-50; 5-100; 10-100; 0.05-50; or 0.10-10—all these ranges being in mg phytase polypeptide protein per kg feed (ppm).

For determining mg phytase polypeptide protein per kg feed, the phytase is purified from the feed composition, and the specific activity of the purified phytase is determined using a relevant assay. The phytase activity of the feed composition as such is also determined using the same assay, and on the basis of these two determinations, the dosage in mg phytase protein per kg feed is calculated.

The same principles apply for determining mg phytase polypeptide protein in feed additives. Of course, if a sample is available of the phytase used for preparing the feed additive or the feed, the specific activity is determined from this sample (no need to purify the phytase from the feed composition or the additive).

Methods for Producing Fermentation Products

Yet another aspect of the present invention relates to the methods for producing a fermentation product, such as, e.g., ethanol, beer, wine, distillers dried grains (DDG), wherein the fermentation is carried out in the presence of a phytase of the present invention. Examples of fermentation processes include, for example, the processes described in WO 01/62947. Fermentation is carried out using a fermenting microorganism, such as, yeast.

In a particular embodiment, the present invention provides methods for producing fermentation product, comprising (a) fermenting (using a fermenting microorganism, such as yeast) a carbohydrate containing material (e.g., starch) in the presence of a phytase of the present invention and (b) producing the fermentation product from the fermented carbohydrate containing material.

In a particular embodiment, the present invention provides methods for producing ethanol, comprising fermenting (using a fermenting microorganism, such as yeast) a carbohydrate containing material (e.g., starch) in the presence of a phytase of the present invention and producing or recovering ethanol from the fermented carbohydrate containing material.

In another embodiment, the present invention provides methods for producing ethanol comprising a) hydrolyzing starch, e.g., by a liquefaction and/or saccharification process, a raw starch hydrolysis process, b) fermenting the resulting starch in the presence of a phytase of the present invention, and c) producing ethanol.

The phytase may be added to the fermentation process at any suitable stage and in any suitable composition, including alone or in combination with other enzymes, such as, one or more alpha-amylases, glucoamylases, proteases, and/or cellulases.

In another embodiment, the present invention provides methods for producing ethanol comprising hydrolyzing biomass, and fermenting (using a fermenting microorganism, such as yeast) the resulting biomass in the presence of a phytase of the present invention.

Signal Peptide

The present invention also relates to nucleic acid constructs comprising a gene encoding a protein operably linked to a first nucleotide sequence consisting of nucleotides 1 to 99 of SEQ ID NO: 9, encoding a signal peptide consisting of amino acids 1 to 33 of SEQ ID NO: 10, wherein the gene is foreign to the first nucleotide sequences.

The present invention also relates to recombinant expression vectors and recombinant host cells comprising such nucleic acid constructs.

The present invention also relates to methods for producing a protein comprising (a) cultivating such a recombinant host cell under conditions suitable for production of the protein; and (b) recovering the protein.

The first nucleotide sequences may be operably linked to foreign genes individually with other control sequences or in combination with other control sequences. Such other control sequences are described supra.

The protein may be native or heterologous to a host cell. The term "protein" is not meant herein to refer to a specific length of the encoded product and, therefore, encompasses peptides, oligopeptides, and proteins. The term "protein" also encompasses two or more polypeptides combined to form the encoded product. The proteins also include hybrid polypeptides which comprise a combination of partial or complete polypeptide sequences obtained from at least two different proteins wherein one or more may be heterologous or native to the host cell. Proteins further include naturally occurring allelic and engineered variations of the above mentioned proteins and hybrid proteins.

Preferably, the protein is a hormone or variant thereof, polypeptide, e.g., enzyme, receptor or portion thereof, antibody or portion thereof, or reporter. In a more preferred aspect, the protein is an oxidoreductase, transferase, hydrolase, lyase, isomerase, or ligase. In an even more preferred aspect, the protein is an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, lipase, mannosidase, mutanase, oxidase, pectinolytic polypeptide, peroxidase, phytase, polyphenoloxidase, proteolytic polypeptide, ribonuclease, transglutaminase or xylanase.

The gene may be obtained from any prokaryotic, eukaryotic, or other source.

Various Embodiments

The following are additional embodiments of the present invention. Also included herein are the corresponding aspects relating to nucleic acid sequences, nucleic acid constructs, recombinant expression vectors, recombinant host cells, methods for production of the polypeptides, transgenic plants and animals, and the various uses, methods of use and feed compositions/additives, all as claimed.

An isolated polypeptide having phytase activity and a residual activity following incubation at 37° C. and in a 0.1 M Glycine/HCl buffer, pH 2.0, for 4 hours of at least 20%, as compared to the activity at time, t=0, the activity being assayed at 37° C. and pH 5.5 on 1% (w/v) Na-phytate, using a 0.25 M Na-acetate buffer pH 5.5, buffer blind subtracted;

preferably with an identity to i) amino acids 1 to 413 of SEQ ID NO: 10, of at least 75%, preferably at least 76%, 77%, 78%, 79%, 80%, 81%, 82%, 83%, 84%, 85%, 86%, 87%, 88%, 89%, 90%, 91%, 92%, 93%, 94%, 95%, 96%, 96.5%, 97%, 97.5%, 98%, 98.5%, 98.7%, 98.8%, 98.9%, 99%, 99.0%, 99.1%, 99.2%, 99.3%, 99.4%, 99.5%, 99.6%, 99.7%, 99.8%, or at least 99.9%.

An isolated polypeptide having phytase activity and a residual activity following incubation at 37° C. and in a 0.1 M Glycine/HCl buffer, pH 2.5, for 24 hours of at least 20%, as compared to the activity at time, t=0, the activity being assayed at 37° C. and pH 5.5 on 1% (w/v) Na-phytate, using a 0.25 M Na-acetate buffer pH 5.5, buffer blind subtracted;

preferably with an identity to i) amino acids 1 to 413 of SEQ ID NO: 10, of at least 75%, preferably at least 76%, 77%, 78%, 79%, 80%, 81%, 82%, 83%, 84%, 85%, 86%, 87%, 88%, 89%, 90%, 91%, 92%, 93%, 94%, 95%, 96%, 96.5%, 97%, 97.5%, 98%, 98.5%, 98.7%, 98.8%, 98.9%, 99%, 99.0%, 99.1%, 99.2%, 99.3%, 99.4%, 99.5%, 99.6%, 99.7%, 99.8%, or at least 99.9%.

An isolated polypeptide having phytase activity, wherein the activity of the polypeptide, at pH 5.0 and 37° C., measured on the substrate pNP-phosphate is less than 11% of the activity of the polypeptide measured on the substrate phytate; preferably with an identity to i) amino acids 1 to 413 of SEQ ID NO: 10, of at least 75%, preferably at least 76%, 77%, 78%, 79%, 80%, 81%, 82%, 83%, 84%, 85%, 86%, 87%, 88%, 89%, 90%, 91%, 92%, 93%, 94%, 95%. 96%, 96.5%, 97%, 97.5%, 98%, 98.5%, 98.7%, 98.8%, 98.9%, 99%, 99.0%, 99.1%, 99.2%, 99.3%, 99.4%, 99.5%, 99.6%, 99.7%, 99.8%, or at least 99.9%.

An isolated polypeptide having phytase activity, wherein the polypeptide has a higher release of phosphorous (P), as compared to the phytase from *Peniophora lycii*; preferably as measured in the in vitro model; and/or, wherein the polypeptide preferably has an identity to i) amino acids 1 to 413 of SEQ ID NO: 10, of at least 75%, preferably at least 76%, 77%, 78%, 79%, 80%, 81%, 82%, 83%, 84%, 85%, 86%, 87%, 88%, 89%, 90%, 91%, 92%, 93%, 94%, 95%, 96%, 96.5%, 97%, 97.5%, 98%, 98.5%, 98.7%, 98.8%, 98.9%, 99%, 99.0%, 99.1%, 99.2%, 99.3%, 99.4%, 99.5%, 99.6%, 99.7%, 99.8%, or at least 99.9%.

An isolated polypeptide having phytase activity, wherein the polypeptide, dosed 0.25 FYT/g feed, releases at least 150% phosphorous (P), relative to the phosphorous released by the phytase from *Peniophora lycii*, also dosed 0.25 FYT/g feed; and/or, wherein the polypeptide preferably has an identity to i) amino acids 1 to 413 of SEQ ID NO: 10, of at least 75%, preferably at least 76%, 77%, 78%, 79%, 80%, 81%, 82%, 83%, 84%, 85%, 86%, 87%, 88%, 89%, 90%, 91%, 92%, 93%, 94%, 95%, 96%, 96.5%, 97%, 97.5%, 98%, 98.5%, 98.7%, 98.8%, 98.9%, 99%, 99.0%, 99.1%, 99.2%, 99.3%, 99.4%, 99.5%, 99.6%, 99.7%, 99.8%, or at least 99.9%.

An isolated polypeptide having phytase activity, wherein the polypeptide, dosed 0.75 FYT/g feed, releases at least 150% phosphorous (P), relative to the phosphorous released by the phytase from *Peniophora lycii*, also dosed 0.75 FYT/g feed; and/or, wherein the polypeptide preferably has an identity to i) amino acids 1 to 413 of SEQ ID NO: 10, of at least 75%, preferably at least 76%, 77%, 78%, 79%, 80%, 81%, 82%, 83%, 84%, 85%, 86%, 87%, 88%, 89%, 90%, 91%, 92%, 93%, 94%, 95%, 96%, 96.5%, 97%, 97.5%, 98%, 98.5%, 98.7%, 98.8%, 98.9%, 99%, 99.0%, 99.1%, 99.2%, 99.3%, 99.4%, 99.5%, 99.6%, 99.7%, 99.8%, or at least 99.9%.

I. An isolated polypeptide having phytase activity, selected from the group consisting of: (a) a polypeptide having an amino acid sequence which has at least 75% identity with (i) amino acids 1 to 413 of SEQ ID NO: 10, and/or (ii) the mature polypeptide part of SEQ ID NO: 10, (b) a polypeptide which is encoded by a polynucleotide which hybridizes under at least medium stringency conditions with (i) nucleotides 100 to 1338 of SEQ ID NO: 9, (ii) the mature polypeptide encoding part of SEQ ID NO: 9, and/or (iii) a complementary strand of any one of (i), or (ii); (c) a variant of any one of the polypeptides of (a)(i)-(a)(ii), comprising a conservative substitution, deletion, and/or insertion of one or more amino acids; and (d) a fragment of any one of the polypeptides of (a)(i)-(a)(ii).

II. An isolated polynucleotide comprising a nucleotide sequence which encodes the polypeptide of section I.

III. An isolated polynucleotide encoding a polypeptide having phytase activity, selected from the group consisting of: (a) a polynucleotide encoding a polypeptide having an amino acid sequence which has at least 75% identity, preferably at least 76%, 77%, 78%, 79%, 80%, 81%, 82%, 83%, 84%, 85%, 86%, 87%, 88%, 89%, 90%, 91%, 92%, 93%, 94%, 95%, 96%, 96.5%, 97%, 97.5%, 98%, 98.5%, 98.7%, 98.8%, 98.9%, 99%, 99.0%, 99.1%, 99.2%, 99.3%, 99.4%, 99.5%, 99.6%, 99.7%, 99.8%, or at least 99.9% identity with amino acids 1 to 413 of SEQ ID NO: 10; (b) a polynucleotide having at least 75% identity, preferably at least 76%, 77%, 78%, 79%, 80%, 81%, 82%, 83%, 84%, 85%, 86%, 87%, 88%, 89%, 90%, 91%, 92%, 93%, 94%, 95%, 96%, 96.5%, 97%, 97.5%, 98%, 98.5%, 98.7%, 98.8%, 98.9%, 99%, 99.0%, 99.1%, 99.2%, 99.3%, 99.4%, 99.5%, 99.6%, 99.7%, 99.8%, or at least 99.9% identity with nucleotides 100 to 1338 of SEQ ID NO: 9; and (c) a polynucleotide which hybridizes under at least medium stringency conditions with (i) nucleotides 100 to 1338 of SEQ ID NO: 9, (ii) the mature polypeptide encoding part of SEQ ID NO: 9, (iii) a complementary strand of any one of (i), or (ii).

IV. The isolated polynucleotide of any one of sections II and III, having at least one mutation in the mature polypeptide coding sequence of SEQ ID NO: 9, in which the mutant nucleotide sequence encodes a polypeptide comprising amino acids 1 to 413 of SEQ ID NO: 10.

V. A nucleic acid construct comprising the polynucleotide of any one of sections II-IV operably linked to one or more control sequences that direct the production of the polypeptide in an expression host.

VI. A recombinant expression vector comprising the nucleic acid construct of section V.

VII. A recombinant host cell comprising the nucleic acid construct of section V.

VIII. A method for producing the polypeptide of section I comprising (a) cultivating a cell, which in its wild-type form is capable of producing the polypeptide, under conditions conducive for production of the polypeptide; and (b) recovering the polypeptide.

IX. A method for producing the polypeptide of section I comprising (a) cultivating a recombinant host cell comprising a nucleic acid construct comprising a nucleotide sequence encoding the polypeptide under conditions conducive for production of the polypeptide; and (b) recovering the polypeptide.

X. A transgenic plant, plant part or plant cell, which has been transformed with a polynucleotide encoding the polypeptide of section I.

XI. A transgenic, non-human animal, or products, or elements thereof, being capable of expressing the polypeptide of section I.

XII. Use of at least one polypeptide of section I in animal feed.

XIII. Use of at least one polypeptide of section I in the preparation of a composition for use in animal feed.

XIV. A method for improving the nutritional value of an animal feed, wherein at least one polypeptide of section I is added to the feed.

XV. An animal feed additive comprising (a) at least one polypeptide of section I; and (b) at least one fat soluble vitamin, (c) at least one water soluble vitamin, and/or (d) at least one trace mineral.

XVI. The animal feed additive of section XV, which further comprises at least one amylase, at least one additional phytase, at least one xylanase, at least one galactanase, at least one alpha-galactosidase, at least one protease, at least one phospholipase, and/or at least one beta-glucanase.

XVII. The animal feed additive of section XVI, wherein the additional phytase has a pH-optimum which is higher than the pH-optimum of the polypeptide having the amino acid sequence of amino acids 1 to 413 of SEQ ID NO: 10.

IIXX. An animal feed composition having a crude protein content of 50 to 800 g/kg and comprising at least one polypeptide of section I.

A polypeptide having phytase activity which comprises, preferably has or consists of, an amino acid sequence which has at least 75% identity, preferably at least 76%, 77%, 78%, 79%, 80%, 81%, 82%, 83%, 84%, 85%, 86%, 87%, 88%, 89%, 90%, 91%, 92%, 93%, 94%, 95%, 96%, 96.5%, 97%, 97.5%, 98%, 98.5%, 98.7%, 98.8%, 98.9%, 99%, 99.0%, 99.1%, 99.2%, 99.3%, 99.4%, 99.5%, 99.6%, 99.7%, 99.8%, or at least 99.9% identity with amino acids 1 to 413 of SEQ ID NO: 10.

A polypeptide having phytase activity which comprises, preferably has, the sequence of (i) amino acids 1 to 413 of SEQ ID NO: 10, and/or (ii) the mature polypeptide part of SEQ ID NO: 10; or which polypeptide (a) is a variant of any one of the polypeptides of (i)-(ii), comprising a deletion, insertion, and/or conservative substitution of one or more amino acids; or (b) is a fragment of any one of the polypeptides of (i)-(ii).

The present invention is further described by the following examples which should not be construed as limiting the scope of the invention.

EXAMPLES

Example 1

Cloning of a *Hafnia alvei* Phytase Gene

A multiple alignment was made of the following histidine acid phosphatases (HAP): appA *Escherichia coli* (SP-TREMBL:Q8GN88), *Citrobacter gillenii* DSM 13694 phytase (geneseqp:aeh04533), *Citrobacter amalonaticus* ATCC 25407 phytase (geneseqp:aeh04535), *Citrobacter braakii* phytase (geneseqp:aeh04827), and ypo1648 *Yersinia pestis* C092 (SPTREMBL:Q8ZFP6). Two degenerate oligonucleotide primers were designed on the basis of consensus sequences:

```
                                          (SEQ ID NO: 1)
2123fw:  5'-CATGGTGTGCGNGCNCCNACNAA-3'

(SEQ ID NO: 2)
2065rev: 5'-CCCACCAGGNGGNGTRTTRTCNGGYTG-3',
``` wherein Y designates T or C, R designates A or G, and N designates A, C, G or T.

The primers were used for PCR screening of a number of bacterial species at annealing temperatures between 40 and 50° C. but typical as touch down program starting with 50° C. and then reduced the annealing temperature with 1° C. for each cycle over the next 10 cycles before conducting standard PCR.

A partial phytase gene in the form of an approximately 950 bp PCR fragment was identified in *Hafnia alvei* (DSM 19197).

The PCR fragment was isolated from agarose gel and the fragment was sequenced using the same PCR primers the fragment was generated with. By translation of the nucleotide sequence, it was confirmed that the DNA fragment was part of a HAP phytase gene.

For obtaining the full length nucleotide sequence of the gene, the DNA WALKING SPEEDUP™ Kit (DWSK-V102 from Seegene, Inc., 2nd Fl., Myungji Bldg., 142-21, Samsung-dong, Kangnam-gu, Seoul, 135-090, Korea) was used, which is designed to capture unknown target sites. For this purpose, 6 specific oligonucleotides were designed and used with the kit.

```
                                          (SEQ ID NO: 3)
2328 TSP1dw: 5'-ACTTGCATCGACGTTGGCTG (SEQ ID NO: 4)
2329 TSP2dw: 5'-ACTGAGCAGCAATGGAACTCTCTG (SEQ ID NO: 5)
2330 TSP3dw: 5'-ACTGGGTTCCAATATCACGAGTC (SEQ ID NO: 6)
2331 TSP1up: 5'-ATGGTGGATCGCTAAATCACACTG (SEQ ID NO: 7)
2332 TSP2up: 5'-ACGTCTGCCCAAACATACACG (SEQ ID NO: 8)
2333 TSP3up: 5'-ACCGCCCATCAGGCTAATC
```

The full length nucleotide sequence encoding the phytase from *Hafnia alvei* DSM 19197 is shown in the sequence listing as SEQ ID NO: 9, and the corresponding encoded amino acid sequence is shown in SEQ ID NO: 10. The first 33 amino acids of SEQ ID NO:10 (i.e. amino acids −33 to −1) are a signal peptide, as predicted by the software Signal P V3.0 (see cbs.dtu.dk/services/SignalP/).

Example 2

Expression of the *Hafnia alvei* Phytase Gene

A 27 amino-acid signal peptide encoding polynucleotide of a native protease, Savinase™, from *Bacillus licheniformis* was fused by PCR in frame to the gene encoding the mature phytase from from *Hafnia alvei*. The signal peptide coding sequence is shown in SEQ ID NO: 11, encoding the signal peptide of SEQ ID NO: 12.

The DNA coding for the fusion polypeptide was integrated by homologous recombination on a *Bacillus subtilis* host cell genome. The gene construct was expressed under the control of a triple promoter system (as described in WO 99/43835), consisting of the promoters from *Bacillus licheniformis* alpha-amylase gene (amyL), *Bacillus amyloliquefaciens* alpha-amylase gene (amyQ), and the *Bacillus thuringiensis* cryIIIA promoter including the mRNA stabilizing sequence. The gene coding for Chloramphenicol acetyl-transferase was used as marker, as described in, e.g., Diderichsen et al., A useful cloning vector for Bacillus subtilis. Plasmid, 30, p. 312, 1993.

Chloramphenicol resistant transformants was cultured in PS-1 medium (10% sucrose, 4% soybean flour, 1% $Na_3PO_4$-$12H_2O$, 0.5% $CaCO_3$, and 0.01% pluronic acid) shaken at 250 RPM at 30° C. After 2-5 days of incubation the supernatant was removed and the phytase activity was identified by applying 20 microliter of the supernatant into 4 mm diameter holes punched out in 1% LSB-agarose plates containing 0.1 M Sodium acetate pH 4.5 and 0.1% Inositol hexaphosphoric acid. The plates were left over night at 37° C. and a buffer consisting of 0.25 M $CaCl_2$ and 500 mM MES (adjusted to pH 6.5 with 4 N NaOH) was poured over the plates. The plates were left at room temperature for 1 h and the inositolphosphate phosphatase, or phytase, activity was then identified as a clear zone.

Several phytase positive transformants were analyzed by DNA sequencing to ensure the correct DNA sequence of the constructs. One correct clone was selected.

Example 3

Fermentation of the *Hafnia* NN020125 Phytase Host

The selected clone of *Bacillus subtilis*, which was harboring the *Hafnia alvei* phytase construct and was capable of expressing the phytase (mature part) was cultivated at 30° C. and with 250 rpm for 6 days in SK-1M medium (Sodium Caseinate (Miprodan 30 from Arla) 40 g, Maltodextrin 01 (Glucidex 6, catalogue no. 332203 from Roquette), 200 g, Soybean Meal 50 g, Dowfax 63N10 (a non-ionic surfactant from Dow) 0.1 ml, tap water up to 1000 ml, $CaCO_3$ tablet 0.5 g/100 ml).

Example 4

Purification of *Hafnia alvei* Phytase

The fermentation supernatant with the phytase was first centrifuged at 7200 rpm and 5° C. for one hour and filtered through a sandwich of four Whatman glass microfibre filters (2.7, 1.6, 1.2 and 0.7 micrometer). Following this the solution was sterile filtered through a Seitz-EKS depth filter using pressure. Next, the filtered supernatant was pre-treated as follows:

The sample solution was washed with water and concentrated using an ultrafiltration unit (Filtron, from Filtron Technology Corporation) equipped with a 10 kDa cut-off ultrafiltration membrane. Then pH was adjusted to 4.5 with 10% (w/v) acetic acid, which caused a minor precipitation. No activity was found in the precipitate and it was removed by filtration through a Fast PES bottle top filter with a 0.22 micrometer cut-off.

After pretreatment the phytase was purified by chromatography on S Sepharose, approximately 50 ml in a XK26 column, using as buffer A 50 mM sodium acetate pH 4.5, and as buffer B 50 mM sodium acetate+1 M NaCl pH 4.5. The fractions from the column were analyzed for activity using the phosphatase assay (see below) and fractions with activity were pooled.

The solution was added solid ammonium sulfate giving a final concentration of 1.5 M and the pH was adjusted to 6.0 using 6 M HCl. The phytase-containing solution was applied to a butyl-sepharose column, approximately 30 ml in a XK26 column, using as buffer A 25 mM bis-tris (Bis-(2-hydroxyethyl)imino-tris(hydroxymethyl)methan))+1.5 M ammonium sulfate pH 6.0, and as buffer B 25 mM bis-tris pH 6.0. The fractions from the column were analyzed for activity using the phosphatase assay (see below) and fractions with activity were pooled. Finally, the solution containing the purified phytase was buffer-changed into 50 mM sodium acetate+ 0.1 M NaCl, pH 4.5 and concentrated using an Amicon ultra-15 filtering device with a 30 kDa cut-off membrane.

The molecular weight, as estimated from SDS-PAGE, was approximately 40 kDa and the purity was >95%.

Example 5

Activity Assays

Determination of Phosphatase Activity 75 microliters phytase-containing enzyme solution is dispensed in a microtiter plate well, e.g., NUNC 269620 and 75 microliter substrate is added (for preparing the substrate, two 5 mg p-nitrophenyl phophate tablets (Sigma, Cat.No. N-9389) are dissolved in 10 ml 0.1 M Na-acetate buffer, pH 5.5). The plate is sealed and incubated 15 min., shaken with 750 rpm at 37° C. After the incubation time 75 microliter stop reagent is added (the stop reagent is 0.1 M di-sodiumtetraborate in water) and the absorbance at 405 nm is measured in a microtiter plate spectrophotometer.

Determination of Phytase Activity 75 microliters phytase-containing enzyme solution, appropriately diluted in 0.25 M sodium acetate, 0.005% (w/v) Tween-20. pH 5.5, is dispensed in a microtiter plate well, e. g. NUNC 269620, and 75 microliter substrate is added (prepared by dissolving 100 mg sodium phytate from rice (Aldrich Cat.No. 274321) in 10 ml 0.25 M sodium acetate buffer, pH 5.5). The plate is sealed and incubated 15 min. shaken with 750 rpm at 37° C. After incubation, 75 microliters stop reagent is added (the stop reagent being prepared by mixing 10 ml molybdate solution (10% (w/v) ammonium heptamolybdate in 0.25% (w/v) ammonia solution), 10 ml ammonium vanadate (0.24% commercial product from Bie&Berntsen, Cat.No. LAB17650), and 20 ml 21.7% (w/v) nitric acid), and the absorbance at 405 nm is measured in a microtiter plate spectrophotometer. The phytase activity is expressed in the unit of FYT, one FYT being the amount of enzyme that liberates 1 micromole inorganic ortho-phosphate per minute under the conditions above. An absolute value for the measured phytase activity may be obtained by reference to a standard curve prepared from appropriate dilutions of inorganic phosphate, or by reference to a standard curve made from dilutions of a phytase enzyme preparation with known activity (such standard enzyme preparation with a known activity is available on request from Novozymes A/S, Krogshoejvej 36, DK-2880 Bagsvaerd).

Determination of Specific Phytase Activity

The specific activity of the phytase was determined in sodium acetate buffer, pH 5.5. The phytase was highly purified as described above, i.e. only one component was identified on an SDS poly acryl amide gel.

The protein concentration was determined by amino acid analysis as follows: An aliquot of the sample was hydrolyzed in 6 M HCl, 0.1% phenol for 16 h at 110° C. in an evacuated glass tube. The resulting amino acids were quantified using an Applied Biosystems 420A amino acid analysis system operated according to the manufacturer's instructions. From the amounts of the amino acids the total mass—and thus also the concentration—of protein in the hydrolyzed aliquot was calculated.

The phytase activity was determined in the units of FYT as described above and the specific activity was calculated as the phytase activity measured in FYT units per mg phytase enzyme protein.

The resulting specific activity was 980 FYT/mg protein. The specific activity was determined on sodium phytate at pH 5.5 and 37° C.

Example 6

Determination of the Phytase pH Profile

The pH profile was determined at 37° C. in the pH range of 2.0 to 7.5 (in 0.5 pH-unit steps) as described above in the section "Determination of phytase activity", except that a buffer cocktail (50 mM glycine, 50 mM acetic acid and 50 mM Bis-Tris was used instead of the 0.25 M sodium acetate pH 5.5 buffer. The results are summarized in table 1 below. The values given for each pH in the range of 2.0-7.5 are the relative activity in % normalized to the value at optimum.

TABLE 1

| | pH profile | | | | | | | | | | | |
|---|---|---|---|---|---|---|---|---|---|---|---|---|
| | pH | | | | | | | | | | | |
| Phytase | 2.0 | 2.5 | 3.0 | 3.5 | 4.0 | 4.5 | 5.0 | 5.5 | 6.0 | 6.5 | 7.0 | 7.5 |
| Hafnia alvei | 46 | 61 | 83 | 95 | 100 | 100 | 88 | 71 | 43 | 18 | 3 | 0 |

Example 7

Determination of the Phytase Isoelectric Point

The isoelectric point, pI, for the phytase was determined using isoelectric focusing gels (Novex pH 310 IEF gel from Invitrogen, catalog number EC6655A2) run as described by the manufacturer. The pI for the *Hafnia alvei* phytase is about 7.4.

Example 8

Phytase Temperature Profile

The temperature profile (phytase activity as a function of temperature) was determined for the *Hafnia alvei* phytase in the temperature range of 20-90° C. essentially as described above ("Determination of phytase activity"). However, the enzymatic reactions (100 microliter phytase-containing enzyme solution+100 microliter substrate) were performed in PCR tubes instead of microtiter plates. After a 15 minute reaction period at desired temperature the tubes were cooled to 20° C. for 20 seconds and 150 microliter of each reaction mixture was transferred to a microtiter plate. 75 microliter stop reagent was added and the absorbance at 405 nm was measured in a microtiter plate spectrophotometer. The results are summarized in Table 2 below. The numbers given for each temperature are relative activity (in %) normalized to the value at optimum.

TABLE 2

Temperature profile

| Temperature ° C.  | 20 | 30 | 40 | 50 | 55 | 60 | 65  | 70 | 80 | 90 |
|---|---|---|---|---|---|---|---|---|---|---|
| Relative activity | 17 | 27 | 45 | 69 | 79 | 85 | 100 | 95 | 7  | 0  |

Example 9

Phytase Thermostability

*Hafnia alvei* phytase expressed in both *Aspergillus oryzae* and *Bacillus subtilis* were subjected to thermostability measurements by Differential Scanning Calorimetry (DSC) and compared to the *E. coli* phytase (commercially available as PHYZYME XP from Danisco A/S).

An aliquot of the protein sample of *Hafnia alvei* phytase (purified as described in Example 4) was dialysed against 2×500 ml 20 mM Na-acetate, pH 4.0 at 4° C. in a 2-3 h step followed by an overnight step. The sample was 0.45 μm filtered and diluted with buffer to approx. 2 A280 units. The exact absorbance values measured are given in the results table shown below. The dialysis buffer was used as reference in Differential Scanning Calorimetry (DSC). The samples were degassed using vacuum suction and stirring for approx. 10 minutes. An aliquot of the *E. coli* phytase from the commercial product PHYZYME XP was purified in a similar fashion as described in Example 4.

A DSC scan was performed at a constant scan rate of 1.5° C./min from 20-80° C. Filtering period: 16 s. Before running the DSC, the phytases were dialyzed against the appropriate buffers (e.g. 0.1M glycine-HCl, pH 2.5 or 3.0; 20 mM sodium acetate pH 4.0; 0.1 M sodium acetate, pH 5.5; 0.1 M Tris-HCl, pH 7.0). Data-handling was performed using the MicroCal Origin software (version 4.10), and the denaturation temperature, Td (also called the melting temperature, Tm) is defined as the temperature at the apex of the peak in the thermogram. To probe the reversibility of the unfolding process, a second scan was performed immediately after a short cooling phase. For the second scan the peak area (the area between the peak and the baseline=enthalpy of unfolding which is compared) is compared to the peak area of the first scan. A large peak (between 75-100% of the peak area of the first scan) is interpreted as a reversible unfolding/folding process.

The results of DSC for *Hafnia alvei* phytase expressed in both *Aspergillus oryzae* and *Bacillus subtilis* and the *E. coli* phytase are summarized in the Table 3 below.

TABLE 3

Comparative Thermostability of *Hafnia alvei* Phytase and *E. coli* Phytase

| Phytase | Buffer | A280 | Td 1st Scan (° C.) | TD 2nd Scan (° C.) | Relative peak size (actual area) on 2 scans |
|---|---|---|---|---|---|
| Aspergillus expressed *H. alvei* | 20 nM NaAc pH 4.0 | 3.2 | 70.2 | 70.3 | large |
| Bacillus expressed *H. alvei* | 20 nM NaAc pH 4.0 | 1.6 | 70.1 | 70.3 | large |
| *E. coli* | 20 nM NaAc pH 4.0 | 2.4 | 62.6 | 62.9 | medium |

As illustrated in the above table, the *Hafnia alvei* phytase had greater thermostability than the *E. coli* phytase. It is also clear that the thermostability of the *Hafnia alvei* phytase was not affected by the expression host.

Example 10

Gastric Proteolytic Resistance of *Hafnia alvei* Phytase and *E. coli* Phytase

Samples of *H. alvei* phytase and *E. coli* phytase (PHYZYME XP, available from Danisco) were treated with pepsin (Pepsin 1:60000 from Porcine Stomach Mucosa, Wako 162-18721, 2900 Units/mg, Lot SDK5232) in 250 mM glycine buffer pH 3.0 (approx. 1000 pepsin Units/mg phytase). Incubation for 30 minutes at 40° C. with shaking (750 rpm). Following incubation with pepsin, the phytase activity was determined as described in Example 5 and compared to the activity of a sample treated in the same way, but without addition of pepsin. The results are summarized in Table 4 below.

TABLE 4

Gastric Proteolytic Resistance of *Hafnia alvei* Phytase and *E. coli* Phytase

| Phytase | Mean (res. act. %) | |
|---|---|---|
| *E. coli* | 96 | result of two runs with results of 95% and 97% residual activity. |
| *H. alvei* | 95.5 | result of two runs with results of 97% and 94% residual activity. |

Thus, the *E. coli* phytase and *H. alvei* phytase had very similar gastro proteolytic resistance properties.

Example 11

Performance in Animal Feed in an In Vitro Model for the *Hafnia alvei* Phytase and *Citrobacter braakii* Phytase The performance in animal feed of the *Hafnia alvei* phytase was compared, in an in vitro model, to the performance of a *Citrobacter braakii* phytase. The in vitro model simulates gastro-intestinal conditions in a monogastric animal and correlates well with results obtained in animal trials in vivo. Phytase activity in the sample is determined as described in Example 5 under "Determination of phytase activity". The comparison was performed as follows:

Feed samples composed of 30% soybean meal and 70% maize meal with added $CaCl_2$ to a concentration of 5 g calcium per kg feed are then prepared and pre-incubated at 40° C. and pH 3.0 for 30 minutes followed by addition of pepsin (3000 U/g feed) and suitable dosages of the phytases (identical dosages are used for all phytases to be tested to allow comparison), for example between 0.1 to 1.0 phytase units FYT/g feed. A blank with no phytase activity was also included as reference. The samples were then incubated at 40° C. and pH 3.0 for 60 minutes followed by pH 4.0 for 30 minutes.

The reactions were stopped and phytic acid and inositol-phosphates extracted by addition of HCl to a final concentration of 0.5 M and incubation at 40° C. for 2 hours, followed by one freeze-thaw cycle and 1 hour incubation at 40° C.

Phytic acid and inositol-phosphates were separated by high performance ion chromatography as described by Chen et al in Journal of Chromatography A (2003) vol. 1018, pp. 41-52 and quantified as described by Skoglund et al in J. Agric. Food Chem. (1997), vol. 45, pp. 431-436.

FIG. 1 shows a dose-response of the *Hafnia alvei* phytase compared to a *Citrobacter braakii* phytase at dosing of 125 FYT/kg feed, 250 FYT/kg feed and 500 FYT/kg feed. The effects of phytases in vitro are shown as the residual inositol-phosphate bound phosphorous (IP-P) remaining in a sample after in vitro incubation and compared to the residual IP-P remaining in a control sample without phytase. All numbers given are average and standard deviation of 4 or 5 replica (in vitro incubations). Dosing 250 FYT/kg of the *Hafnia* phytase reduced the amount of residual IP-P in the in vitro sample to about the same degree as 125 FYT/kg of the *Citrobacter* phytase.

Accordingly, the *Hafnia* phytase was able to obtain a very good reduction in the amount of residual inositol-phosphate bound phosphorous.

Example 12

Figure 2:
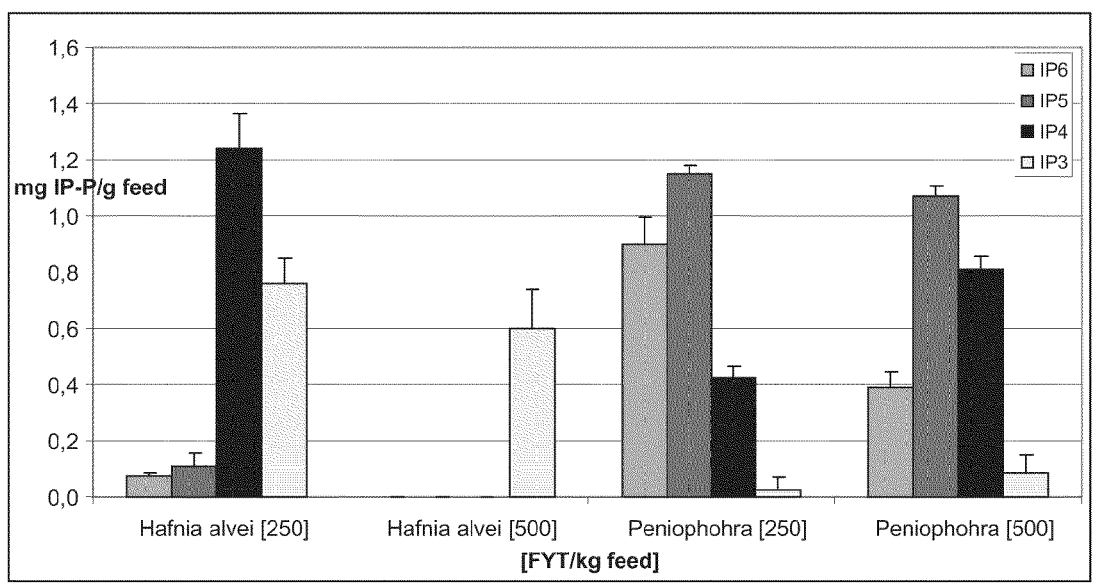
FIG. 2 shows a comparison of the residual inositol-phosphate bound phosphorous after in vitro incubation between the *Hafnia alvei* phytase and a *Peniophora lycii* phytase phytase dosed at 250 FYT/kg Feed and 500 FYT/kg Feed.

Performance in Animal Feed in an In Vitro Model for the *Hafnia alvei* Phytase and *Peniophora lycii* Phytase Phytase The performance in animal feed of the *Hafnia alvei* phytase in an in vitro model was also compared to the performance of a *Peniophora lycii* phytase at dosing of 250 FYT/kg and 500 FYT/kg feed. The results were obtained following the experimental protocol as described in Example 11. As shown in FIG. 2, the *Hafnia alvei* phytase reduced the amount of residual IP-P in the in vitro sample better than the *Peniophora lycii* phytase.

The invention claimed is:

1. An isolated polypeptide having phytase activity, which has at least 90% identity with (i) amino acids 1 to 413 of SEQ ID NO: 10, and/or (ii) the mature polypeptide part of SEQ ID NO: 10.

2. The polypeptide of claim 1, which has at least 92% identity with the sequence of amino acids 1 to 413 of SEQ ID NO: 10.

3. The polypeptide of claim 1, which has at least 94% identity with the sequence of amino acids 1 to 413 of SEQ ID NO: 10.

4. An animal feed additive comprising
   (a) at least one polypeptide of claim 1; and
   (b) at least one fat soluble vitamin, at least one water soluble vitamin, at least one trace mineral or combinations thereof.

5. The animal feed additive of claim 4, which further comprises at least one amylase, at least one additional phytase, at least one xylanase, at least one galactanase, at least one alpha-galactosidase, at least one protease, at least one phospholipase, and/or at least one beta-glucanase.

6. An animal feed composition having a crude protein content of 50 to 800 g/kg and comprising at least one polypeptide of claim 1.

7. A method for improving the nutritional value of an animal feed, comprising adding at least one polypeptide of claim 1 to the animal feed.

8. A method for producing a fermentation product, comprising
   (a) fermenting using a fermenting microorganism a carbohydrate containing material in the presence of a polypeptide of claim 1 and
   (b) producing the fermentation product or fermentation coproduct from the fermented carbohydrate containing material.

9. The method of claim 8, wherein the fermentation product is ethanol, beer, wine, or distillers dried grains (DDG).

* * * * *

SEQUENCE LISTING

```
<160> NUMBER OF SEQ ID NOS: 12

<210> SEQ ID NO 1
<211> LENGTH: 23
<212> TYPE: DNA
<213> ORGANISM: Artificial sequence
<220> FEATURE:
<223> OTHER INFORMATION: Primer 2123fw
<220> FEATURE:
<221> NAME/KEY: misc_feature
<222> LOCATION: (12)..(12)
<223> OTHER INFORMATION: N designates A, C, G or T.
<220> FEATURE:
<221> NAME/KEY: misc_feature
<222> LOCATION: (15)..(15)
<223> OTHER INFORMATION: N designates A, C, G or T.
<220> FEATURE:
<221> NAME/KEY: misc_feature
<222> LOCATION: (18)..(18)
<223> OTHER INFORMATION: N designates A, C, G or T.
<220> FEATURE:
<221> NAME/KEY: misc_feature
<222> LOCATION: (21)..(21)
<223> OTHER INFORMATION: N designates A, C, G or T.

<400> SEQUENCE: 1
catggtgtgc gngcnccnac naa                                           23

<210> SEQ ID NO 2
<211> LENGTH: 27
<212> TYPE: DNA
<213> ORGANISM: Artificial sequence
<220> FEATURE:
<223> OTHER INFORMATION: Primer 2065rev
<220> FEATURE:
<221> NAME/KEY: misc_feature
<222> LOCATION: (10)..(10)
<223> OTHER INFORMATION: N designates A, C, G or T.
<220> FEATURE:
<221> NAME/KEY: misc_feature
<222> LOCATION: (13)..(13)
<223> OTHER INFORMATION: N designates A, C, G or T.
<220> FEATURE:
<221> NAME/KEY: misc_feature
<222> LOCATION: (16)..(16)
<223> OTHER INFORMATION: R designates A or G.
<220> FEATURE:
<221> NAME/KEY: misc_feature
<222> LOCATION: (19)..(19)
<223> OTHER INFORMATION: R designates A or G.
<220> FEATURE:
<221> NAME/KEY: misc_feature
```

```
<222> LOCATION: (22)..(22)
<223> OTHER INFORMATION: N designates A, C, G or T.
<220> FEATURE:
<221> NAME/KEY: misc_feature
<222> LOCATION: (25)..(25)
<223> OTHER INFORMATION: Y designates T or C.

<400> SEQUENCE: 2
cccaccaggn ggngtrttrt cnggytg                                              27

<210> SEQ ID NO 3
<211> LENGTH: 20
<212> TYPE: DNA
<213> ORGANISM: Artificial sequence
<220> FEATURE:
<223> OTHER INFORMATION: Primer 2328 TSP1dw

<400> SEQUENCE: 3
acttgcatcg acgttggctg                                                      20

<210> SEQ ID NO 4
<211> LENGTH: 24
<212> TYPE: DNA
<213> ORGANISM: Artificial sequence
<220> FEATURE:
<223> OTHER INFORMATION: Primer 2329 TSP2dw

<400> SEQUENCE: 4
actgagcagc aatggaactc tctg                                                 24

<210> SEQ ID NO 5
<211> LENGTH: 23
<212> TYPE: DNA
<213> ORGANISM: Artificial sequence
<220> FEATURE:
<223> OTHER INFORMATION: Primer 2330 TSP3dw

<400> SEQUENCE: 5
actgggttcc aatatcacga gtc                                                  23

<210> SEQ ID NO 6
<211> LENGTH: 24
<212> TYPE: DNA
<213> ORGANISM: Artificial sequence
<220> FEATURE:
<223> OTHER INFORMATION: Primer 2331 TSP1up

<400> SEQUENCE: 6
atggtggatc gctaaatcac actg                                                 24

<210> SEQ ID NO 7
<211> LENGTH: 21
<212> TYPE: DNA
<213> ORGANISM: Artificial sequence
<220> FEATURE:
<223> OTHER INFORMATION: Primer 2332 TSP2up

<400> SEQUENCE: 7
acgtctgccc aaacatacac g                                                    21

<210> SEQ ID NO 8
<211> LENGTH: 19
<212> TYPE: DNA
<213> ORGANISM: Artificial sequence
<220> FEATURE:
<223> OTHER INFORMATION: Primer 2333 TSP3up

<400> SEQUENCE: 8
```

```
accgcccatc aggctaatc                                              19
```

<210> SEQ ID NO 9
<211> LENGTH: 1338
<212> TYPE: DNA
<213> ORGANISM: Hafnia alvei
<220> FEATURE:
<221> NAME/KEY: CDS
<222> LOCATION: (1)..(1338)
<220> FEATURE:
<221> NAME/KEY: sig_peptide
<222> LOCATION: (1)..(99)
<220> FEATURE:
<221> NAME/KEY: mat_peptide
<222> LOCATION: (100)..(1338)

<400> SEQUENCE: 9

```
atg aca atc tct ctg ttt aac cgt aat aaa ccc gct att gca cag cgt      48
Met Thr Ile Ser Leu Phe Asn Arg Asn Lys Pro Ala Ile Ala Gln Arg
            -30                 -25                 -20 att tta tgt cct ctg atc gtg gct tta ttc tca ggt tta ccg gca tac      96
Ile Leu Cys Pro Leu Ile Val Ala Leu Phe Ser Gly Leu Pro Ala Tyr
        -15                 -10                  -5 gcc agt gat acc gcc cct gct ggg ttc cag ttg gaa aag gtt gtt atc     144
Ala Ser Asp Thr Ala Pro Ala Gly Phe Gln Leu Glu Lys Val Val Ile
 -1   1           5                  10                  15 cta agc aga cat ggt gta cgc gcg cca acc aaa atg aca caa acg atg     192
Leu Ser Arg His Gly Val Arg Ala Pro Thr Lys Met Thr Gln Thr Met
             20                  25                  30 cgc gac gtc aca cct cac cag tgg cct gaa tgg ccg gta aaa ctc ggc     240
Arg Asp Val Thr Pro His Gln Trp Pro Glu Trp Pro Val Lys Leu Gly
         35                  40                  45 tat atc acg cca cgc ggc gaa cat ctg att agc ctg atg ggc ggt ttt     288
Tyr Ile Thr Pro Arg Gly Glu His Leu Ile Ser Leu Met Gly Gly Phe
     50                  55                  60 tat cga gag cgc ttt cag caa caa ggt tta tta cct aag gat aac tgt     336
Tyr Arg Glu Arg Phe Gln Gln Gln Gly Leu Leu Pro Lys Asp Asn Cys
 65                  70                  75 cct aca cca gat gcc gtg tat gtt tgg gca gac gtc gat caa cgc aca     384
Pro Thr Pro Asp Ala Val Tyr Val Trp Ala Asp Val Asp Gln Arg Thr
 80                  85                  90                  95 cgt aaa acc ggc gag gct ttc tta gca ggt ctt gct ccc cag tgt gat     432
Arg Lys Thr Gly Glu Ala Phe Leu Ala Gly Leu Ala Pro Gln Cys Asp
                100                 105                 110 tta gcg atc cac cat cag caa aac act cag cag gcc gat ccg ctg ttc     480
Leu Ala Ile His His Gln Gln Asn Thr Gln Gln Ala Asp Pro Leu Phe
             115                 120                 125 cac cct gtg aaa gcc ggt att tgt tcg atg gat aaa tca cag gta cac     528
His Pro Val Lys Ala Gly Ile Cys Ser Met Asp Lys Ser Gln Val His
         130                 135                 140 gcc gcg gtt gaa aag cag gca ggc aca ccg att gag acg ctc aat caa     576
Ala Ala Val Glu Lys Gln Ala Gly Thr Pro Ile Glu Thr Leu Asn Gln
     145                 150                 155 cgc tat caa gcc tct tta gcg ctg atg agt tcg gta ctc gat ttt cca     624
Arg Tyr Gln Ala Ser Leu Ala Leu Met Ser Ser Val Leu Asp Phe Pro
160                 165                 170                 175 aaa tcc ccc tat tgt cag cag cac aac att ggc aaa ctc tgc gat ttt     672
Lys Ser Pro Tyr Cys Gln Gln His Asn Ile Gly Lys Leu Cys Asp Phe
                180                 185                 190 tca cag gcg atg cct agc aga ctg gcg ata aat gac gac ggt aat aaa     720
Ser Gln Ala Met Pro Ser Arg Leu Ala Ile Asn Asp Asp Gly Asn Lys
             195                 200                 205
```

```
gtg gct ctc gaa ggt gcc gtg gga ctt gca tcg acg ttg gct gaa att    768
Val Ala Leu Glu Gly Ala Val Gly Leu Ala Ser Thr Leu Ala Glu Ile
        210                 215                 220 ttc ctg ctg gaa cac gct cag gga atg cct aaa gtg gct tgg ggg aat    816
Phe Leu Leu Glu His Ala Gln Gly Met Pro Lys Val Ala Trp Gly Asn
225                 230                 235 att cac act gag cag caa tgg aac tct ctg ttg aaa ttg cat aat gcg    864
Ile His Thr Glu Gln Gln Trp Asn Ser Leu Leu Lys Leu His Asn Ala
240                 245                 250                 255 cag ttt gac ttg atg tcg cgc acg ccc tat atc gcc aag cat aac ggt    912
Gln Phe Asp Leu Met Ser Arg Thr Pro Tyr Ile Ala Lys His Asn Gly
                260                 265                 270 act cca ctg ctg caa acc atc gcc cac gca ctg ggt tcc aat atc acg    960
Thr Pro Leu Leu Gln Thr Ile Ala His Ala Leu Gly Ser Asn Ile Thr
            275                 280                 285 agt cgc cca ctg ccg gat att tcg cca gac aat aag atc ctg ttt att   1008
Ser Arg Pro Leu Pro Asp Ile Ser Pro Asp Asn Lys Ile Leu Phe Ile
        290                 295                 300 gcc ggt cac gac acc aat att gcc aat att tct ggc atg tta ggg atg   1056
Ala Gly His Asp Thr Asn Ile Ala Asn Ile Ser Gly Met Leu Gly Met
305                 310                 315 aca tgg aca ctt ccg gga caa cca gat aac acg cct ccg ggt ggc gct   1104
Thr Trp Thr Leu Pro Gly Gln Pro Asp Asn Thr Pro Pro Gly Gly Ala
320                 325                 330                 335 ttg gtg ttt gaa cgc tgg gta gat aac gcg ggg aaa ccg tat gtt agc   1152
Leu Val Phe Glu Arg Trp Val Asp Asn Ala Gly Lys Pro Tyr Val Ser
                340                 345                 350 gtg aat atg gtg tat caa aca ctg gca cag ttg cac gac cag gcg ccg   1200
Val Asn Met Val Tyr Gln Thr Leu Ala Gln Leu His Asp Gln Ala Pro
            355                 360                 365 cta acg ttg cag cat cct gcg ggc agc gta cga cta aac ata ccg ggt   1248
Leu Thr Leu Gln His Pro Ala Gly Ser Val Arg Leu Asn Ile Pro Gly
        370                 375                 380 tgc agc gat caa acg ccc gat ggc tat tgc ccg ctc tcc acc ttc agc   1296
Cys Ser Asp Gln Thr Pro Asp Gly Tyr Cys Pro Leu Ser Thr Phe Ser
385                 390                 395 cgc tta gtc agc cac agc gtt gag cct gcg tgc cag ctt cct            1338
Arg Leu Val Ser His Ser Val Glu Pro Ala Cys Gln Leu Pro
400                 405                 410

<210> SEQ ID NO 10
<211> LENGTH: 446
<212> TYPE: PRT
<213> ORGANISM: Hafnia alvei

<400> SEQUENCE: 10

Met Thr Ile Ser Leu Phe Asn Arg Asn Lys Pro Ala Ile Ala Gln Arg
            -30                 -25                 -20

Ile Leu Cys Pro Leu Ile Val Ala Leu Phe Ser Gly Leu Pro Ala Tyr
        -15                 -10                 -5

Ala Ser Asp Thr Ala Pro Ala Gly Phe Gln Leu Glu Lys Val Val Ile
-1  1               5                   10                  15

Leu Ser Arg His Gly Val Arg Ala Pro Thr Lys Met Thr Gln Thr Met
                20                  25                  30

Arg Asp Val Thr Pro His Gln Trp Pro Glu Trp Pro Val Lys Leu Gly
            35                  40                  45

Tyr Ile Thr Pro Arg Gly Glu His Leu Ile Ser Leu Met Gly Gly Phe
        50                  55                  60

Tyr Arg Glu Arg Phe Gln Gln Gln Gly Leu Leu Pro Lys Asp Asn Cys
65                  70                  75
```

Pro Thr Pro Asp Ala Val Tyr Val Trp Ala Asp Val Asp Gln Arg Thr
80                  85                  90                  95

Arg Lys Thr Gly Glu Ala Phe Leu Ala Gly Leu Ala Pro Gln Cys Asp
            100                 105                 110

Leu Ala Ile His His Gln Asn Thr Gln Gln Ala Asp Pro Leu Phe
        115                 120                 125

His Pro Val Lys Ala Gly Ile Cys Ser Met Asp Lys Ser Gln Val His
        130                 135                 140

Ala Ala Val Glu Lys Gln Ala Gly Thr Pro Ile Glu Thr Leu Asn Gln
        145                 150                 155

Arg Tyr Gln Ala Ser Leu Ala Leu Met Ser Ser Val Leu Asp Phe Pro
160                 165                 170                 175

Lys Ser Pro Tyr Cys Gln Gln His Asn Ile Gly Lys Leu Cys Asp Phe
                180                 185                 190

Ser Gln Ala Met Pro Ser Arg Leu Ala Ile Asn Asp Asp Gly Asn Lys
            195                 200                 205

Val Ala Leu Glu Gly Ala Val Gly Leu Ala Ser Thr Leu Ala Glu Ile
        210                 215                 220

Phe Leu Leu Glu His Ala Gln Gly Met Pro Lys Val Ala Trp Gly Asn
225                 230                 235

Ile His Thr Glu Gln Gln Trp Asn Ser Leu Leu Lys Leu His Asn Ala
240                 245                 250                 255

Gln Phe Asp Leu Met Ser Arg Thr Pro Tyr Ile Ala Lys His Asn Gly
            260                 265                 270

Thr Pro Leu Leu Gln Thr Ile Ala His Ala Leu Gly Ser Asn Ile Thr
            275                 280                 285

Ser Arg Pro Leu Pro Asp Ile Ser Pro Asp Asn Lys Ile Leu Phe Ile
        290                 295                 300

Ala Gly His Asp Thr Asn Ile Ala Asn Ile Ser Gly Met Leu Gly Met
        305                 310                 315

Thr Trp Thr Leu Pro Gly Gln Pro Asp Asn Thr Pro Pro Gly Gly Ala
320                 325                 330                 335

Leu Val Phe Glu Arg Trp Val Asp Asn Ala Gly Lys Pro Tyr Val Ser
                340                 345                 350

Val Asn Met Val Tyr Gln Thr Leu Ala Gln Leu His Asp Gln Ala Pro
            355                 360                 365

Leu Thr Leu Gln His Pro Ala Gly Ser Val Arg Leu Asn Ile Pro Gly
        370                 375                 380

Cys Ser Asp Gln Thr Pro Asp Gly Tyr Cys Pro Leu Ser Thr Phe Ser
385                 390                 395

Arg Leu Val Ser His Ser Val Glu Pro Ala Cys Gln Leu Pro
400                 405                 410

<210> SEQ ID NO 11
<211> LENGTH: 81
<212> TYPE: DNA
<213> ORGANISM: Bacillus licheniformis
<220> FEATURE:
<221> NAME/KEY: CDS
<222> LOCATION: (1)..(81)
<223> OTHER INFORMATION: Savinase signal peptide

<400> SEQUENCE: 11 atg aag aaa ccg ttg ggg aaa att gtc gca agc acc gca cta ctc att      48
Met Lys Lys Pro Leu Gly Lys Ile Val Ala Ser Thr Ala Leu Leu Ile
1               5                   10                  15

```
                                                  -continued
tct gtt gct ttt agt tca tcg atc gca tcg gct                                           81
Ser Val Ala Phe Ser Ser Ser Ile Ala Ser Ala
            20                  25

<210> SEQ ID NO 12
<211> LENGTH: 27
<212> TYPE: PRT
<213> ORGANISM: Bacillus licheniformis

<400> SEQUENCE: 12

Met Lys Lys Pro Leu Gly Lys Ile Val Ala Ser Thr Ala Leu Leu Ile
1               5                   10                  15

Ser Val Ala Phe Ser Ser Ser Ile Ala Ser Ala
            20                  25
```